United States Patent
Buse et al.

(10) Patent No.: US 11,279,967 B2
(45) Date of Patent: Mar. 22, 2022

(54) SYSTEM AND METHOD FOR CONDUCTING AN ASSAY

(71) Applicant: Gen-Probe Incorporated, San Diego, CA (US)

(72) Inventors: David A. Buse, San Diego, CA (US); David Howard Combs, San Diego, CA (US); Byron J. Knight, San Diego, CA (US); Norbert D. Hagen, Carlsbad, CA (US); David Opalsky, San Diego, CA (US); Jason F. Rhubottom, Oceanside, CA (US); Keith Moravick, Los Gatos, CA (US); Tyler Moore, Los Gatos, CA (US); Anita Prasad, Los Gatos, CA (US); Bruce Richardson, Los Gatos, CA (US)

(73) Assignee: GEN-PROBE INCORPORATED, San Diego, CA (US)

( * ) Notice: Subject to any disclaimer, the term of this patent is extended or adjusted under 35 U.S.C. 154(b) by 0 days.

(21) Appl. No.: 17/036,730

(22) Filed: Sep. 29, 2020

(65) Prior Publication Data

US 2021/0017579 A1    Jan. 21, 2021

Related U.S. Application Data

(63) Continuation of application No. 17/033,395, filed on Sep. 25, 2020, which is a continuation of application
(Continued)

(51) Int. Cl.
*C12Q 1/6806* (2018.01)
*G01N 35/04* (2006.01)
(Continued)

(52) U.S. Cl.
CPC ........ *C12Q 1/6806* (2013.01); *B01L 3/50825* (2013.01); *B01L 3/565* (2013.01);
(Continued)

(58) Field of Classification Search
None
See application file for complete search history.

(56) References Cited

U.S. PATENT DOCUMENTS

| | | |
|---|---|---|
| 3,635,394 A | 1/1972 | Natelson |
| 3,653,528 A | 4/1972 | Wimmer |

(Continued)

FOREIGN PATENT DOCUMENTS

| | | |
|---|---|---|
| CA | 2571921 A1 | 1/2006 |
| CA | 2698253 A1 | 4/2009 |

(Continued)

OTHER PUBLICATIONS

USPTO Non-Final Rejection, U.S. Appl. No. 16/829,230, filed Jun. 4, 2020.
(Continued)

*Primary Examiner* — Brian R Gordon
(74) *Attorney, Agent, or Firm* — Richard Wydeven; Rothwell, Figg, Ernst & Manbeck, P.C.; Charles B. Cappellari

(57) ABSTRACT

A system for performing a nucleic acid amplification assay that includes a receptacle holder formed from a thermally conductive material and having a receptacle well for receiving a lower portion of a vial; a thermal element for cycling the temperature of the receptacle holder; a signal detection module in optical communication with the receptacle well; and a robotic pipettor. The receptacle holder supports a capped vial having a plastic, opaque cap in a snap-fit with a single plastic vial containing a nucleic acid amplification reagent. An upper portion of the cap includes a probe recess
(Continued)

that is configured to be removably engaged by an end of a probe of the robotic pipettor. A lower portion of the vial is contained within the receptacle well, and the cap is situated above a top surface of the receptacle holder.

25 Claims, 65 Drawing Sheets

Related U.S. Application Data

No. 16/829,230, filed on Mar. 25, 2020, now Pat. No. 10,889,851, which is a continuation of application No. 15/675,206, filed on Aug. 11, 2017, now Pat. No. 10,711,297, which is a continuation of application No. 14/213,900, filed on Mar. 14, 2014, now Pat. No. 9,732,374.

(60) Provisional application No. 61/784,994, filed on Mar. 14, 2013.

(51) Int. Cl.
  B01L 3/00 (2006.01)
  B01L 7/00 (2006.01)
  C12Q 1/686 (2018.01)

(52) U.S. Cl.
  CPC ............ B01L 7/5255 (2013.01); C12Q 1/686 (2013.01); G01N 35/04 (2013.01); B01L 3/527 (2013.01); B01L 2200/026 (2013.01); B01L 2200/0689 (2013.01); B01L 2300/046 (2013.01); G01N 2035/0418 (2013.01); G01N 2035/0436 (2013.01)

(56) References Cited

U.S. PATENT DOCUMENTS

| | | | |
|---|---|---|---|
| 4,162,003 A | 7/1979 | Bartos et al. | |
| 4,338,936 A | 7/1982 | Nelson | |
| 4,799,599 A * | 1/1989 | Herrmann | B01L 3/5082 215/307 |
| 4,829,006 A * | 5/1989 | Smith | B01L 3/5021 215/354 |
| 4,967,763 A | 11/1990 | Nugent et al. | |
| 5,119,560 A | 6/1992 | Noble | |
| 5,164,318 A | 11/1992 | Sato et al. | |
| 5,250,261 A | 10/1993 | Porte | |
| 5,346,672 A | 9/1994 | Stapleton et al. | |
| 5,473,437 A | 12/1995 | Blumenfeld et al. | |
| 5,475,610 A | 12/1995 | Atwood et al. | |
| 5,588,949 A | 12/1996 | Taylor et al. | |
| 5,656,493 A | 8/1997 | Mullis et al. | |
| 5,673,790 A | 10/1997 | Schramm | |
| 5,686,271 A | 11/1997 | Mian et al. | |
| 5,785,925 A | 7/1998 | U'Ren | |
| 5,786,182 A | 7/1998 | Catanzariti et al. | |
| 5,804,144 A | 9/1998 | Tervamaki | |
| 5,846,489 A | 12/1998 | Bienhaus et al. | |
| 5,863,791 A | 1/1999 | Baldszun et al. | |
| 5,897,008 A | 4/1999 | Hansen | |
| 5,935,524 A | 8/1999 | Bass et al. | |
| 6,134,000 A | 10/2000 | Schmid et al. | |
| 6,143,250 A | 11/2000 | Tajima | |
| 6,143,496 A | 11/2000 | Brown et al. | |
| 6,144,448 A * | 11/2000 | Mitoma | B01L 7/52 250/458.1 |
| D439,673 S | 3/2001 | Brophy et al. | |
| 6,197,572 B1 | 3/2001 | Schneebeli | |
| 6,216,340 B1 | 4/2001 | Fassbind et al. | |
| 6,224,573 B1 | 5/2001 | Yeager et al. | |
| 6,312,886 B1 | 11/2001 | Lee et al. | |
| 6,326,147 B1 | 12/2001 | Oldham et al. | |
| 6,403,037 B1 | 6/2002 | Chang et al. | |
| 6,442,440 B1 | 8/2002 | Miller | |
| 6,455,325 B1 | 9/2002 | Tajima | |
| 6,660,228 B1 | 12/2003 | Chang et al. | |
| 6,699,713 B2 | 3/2004 | Benett et al. | |
| 6,703,236 B2 | 3/2004 | Atwood | |
| 6,746,864 B1 | 6/2004 | McNeil et al. | |
| 6,800,452 B1 | 10/2004 | McNeil et al. | |
| 6,830,731 B1 | 12/2004 | Buechler et al. | |
| 6,875,602 B2 | 4/2005 | Gutierrez | |
| 6,890,488 B2 | 5/2005 | Mathus | |
| 6,909,974 B2 | 6/2005 | Yung et al. | |
| D511,214 S | 11/2005 | Sasano et al. | |
| 7,141,213 B1 | 11/2006 | Pang et al. | |
| 7,185,288 B2 | 2/2007 | McKeever | |
| 7,238,517 B2 | 7/2007 | Atwood et al. | |
| 7,390,458 B2 | 6/2008 | Burow et al. | |
| 7,416,700 B2 | 8/2008 | Buechler et al. | |
| D583,058 S | 12/2008 | Short | |
| D583,481 S | 12/2008 | Yamamoto | |
| 7,491,367 B2 | 2/2009 | Yung et al. | |
| 7,550,291 B2 | 6/2009 | Belz et al. | |
| 7,666,355 B2 | 2/2010 | Alavie et al. | |
| 7,691,332 B2 | 4/2010 | Kacian et al. | |
| 7,951,336 B2 | 5/2011 | Tajima | |
| 8,216,530 B2 | 7/2012 | Handique et al. | |
| 8,460,620 B2 | 6/2013 | Bartfeld et al. | |
| D687,567 S | 8/2013 | Jungheim et al. | |
| D709,624 S | 7/2014 | Baum et al. | |
| D723,181 S | 2/2015 | Kawamura | |
| 9,162,228 B2 | 10/2015 | Knight | |
| 9,248,449 B2 | 2/2016 | Knight | |
| 9,381,320 B2 | 7/2016 | Vincent et al. | |
| D762,873 S | 8/2016 | Baum et al. | |
| 9,732,374 B2 | 8/2017 | Buse et al. | |
| D805,636 S | 12/2017 | Pike | |
| D833,030 S | 11/2018 | Sasano | |
| 10,159,981 B2 | 12/2018 | Knight | |
| D857,883 S | 8/2019 | Knight | |
| 10,711,297 B2 | 7/2020 | Buse et al. | |
| 10,889,851 B2 | 1/2021 | Buse et al. | |
| 2001/0019826 A1 | 9/2001 | Ammann | |
| 2001/0049134 A1 | 12/2001 | Lee et al. | |
| 2002/0030044 A1 | 3/2002 | Brown | |
| 2002/0168299 A1 | 11/2002 | Chang et al. | |
| 2002/0190178 A1 | 12/2002 | Gorfain | |
| 2002/0191058 A1 | 12/2002 | Anderson et al. | |
| 2003/0033091 A1 | 2/2003 | Opalsky et al. | |
| 2003/0162285 A1 | 8/2003 | Tajima | |
| 2003/0215357 A1 | 11/2003 | Malterer et al. | |
| 2003/0219754 A1 | 11/2003 | Olesky et al. | |
| 2003/0225477 A1 | 12/2003 | Gilman et al. | |
| 2004/0032430 A1 | 2/2004 | Yung et al. | |
| 2004/0067169 A1 | 4/2004 | Krause | |
| 2004/0106097 A1 | 6/2004 | Hutter et al. | |
| 2004/0182888 A1 | 9/2004 | Hickert | |
| 2004/0228765 A1 | 11/2004 | Witty et al. | |
| 2005/0013742 A1 | 1/2005 | Shaw | |
| 2005/0123457 A1 | 6/2005 | Tajima et al. | |
| 2005/0203353 A1 | 9/2005 | Ma et al. | |
| 2005/0206895 A1 | 9/2005 | Salmelainen | |
| 2005/0221504 A1 | 10/2005 | Petruno et al. | |
| 2005/0221505 A1 | 10/2005 | Petruno et al. | |
| 2005/0271553 A1 | 12/2005 | Ramstad et al. | |
| 2005/0282266 A1 | 12/2005 | Teng et al. | |
| 2006/0014272 A1 | 1/2006 | Tajima et al. | |
| 2006/0153736 A1 | 7/2006 | Kalra et al. | |
| 2006/0205064 A1 | 9/2006 | Tajima | |
| 2006/0249558 A1 | 11/2006 | Roach et al. | |
| 2007/0132723 A1 | 6/2007 | Lurz et al. | |
| 2007/0183937 A1 | 8/2007 | Sarstedt | |
| 2007/0248494 A1 | 10/2007 | Mokelke et al. | |
| 2008/0072609 A1 | 3/2008 | Kacian et al. | |
| 2008/0227186 A1 | 9/2008 | Polaniec et al. | |
| 2008/0247914 A1 | 10/2008 | Edens et al. | |
| 2008/0254545 A1 | 10/2008 | Kitaoka | |
| 2008/0268529 A1 | 10/2008 | Furusato et al. | |
| 2009/0074624 A1 | 3/2009 | Liang | |
| 2009/0117620 A1 | 5/2009 | Fritchie et al. | |
| 2009/0130745 A1 | 5/2009 | Williams et al. | |

(56) References Cited

U.S. PATENT DOCUMENTS

| | | |
|---|---|---|
| 2009/0132204 A1 | 5/2009 | Bodlaender et al. |
| 2009/0136951 A1 | 5/2009 | Hart et al. |
| 2009/0149351 A1 | 6/2009 | Tajima |
| 2009/0170183 A1 | 7/2009 | Büchs |
| 2009/0227006 A1 | 9/2009 | Kopp et al. |
| 2010/0136632 A1 | 6/2010 | Lipscomb et al. |
| 2010/0209298 A1 | 8/2010 | Kalra et al. |
| 2010/0224632 A1 | 9/2010 | Aneas |
| 2010/0248245 A1 | 9/2010 | Ying et al. |
| 2010/0264155 A1 | 10/2010 | Harder et al. |
| 2010/0297640 A1 | 11/2010 | Kumar et al. |
| 2011/0091885 A1 | 4/2011 | Schmitt et al. |
| 2011/0129825 A1 | 6/2011 | Ketchum |
| 2011/0312102 A1 | 12/2011 | Jo |
| 2012/0012779 A1 | 1/2012 | Foo et al. |
| 2012/0291872 A1 | 11/2012 | Brady et al. |
| 2013/0065797 A1 | 3/2013 | Silbert et al. |
| 2013/0318915 A1 | 12/2013 | Iskarous et al. |
| 2014/0260118 A1 | 9/2014 | Knight |
| 2014/0263153 A1 | 9/2014 | Knight |
| 2016/0008810 A1 | 1/2016 | Knight |
| 2016/0023211 A1 | 1/2016 | Knight |
| 2016/0032358 A1 | 2/2016 | Buse et al. |
| 2016/0114318 A1 | 4/2016 | Knight |
| 2019/0134626 A1 | 5/2019 | Knight |
| 2021/0017578 A1 | 1/2021 | Knight et al. |
| 2021/0079452 A1 | 3/2021 | Buse et al. |

FOREIGN PATENT DOCUMENTS

| | | |
|---|---|---|
| CN | 1352576 A | 6/2002 |
| CN | 101128262 A | 2/2008 |
| CN | 101147070 A | 3/2008 |
| CN | 101802164 A | 8/2010 |
| CN | 102155971 A | 8/2011 |
| DE | 2806089 A1 | 8/1979 |
| DE | 19536789 A1 | 4/1997 |
| DE | 102005062052 A1 | 6/2007 |
| DE | 102006021404 A1 | 11/2007 |
| EP | 0488769 A2 | 6/1992 |
| EP | 0571033 A1 | 11/1993 |
| EP | 0580362 A1 | 1/1994 |
| EP | 0583066 A1 | 2/1994 |
| EP | 0676643 A2 | 10/1995 |
| EP | 0686699 A2 | 12/1995 |
| EP | 1508527 A1 | 2/2005 |
| EP | 1930078 A1 | 6/2008 |
| EP | 2030687 A1 | 3/2009 |
| FR | 2281768 A1 | 3/1976 |
| JP | S6472071 A | 3/1989 |
| JP | 2004-294428 A | 10/2004 |
| JP | 2005-003425 A | 1/2005 |
| JP | 2007-222105 A | 9/2007 |
| JP | 2007-287019 A | 11/2007 |
| JP | 2008-245523 A | 10/2008 |
| JP | 2009-039046 A | 2/2009 |
| JP | 2010508813 A | 3/2010 |
| JP | 2011-050699 A | 3/2011 |
| WO | 89/04487 A1 | 5/1989 |
| WO | 99/57304 A1 | 11/1999 |
| WO | 99/57561 A2 | 11/1999 |
| WO | 00/12675 A1 | 3/2000 |
| WO | 00/58013 A1 | 10/2000 |
| WO | 00/60362 A1 | 10/2000 |
| WO | 01/55708 A2 | 8/2001 |
| WO | 01/60967 A1 | 8/2001 |
| WO | 03/42697 A1 | 5/2003 |
| WO | 2004/105947 A2 | 12/2004 |
| WO | 2005/118772 A1 | 12/2005 |
| WO | 2006/005371 A1 | 1/2006 |
| WO | 2006/079814 A2 | 8/2006 |
| WO | 2006/085071 A2 | 8/2006 |
| WO | 2007/122226 A2 | 11/2007 |
| WO | 2008/057375 A2 | 5/2008 |
| WO | 2008/123882 A1 | 10/2008 |
| WO | 2009/035792 A1 | 3/2009 |
| WO | 2009/054870 A2 | 4/2009 |
| WO | 2010/114842 A1 | 10/2010 |
| WO | 2010/144859 A2 | 12/2010 |
| WO | 2012/012779 A2 | 1/2012 |
| WO | 2012/074738 A1 | 6/2012 |
| WO | 2012/173919 A1 | 12/2012 |

OTHER PUBLICATIONS

U.S. Appl. No. 16/829,230, filed Sep. 2, 2020. Notice of Allowance.
USPTO Non-Final Rejection, U.S. Appl. No. 16/238,239, filed Mar. 15, 2021.
USPTO Notice of Allowance, U.S. Appl. No. 29/670,399, filed Apr. 4, 2019.
APO Examination Report No. 1, Australian Patent Application No. 2019206128, dated Mar. 6, 2020.
APO Notice of Acceptance for Patent Application, Australian Patent Application No. 2019206128, dated Feb. 23, 2021.
APO Examination Report No. 1, Australian Patent Application No. 2020233639, dated Jan. 29, 2021.
APO Notice of Acceptance for Patent Application, Australian Patent Application No. 2020233639, dated Feb. 26, 2021.
CNIPA Second Office Action, Chinese Patent Application No. 201710826817.8, dated Jan. 22, 2020.
CNIPA First Office Action, Chinese Patent Application No. 201810251881.2, dated Mar. 22, 2021.
CNIPA First Office Action, Chinese Patent Application No. 201810249771.2, Mar. 9, 2021.
CNIPA Search Report, Chinese Patent Application No. 201810249771.2, dated Mar. 1, 2021.
EPO Extended European Search Report, European Patent Application No. 19161986.5, dated Sep. 25, 2019.
EPO Communication under Rule 71(3) EPC, European Patent Application No. 19161986.5, dated Oct. 29, 2020.
EPO Extended European Search Report, European Patent Application No. 19161987.3, dated Aug. 7, 2019.
EPO Communication under Rule 71(3) EPC, European Patent Application No. 19161987.3, dated Nov. 2, 2020.
JPO Official Action, Japanese Patent Application No. 2019-019717, dated Jan. 31, 2020.
PCT International Search Report and Written Opinion, International Application No. PCT/US2014/026789, dated Oct. 15, 2014.
PCT International Search Report and Written Opinion, International Application No. PCT/US2014/029538, dated Nov. 24, 2014.
PCT International Search Report and Written Opinion, International Application No. PCT/US2013/52966, dated Feb. 7, 2014.
PCT International Preliminary Report on Patentability, International Application No. PCT/US2013/52966, dated Feb. 12, 2015.
USPTO Non-Final Rejection, U.S. Appl. No. 13/956,022, dated Oct. 27, 2015.
USPTO Final Rejection, U.S. Appl. No. 13/956,022, dated May 13, 2016.
USPTO Advisory Action, U.S. Appl. No. 13/956,022, dated Sep. 28, 2016.
USPTO Non-Final Rejection, U.S. Appl. No. 13/956,022, dated Feb. 22, 2017.
USPTO Final Rejection, U.S. Appl. No. 13/956,022, dated Sep. 15, 2017.
USPTO Non-Final Rejection, U.S. Appl. No. 13/956,022, dated Mar. 7, 2018.
USPTO Final Rejection, U.S. Appl. No. 13/956,022, dated Aug. 7, 2018.
USPTO Advisory Action, U.S. Appl. No. 13/956,022, dated Oct. 16, 2018.
USPTO Non-Final Rejection, U.S. Appl. No. 13/956,022, dated Mar. 1, 2019.
USPTO Interview Summary, U.S. Appl. No. 13/956,022, dated Jun. 6, 2019.
USPTO Notice of Allowance, U.S. Appl. No. 13/956,022, dated Jul. 3, 2019.
USPTO Corrected Notice of Allowance, U.S. Appl. No. 13/956,022, dated Nov. 8, 2019.

(56) References Cited

OTHER PUBLICATIONS

USPTO Non-Final Rejection, U.S. Appl. No. 14/210,042, dated Apr. 8, 2015.
USPTO Notice of Allowance, U.S. Appl. No. 14/210,042, dated Jun. 23, 2015.
USPTO Non-Final Rejection, U.S. Appl. No. 14/210,163, dated May 21, 2015.
USPTO Notice of Allowance, U.S. Appl. No. 14/210,163, dated Sep. 16, 2015.
USPTO Notice of Allowance, U.S. Appl. No. 14/210,163, dated Dec. 16, 2015.
USPTO Corrected Notice of Allowance, U.S. Appl. No. 14/210,163, dated Dec. 24, 2015.
USPTO Non-Final Rejection, U.S. Appl. No. 14/212,261, dated Oct. 28, 2016.
USPTO Final Rejection, U.S. Appl. No. 14/212,261, dated Jul. 6, 2017.
USPTO Non-Final Rejection, U.S. Appl. No. 14/212,261, dated Dec. 29, 2017.
USPTO Interview Summary, U.S. Appl. No. 14/212,261, dated Apr. 26, 2018.
USPTO Final Rejection, U.S. Appl. No. 14/212,261, dated May 29, 2018.
USPTO Non-Final Rejection, U.S. Appl. No. 14/212,261, dated Dec. 5, 2018.
USPTO Non-Final Rejection, U.S. Appl. No. 14/212,261, dated Jun. 19, 2019.
USPTO Non-Final Rejection, U.S. Appl. No. 14/213,900, dated Jun. 24, 2016.
USPTO Notice of Allowance, U.S. Appl. No. 14/213,900, dated Apr. 10, 2017.
USPTO Non-Final Rejection, U.S. Appl. No. 14/858,453, dated Apr. 7, 2016.
USPTO Final Rejection, U.S. Appl. No. 14/858,453, dated Jan. 6, 2017.
USPTO Non-Final Rejection, U.S. Appl. No. 14/992,663, dated Dec. 21, 2016.
USPTO Final Rejection, U.S. Appl. No. 14/992,663, dated Sep. 5, 2017.
USPTO Non-Final Rejection, U.S. Appl. No. 14/992,663, dated Feb. 28, 2018.
USPTO Notice of Allowance, U.S. Appl. No. 14/992,663, dated Jul. 12, 2018.
USPTO Corrected Notice of Allowance, U.S. Appl. No. 14/992,663, dated Nov. 13, 2018.
USPTO Non-Final Rejection, U.S. Appl. No. 15/675,206, dated Mar. 13, 2019.
USPTO Interview Summary, U.S. Appl. No. 15/675,206, dated Sep. 9, 2019.
USPTO Notice of Allowance, U.S. Appl. No. 15/675,206, dated Feb. 26, 2020.
USPTO Notice of Allowance, U.S. Appl. No. 16/829,230, dated Sep. 12, 2020.
USPTO Non-Final Rejection, U.S. Appl. No. 17/036,307, dated Feb. 5, 2021.
APO Patent Examination Report No. 1, Australian Patent Application No. 2013202778, dated Jun. 3, 2014.
APO Patent Examination Report No. 1, Australian Patent Application No. 2013202793, dated Feb. 28, 2014.
APO Notice of Acceptance, Australian Patent Application No. 2013202793, dated Sep. 4, 2014.
APO Patent Examination Report No. 1, Australian Patent Application No. 2013202805, dated Aug. 25, 2014.
APO Notice of Acceptance, Australian Patent Application No. 2013202805, dated Jul. 6, 2015.
APO Patent Examination Report No. 1, Australian Patent Application No. 2014236196, dated Nov. 20, 2015.
APO Patent Examination Report No. 1, Australian Patent Application No. 2014236667, dated Oct. 21, 2015.
APO Patent Examination Report No. 1, Australian Patent Application No. 2014277774, dated Apr. 28, 2016.
APO Notice of Acceptance, Australian Patent Application No. 2014277774, dated Apr. 21, 2017.
APO Patent Re-examination Report, Australian Patent Application No. 2014277774, dated Oct. 26, 2018.
APO Patent Re-examination Report, Australian Patent Application No. 2014277774, dated Feb. 8, 2019.
APO Patent Examination Report No. 1, Australian Patent Application No. 2016247157, dated Nov. 8, 2016.
APO Notice of Acceptance for Patent Application, Australian Patent Application No. 2016247157, dated Oct. 27, 2017.
APO Patent Examination Report No. 1, Australian Patent Application No. 2016262653, dated Nov. 6, 2017.
APO Notice of Acceptance, Australian Patent Application No. 2016262653, dated Jun. 22, 2018.
APO Examination Report No. 1, Australian Patent Application No. 2017210511, dated Jul. 19, 2018.
CIPO Examination Report, Canadian Patent Application No. 2,903,105, dated Nov. 4, 2015.
CIPO Examination Report, Canadian Patent Application No. 2,903,105, dated Nov. 23, 2015.
CIPO Examination Report, Canadian Patent Application No. 2913698, dated Jan. 25, 2016.
CIPO Examination Report, Canadian Patent Application No. 2913701, dated Jan. 26, 2016.
CIPO Examination Report, Canadian Patent Application No. 2913701, dated Jun. 2, 2016.
CIPO Examination Report, Canadian Patent Application No. 2913701, dated Mar. 20, 2018.
CIPO Examiner's Report, Canadian Patent Application No. 2,913,701, dated Feb. 6, 2020.
CIPO Examination Report, Canadian Patent Application No. 2,913,705, dated Jan. 26, 2016.
CIPO Notice of Allowance, Canadian Patent Application No. 2,913,705, dated May 19, 2016.
SIPO Search Report, Chinese Patent Application No. 201380046526.7, dated Dec. 7, 2015.
SIPO First Office Action, Chinese Patent Application No. 201380046526.7, dated Dec. 23, 2015.
SIPO Second Office Action, Chinese Patent Application No. 201380046526.7, dated Sep. 14, 2016.
SIPO Third Office Action, Chinese Patent Application No. 201380046526.7, dated Feb. 28, 2017.
SIPO Search Report, Chinese Patent Application No. 201380046526.7, dated Jun. 19, 2017.
SIPO Notification of Fulfilling of Registration Formality, Chinese Patent Application 201380046526.7, dated Jun. 29, 2017.
SIPO First Office Action, Chinese Patent Application No. 201480015079.3, dated Jun. 7, 2016.
SIPO Second Office Action, Chinese Patent Application No. 201480015079.3, dated Mar. 7, 2017.
SIPO Search Report, Chinese Patent Application No. 201480015079.3, dated Feb. 23, 2017.
SIPO Third Office Action, Chinese Patent Application No. 201480015079.3, dated Feb. 24, 2018.
SIPO Notification of Registering the Patent, Chinese Patent Application No. 201480015079.3, dated Nov. 28, 2018.
SIPO Search Report, Chinese Patent Application No. 201480015048.8, dated Jun. 1, 2016.
SIPO Office Action No. 2, Chinese Patent Application No. 201480015048.8, dated Nov. 22, 2016.
CNIPA Search Report, Chinese Patent Application No. 201710826817.8, dated Mar. 20, 2019.
CNIPA First Office Action, Chinese Patent Application No. 201710826817.8, dated Mar. 28, 2019.
CNIPA Search Report, Chinese Patent Application No. 201810251881.2, dated Mar. 12, 2021.
SIPO First Office Action, Chinese Patent Application No. 201810249772.7, dated Jan. 21, 2020.
EPO Extended European Search Report, European Patent Application No. 13826240.7, dated Feb. 29, 2016.

(56) References Cited

OTHER PUBLICATIONS

EPO Communication Pursuant to Art. 94(3) EPC, European Patent Application No. 13826240.7, dated Feb. 15, 2017.
EPO Communication Pursuant to Art. 71(3) EPC, European Patent Application No. 13826240.7, dated May 7, 2018.
EPO Communication Pursuant to Art. 71(3) EPC, European Patent Application No. 13826240.7, dated Sep. 24, 2018.
EPO Communication pursuant to Art. 94(3) EPC, European Patent Application No. 14717958.4, dated Aug. 5, 2016.
EPO Communication pursuant to Art. 94(3) EPC, European Patent Application No. 14717958.4, dated Mar. 13, 2017.
EPO Communication under Rule 71(3) EPC, European Patent Application No. 14717958.4, dated Apr. 20, 2018.
EPO Communication pursuant to Article 94(3) EPC, European Patent Application No. 14720813.6, dated Nov. 24, 2016.
EPO Communication under Rule 71(3) EPC, European Patent Application No. 14720813.6, dated Apr. 12, 2017.
EPO Communication pursuant to Rule 62 EPC, European Patent Application No. 18197232.4, dated Jan. 21, 2019.
EPO Communication pursuant to Rule 94(3) EPC, European Patent Application No. 18197232.4, dated Feb. 7, 2020.
EPO Partial European Search Report, European Patent Application No. 19161986.5, dated Aug. 8, 2019.
JPO Office Action, Japanese Patent Application No. 2015-525551, dated Apr. 24, 2017.
JPO Office Action, Japanese Patent Application No. 2015-525551, dated Dec. 6, 2017.
JPO Final Office Action, Japanese Patent Application No. 2015-525551, dated Nov. 2, 2018.
JPO Notice of Allowance, Japanese Patent Application No. 2015-525551, dated May 13, 2019.
JPO Official Action, Japanese Patent Application No. 2016-502247, dated Jul. 27, 2016.
JPO Official Action, Japanese Patent Application No. 2016-502247, dated Mar. 8, 2017.
JPO Notice of Allowance, Japanese Patent Application No. 2016-502247, dated Jun. 7, 2017.
JPO Office Action No. 1, Japanese Patent Application No. 2016-503127, dated Jul. 14, 2016.
JPO Office Action No. 2, Japanese Patent Application No. 2016-503127, dated Apr. 24, 2017.
JPO Notice of Allowance, Japanese Patent Application No. 2016-503127, dated Mar. 26, 2018.
JPO Office Action, Japanese Patent Application No. 2017-005256, dated Dec. 13, 2017.
JPO Office Action, Japanese Patent Application No. 2017-205176, dated Oct. 25, 2018.
JPO Office Action, Japanese Patent Application No. 2019-019716, dated Feb. 4, 2020.
Heid et al., "Real Time Quantitative PCR," Genome Research, 1996, 6(10):986-994, Cold Spring Harbor Laboratory.
Innis et al., "PCR Protocols," pp. 237-244, HBJ Shuppankyoku, 1991, Japan.
Nakano et al., "Development of Single Molecule RT-PCR Method Using W/O Emulsion", The Society of Chemical Engineers, The Collected Abstracts of Research Presentations of the 36th Autumn Meeting, Aug. 18, 2003, DOI 10.11491/scej.2003f.0.676.0.
Qi et al., "Implication of C-Terminal Deletion on the Structure and Stability of Bovine β-casein," Protein J., 2005, 24 (7-8):431-444, Springer Science + Business Media, Inc., U.S.

* cited by examiner

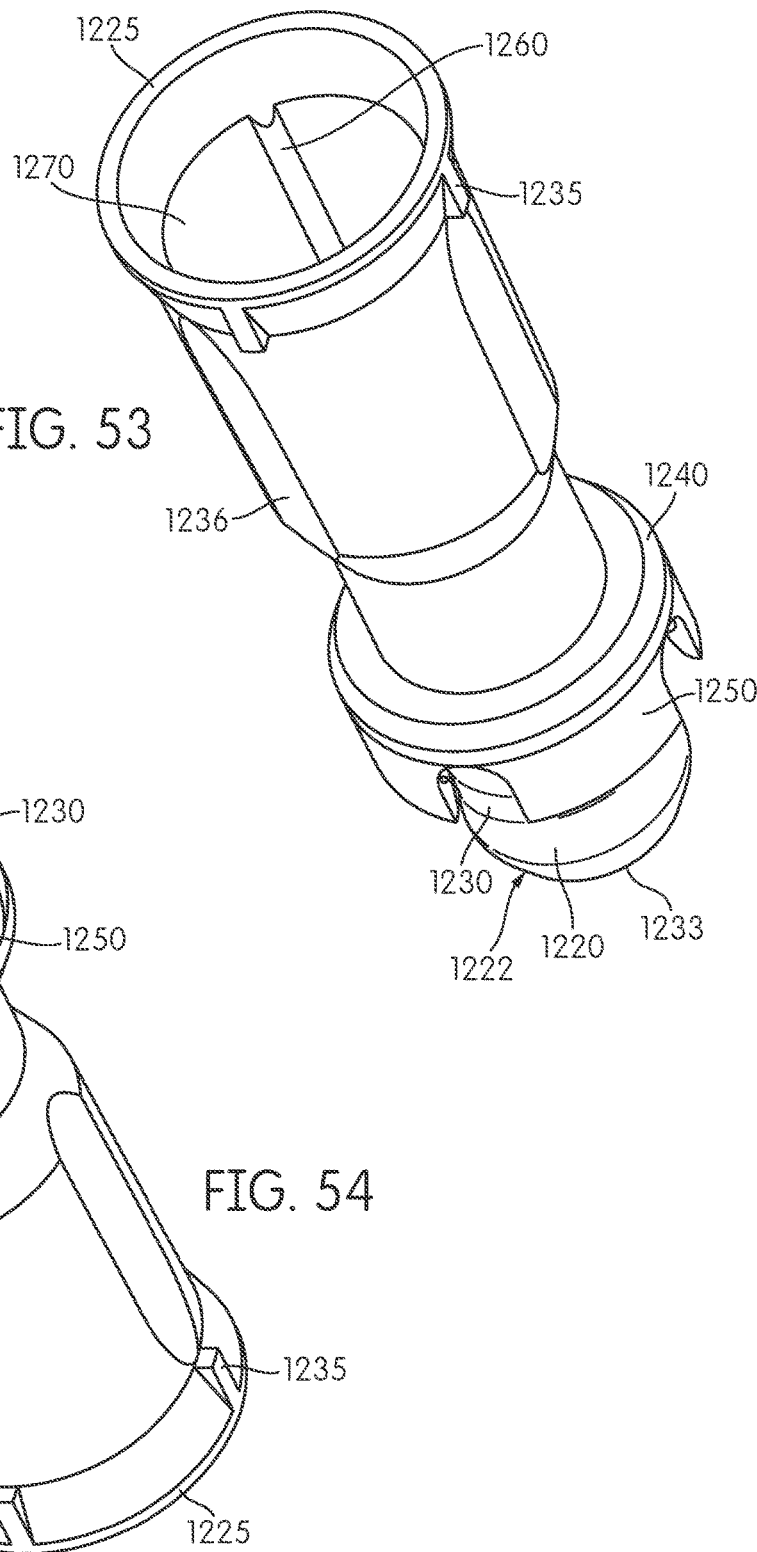

SYSTEM AND METHOD FOR CONDUCTING AN ASSAY

CROSS-REFERENCE TO RELATED APPLICATIONS

This is a continuation application claiming the benefit under 35 U.S.C. § 120 of the filing date of U.S. application Ser. No. 17/033,395, filed Sep. 25, 2020, which is a continuation application claiming the benefit under 35 U.S.C. § 120 of the filing date of U.S. application Ser. No. 16/829,230, filed Mar. 25, 2020, now U.S. Pat. No. 10,889,851, which is a continuation application claiming the benefit under 35 U.S.C. § 120 of the filing date of U.S. application Ser. No. 15/675,206, filed Aug. 11, 2017, now U.S. Pat. No. 10,711,297, which is a continuation application claiming the benefit under 35 U.S.C. § 120 of the filing date of U.S. application Ser. No. 14/213,900, filed Mar. 14, 2014, now U.S. Pat. No. 9,732,374, which claims the benefit under 35 U.S.C. § 119(e) of the filing date of U.S. Provisional Application No. 61/784,994, filed Mar. 14, 2013, the disclosures of which are hereby incorporated by reference herein.

FIELD

The present disclosure relates to systems and methods for performing molecular assays that comprise target nucleic acid amplification reactions by heating the contents of a capped vial containing a reaction mixture and measuring an optical signal from the contents of the vial.

BACKGROUND

None of the references described or referred to herein are admitted to be prior art to the claimed invention.

Molecular assays are nucleic acid-based tests that are used in clinical diagnosis, screening, monitoring, industrial and environmental testing, health science research, and other applications to detect the presence or amount of an analyte of interest in a sample, such as a microbe or virus, or to detect genetic abnormalities or mutations in an organism. Molecular assays enabling quantification may permit practitioners to better calculate the extent of infection or disease and to determine the state of a disease over time. Quantitative molecular assays are also useful for monitoring the effectiveness of a therapy. A variety of known molecular assays can be employed to detect various diagnostic indicators.

Molecular assays generally include multiple steps leading to the detection or quantification of a target nucleic acid in a sample. Targeted nucleic acids often include a region that is specific to an identifiable "group" of organisms or viruses, where the group is defined by at least one shared sequence of nucleic acid that is common to all members of the group and is specific to the group in the particular sample being assayed. Examples of nucleic acid-based detection methods are disclosed by Kohne in U.S. Pat. No. 4,851,330 and Hogan et al. in U.S. Pat. No. 5,541,308.

Most molecular assays include a detection step in which the sample is exposed to a detection probe or amplification primer that is designed or selected to exhibit specificity under the particular conditions of use for a nucleic acid sequence belonging to an organism or virus of interest. The detection probe or amplification primer can be labeled for detection with a reporter moiety, such as a chemiluminescent or fluorescent agent, or an intercalating dye can be used to indiscriminately detect the presence of double-stranded nucleic acids in a sample. See, e.g., Livak et al. in U.S. Pat. No. 5,538,848, Hogan et al. in U.S. Pat. No. 5,541,308, Tyagi et al. in U.S. Pat. No. 5,925,517, Higuchi in U.S. Pat. No. 5,994,056, Wittwer et al. in U.S. Pat. No. 6,174,670, Whitcombe et al. in U.S. Pat. No. 6,326,145, and Wittwer et al. in U.S. Pat. No. 6,569,627. To render a nucleic acid available for hybridization to the detection probe or amplification primer, cells may be lysed or permeabilized by a variety of known techniques, including by chemical (e.g., detergent), mechanical (e.g., sonication), and/or thermal procedures. See, e.g., Clark et al. in U.S. Pat. No. 5,786,208.

Before or after exposing a target nucleic acid to a detection probe or amplification primer, the target nucleic acid can be immobilized on a solid support (e.g., particles or beads comprising a magnetically-responsive material) that directly or indirectly binds the target nucleic acid. A solid-phase extraction method for directly binding nucleic acids onto silica beads in the presence of a chaotropic substance is described by Boom et al. in U.S. Pat. No. 5,234,864. An example of indirect immobilization is described Weisburg et al. in U.S. Pat. No. 6,534,273, which discloses the use of a capture probe that binds to the target nucleic acid under a first set of sample conditions and to an oligonucleotide covalently attached to the solid support under a second set of sample conditions. If the solid support comprises a magnetically-responsive particle or bead, magnets can be used to attract the solid support to the side of a receptacle containing the solid support. Once the immobilized target nucleic acid is isolated within the receptacle, the isolated target nucleic acid can be separated from at least a portion of the fluid contents of the sample by, for example, contacting and aspirating the fluid contents of the receptacle with a robotic pipettor or other substance transfer device. See, e.g., Ammann et al. in U.S. Pat. No. 6,605,213. One or more wash steps with a buffered solution or water may be performed to further purify the isolated nucleic acid.

To increase the sensitivity of an assay, a target nucleic acid can be amplified by a nucleic acid amplification reaction, many of which are well known in the art. Known methods of amplification include Polymerase Chain Reaction ("PCR") (see, e.g., Mullis et al. in U.S. Pat. Nos. 4,683,195, 4,683,202 and 4,800,159; and Mullis et al., *Methods in Enzymology,* 155:335-350 (1987)); Strand Displacement Amplification ("SDA") (see, e.g., Walker, *PCR Methods and Applications,* 3:25-30 (1993); Walker et al., *Nucleic Acids Res.,* 20:1691-1996 (1992); and Walker et al., *Proc. Natl. Acad. Sci.,* 89:392-396 (1991)); Ligase Chain Reaction ("LCR") (see, e.g., Birkenmeyer in U.S. Pat. No. 5,427,930 and Carrino et al., in U.S. Pat. No. 5,686,272); and transcription-based methods of amplification (Boothroyd et al. in U.S. Pat. No. 5,437,990; Kacian et al., in U.S. Pat. Nos. 5,399,491 and 5,480,784; Davey et al. in U.S. Pat. No. 5,409,818; Malek et al. in U.S. Pat. No. 5,130,238; and Gingeras et al. in International Publication Nos. WO 88/01302 and WO 88/10315). A review of many amplification reactions, including PCR and Transcription-Mediated Amplification ("TMA"), is provided in Lee et al., Nucleic Acid Amplification Technologies, *BioTechniques Books* (1997).

PCR is the oldest and most common form of amplification. Like other amplification methods, PCR amplifies one or more copies of a region of nucleic acid by several orders of magnitude, generating thousands to millions of copies of a particular nucleic acid sequence. PCR has broad applications in clinical and biological research labs. The uses of this procedure are too enumerable, and well known at this time, to recite in this patent application.

PCR employs thermal cycling, which consists of repeated cycles of heating and cooling of a reaction mixture. The reaction is generally initiated with primers (short DNA fragments containing sequences complementary to the target nucleic acid region), along with enzymes and additional reaction materials. Once under way, the replicated nucleic acid can be used as an additional template in the amplification reaction, thereby leading to the exponential amplification of a target nucleic acid sequence.

Because a probe hybridizes to the targeted sequence, the strength of a signal associated with the probe is proportional to the amount of target nucleic acid sequence that is present in a sample. Accordingly, by periodically measuring, during the amplification process, a signal indicative of the presence of amplicon, the growth of amplicon over time can be detected. Based on the data collected during this "real-time" monitoring of the amplification process, the amount of the target nucleic acid that was originally in the sample can be ascertained. In one context, collecting data in "real-time" means collecting data while a reaction or other process is in progress, as opposed to collecting data at the conclusion of the reaction or process. Systems and methods for real-time detection and for processing real-time data to ascertain nucleic acid levels are disclosed by, for example, Lair et al. in U.S. Pat. No. 7,932,081.

To detect different nucleic acids in a single assay, distinct probes may be designed or selected to separately hybridize to the different nucleic acids, where the probes may include reporter moieties that can be differentiated from each other. See, e.g., Livak et al. in U.S. Pat. No. 5,538,848, Tyagi et al. in U.S. Pat. No. 5,925,517, Morrison in U.S. Pat. No. 5,928,862, Mayrand in U.S. Pat. No. 5,691,146, and Becker et al. in U.S. Pat. No. 5,928,862. For example, different probes designed or selected to hybridize to different targets can have fluorophores that fluoresce at a predetermined wavelength when exposed to excitation light of a prescribed excitation wavelength. Assays for detecting different target nucleic acids can be performed in parallel by alternately exposing the sample material to different excitation wavelengths and detecting the level of fluorescence at the wavelength of interest corresponding to the probe for each target nucleic acid during the real-time monitoring process. Parallel processing can be performed using different signal detecting devices configured to periodically measure signal emissions during the amplification process, and with different signal detecting devices being configured to generate excitation signals of different wavelengths and to measure emission signals of different wavelengths.

SUMMARY

Aspects of the present disclosure are embodied in systems, apparatuses, and processes that, inter alia, enhance the functionality of certain diagnostic first modules by supporting processing capabilities that are not available in the base first module or existing modules within the base first module. In one embodiment, the systems, apparatuses, and processes extend the functionality of a nucleic acid diagnostic first module by supporting PCR assay processing and analysis capabilities in addition to isothermal amplification processing and analysis capabilities. A second module is operatively coupled to the base first module to extend the overall system capabilities of the diagnostic system. Providing this extension module imparts sample-to-answer capabilities for a single automated instrument that, when incorporated, will be capable of automatically performing both thermal cycling and isothermal amplification assays, and which may incorporate end-point and real-time formats using chemiluminescent and/or fluorescent labels.

In some embodiments, a diagnostic system can be configured to perform a first nucleic acid amplification reaction and a second nucleic acid amplification reaction different than the first nucleic acid amplification reaction. The diagnostic system comprises at least one bulk reagent container compartment configured to store at least a first bulk reagent container comprising a first bulk reagent for performing a sample preparation process, and a second bulk reagent container comprising a second bulk reagent for performing the first nucleic acid amplification reaction. The at least one bulk reagent container compartment is further configured to store a unit-dose reagent compartment configured to store at least one unit-dose reagent pack comprising a plurality of unit-dose reagents for performing the second nucleic acid amplification reaction. The diagnostic system is configured to perform the sample preparation process using the first bulk reagent on a first subset of the plurality of samples provided to the diagnostic system. The diagnostic system is also configured to perform the first nucleic acid amplification reaction using a second bulk reagent on the first subset of the plurality of samples. And the diagnostic system is configured to perform the second nucleic acid amplification reaction using the plurality of unit-dose reagents on a second subset of the plurality of samples.

In some embodiments, an automated method for analyzing a plurality of samples comprises performing a first assay on a first sample subset of the plurality of samples. The first assay comprises a first reaction that uses a first unit-dose reagent. The method also comprises performing a second assay on a second sample subset of the plurality of samples. The second assay comprises a second reaction that uses at least one of (a) a second unit-dose reagent different than the first unit-dose reagent and (b) a first bulk reagent. Performing the first assay and performing the second assay occur within a same diagnostic system that stores the first unit-dose reagent and at least one of the second unit-dose reagent and the first bulk reagent.

In one exemplary embodiment, the base first module comprises a dual format molecular diagnostic instrument designed to run specific target-amplified assays, utilizing chemiluminescence and fluorescence detection technologies for both qualitative and real-time quantitative assays. With the addition of the second module, additional automated assays, such as PCR assays, can be run (intermixed) with assays performed by the base first module and achieve similar throughput that is achieved by the base first module.

In one exemplary embodiment, the second module comprises a thermal cycler with real-time fluorescence detection capabilities, a reagent pack storage bay that allows for loading and cooled storage of new reagent packs containing reagents (e.g., PCR reagents), additional disposable pipette tip trays, PCR- and assay-specific reagents, and one or more pipettor systems to perform the assay steps needed for the PCR or other reaction and/or receptacle transport. The second module may rely on the base first module for sample input, sample preparation, target capture, and other processing steps, such as the addition of elution for subsequent PCR assays, and thus the second module further leverages those capabilities of the base first module and supports additional processing and detection capabilities without requiring that the sample input and preparation functionality be built into the second module.

Aspects of the disclosure are embodied in a second module for enhancing the capabilities of a first module configured to process substances within each of a plurality of receptacles and including a first substance transfer device configured to dispense substances into each receptacle and a receptacle transfer device configured to move receptacles within the first module. The second module is configured to be coupled to or decoupled from the first module and comprises a container transport configured to transport at least one container from a location within the second module to a location within the first module that is accessible to the first substance transfer device to transfer substance from the container to a receptacle within the first module, a receptacle distribution module configured to receive a receptacle from the receptacle transfer device of the first module, transfer the receptacle into the second module, and move the receptacle between different locations within the first module, and a second substance transfer device configured to dispense substances into or remove substances from the receptacle within the second module.

According to some aspects of the disclosure, the receptacle distribution module comprises a receptacle distributor configured to move a receptacle onto the receptacle distributor at a first location on the second module, carry the receptacle from the first location to a second location on the second module that is different from the first location, and move the receptacle off the receptacle distributor at the second location on the second module. A receptacle handoff device can be configured to receive a receptacle from the receptacle transfer device of the first module and to reposition the receptacle to present the receptacle to the receptacle distributor to be moved by the receptacle distributor from the receptacle handoff device onto the receptacle distributor.

According to some aspects of the disclosure, the receptacle distributor is configured to rotate about an axis of rotation to move a receptacle carried thereby in an arced path between locations within the second module. Other configurations for moving a receptacle between locations within the second module are contemplated. Therefore, the disclosure is not limited to receptacle distributors that rotate about an axis of rotation.

According to some aspects of the disclosure, the second module further comprises receptacle storage stations for holding one or more receptacles transferred from the first module to the second module, wherein the receptacle storage stations are arranged in a configuration corresponding to the arced path of the receptacle distributor.

According to some aspects of the disclosure, the receptacle distributor is configured to move vertically a receptacle carried thereby between different vertically-disposed locations within the second module.

According to some aspects of the disclosure, the receptacle handoff device is configured to rotate between a first position for receiving a receptacle from the receptacle transfer device of the first module and a second position for presenting the receptacle to the receptacle distributor.

According to some aspects of the disclosure, the second module further comprises a container compartment, configured to hold one or more fluid containers. In certain embodiments, the container compartment can be a container drawer configured to be moved between an open position and a closed position and to, when moved to the closed position, place at least one fluid container into an operative position with respect to the container transport so that the container can be transported by the container transport from the container compartment into the first module. In an alternate embodiment, the container compartment can comprise a door with a sliding tray that is configured to be moved between an open position and a closed position and to, when moved to the closed position, place at least one fluid container into an operative position with respect to the container transport so that the container can be transported by the container transport from the container compartment into the first module.

According to some aspects of the disclosure, the second module further comprises a container carriage configured to carry one or more containers and to be movable with the container compartment and further configured to be engaged by the container transport when the container compartment is in the closed position such that the container transport is operable to move the container carriage and the one or more containers carried thereby from the container compartment into the first module.

According to some aspects of the disclosure, the second module further comprises a carriage transport and a carriage lock. The carriage transport is moveable with the container receptacle and configured to carry the container carriage between a first position when the container receptacle is in the open position and a second position when the container receptacle is in the closed position. The carriage lock is configured to lock the container carriage to the carriage transport when the carriage transport is in the first position and to release the container from the carriage transport when the carriage transport is in the second position to permit the container carriage to be removed from the carriage transport by the container transport.

According to some aspects of the disclosure, the container transport comprises a track extending from the container compartment into the first module, a carriage hook configured to engage the container carriage when the container compartment is in the closed position, and a motorized carriage hook drive system configured to move carriage hook along the carriage track.

According to some aspects of the disclosure, the motorized carriage hook drive system comprises a motor and a belt driven by the motor and coupled to the carriage hook.

According to some aspects of the disclosure, the processing apparatus further comprises one or more position sensors disposed at one or more locations along the track to detect a position of the carriage on the track.

According to some aspects of the disclosure, the second module further comprises a reagent pack changer comprising a pack input device and a pack storage compartment. The pack input device is configured to enable an operator to place a reagent pack containing at least one reagent into the second module or remove a reagent pack from the second module. The pack storage compartment is configured to hold a plurality of reagent packs until a reagent pack is needed for processing within the second module. The receptacle distribution module is further configured to move a reagent pack between the pack input device and the pack storage compartment.

According to some aspects of the disclosure, the second module further comprises one or more reagent pack loading stations, each configured to hold a reagent pack in a manner that permits the second substance transfer device to transfer a substance to or from the reagent pack. Therefore, in some embodiments, the reagent pack loading station is configured to change the orientation of the reagent pack from an initial loaded position to a position aligned with the second substance transfer device.

According to some aspects of the disclosure, the second module further comprises a charged field generator operatively associated with at least one of the pack input device, the pack storage compartment, and the reagent pack loading stations and configured to generate electrostatic forces to position and hold a reagent present in a reagent pack held in the pack input device or pack storage compartment. In related aspects the charged field generator is situated below at least one of the pack input device, the pack storage compartment, and the reagent pack loading stations such that electromagnetic forces are applied to, or adjacent to, the bottom of one or more wells of a reagent pack, when present.

According to some aspects of the disclosure, wherein the pack input device comprises a reagent pack carousel that is rotatable about an axis of rotation, wherein the pack carousel includes a plurality of reagent pack stations, each configured to hold a reagent pack, disposed around the axis of rotation.

According to some aspects of the disclosure, the pack carousel is disposed in a compartment, such as a drawer, that is movable between an open position providing access to the pack carousel and a closed position closing off access to the pack carousel. The pack carousel can also be accessed through an access panel revealing a slidable tray on which is mounted the pack carousel.

According to some aspects of the disclosure, the second module further comprises a code reader operatively disposed with respect to the pack input device and configured to read a machine readable code on each reagent pack carried in the pack input device. In some embodiments, the code reader reads the machine readable code on a respective reagent pack in close proximity to the code reader.

According to some aspects of the disclosure, the second module further comprises a pack storage carousel disposed within the pack storage compartment. The pack storage carousel is rotatable about an axis of rotation and includes a plurality of reagent pack stations, each configured to hold a reagent pack, disposed around the axis of rotation.

According to some aspects of the disclosure, the reagent pack stations of the pack storage carrousel are disposed on more than one level of the second module.

According to some aspects of the disclosure, the second module further includes a cooling system for maintaining the storage compartment at a lower than ambient temperature.

According to some aspects of the disclosure, the second substance transfer device comprises a robotic pipettor having a pipettor probe, and the second module further comprises one or more disposable tip compartments configured to hold a plurality of disposable tips configured to be placed on the pipettor probe of the robotic pipettor.

According to some aspects of the disclosure, the second module further comprises a cap/vial tray configured to hold a plurality of processing vials and/or associated caps. Each cap is configured to be coupled to an associated vial to close the associated vial. The vials are accessible by the robotic pipettor to dispense processing material into the vials, and the associated caps are accessible by the robotic pipettor to move each cap into an associated vial to form a cap/vial assembly. The robotic pipettor is configured to move the cap/vial assembly from the cap/vial tray to another location on the second module.

According to some aspects of the disclosure, the second module further comprises a centrifuge, wherein the robotic pipettor is configured to move a cap/vial assembly from the cap/vial tray to the centrifuge.

According to some aspects of the disclosure, the second module further comprises a thermal cycler configured to hold a plurality of cap/vial assemblies and to subject the contents of the plurality of cap/vial assemblies to cyclically varying temperatures and a robotic vial transfer arm configured to move a cap/vial assembly from the centrifuge to the thermal cycler.

According to some aspects of the disclosure, the second module further comprises one or more magnetic receptacle holding slots configured to hold a receptacle transferred from the first module to the second module. Each magnetic receptacle holding slot comprises a magnet and is configured to draw magnetic particles contained within the receptacle to a wall of the receptacle and out of solution within the fluid contents of the receptacle.

According to some aspects of the disclosure, the first module and the second module are configured to conduct nucleic acid amplification reactions.

According to some aspects of the disclosure, the nucleic acid amplification reactions conducted in the first module and the second module are different types of amplification reactions.

According to some aspects of the disclosure, the nucleic acid amplification reaction conducted in the first module comprises a qualitatively monitored reaction and the nucleic acid amplification reaction conducted in the second module comprises a quantitatively monitored reaction.

According to some aspects of the disclosure, the nucleic acid amplification reaction conducted in the second module comprises a reaction monitored in real-time.

According to some aspects of the disclosure, wherein the nucleic acid amplification reaction conducted in the first module is an isothermal reaction, and the nucleic acid amplification reaction conducted in the second module comprises the use of a polymerase chain reaction.

Aspects of the disclosure are further embodied in an automated system capable of performing multiple molecular assays on a single sample. The system comprises a sample input portal configured to accept samples contained in one or more receptacles, a sample preparation module configured to prepare a sample provided to the sample input portal for a nucleic acid amplification reaction, a first module configured to conduct an isothermal nucleic acid amplification assay with the sample, a second module configured to conduct a nucleic acid amplification assay involving temperature cycling with the sample, and a transport mechanism configured to effect automated transport of one or more receptacles containing the sample between the sample input portal, the sample preparation module, the first module, and the second module.

According to some aspects of the disclosure, the automated system further comprises a substance transfer device configured to access the sample when present in the sample second module, the first module, or the second module.

According to some aspects of the disclosure, the system further comprises a reagent storage compartment configured to hold a plurality of reagent containers, wherein the reagent storage compartment is held at a temperature below ambient temperature.

According to some aspects of the disclosure, the system further comprises a reagent container transport mechanism configured to transport one or more reagent containers between the reagent storage compartment and a separate location within the second module.

According to some aspects of the disclosure, the reagent container transport mechanism is configured to transport the reagent containers within the second module and to transport the receptacles within the second module.

Some aspects of the disclosure are embodied in a method for improved thermal cycling of low volume nucleic acid amplification reaction mixtures. The method comprises combining a fluid sample together with one or more amplification reaction reagents in a reaction receptacle using an automated pipettor, transporting the reaction receptacle to a centrifuge using the automated pipettor, centrifuging the fluid contents of the reaction receptacle, automatically removing the reaction receptacle from the centrifuge after centrifugation and placing the reaction receptacle in a thermal cycler, and subjecting the fluid contents of the reaction receptacle to one or more temperature cycles within the thermal cycler.

According to some aspects of the disclosure, the reaction receptacle is removed from the centrifuge and transported to the thermal cycler using the vial transfer arm.

According to some aspects of the disclosure, the reaction receptacle is placed in the centrifuge at a first location, and the reaction receptacle is removed from the centrifuge at a second, different location.

According to some aspects of the disclosure, the method further comprises a second automated pipettor, and the second automated pipettor automatically removes the reaction receptacle from the centrifuge after centrifugation and places the reaction receptacle in the thermal cycler.

According to some aspects of the disclosure, the receptacle is sealed by a cap before transporting the sealed receptacle to the centrifuge.

According to some aspects of the disclosure, the automated pipettor transports the cap to the receptacle and seals the receptacle by coupling the cap to the receptacle.

Some aspects of the disclosure are embodied in an improved method of preparing multiple different nucleic acid reaction mixtures within the workflow of an automated molecular instrument. The method comprises providing two or more reaction receptacles, providing two or more unit dose reagent containers, each unit dose reagent container corresponding to a respective reaction receptacle, and each unit dose reagent container containing a nucleic acid amplification reagent that is specific for one or more target nucleic acids, providing a receptacle containing a first bulk reagent, and combining at least a portion of the sample with at least a portion of the unit dose reagent and at least a portion of the bulk reagent in each of the two or more reaction receptacles. After combination, each reaction receptacle contains a different sample, a different unit dose reagent, and the same first bulk reagent.

According to further aspects of the disclosure, the method further comprises a receptacle containing a second bulk reagent, wherein the second bulk reagent is dispensed into each of the two or more unit dose reagent containers before combining at least a portion of the sample with at least a portion of the unit dose reagent and at least a portion of the bulk reagent in each of the two or more reaction receptacles.

According to some aspects of the disclosure, the second bulk reagent comprises a reconstitution reagent.

According to some aspects of the disclosure, the method further comprises transporting each of the two or more reaction receptacles to a heater, such as a heated incubator or a heating plate, to conduct a nucleic acid amplification assay.

Other features and characteristics of the present disclosure, as well as the methods of operation, functions of related elements of structure and the combination of parts, and economies of manufacture, will become more apparent upon consideration of the following description and the appended claims with reference to the accompanying drawings, all of which form a part of this specification, wherein like reference numerals designate corresponding parts in the various figures.

DESCRIPTION OF THE DRAWINGS

The accompanying drawings, which are incorporated herein and form part of the specification, illustrate various, non-limiting embodiments of the present disclosure. In the drawings, common reference numbers indicate identical or functionally similar elements.

FIG. 45 is a side view of the receptacle. FIG. 46 is a cross-sectional view of the receptacle taken along a vertical axis of view shown in FIG. 45. FIG. 47 top view of the receptacle. FIG. 48 is a perspective view of the receptacle.

FIGS. 49-54 show a cap of the present disclosure. FIG. 49 is a side view of the cap. FIG. 50 is a cross-sectional view of the cap taken along a vertical axis of the view shown in FIG. 49. FIG. 51 is a top view of the cap. FIG. 52 is a bottom view of the cap. FIGS. 53 and 54 are top and bottom perspective views of the cap.

DETAILED DESCRIPTION

Figure 1:
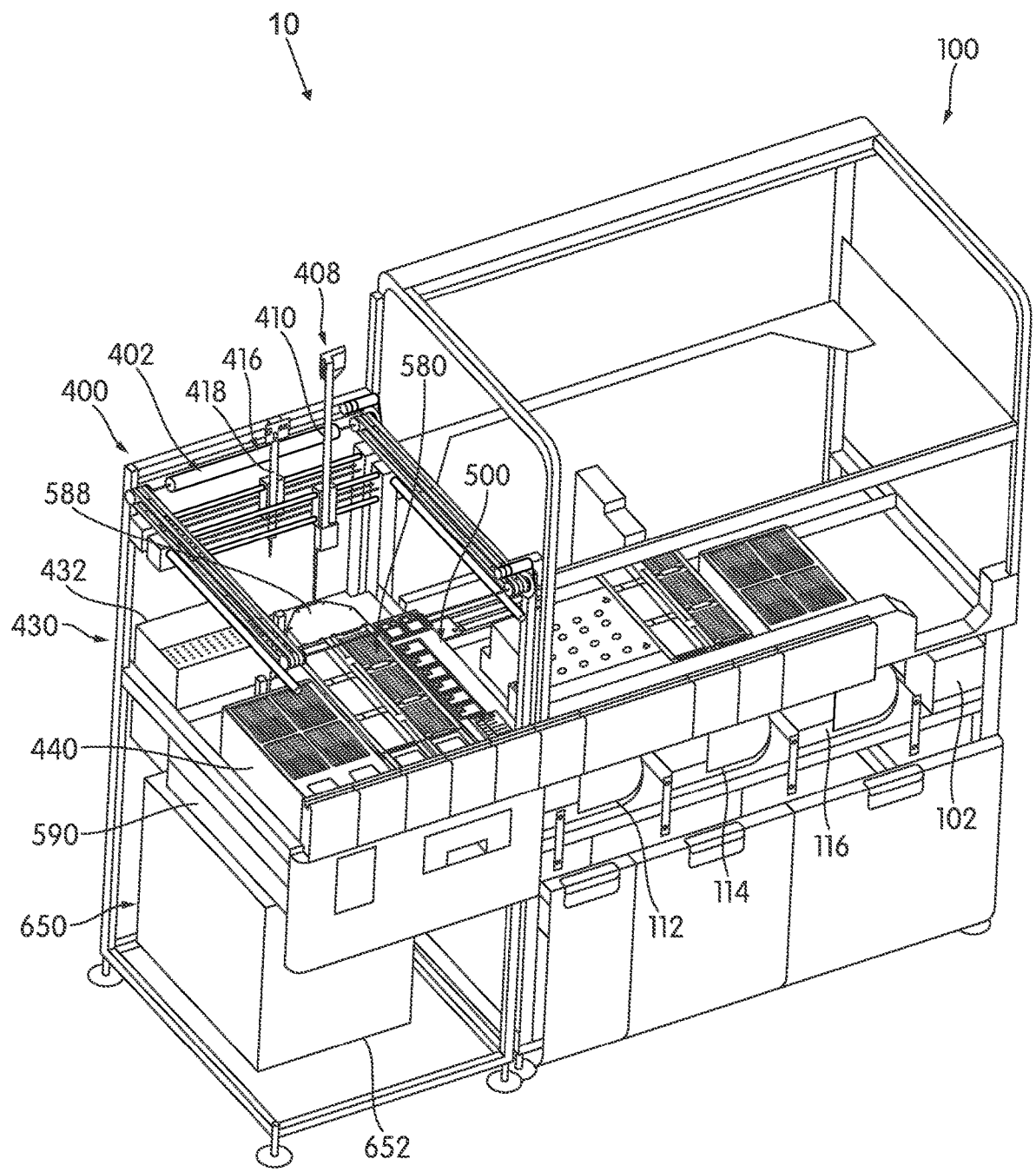
FIG. 1 is a perspective view of a diagnostic system comprising a first module and a second module according to an embodiment.

Unless defined otherwise, all terms of art, notations and other scientific terms or terminology used herein have the same meaning as is commonly understood by one of ordinary skill in the art to which this disclosure belongs. Many of the techniques and procedures described or referenced herein are well understood and commonly employed using conventional methodology by those skilled in the art. As appropriate, procedures involving the use of commercially available kits and reagents are generally carried out in accordance with manufacturer defined protocols and/or parameters unless otherwise noted. All patents, applications, published applications and other publications referred to herein are incorporated by reference in their entirety. If a definition set forth in this section is contrary to or otherwise inconsistent with a definition set forth in the patents, applications, published applications, and other publications that are herein incorporated by reference, the definition set forth in this section prevails over the definition that is incorporated herein by reference.

References in the specification to "one embodiment," "an embodiment," a "further embodiment," "an example embodiment," "some aspects," "a further aspect," "aspects," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, such feature, structure, or characteristic is also a description in connection with other embodiments whether or not explicitly described.

As used herein, "a" or "an" means "at least one" or "one or more."

As used herein, "sample" refers to any substance suspected of containing a virus or organism of interest or, alternatively, nucleic acid derived from the virus or organism of interest, or any substance suspected to have a nucleic acid of interest, such as a nucleic acid suspected of having genetic abnormalities or mutations. The substance may be, for example, an unprocessed clinical specimen, such as a blood or genitourinary tract specimen, a buffered medium containing the specimen, a medium containing the specimen and lytic agents for releasing nucleic acid belonging to the virus or organism, or a medium containing nucleic acid derived from the virus or organism which has been isolated and/or purified in a reaction receptacle or on a reaction material or device. For this reason, the term "sample" will be understood to mean a specimen in its raw form or to any stage of processing to release, isolate and purify nucleic acid derived from the virus or organism. Thus, references to a "sample" may refer to a substance suspected of containing nucleic acid derived from a virus or organism at different stages of processing and is not limited to the initial form of the substance.

This description may use relative spatial and/or orientation terms in describing the position and/or orientation of a component, apparatus, location, feature, or a portion thereof. Unless specifically stated, or otherwise dictated by the context of the description, such terms, including, without limitation, top, bottom, above, below, under, on top of, upper, lower, left of, right of, inside, outside, inner, outer, proximal, distal, in front of, behind, next to, adjacent, between, horizontal, vertical, diagonal, longitudinal, transverse, etc., are used for convenience in referring to such component, apparatus, location, feature, or a portion thereof in the drawings and are not intended to be limiting.

The section headings used in the present application are merely intended to orient the reader to various aspects of the disclosed system. The section headings are not intended to limit the disclosed and claimed inventions. Similarly, the section headings are not intended to suggest that materials, features, aspects, methods, or procedures described in one section do not apply in another section. Therefore, descriptions of materials, features, aspects, methods or procedures described in one section are intended to apply to other sections.

Nucleic Acid Diagnostic Assays

Aspects of the present disclosure involve diagnostic systems and methods that can be used in conjunction with nucleic acid diagnostic assays, including "real-time" amplification assays and "end-point" amplification assays.

Real-time amplification assays can be used to determine the presence and amount of a target nucleic acid in a sample which, by way of example, is derived from a pathogenic organism (e.g., bacterium, fungus, or protozoan) or virus. Thus, real-time amplification assays are often referred to as quantitative assays. By determining the quantity of a target nucleic acid in a sample, a practitioner can approximate the amount or load of the organism or virus in the sample. In one application, a real-time amplification assay may be used to screen blood or blood products intended for transfusion for blood borne pathogens, such as hepatitis C virus (HCV) and human immunodeficiency virus (HIV). In another application, a real-time assay may be used to monitor the efficacy of a therapeutic regimen in a patient infected with a pathogenic organism or virus, or that is afflicted with a disease characterized by aberrant or mutant gene expression. Real-time amplification assays may also be used for diagnostic purposes, as well as in gene expression determinations. Exemplary systems and methods for performing real-time amplification assays are disclosed by Macioszek et al. in U.S. Pat. No. 7,897,337.

In addition to implementation of embodiments of the disclosure in conjunction with real-time amplification assays, embodiments of the disclosure may also be implemented in conjunction with end-point amplification assays. In end-point amplification assays, the presence of amplification products containing the target sequence or its complement is determined at the conclusion of an amplification procedure. Thus, end-point amplification assays are often referred to as qualitative assays in that such assays do not indicate the amount of a target analyte present, but provide a qualitative indication regarding the presence or absence of the target analyte. Exemplary systems and methods for end-point detection are disclosed by Ammann et al. in U.S. Pat. No. 6,335,166. The determination may occur in a detection station that is integral with or at an external location relative to the incubator(s) in which the amplification reactions occur. In contrast, in "real-time" amplification assays, the amount of amplification products containing the target sequence or its complement is determined during an amplification procedure. In a real-time amplification assay, the concentration of a target nucleic acid can be determined using data acquired by making periodic measurements of signals that are a function of the amount of amplification product in the sample containing the target sequence or its complement, and calculating the rate at which the target sequence is being amplified from the acquired data. An example of such a real-time amplification assay is described by Light II et al. in U.S. Pat. No. 8,615,368.

In an exemplary real-time amplification assay, the interacting labels include a fluorescent moiety, or other emission moiety, and a quencher moiety, such as, for example, 4-(4-dimethylaminophenylazo) benzoic acid (DABCYL). The fluorescent moiety emits light energy (i.e., fluoresces) at a specific emission wavelength when excited by light energy at an appropriate excitation wavelength. When the fluorescent moiety and the quencher moiety are held in close proximity, light energy emitted by the fluorescent moiety is absorbed by the quencher moiety. But when a probe hybridizes to a nucleic acid present in the sample, the fluorescent and quencher moieties are separated from each other and light energy emitted by the fluorescent moiety can be detected. Fluorescent moieties having different and distinguishable excitation and emission wavelengths are often combined with different probes. The different probes can be added to a sample, and the presence and amount of target nucleic acids associated with each probe can be determined by alternately exposing the sample to light energy at different excitation wavelengths and measuring the light emission from the sample at the different wavelengths corresponding to the different fluorescent moieties. In another embodiment, different fluorescent moieties having the same excitation wavelength, but different and distinguishable emission wavelengths are combined with different probes. The presence and amount of target nucleic acids associated with each probe can be determined by exposing the sample to a specific wavelength light energy and the light emission from the sample at the different wavelengths corresponding to the different fluorescent moieties is measured.

A variety of different labeled probes and probing mechanisms are known in the art, including those where the probe does not hybridize to the target sequence. See, e.g., Brow et al. in U.S. Pat. No. 5,846,717 and Chun et al. in U.S. Patent Application Publication No. 2013/0109588. Some embodiments of the present disclosure operate regardless of the particular labeling scheme utilized, provided the moiety to be detected can be excited by a particular wavelength of light and emits a distinguishable emission spectra.

Where a nucleic acid amplification reaction is used to increase the amount of target sequence and/or its complement present in a sample before detection, it is desirable to include a "control" to ensure that amplification has taken place. See, for example, the amplification controls described by Wang in U.S. Pat. No. 5,476,774. Such a control can be a known nucleic acid sequence that is unrelated to the sequence(s) of interest. A probe (i.e., a control probe) having specificity for the control sequence and having a unique fluorescent dye (i.e., the control dye) and quencher combination is added to the sample, along with one or more amplification reagents needed to amplify the control sequence, as well as the target sequence(s). After exposing the sample to appropriate amplification conditions, the sample is alternately exposed to light energy at different excitation wavelengths (including the excitation wavelength for the control dye) and emission light is detected. Detection of emission light of a wavelength corresponding to the control dye confirms that the amplification was successful (i.e., the control sequence was indeed amplified), and thus, any failure to detect emission light corresponding to the probe(s) of the target sequence(s) is not likely due to a failed amplification. Conversely, failure to detect emission light from the control dye may be indicative of a failed amplification, thus calling into question the results from that assay. Alternatively, failure to detect emission light may be due to failure or deteriorated mechanical and/or electrical performance of an instrument for detecting the emission light.

In some embodiments, the assays performed in accordance with the description herein capture, amplify, and detect nucleic acids from target organisms in patient samples employing technologies, such as target capture, reverse transcription, and real-time polymerase chain reaction. The combination of reverse transcription and PCR is abbreviated "RT-PCR." The following is a generalized assay processing description of the different technologies that may be implemented in accordance with aspects of the disclosure.

The target capture process isolates nucleic acid of the target (e.g., virus, bacterium, fungus, protozoan, mammalian cells, etc.) and purifies nucleic acid for amplification. The target organism, which can be in a variety of biological matrices from urine to blood, can be lysed by target capture reagents ("TCR"), whereby the nucleic acid is released. In one approach, capture oligonucleotide probes hybridize to a target nucleic acid. The capture probe/target nucleic acid complexes attach to magnetic particles in the TCR through nucleic acid hybridization. Exemplary disclosures for performing these methods are provided by U.S. Pat. Nos. 6,140,678, 5,234,809, 5,693,785, and 5,973,138, and EP Patent No. 0 389 063. The magnetic particles are pulled to the side of a container and isolated by a magnet, and potential inhibitory substances are washed away (multiple wash cycles may be performed) to thereby provide a target nucleic acid. Hogan et al. provide an exemplary disclosure of this protocol in U.S. Pat. No. 7,172,863. See also International Publication No. WO 2003/097808 by Fort et al. If the target capture process is specific for the target nucleic acid, then it is the target nucleic acid that will primarily remain after the purification step. As a result, target capture enables the enrichment of a variety of sample types and significantly reduces the inhibition rate and can increase assay sensitivity. Exemplary methods of target nucleic acid capture are disclosed by, for example, Boom et al. in U.S. Pat. No. 5,234,864, Hawkins in U.S. Pat. No. 5,705,628, Collins et al. in U.S. Pat. No. 5,750,338, and Weisburg et al. in U.S. Pat. No. 6,534,273.

After completing the target capture process, the magnetic particles on which the target nucleic acid is immobilized are re-suspended, for example, with 20-60 µL of a wash solution comprising a low salt buffer or water. This will de-hybridize the target nucleic acid from the magnetic particles and, in the presence of a strong magnet, allow 5-50 µL of purified nucleic acid to be recovered as input into the amplification process.

Reverse transcription and PCR can be optimized to run in a single receptacle using common reagents as a one-step process. This method provides a sensitive means to detect low-abundance RNAs, and, although the method is not necessarily quantitative, specific controls can be included in the experiment if quantitative results are desired. (A reverse-transcription step is not required if the target nucleic acid is DNA.) In an exemplary implementation, before performing the real-time PCR reaction, RNAs are incubated with a retroviral enzyme (reverse transcriptase) under oil at 42° C. for approximately 30 minutes. This process creates a single-stranded DNA copy of the RNA target sequence. If the goal is to copy all RNAs present in the source material into DNA, non-specific primers or primer sets are used. In the case of mRNA, which has a polyadenylated (poly A) tail, an oligo dT primer can be used. Alternatively, a collection of randomized hexanucleotide primers can be used to ensure an primer will be present that is complementary to each of the messages. If only one RNA target is sought, a sequence-specific primer complementary to the 3' end of the desired amplification product is used. RNase H is used to degrade the RNA molecule contained in the hybrid RNA-DNA duplex, so that the DNA strand is available to direct second-strand synthesis. Single-stranded DNA thus generated can serve as the template for PCR using sequence-specific primers to amplify the region of interest.

The polymerase is inactive at low temperatures and can be heat activated at 95° C. for several minutes (for example, approximately 10 minutes) before beginning PCR. Both reactions occur inside a thermal cycler (i.e., a module configured to expose the contents of the receptacle to temperatures that are cycled between two or more different temperatures), but real-time PCR requires accurate/rapid thermal cycling between denaturation (~95° C.), annealing (~55° C.), and synthesis (~72° C.) temperatures. Fluorescence monitoring occurs at one or many color wavelengths—relating to one or many probes adapted to detect one or many target analytes—during each cycle or at another predetermined interval. PCR components may include, for example, the forward and reverse primers and a fluorogenic probe containing a reporter fluorescent dye on the 5' end and a quencher dye on the 3' end. (See, e.g., Holland et al., Proc. Natl. Acad. Sci. USA, 88(16):7276-7280 (1991).) During PCR, nucleic acid primers hybridize to opposite strands of the target nucleic acid and are oriented with their 3' ends facing each other so that synthesis by a nucleic acid polymerization enzyme, such as a DNA polymerase, extends across the segment of the nucleic acid between them. While the probe is intact, the proximity of the quencher dye to the reporter dye greatly reduces the fluorescence emitted by the reporter dye. During amplification if the target nucleic acid is present, the fluorogenic probe anneals downstream from one of the primer sites and is cleaved by the 5' nuclease activity of the polymerization enzyme during primer extension. The cleavage of the probe separates the reporter dye from the quencher dye, thus rendering detectable the reporter dye signal and removing the probe from the target strand, allowing primer extension to continue to the end of the template strand.

One round of PCR synthesis will result in new strands of indeterminate length which, like the parental strands, can hybridize to the primers upon denaturation and annealing. These products accumulate arithmetically with each subsequence cycle of denaturation, annealing to primers, and synthesis. The second cycle of denaturation, annealing, and synthesis produces two single-stranded products that together compose a discrete double-stranded product which is exactly the length between the primer ends. Each strand of this discrete product is complementary to one of the two primers and can therefore participate as a template in subsequent cycles. The amount of this product doubles with every subsequent cycle of synthesis, denaturation and annealing. This accumulates exponentially so that 30 cycles should result in a $2^{28}$-fold (270 million-fold) amplification of the discrete product.

Multiple Receptacle Devices

Figure 2:
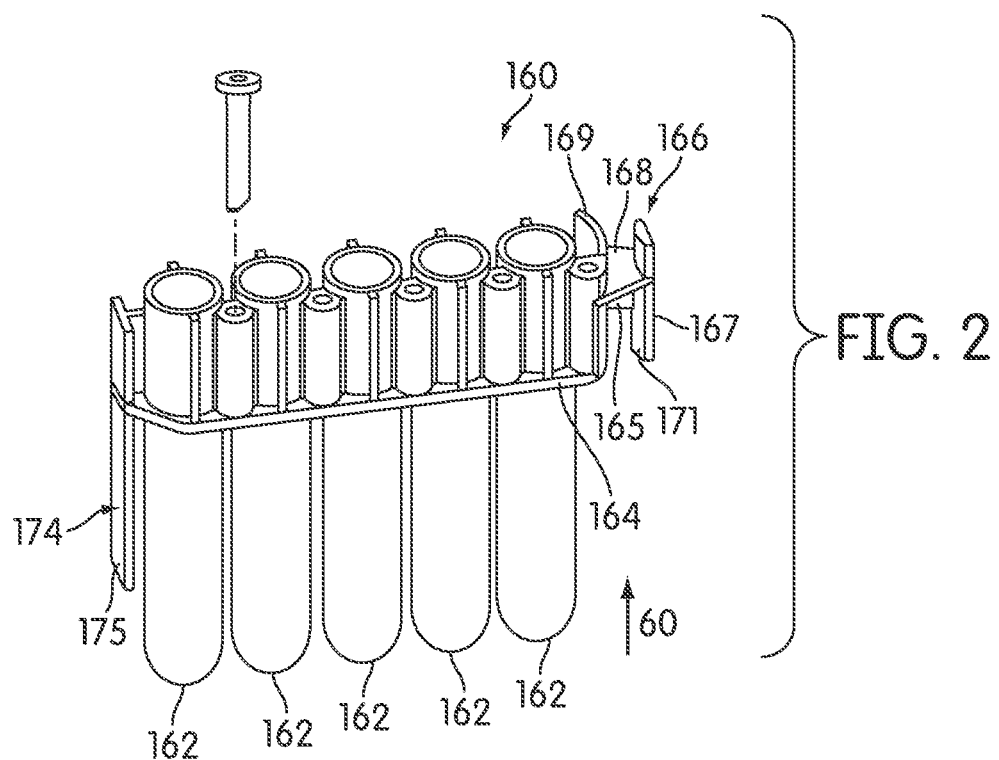
FIG. 2 is a perspective view of a multiple receptacle device ("MRD") according to an embodiment.

FIG. 2 illustrates one embodiment of MRD 160 that comprises a plurality of individual receptacles, or tubes, 162, preferably five. The receptacles 162 are formed to have open top ends and closed bottom ends (preferably in the form of cylindrical tubes), and are connected to one another by a connecting rib structure 164 which defines a downwardly facing shoulder extending longitudinally along either side of the MRD 160.

Alternatively, the receptacle may be any container suitable for holding a fluid or liquid, including, for example, a cuvette, vial, beaker, well of a microtiter plate, test tube, and in some embodiments, a pipette tip. Unless explicitly stated or the context dictates otherwise, descriptions of an MRD or receptacle of an MRD are exemplary and should not be construed as limiting of the scope of the disclosure, as aspects of the disclosure are applicable to any suitable "receptacle."

The MRD 160 in certain embodiments is formed from injection molded polypropylene, such as those sold by Montell Polyolefins, of Wilmington, Del., product number PD701NW or Huntsman, product number P5M6K-048. In an alternative embodiment, the receptacles 162 of the MRD are releasably fixed with respect to each other by means such as, for example, a sample tube rack or other holding structure.

An arcuate shield structure 169 can be provided at one end of the MRD 160. An MRD manipulating structure 166 extends from the shield structure 169. In certain embodiments, the manipulating structure 166 is configured to be engaged by an extendible and retractable hook of a receptacle distributor or a transport mechanism for moving the MRD 160 between different components of a first module of a diagnostic system. An exemplary transport mechanism that is compatible with the MRD 160 is disclosed by Ammann et al. in U.S. Pat. No. 6,335,166. The transport mechanism, in certain embodiments, engages the manipulating structure 166 from the underside of the manipulating structure as shown with arrow 60. In certain embodiments, the MRD manipulating structure 166 comprises a laterally extending plate 168 extending from shield structure 169 with a vertically extending piece 167 on the opposite end of the plate 168. A gusset wall 165 can extend downwardly from lateral plate 168 between shield structure 169 and vertical piece 167.

Figure 3:
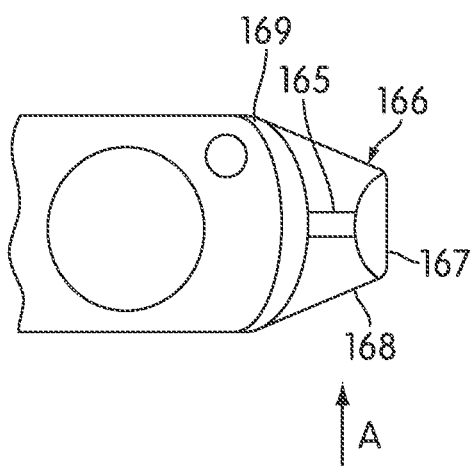
FIG. 3 is a partial bottom view of the MRD of FIG. 2.

As shown in FIG. 3, the shield structure 169 and vertical piece 167 have mutually facing convex surfaces. This, however, is just one way that the shield structure 169 and vertical piece 167 can be configured. The MRD 160 may be engaged by a receptacle distributor, a transport mechanism, and other components, by moving an engaging member, such as an extendible and retractable hook, laterally (in the direction "A") into the space between the shield structure 169 and the vertical piece 167. The convex surfaces of the shield structure 169 and vertical piece 167 provide for wider points of entry for an engaging member undergoing a lateral relative motion into the space between the shield structure 169 and the vertical piece 167. Of course, as the engaging member is robotically controlled, it is understood that the convex surfaces are merely a design choice of the present embodiment and that other shaped surfaces are contemplated.

A label-receiving structure 174 having a flat label-receiving surface 175 can be provided on an end of the MRD 160 opposite the shield structure 169 and MRD manipulating structure 166. Human and/or machine-readable labels, such as scannable bar codes, can be placed on the surface 175 to provide identifying and instructional information on the MRD 160.

Further details regarding a representative MRD 160 are disclosed by Homer et al. in U.S. Pat. No. 6,086,827.

Diagnostic System

FIG. 1 illustrates a diagnostic system 10 according to an embodiment. Diagnostic system 10 can be configured to perform a plurality of different molecular assays on a plurality of samples. In some embodiments, diagnostic system 10 can be configured to perform different target nucleic acid amplification reactions. For example, diagnostic system 10 can be configured to perform a first target nucleic acid amplification reaction on a first subset of a plurality of samples, and perform a second, different target nucleic acid amplification reaction on a second subset of the plurality of samples.

In some embodiments, diagnostic system 10 comprises a first module 100 configured to perform at least one of the steps of a first target nucleic acid amplification reaction, and a second module 400 configured to perform at least one of the steps of a second target nucleic acid amplification.

In some embodiments, diagnostic system 10 is an integral, self-contained structure—first module 100 cannot be selectively coupled to and decoupled from second module 400.

In some embodiments, diagnostic system 10 is configured such that first module 100 can be selectively and operatively coupled to second module 400, and first module 100 can be selectively decoupled from second module 400. In some embodiments, first module 100 can be selectively coupled to second module 400 using, for example, mechanical fasteners (for example, bolts or screws), clamps, any combination thereof, or any other suitable attachment device. In some embodiments, suitable power and/or data lines are provided between the second module 400 and the first module 100. For example, in embodiments in which first module 100 can be selectively coupled to second module 400, second module 400 can extend the overall system capabilities of a diagnostic system including only first module 100 that was previously purchased by a customer.

The configurations and functions of first module 100 and second module 400 according to various embodiments are described below.

First Module

Figure 4:
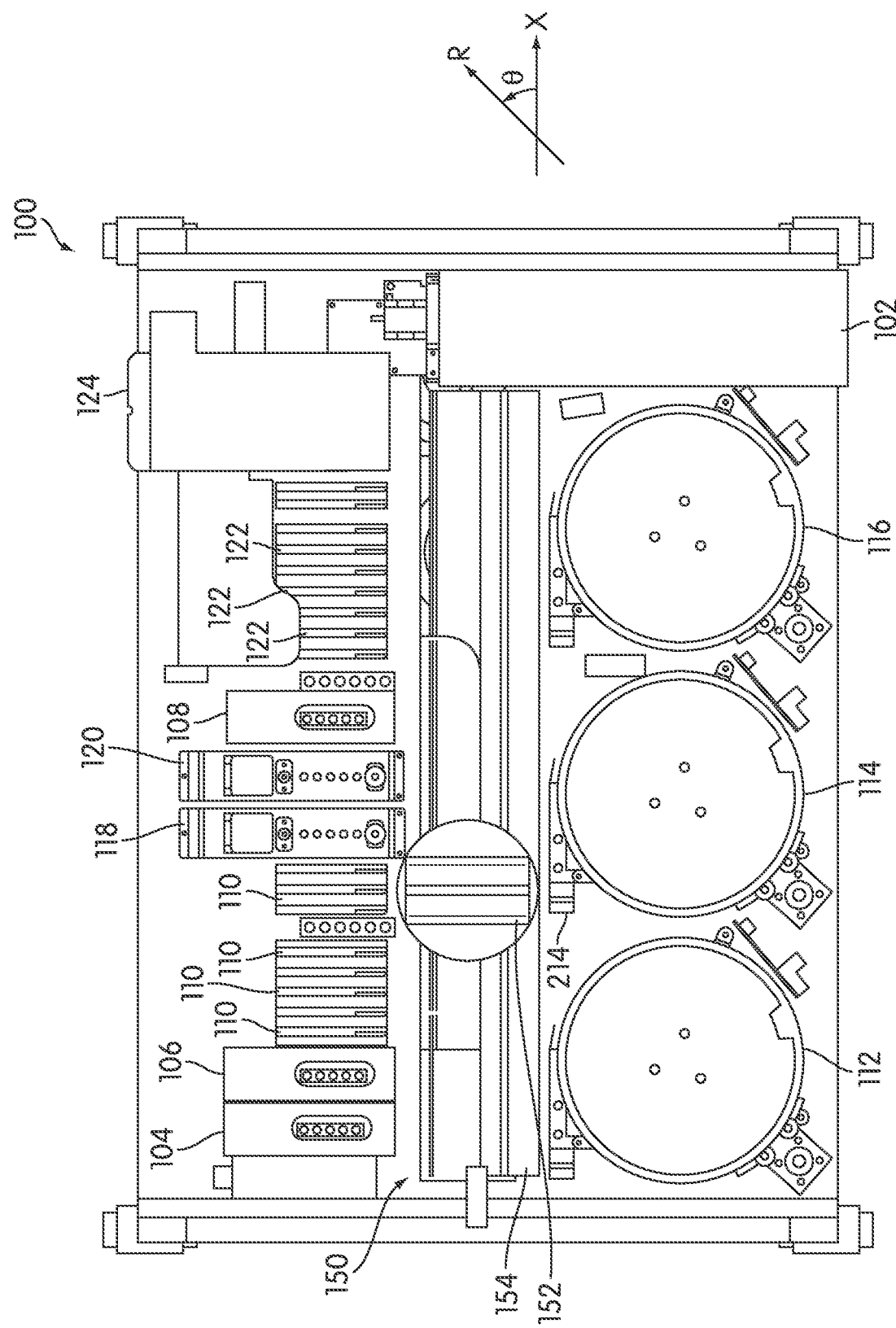
FIG. 4 is a top plan view of a first module of a diagnostic system according to an embodiment.

A first module 100 in which embodiments of the present disclosure may be implemented is shown schematically in plan view and designated by reference number 100 in FIG. 4. The first module 100 includes various devices configured to receive one or more reaction receptacles (described in more detail below), within each of which is performed one or more steps of a multi-step nucleic acid test (NAT) designed to detect a virus or organism (e.g., bacterium, fungus, or protozoan). First module 100 can include receptacle-receiving components configured to receive and hold one or more reaction receptacles and, in some instances, to perform processes on the contents of the receptacles. Exemplary processes include, but are not limited to, adding substances such as sample fluid, reagents (e.g., target capture reagents, amplification reagents, buffers, oils, labels, probes, or any other reagent) and/or removing substances from a reaction receptacle; agitating a receptacle to mix the contents thereof; maintaining and/or altering the temperature of the contents of a reaction receptacle; heating or chilling the contents of a reaction receptacle; altering the concentration of one or more components of the contents of a reaction receptacle; separating or isolating constituent components of the contents of a reaction receptacle; detecting an electromagnetic signal emission (e.g., light) from the contents of a reaction receptacle; deactivating or halting an on-going reaction; or any combination of two or more of such processes.

In some embodiments, the first module 100 may include a receptacle input device 102 that includes structure for receiving and holding one or more empty reaction receptacles before the receptacles are used for performing one or more process steps of a NAT. The receptacle input device 102 may comprise a compartment, for example, a drawer or cabinet, that may be opened and loaded with a plurality of receptacles and may include a receptacle feeding device for moving receptacles, for example, one or more at a time, into a receptacle pick-up position. In some embodiments, the receptacle pick-up position comprises a registered or known position of the receptacle to facilitate removal of the receptacle by a receptacle distributor.

In some embodiments, the first module 100 may further include one or more bulk reagent container compartments configured to store one or more bulk containers that hold bulk reagents or hold waste material. In some embodiments, the bulk reagents include fluids such as water, buffer solution, target capture reagents, nucleic acid amplification reagents. In some embodiments, the bulk reagent container compartments may be configured to maintain the contents of such containers at prescribed storage temperatures and/or to agitate such containers to maintain the contents of the containers in solution or suspension.

In some embodiments, first module 100 comprises a first bulk reagent container compartment configured to store at least one bulk container that holds a nucleic acid amplification reagent, for example, a reagent for performing TMA, and a separate second bulk reagent container compartment configured to store at least one bulk container that holds a sample preparation reagent, for example, a target capture reagent. In some embodiments, first module 100 comprises a bulk reagent container compartment that stores both a bulk container that holds a nucleic acid amplification reagent and a bulk container that holds a sample preparation reagent, for example, a target capture reagent. In some embodiments, a bulk reagent container compartment that is configured to store at least one bulk container can be a compartment that houses a mixer, for example, an orbital mixer, that is configured to carry a container holding a sample preparation reagent, for example, a target capture reagent. In some embodiments, the one or more bulk container compartments can comprise a holding structure for carrying and agitating containers (e.g., containers of TCR with magnetically-responsive solid supports). Buse et al. in U.S. Provisional Application No. 61/783,670, "Apparatus for Indexing and Agitating Fluid Containers," filed Mar. 14, 2013, which enjoys common ownership herewith, discloses an exemplary holding structure. In some embodiments, one or more bulk container compartments comprise a slidable tray that defines at least one recess configured to closely receive respective bulk containers.

In some embodiments, one or more of the bulk reagent container compartments of first module 100 can be configured to store at least two containers containing sample preparation reagents, for example, target capture reagents. In some embodiments, each target capture reagent is specific for a particular assay type (i.e., target nucleic acid), the type of nucleic acid (e.g., RNA or DNA), and/or the sample type (e.g., stool, urine, blood, etc.). For example, the target capture reagents can comprise probes having a region specific for the target nucleic acid. See, e.g. Weisburg et al. in U.S. Pat. No. 6,534,273.

The first module 100 may further include a sample loading device configured to receive and hold containers, such as test tubes, containing samples. The first module 100 may also include one or more substance transfer devices for transferring fluids, for example, sample fluids, reagents, bulk fluids, waste fluids, etc., to and from reaction receptacles and/or other containers. In some embodiments, the substance transfer devices may comprise one or more robotic pipettors configured for controlled, automated movement and access to the reaction receptacles, bulk containers holding reagents, and containers holding samples. In some embodiments, the substance transfer devices may also include fluid dispensers, for example, nozzles, disposed within other devices and connected by suitable fluid conduits to containers, for example, bulk containers holding the reagents, and to pumps or other devices for causing fluid movement from the containers to the dispensers.

In some embodiments, the first module 100 may further include a plurality of load stations, such as load stations 104, 106, 108 depicted in FIG. 4, which are configured to receive racks and other forms of holders for carrying sample receptacles and various reagent containers that can be accessed by a substance transfer device. Examples of a load station and receptacle holder that can be used with embodiments are illustrated and described by Clark et al. in U.S. Pat. No. 8,309,036. In an embodiment where the first module 100 comprises a platform for performing a NAT, reaction reagents may comprise target capture reagents, lysis reagents, nucleic acid amplification reagents (e.g., the polymerases and nucleoside triphosphates needed for amplification), and/or nucleic acid detection reagents, such as detectable probes or intercalating dyes.

In some embodiments, the first module 100 may further comprise temperature ramping stations 110 configured to hold one or more reaction receptacles in an environment that is maintained at higher than ambient temperatures so as to raise the temperature of the contents of the receptacles. Exemplary temperature ramping stations are disclosed by Ammann et al. in U.S. Pat. No. 8,192,992.

In some embodiments, the first module 100 may further include one or more heater modules. The illustrated first module 100 includes three heated incubators 112, 114, 116, each of which is configured to receive a plurality of reaction receptacles and maintain the receptacles in an elevated temperature environment. Exemplary incubators are disclosed by Macioszek et al. in U.S. Pat. No. 7,964,413 and Heinz et al. in U.S. Patent Application Publication No. 2012/0221252. A heater module may alternatively be a heating plate. In certain embodiments, it is possible to have a heater module configured with one or more heated incubators and one or more heating plates.

Also, in an embodiment in which the first module 100 comprises a platform for performing a NAT, the first module may include sample-processing components, such as magnetic separation wash stations 118, 120, adapted to separate or isolate a target nucleic acid immobilized on a magnetically-responsive solid support from the remaining contents of the receptacle. Exemplary magnetic separation wash stations are disclosed by Hagen et al. in U.S. Patent Application Publication No. 2010/0288395 and Ammann et al. in U.S. Pat. No. 6,605,213.

Figure 21:
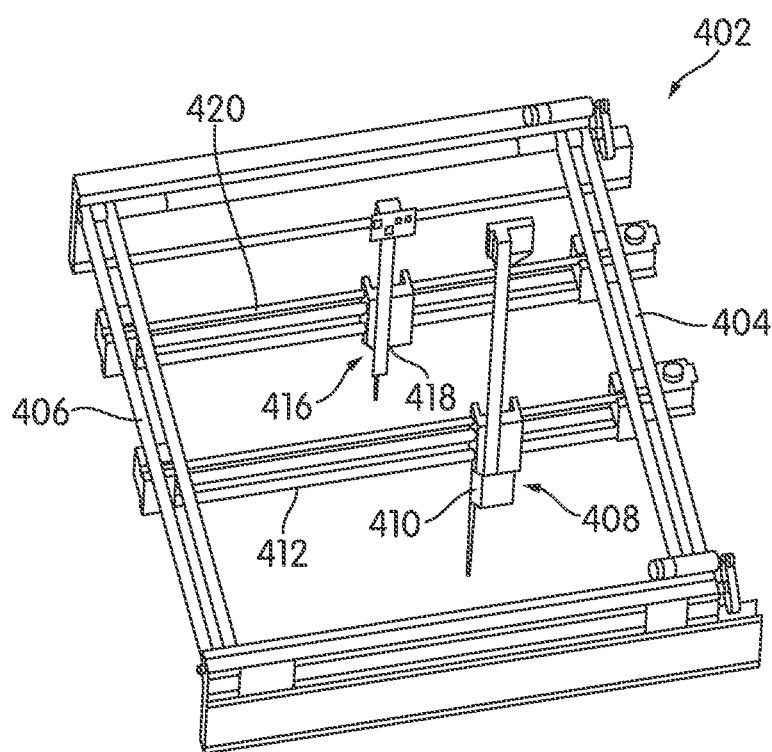
FIG. 21 is a perspective view of a robotic pipettor of the second module according to an embodiment.

Although not exemplified in the plan drawings of first module 100, the first module 100 may comprise one or more substance transfer devices, for example, robotic pipettors, in some embodiments. FIG. 21, which is a perspective view of the robotic pipettor of the second module 400, exemplifies at least one way to configure a substance transfer device for the first module 100.

In some embodiments, the first module 100 may further include chiller modules 122 adapted to receive one or more reaction receptacles and hold the receptacles in a lower than ambient temperature environment so as to reduce the temperature of the contents of the receptacles.

And in some embodiments, the first module 100 may include a detector 124 configured to receive a reaction receptacle and detect a signal (e.g., an optical signal) emitted by the contents of the reaction receptacle. In one implementation, detector 124 may comprise a luminometer for detecting luminescent signals emitted by the contents of a receptacle and/or a fluorometer for detecting fluorescent emissions. The first module 100 may also include one or more signal detecting devices, such as fluorometers, coupled to one or more of the incubators 112, 114, 116 and which are configured and controlled to detect, preferably at specified, periodic intervals, signals emitted by the contents of the receptacles contained in the incubator while a process, such as nucleic acid amplification, is occurring within the reaction receptacles. An exemplary luminometer and an exemplary fluorometer are disclosed by Macioszek et al. in U.S. Pat. No. 7,964,413 and another exemplary fluorometer is disclosed by Heinz et al. in U.S. Patent Application Publication No. 2012/0221252.

The first module 100 further includes a receptacle transfer device, which, in the illustrated embodiment, comprises a receptacle distributor 150. The components of first module 100, for example, incubators 112, 114, 116, load stations 104, 106, 108, temperature ramping stations 110, wash stations 118, 120, and chiller modules 122, can also include a receptacle transfer portal through which receptacles can be inserted into or removed from the respective components. Each component may or may not include an openable door covering its receptacle portal. The receptacle distributor 150 is configured to move receptacles between the various components and retrieve receptacles from the components and deposit receptacles into the components. In one exemplary embodiment, the receptacle distributor 150 includes a receptacle distribution head 152 configured to move in an X direction along a transport track assembly 154, rotate in a theta (θ) direction, and move receptacles in an R direction into and out of the receptacle distribution head 152 and one of the components of first module 100. An exemplary receptacle distributor is disclosed by Hagen et al. in U.S. Patent Application Publication No. 2012/0128451.

Second Module

Aspects of the disclosure are embodied in a second module 400 a diagnostic system. In some embodiments, the second module 400 is integral with the first module 100, and in other embodiments, the second module 400 may be selectively and operatively coupled to the first module 100 as described above. In some embodiments, the first module 100 to which the second module 400 can be operatively coupled include, for example, molecular instruments, such as the Panther® instrument system available from Hologic, Inc.

In one exemplary embodiment, the second module 400 is configured to perform nucleic acid amplification reactions, for example, PCR, and, in certain embodiments, to measure fluorescence in real-time (i.e., as the amplification reaction is occurring). A controller directs the components of the first module 100 and components of the second module 400 to perform the assay steps. In one exemplary embodiment, the first module 100 houses a computer and all fluids, reagents, consumables, and mechanical modules needed to perform the specified amplification-based assays, such as assays based on transcription-based amplification methods, for example, TMA or nucleic acid sequence-based amplification (NASBA). (TMA methods are described by Kacian et al. in U.S. Pat. Nos. 5,399,491 and 5,480,784; and NASBA methods are described by Davey et al. in U.S. Pat. No. 5,409,818 and Malek et al. in U.S. Pat. No. 5,130,238.) As explained above, the controller may comprise a computer and preferably can accommodate LIS ("laboratory information system") connectivity and as well as remote user access. In some embodiments, second module 400 houses component modules that enable second amplification assays, melting analyses, and optionally additional functionalities. Other components may include a printer and an optional uninterruptible power supply.

Figure 5:
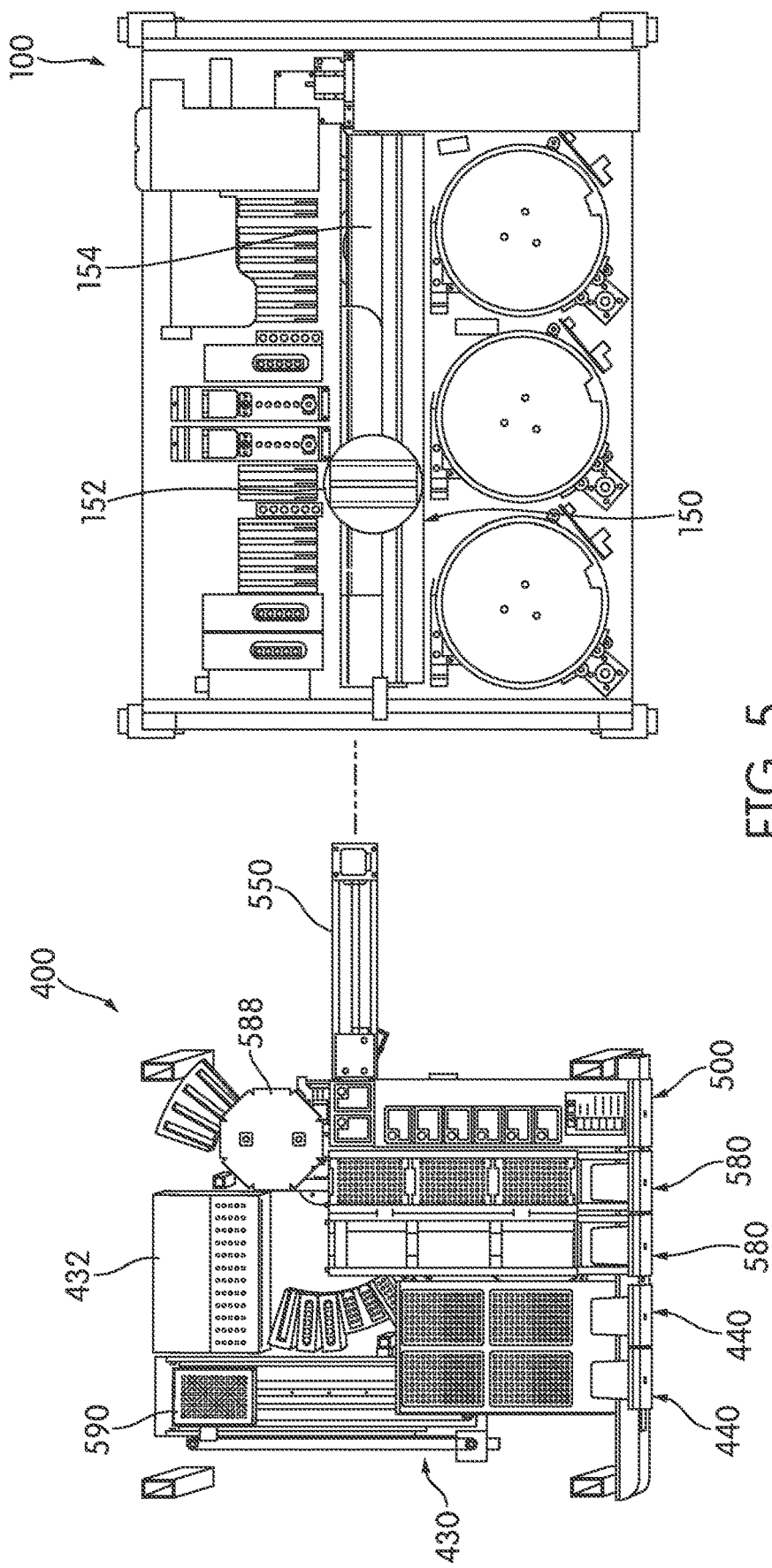
FIG. 5 is an exploded, top plan view of the first module and the second module according to an embodiment.
Figure 6:
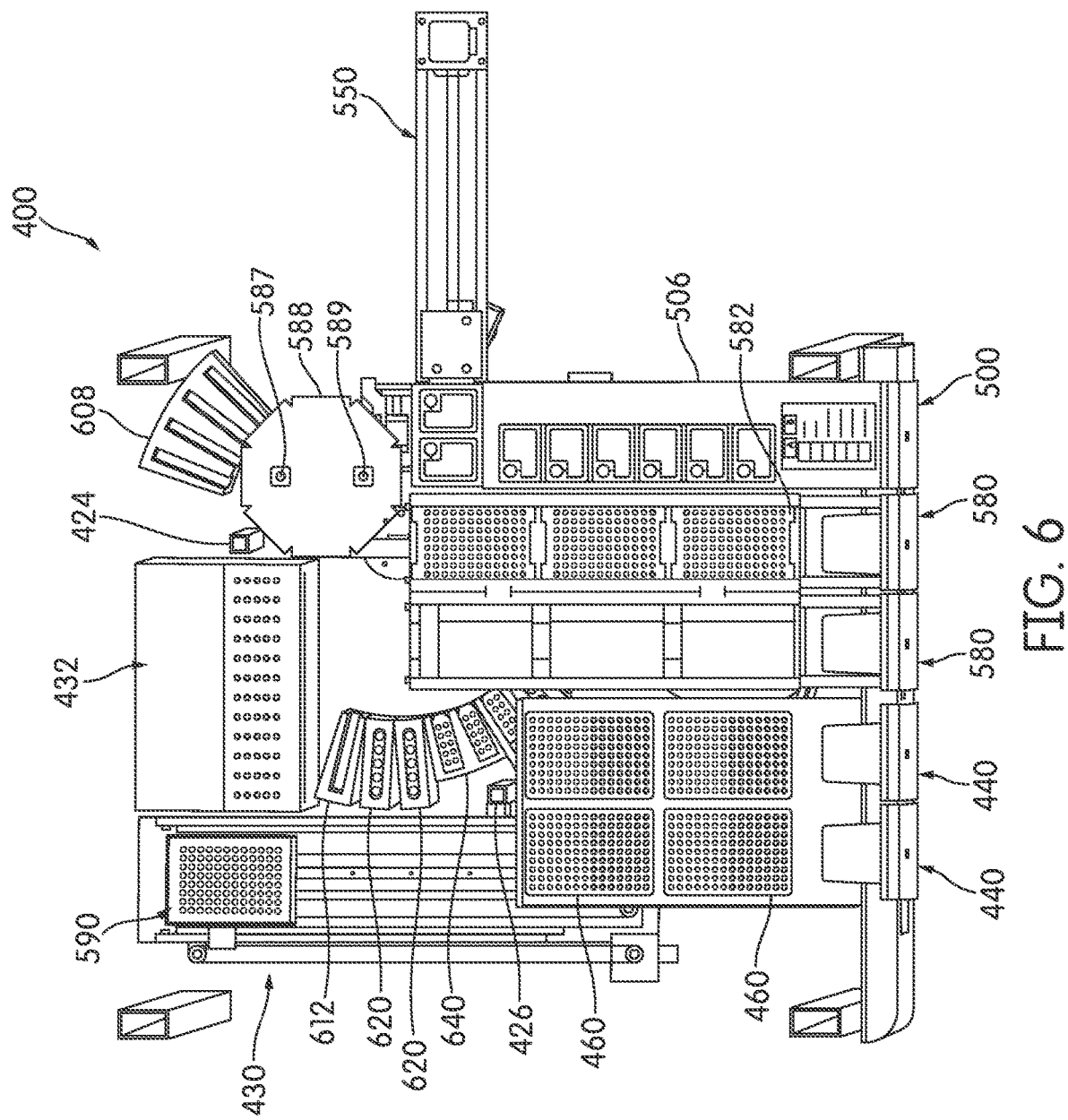
FIG. 6 is a top plan view of an amplification processing deck of the second module according to an embodiment.
Figure 14:
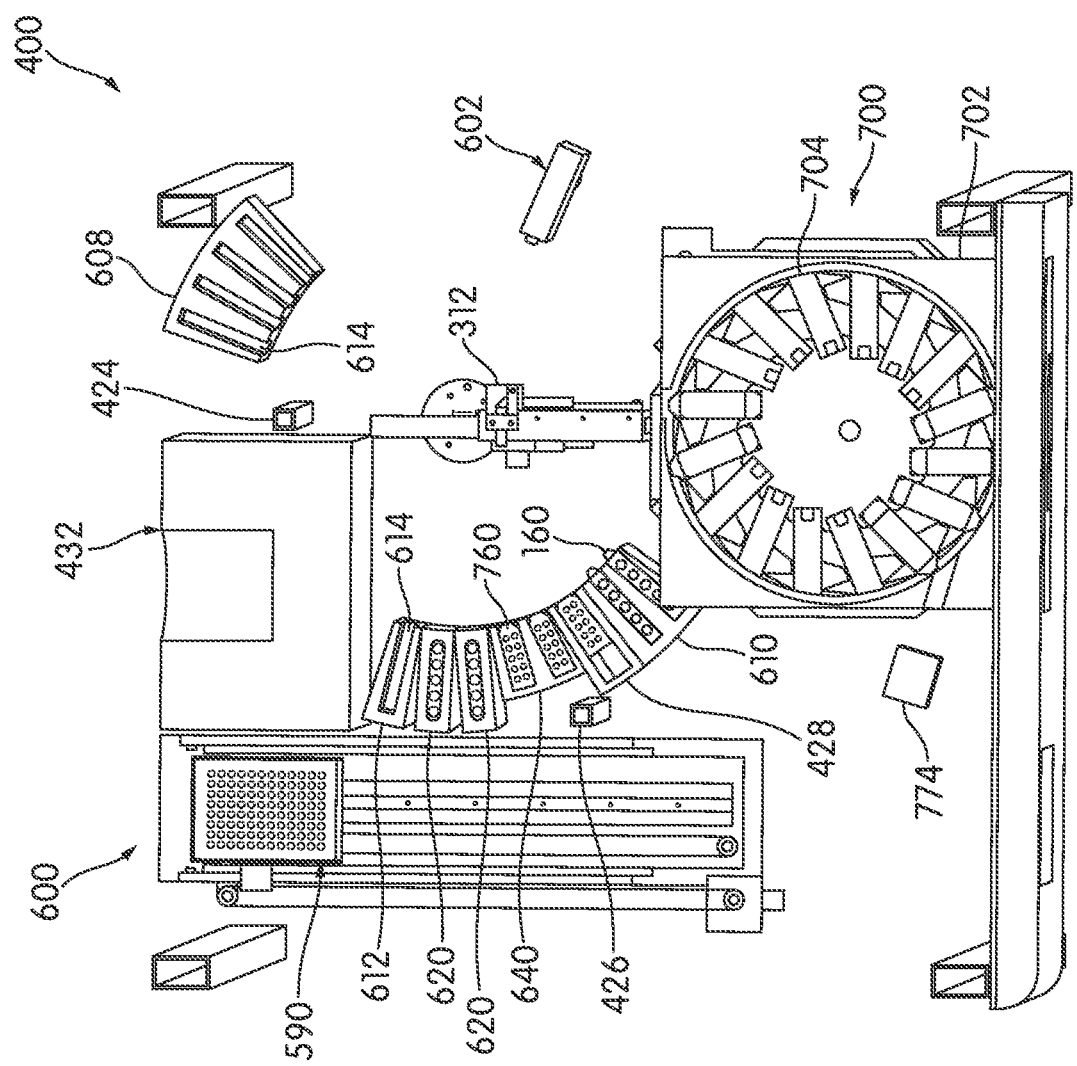
FIG. 14 is a top perspective view of a receptacle processing deck of the second module according to an embodiment.

Embodiments of the general configuration of the second module 400 are shown in FIGS. 1, 5, 6, and 14. FIG. 1 is a perspective view of diagnostic system 10 comprising a second module 400 and the first module 100. FIG. 5 is a top plan view of the second module 400 separated from the first module 100. FIG. 6 is a top plan view of an amplification processing deck 430, for example, a deck containing components for performing PCR, of the second module 400. FIG. 14 is a top plan view of a receptacle processing deck 600 of the second module 400. Referring to FIGS. 1, 5, 6, and 14, the component of the second module 400 can include, for example, a substance transfer device (for example, a robotic pipettor 402), a thermal cycler/signal detector 432, tip compartments 580 (e.g., two or more) configured to contain trays of disposable tips for the pipettor(s), processing cap/vial compartments 440 (e.g., two or more) configured to contain trays of disposable processing vials and associated caps, a bulk reagent container compartment 500, a bulk reagent container transport 550, a receptacle distribution system comprising a receptacle handoff device 602 and a receptacle distributor 312, which, in the exemplary embodiment shown, comprises a rotary distributor, MRD storage units 608, 610, 612 configured to store MRDs 160, magnetic elution slots 620 (e.g., two or more), a waste bin access door 652, a waste bin 652, a centrifuge 588, a reagent pack changer 700, reagent pack loading stations (e.g., two or more) 640, and a compartment 590 configured to store accessories, including, for example, consumables, output cards, and/or post-processing cap/vial assemblies.

As shown in FIG. 1, the components may be positioned on different levels, or decks, arranged vertically through the module 400. In some embodiments, the substance transfer and handling device 402 can be a robotic pipettor 402 as shown in FIG. 1. The robotic pipettor 402 is disposed near the top of the second module 400, above all other components, in some embodiments. The depicted configurations represent only a single embodiment. The vertical order of the decks and components may vary according to the intended use of diagnostic system 10. In the depicted embodiment, below the robotic pipettor 402, the amplification processing deck 430 includes the bulk reagent container compartment 500 and bulk reagent container transport 520, the centrifuge 588, the top of the thermal cycler/signal detector 432, the tip compartments 580, and the processing cap/vial compartments 440. Below the amplification processing deck 430, the receptacle processing deck 600 includes the receptacle handoff device 602, the rotary distributor 312, the MRD storage units 608, 610, 612, the magnetic elution slots 620, the reagent pack changer 700, and the reagent pack loading stations 640. As can be seen in FIG. 6, the magnetic elution slots 620 and the reagent pack loading stations 640 on the receptacle processing deck 600 are accessible by the robotic pipettor 402 through a gap between modules of the amplification processing deck 430.

The receptacle distribution system comprising the receptacle handoff device 602 and the rotary distributor 312, is configured to receive a receptacle or group of receptacles (e.g., MRD 160) from the receptacle transfer device (e.g., the receptacle distributor 150) of the first module 100 and transfer the receptacle to the second module 400 and configured to move the receptacle into different positions in the second module 400. The rotary distributor 312 and the receptacle handoff device 602 are shown schematically in FIG. 14. Further details regarding these components are described below.

In some embodiments, the second module 400 is operatively positioned adjacent to the first module 100, with the bulk reagent container transport 550 extending into the first module 100 so that elution containers 502, 504 can be transported by the bulk reagent container transport 550 from the bulk reagent container compartment 500 to a position in the first module 100 at which a substance transfer device, for example, a robotic pipettor, in the first module 100 can access the containers 502, 504.

In some embodiments, the second module 400 is generally self-supporting relative to first module 100 such that the second-module/first-module assembly is not over-constrained. Thus, in some embodiments, the second module 400 does not include any feet that contact the ground beneath the second module and support some or all of the weight of the module. In some embodiments, if the second module 400 includes its own rigid feet (e.g., two, three, or four feet), the feet of the first module 100 and the feet of the second module 400 could create an over-constrained geometry. In this case, one would carefully level all feet of the second module 400 and the first module 100 relative to each other to ensure that the assembly is level and that excessive stresses are not applied to attachment points between the second module 400 and the first module 100. To avoid such a potentially over-constrained geometry, the second module 400, in some embodiments, is cantilevered off the first module 100 if the first module feet can support the additional weight of the second module. In some embodiments, some of the weight of the second module 400 may be supported by a single foot on a far edge of the second module 400 away from the first module 100.

In some embodiments, second module 400 and first module 100 are mounted to an integral frame.

In some embodiments, the interface between the second module 400 and the first module 100 is blocked and sealed where possible to prevent airflow between the two modules. Existing air inlets on the side of the first module 100 facing the second module 400 may be ducted through the second module 400 to a fresh air source. The side wall of the second module 400 facing the first module 100 can be covered by panels to block airflow into the first module 100. Such panels can include openings where necessary for receptacle or container transfer between the second module 400 and first module 100, cable routing, etc.

Components of exemplary embodiments of the second module 400 are described below.

Reagent Packs

In some embodiments, amplification reagents and other reagents may be provided in the second module 400 in lyophilized form in a reagent pack comprising a cartridge that includes wells within which the lyophilized reagent may be reconstituted. Examples of cartridges that can be used in this embodiment are disclosed by Knight et al. in U.S. Provisional Application No. 61/782,320, "Systems, Methods, and Apparatus for Performing Automated Reagent-Based Assays," filed Mar. 14, 2014, which enjoys common ownership herewith (these cartridges are both identified by reference number 500 in FIGS. 10A and 10B). The reagent pack is further configured to be stored within the second module 400 and, in some embodiments, to be moved within the second module 400 by the distributor 312, and inserted and removed from the reagent pack changer 700.

Figure 19:
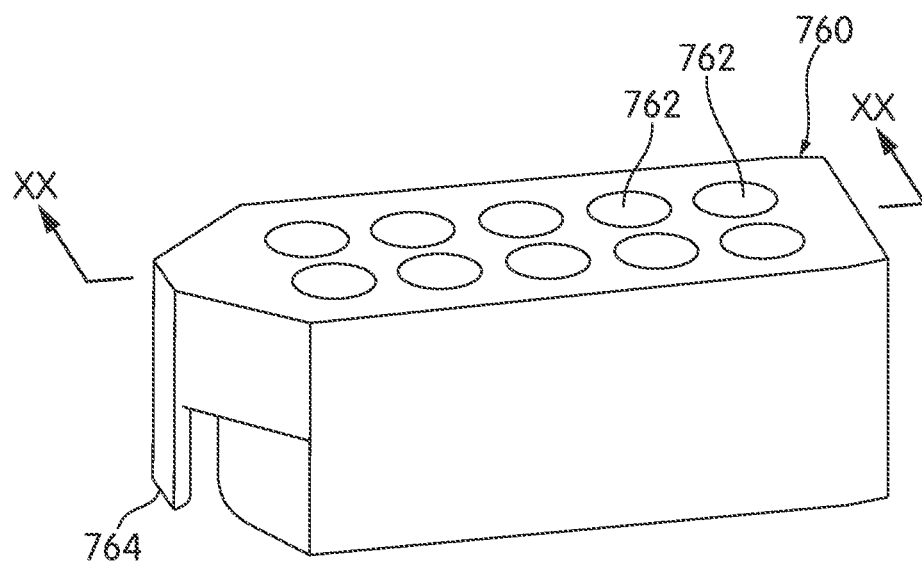
FIG. 19 is a top perspective view of a reagent pack embodying aspects of the present disclosure according to an embodiment.
Figure 20:
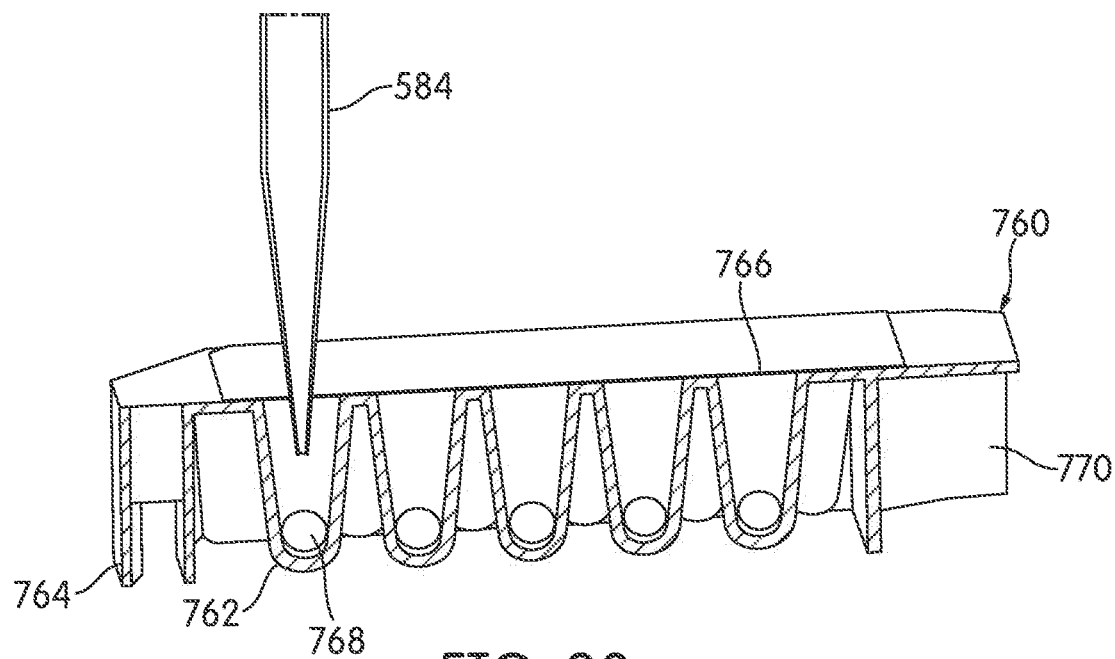
FIG. 20 is a top perspective, cross-sectional view of a reagent pack along the line XX-XX in FIG. 19 according to an embodiment.

Details of a reagent pack 760, according to one embodiment, are shown in FIGS. 19 and 20. The reagent pack 760 may include a plurality of mixing wells 762, each of which contains a lyophilized unit-dose, assay-specific reagent 768, which may be in pellet form. (As used herein, "unit-dose" or "unitized" means an amount or concentration of a reagent sufficient to perform one or more steps of a single assay for a single sample.) In some embodiments, the unit-dose reagent 768 comprises a component for performing a nucleic acid amplification reaction. For example, the nucleic acid amplification reaction component can be a polymerase, nucleoside triphosphates, or any other suitable component. In the illustrated embodiment, the reagent pack 760 includes ten mixing wells 762. But in some embodiments, the reagent pack 760 may include more or fewer than ten mixing wells. Each mixing well 762 of a single reagent pack 760 may hold the same reagent, or the wells 762 may hold different reagents, or some wells 762 may hold the same reagent and some may hold different reagents. Exemplary assay specific reagents 768 held in the reagent pack 760 include unitized reagents for performing a single amplification reaction, for example, PCR and/or a detection reaction utilizing a sample. Such reagents may be specific for one target nucleic acid or a plurality of different target nucleic acids. For example, the plurality of different target nucleic acids may be part of a respiratory panel, and the unitized reagents are sufficient to conduct a PCR reaction targeting Flu A, Flu B, RSV, parainfluenza 1, 2, and 3, Human Metapneumovirus, Adenoviris, H1, H3, 2009 H1N1, and/or Tamiflu resistance. In an embodiment, each reagent pellet 768 is held at the bottom of the associated mixing well 762 with an electrostatic charge imparted to the pellet 768 and/or the mixing well 762. In other embodiments, each reagent pellet 768 is held at the bottom of the associated mixing well 762 with one or more physical feature present in the mixing well 762, for example, those disclosed by Knight et al. in U.S. Provisional Application No. 61/782,320.

In some embodiments, the mixing wells 762 are covered by a pierceable foil 766 adhered to the top of the reagent pack 760. Foil 766 can be pierced by a pipette tip 584 to enable reconstitution agents or other substances to be dispensed into the mixing well 762 and to enable reconstituted reagent to be aspirated from the mixing well 762.

In some embodiments, the reagent pack 760 further includes a manipulating structure 764, for example, a manipulating hook, that is similar to the manipulating structure 166 of the MRD 160 and is configured to be engageable by a manipulating structure, for example, a hook, of the rotary distributor 312. The reagent pack 760 may include a rear recess 770 that is configured to align the reagent pack within a reagent pack carrier, as will be described below.

Tip Compartments

As shown in FIGS. 1, 5, and 6, tip compartments 580 are configured to hold trays 582 of disposable pipette tips in a manner that enables the tips held in the drawers 580 to be accessed by the robotic pipettor 402. In the illustrated embodiment, the second module 400 includes two tip compartments 580, each configured to hold up to three trays 582 of disposable pipette tips. The compartments 580 may be configured to accept commercially-available trays of disposable pipette tips. Exemplary, commercially available pipette tips and trays are available from TECAN (TECAN U.S. Inc., Research Triangle Park, N.C.). Such tips are available in a variety of volumetric capacities, and each tip may be conductive to facilitate capacitive liquid level sensing and tip-present detection, as is well known in the art. Exemplary trays hold ninety-six pipette tips.

The tip compartments 580 are configured to be accessible to an operator for reloading of trays 582. In one contemplated embodiment, the tip compartment 580 comprises a drawer configured to be pulled out of the second module 400 to enable an operator to place the trays 582 of tips into the drawers 580 and to remove empty trays from the drawers 580. A door or cover panel that is either part of each drawer 580 or the housing of diagnostic system 10 is opened to access each tip compartment 580 behind it. The door or cover panels may provide an esthetically pleasing appearance to the front of the second module 400. Manual or automated locks, controlled by the system controller, may be provided to prevent the compartment 580 from being opened when the second module 400 is operating. In some embodiments, visible and/or audible warning signals may be provided to indicate that a compartment 580 is not closed properly. In an alternative embodiment, compartment 580 comprises an access door and a slidable tray, wherein the tray is configured to slide out from second module to thereby provide loading access to an operator.

Substance Transfer and Handling System

Figure 22:
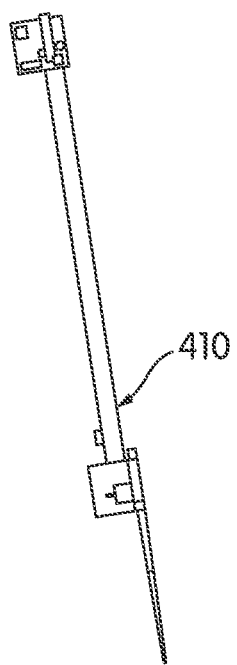
FIG. 22 is a perspective view of a substance transfer pipettor of the robotic pipettor according to an embodiment.

The substance transfer and handling system 402, for example, a robotic pipettor, shown in FIGS. 1, 21, and 22 is a dual arm system comprising a front arm 408 and a back arm 416. However, other robotic pipettor and handling configurations are contemplated, and the presently depicted embodiment is only exemplary. Substance transfer and handling system 402 can be configured to dispense and/or aspirate substances into and/or from a container, receptacle, well, etc., in second module 400. In an exemplary embodiment, the front arm 408 includes a substance transfer pipettor 410 configured to aspirate fluid and dispense fluid and includes a pump, for example, an integrated syringe pump, and the back arm 416 includes a vial transfer arm 418 and does not perform substance transfer. The robotic pipettor system 402 comprises a Cartesian gantry assembly with two transverse tracks 404, 406, a back arm longitudinal track 420, and a front arm longitudinal track 412. The designations "longitudinal" and "transverse" are merely for distinguishing the two sets of tracks, which may be orthogonal to one another, but otherwise the designations are arbitrary.

The substance transfer pipettor 410 may be driven back and forth along the front arm longitudinal track 412 by a belt, drive screw, or other motion transmission device coupled to a motor, and the vial transfer arm 418 may be driven back and forth along the back arm longitudinal track 420 by a belt, drive screw, or other motion transmission device coupled to a motor. The front arm longitudinal track 412 may be driven back and forth along the transverse tracks 404, 406 by a belt, drive screw, or other motion transmission device coupled to a motor, and the back arm longitudinal track 420 may be driven back and forth along the transverse tracks 404, 406 by a belt, drive screw, or other motion transmission device coupled to a motor. The substance transfer pipettor 410 and the vial transfer arm 418 include probes that are driven along the Z, or vertical, axis, for example, by a motor coupled to the probes, e.g., by a gear, a rack and pinion, a lead screw, or other suitable device. The motors may be under the control of a system controller. The motors may be stepper motors and may include rotary encoders for controlling and monitoring the position of the track or pipettor to which it is coupled. Each of the tracks has home sensors (or limit switches) for indicating when the substance transfer pipettor 410 or the vial transfer arm 418 is in one or more designated positions, such as a designated "home" position. Similarly, each device may have a vertical home sensor for indicating when the probe is in one or more designated vertical positions, such as a designated vertical "home" position. Such sensors for indicating a home position may include optical sensors (e.g., slotted optical sensors), proximity sensors, magnetic sensors, capacitive sensors, etc.

In one exemplary embodiment, the substance transfer pipettor 410 is configured to accept TECAN 1 mL disposable pipette tips by inserting the probe thereof into a disposable pipette tip, and an interference fit between the probe and the pipette tip frictionally secures the pipette tip to the end of the probe. The front arm 408 and the substance transfer pipettor 410 are configured to access at least parts of both the amplification processing deck 430 and the receptacle processing deck 600 on the second module 400. The substance transfer pipettor 410 may include integrated tip sensing for confirming the presence or absence of a disposable pipette tip, capacitive level sensing for detecting contact by the pipette tip with the surface of the fluid contents of a reaction receptacle or other container and determining the level of the fluid contents based on the detected vertical position of the pipettor, and pressure sensing for sensing pressure fluctuations within the substance transfer system during fluid dispensing or aspiration. The substance transfer pipettor 410 is capable of transferring fluids, caps, or cap/processing vial assemblies such as those described below.

The vial transfer arm 418 is a "pick and place" device configured pick up a cap/vial assembly by inserting the probe thereof into a cap that is coupled to a vial, as will be described below.

Pipettor Pump

In an exemplary embodiment, the pump for the substance transfer pipettor 410 comprises a ceramic piston driven by a servomotor and a lead screw. The servomotor is controlled by the system controller, and the device can include rotary encoder feedback to the system controller and home sensors for monitoring the position of the piston. The syringe may have a volume of between 0.5 and 3 mL (preferably 1.05 mL) and, in certain embodiments, is a ceramic. The pump can preferably dispense very small volumes (5 µL) of fluid with +/−5% coefficient of variation (CV) measured across 30 discrete dispenses. To achieve this performance, in certain embodiments, the pump includes a solenoid valve to release pressure at the end of the stroke to ensure consistent fluid shear.

Processing Cap/Vial Assembly

In general, the processing vial provides a receptacle for containing reaction fluids for performing PCR or other process. The cap is configured to be placed into or onto the vial in an automated manner so as to close off the vial. In some embodiments, the cap is configured to receive the end of the vial transfer arm 418 with a friction fit, so that the transfer arm 418 can thereafter pick up the cap and place it into or onto the vial. The cap and vial are configured to lock together so that, once the cap is placed into or onto the vial, the cap and the vial are interlocked to form a cap/vial assembly. The robotic pipettor, with the probe of the transfer arm 418 inserted into the cap, can then pick up the cap/vial assembly and transfer it from one location within the second module 400 to another location. Exemplary caps and processing vials are disclosed by, for example, Knight et al. in U.S. Provisional Application No. 61/782,320.

Figure 23:
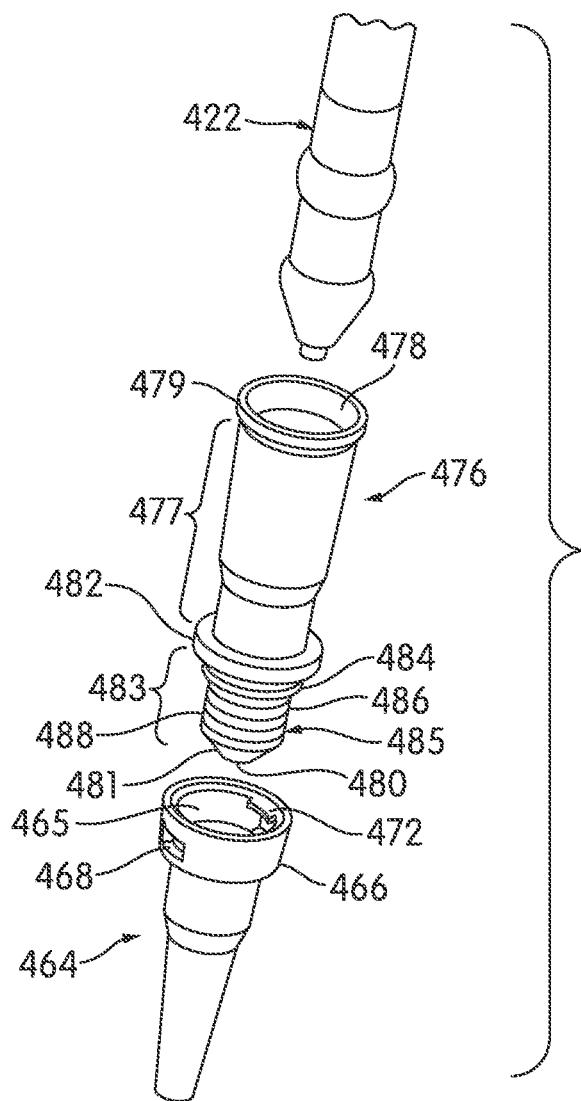
FIG. 23 is an exploded, perspective view of a processing vial, a processing vial cap, and a pipettor probe according to an embodiment.
Figure 24:
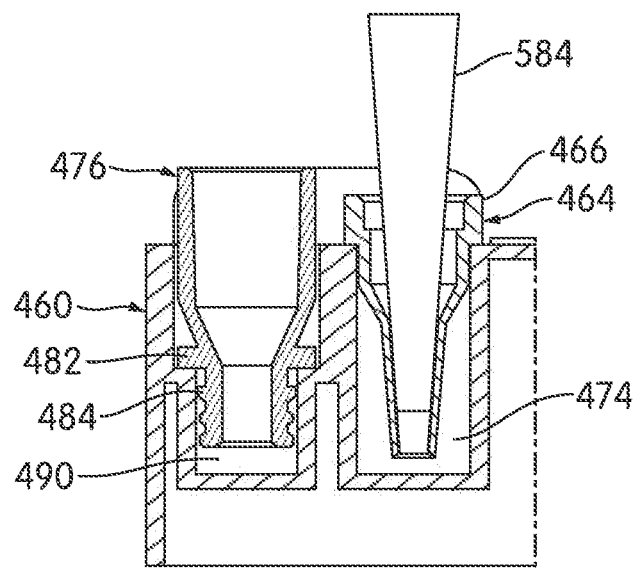
FIG. 24 is a transverse cross-section of the processing vial and the processing vial cap disposed within a processing vial well and a cap well, respectively, of a processing cap/vial compartment tray according to an embodiment.
Figure 25:
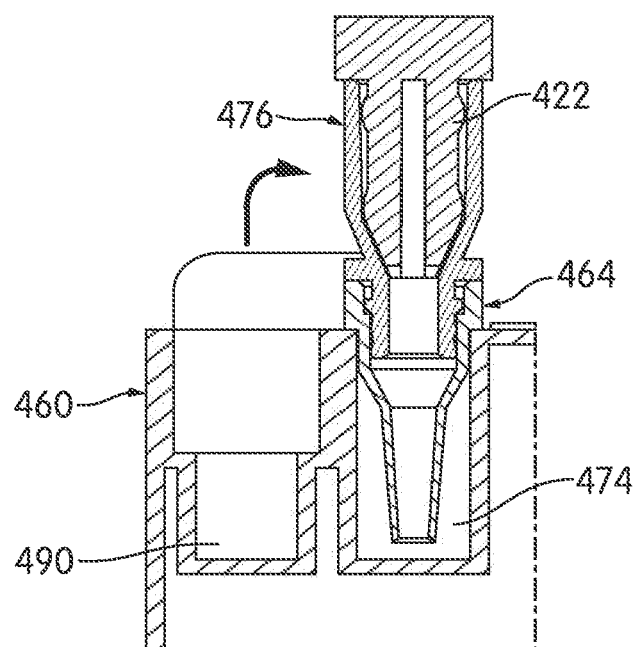
FIG. 25 is a transverse cross-section of the processing vial cap removed from the cap well and inserted into the processing vial with the processing vial disposed within the processing vial well according to an embodiment.

Details of an exemplary embodiment of the processing vial 464, the processing vial cap 476, and a vial transfer arm probe 422 (which may be the probe of the substance transfer pipettor 410 or the vial transfer arm 418) are shown in FIGS. 23-25.

In the embodiment shown in FIGS. 23-25, the processing vial 464 may have a conical shape and an open top end 465 surrounded by a locking collar 466 forming a peripheral wall around the open end 465. Lateral through holes 468 are formed through the locking collar 466 at diametrically opposed locations. A latch hook, or tab or radial protrusion, 472 is located above each through hole 468 and protrudes radially inwardly from the locking collar 466.

The processing vial cap 476 has an upper portion 477 with an open top end 478 that defines a probe recess to receive probe 422 and lower portion 483 with a closed lower end 480 at a distal end of the processing vial cap 476. A peripheral chamfer 481 extends about the lower (distal) end 480 and forms a convex distal end surface of the cap 476. An annular collar 482 extends about the cap 476 at a position between the upper portion 477 and the lower portion 483. Collar 482 of the vial 476 sits atop the thermal cycler when the vial 476 is placed therein, ensuring a close fit of the vial within the wells of the thermal cycler. An exemplary thermal cycler for use with processing vial 476 is disclosed by Buse et al. in U.S. Patent Application Publication No. 2014/0038192. The lower portion 483 of the cap 476 beneath the collar 482 defines a plug 485 that fits into the open top end 465 of the processing vial 464. This plug 485 is sized so as to fit into the processing vial 464 with an interference, friction fit. A latch collar 484—a radial protrusion—extends about the cap 476 and protrudes radially outwardly to provide a locking ridge at a position below the collar 482. Seal rings 486, 488 extend about the lower portion 483 of the cap 476 at positions below the latch collar 484.

FIGS. 24 and 25 show, in cross-section, a processing vial cap 464, initially held in a cap well 490 of a cap/vial tray 460, and a processing vial 464 held in a vial well 474 of the cap/vial tray 460. After fluids are dispensed into the processing vial 464 with the disposable pipette tip 584 (connected to a robotic pipettor), the processing vial 464 is capped by a processing vial cap 476 by inserting the closed lower end 480 of the cap 476 into the open top end 465 of the vial 464, until a bottom surface of the collar 482 of the cap 476 abuts a top surface of the locking collar 466 of the vial 464. The latch collar 484 of the cap 476 snaps in beneath the mating latch hooks 472 of the vial 464 which may function as locking detents to secure the cap 476 to the vial 464. The cap 476 and the vial 464 are thereafter locked together and the cap/vial assembly may be picked up and moved by the pipettor. The cap/vial assembly can be removed from the pipettor probe 422 by an eject device engaging a rim 479 surrounding open end 478 to pull the cap/vial assembly off the probe 422. The seal rings 486, 488 of the cap 476 preferably have outer diameters that are slightly larger than the inner diameter of the upper portion of the vial 464, thereby forming a tight seal between the cap 476 and the vial 464 as the cap and vial are made of materials, such as suitable plastics, that are at least partially resilient.

Figure 26:
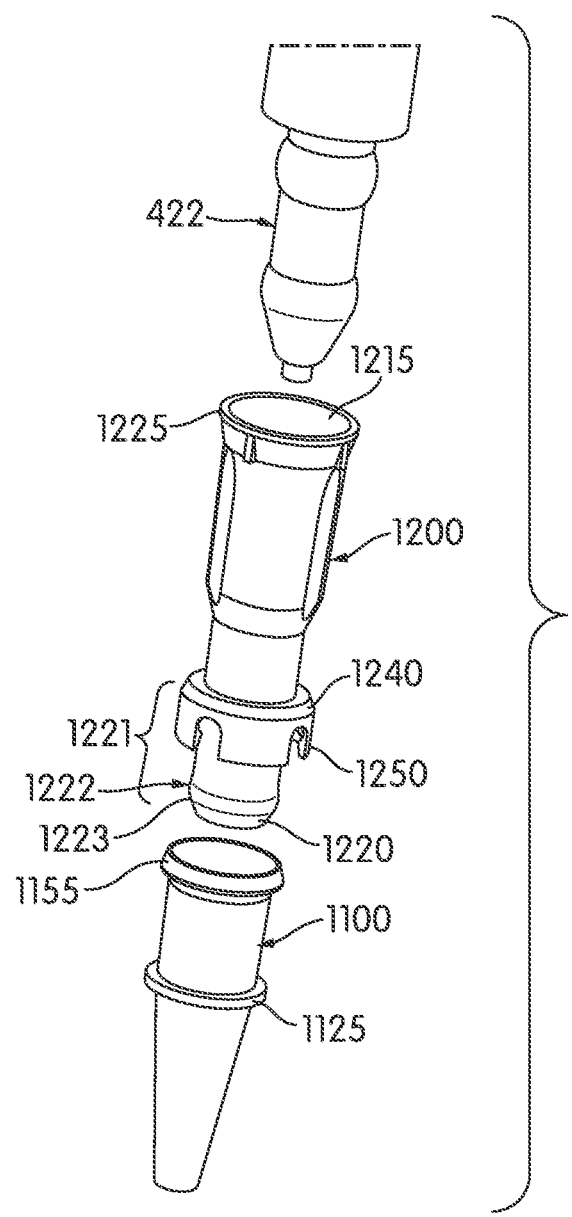
FIG. 26 is an exploded, perspective view of an alternative embodiment of a processing vial, a processing vial cap, and a pipettor probe.

An alternative processing cap/vial assembly is shown in FIG. 26, which is an exploded perspective view of a processing vial 1100 and a processing vial cap 1200. Processing vial cap 1200 includes a lower portion 1221 with a closed lower end 1220 defining a plug 1222, a tapered opening, or open end, 1215 forming or defining a probe recess, and a latch collar 1240 having latch fingers 1250 (or locking fingers or locking members). A peripheral chamfer 1223 extends about the lower (distal) end 1220 and forms a convex distal end surface of the vial cap 1200. The vial 1100 includes a radially-outwardly protruding lock collar, or lip, 1155 surrounding the open top end of the vial 1100 and a collar 1125. Collar 1125 of vial 1100 sits atop the thermal cycler when the vial 1100 is placed therein, ensuring a close fit of the vial within the wells of the thermal cycler. After fluid is dispensed into the vial 1100, the vial is capped by first inserting the pipettor probe 422 into the tapered opening 1215 of the processing vial cap 1200 to frictionally secure the cap 1200 to the pipettor probe 422 and then picking up the cap 1200 with the pipettor and inserting the plug 1222 of the closed lower end 1220 of the cap 1200 into the open top end of the vial 1100 until the latch fingers 1250 lockingly snap onto the lock collar 1155 of the vial 1100. The cap 1200 and the vial 1100 are thereafter locked together and the cap/vial assembly may be picked up and moved by the pipettor. The cap/vial assembly can be removed from the probe 422 by an eject device engaging a rim 1225 surrounding opening 1215 to pull the cap/vial assembly off the probe 422.

Details of the vial and cap of FIG. 26 are shown in FIGS. 45-55.

As shown in FIGS. 45-48, the vial 1100 is a single-piece receptacle that includes a body 1105 having a generally cylindrical upper portion 1110 and a tapered lower portion 1120. Formed on an outer surface of the body 1105 is collar 1125, which separates the upper and lower portions of the body. The upper portion 1110 of the body 1105 has an open end 1145 through which fluid samples are deposited or removed from the vial 1100. The tapered lower portion 1120 has a closed end 1150 that may either be flat or rounded to provide optical communication with an optical system, for example, one or more optical fibers (not shown) of a biochemical analyzer. In various embodiments, the bottom surface of the closed-ended lower portion may be flat or curved.

The vial 1100 optionally containing a sample or reaction mixture is configured for insertion into a receptacle holder of an automated biochemical analyzer (not shown). As used herein, a receptacle that is "configured for insertion" refers to the exterior surface of the body 1105 of the vial 1100 being sized and shaped to maximize contact between the receptacle and a receptacle well of a receptacle holder. In certain embodiments, this maximal contact refers to physical contact of the receptacle well with at least a portion of the vial 1100. Also in certain embodiments, this maximal contact refers to physical contact of the receptacle well with the tapered lower portion 1120 of the vial 1100, or at least a portion the tapered lower portion 1120 of the vial 1100.

Formed in the inner surface 1140 of the upper portion 1110 of the body 1105 is one or more longitudinally oriented grooves 1135 to facilitate the venting of air displaced from the interior upon deposit of the test sample or attachment of a cap 1200 to the vial 1100. In various embodiments, a plurality (i.e., 2, 3, 4, 5, 6, 7, or 8) of longitudinally oriented grooves may be formed in the inner surface 1140 of the upper portion 1110, and the grooves 1135 may be equally spaced apart from one another around the entire circumference of the body 1105.

Circumscribing the open end 1145 of the upper portion 1110 of the body 1105 is lock collar 1155 extending radially outward from a central axis thereof. In various embodiments, the lock collar 1155 tapers from the outer-most portion of the radially-extended lip towards the open end of the body, and is configured for securable attachment to a cap 1200 (FIGS. 49-55).

Figures 49, 50:
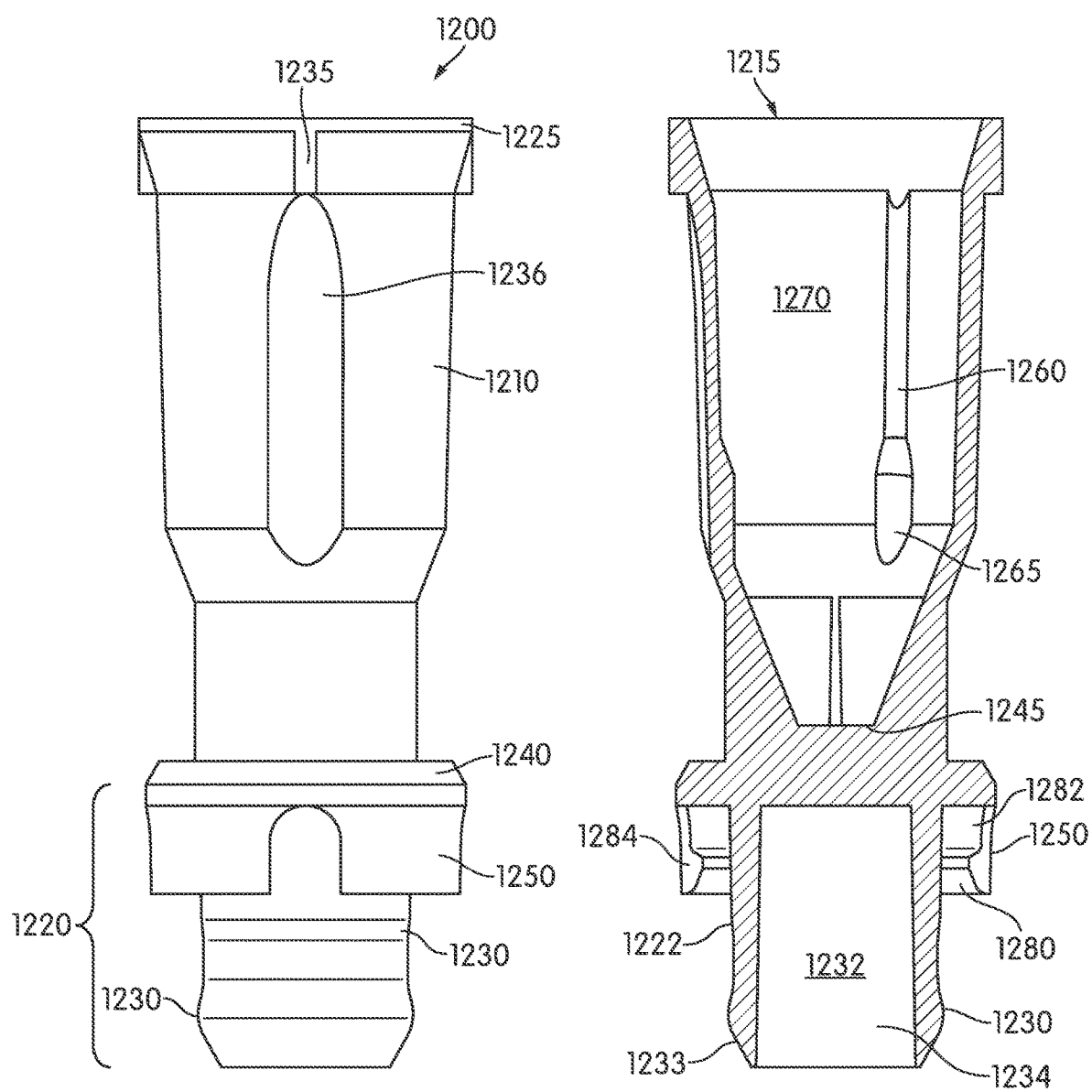
Figure 51:
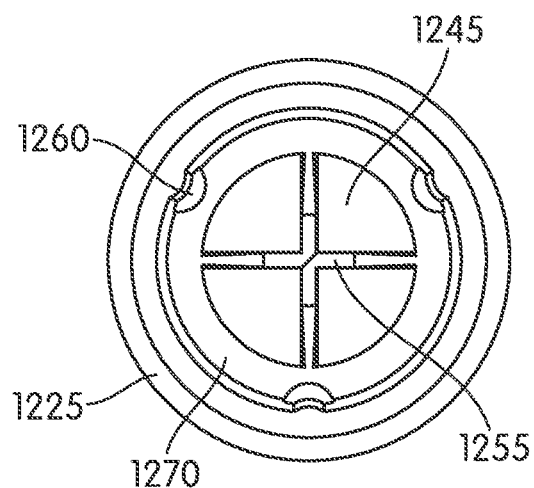
Figure 52:
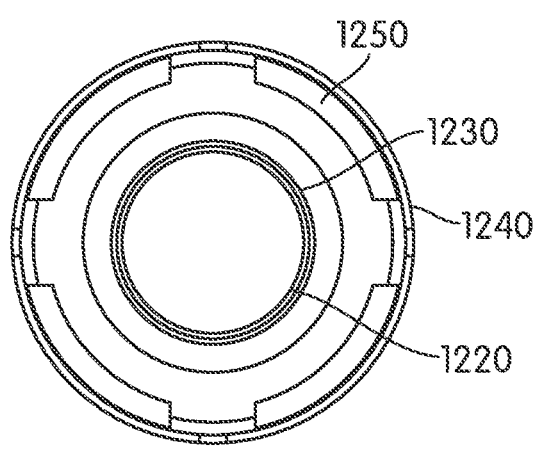
Figure 55:
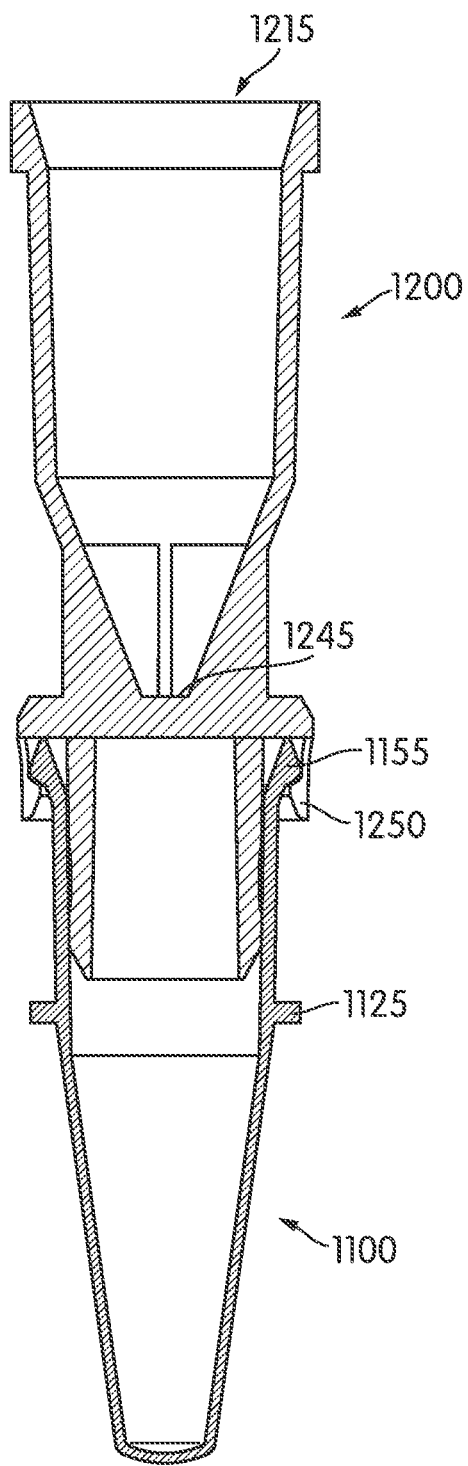
FIG. 55 is a cross-sectional view of the cap secured to the receptacle, and insertion of an automated pipettor into the open end of the cap.

With reference now to FIGS. 49-52, the securable cap 1200 includes lower portion 1221 having an outer surface defining plug 1222 for sealing engagement of the inner surface 1140 of the upper portion 1110 of the vial 1100 and an upper portion 1210. To ensure an essentially leak-proof seal when the cap 1200 is securely attached to the open end 1145 of the upper portion 1110 of the vial 1100, the outer surface of the lower portion 1221 of the cap 1200 is formed with one or more ribs 1230 circumscribing the plug 1222 for contacting the inner surface 1140 of the upper portion 1110 of the vial 1100. In various embodiments, the lower portion 1221 of the cap 1200 is formed with 1, 2, or 3 ribs 1230 for contacting the inner surface 1140 of the upper portion 1110 of the vial 1100. As shown in FIG. 50, lower portion 1221 has an open distal end 1234 defining an inner surface 1232, which is different from the embodiment shown in FIG. 26 in which lower portion 1221 has a closed lower end 1220. In an embodiment, a peripheral chamfer 1233 extends about the open distal end 1234 and forms a convex distal end surface of the vial cap 1200.

The upper portion 1210 of the cap 1200 includes tapered opening 1215 forming or defining a probe recess for frictional attachment to a receptacle transport mechanism (FIG. 26), such as the probe 422 of a pipettor or pick-and-place robot. Guiding insertion of the receptacle transport mechanism 422 into the open end 1215 of the upper portion 1210 of the cap 200 are one or more linear ribs 1260 formed in the inner surface 1270 of the upper portion 1210. The linear ribs 1260 protrude towards an axial center of the cap 1200, thereby decreasing the inner fitment diameter of the upper portion 1210 of the cap 1200. These linear ribs 1260 can, among other things, enhance the frictional attachment to the receptacle transport mechanism 422. In various embodiments, 1, 2, 3, 4, 5, 6, 7, or 8 linear ribs 1260 are formed in the inner surface 1270 of the cap 1200 and extend at least a portion of the way down the length of the upper portion 1210 thereof.

At least one of the linear ribs 1260 may be formed with a portion 1265 thereof that gradually tapers radially inward toward a central axis of the upper portion 1210 of the cap. In other words, the amount of protrusion of the linear rib 1260 may gradually increase in size as the linear rib 1260 approaches the bottom 1245 of the upper portion 1210 of the cap 1200. Alternatively, or in addition thereto, in certain embodiments, the linear rib 1260 may gradually increase in overall thickness as it approaches the bottom 1245 of the upper portion 1210 of the cap 1200. Thus, gradual increase in thickness or radial geometry is contemplated for the gradual tapering of the one or more linear ribs 1260, which serves to stabilize and center the receptacle transport mechanism 422 as it is lowered into the cap 1200 for transport.

Corresponding with each linear rib 1260 and disposed on the exterior surface of the upper portion 1210 of the cap 1200 are one or more indentations 1236 that extend along at least part of the length thereof. The indentations may be formed in any shape such as, for example, concave, notched, squared, etc. Thus, at least one indentation 1236 is formed in the exterior surface of the upper portion 1210 of the cap 1200. In various embodiments, the length of the indentation 1236 is the same as the length of the corresponding linear rib 1260, and each linear rib 1260 is positioned such that it lies on the inner surface 1270 of the cap 1200 in a location that directly opposes the position of the at least one indentation 1236 formed on the outer surface of the cap 1200 in a one-to-one relationship. The coupling of a linear rib 1260 with an indentation in this manner enhances the predictability of the frictional attachment of the cap 1200 to a receptacle transport mechanism 422. In certain embodiments, as the receptacle transport mechanism 422 is lowered into the open end 1215 of the cap 1200, it contacts the one or more linear ribs 1260, thereby pressing against the one or more linear ribs 1260. Such pressing against the linear ribs 1260 causes the cap 1200, and indentations 1236 to flex and/or expand radially outward with respect to the axial center thereof to accommodate the receptacle transport mechanism 422 and enhance fictional attachment thereto. Accordingly, 1, 2, 3, 4, 5, 6, 7, or 8 indentations 1236 may be formed on the exterior surface of the upper portion 1210 of the cap 1200.

Circumscribing the opening 1215 of the upper portion 1210 of the cap 1200 is the rim 1225 extending radially outward from a central axis thereof. In various embodiments, the rim 1225 tapers from the open end 1215 towards the lower portion 1221. Protruding from the taper of the rim 1225 are a plurality of protrusions 1235. The protrusions 1235 may be equally spaced apart from one another and facilitate stacking and/or docking within a well of a consumable card for use in an automated biochemical analyzer. In various embodiments, 1, 2, 3, 4, 5, 6, 7, or 8 protrusions 400 are formed in the taper of the rim 1225.

Separating the upper portion 1210 from the lower portion 1221 of the cap 1200 is the latch collar 1240 that extends radially away from an axial center thereof such that the top and bottom of the latch collar 1240 form radially-extending, annular surfaces. The latch collar 1240 includes one or more locking members, such as the plurality of locking fingers 1250 that extend from the latch collar 1240 toward the lower portion 1221 of the cap 1200. The locking fingers 1250 are shaped for securely engaging the lock collar 1155 of the vial 1100, and may be disposed to allow for removable attachment of the cap 1200 to the vial 1100, while maintaining a leak-proof seal of the contents thereof. In various embodiments, 1, 2, 3, 4, 5, 6, 7, or 8 locking fingers 1250 are formed in the cap 1200. In an embodiment, as shown in FIG. 50, each locking finger 1250 may include a distal, beveled end 1280, such that the locking finger(s) 1250 together define a radial locking groove 1282 surrounding the plug 1222 and a radially-protruding locking ridge 1284 surrounding the plug 1222 and disposed distally from the radial locking groove 1282. The locking ridge 1284 operatively engages the mating, lock collar 1155 of the vial 1100, which is received within the radial locking groove 1282 above the radial locking ridge 1284 when the plug 1222 of the closed lower end 1200 of the cap 1200 is inserted into the open top end of the vial 1100 and the locking finger(s) 1250 engage the lock collar 1155.

The latch collar 1240 of the cap 1200 additionally serves to form a bottom 1245 to separate the upper portion 1210 from the lower portion 1221, thereby closing the interior of the vial 1100 from the environment. However, in certain embodiments, the bottom 1245 is scored 1255 for piercing by a mechanism for collecting and/or adding reagents to the test sample within the vial 1100. Such piercing avoids the need to remove the secured cap 200 from engagement with the vial 1100, while providing access to the contents therein.

The vial 1100 and cap 1200 of the present invention may be prepared from a number of different polymer and heteropolymer resins, including, but not limited to, polyolefins (e.g., high density polyethylene ("HDPE"), low density polyethylene ("LDPE"), a mixture of HDPE and LDPE, or polypropylene), polystyrene, high impact polystyrene and polycarbonate. An example of an HDPE is sold under the tradename Alathon M5370 and is available from Polymerland of Huntsville, N.C.; an example of an LDPE is sold under the tradename 722 and is available from The Dow Chemical Company of Midland, Mich.; and an example of a polypropylene is sold under the tradename Rexene 13T10ACS279 and is available from the Huntsman Corporation of Salt Lake City, Utah. Although LDPE is a softer, more malleable material than HDPE, the softness of LDPE provides flexibility in the locking members 1250 of the cap 1200 to securably engage the lip 1155 of the vial 100. And, while a cap made of HDPE is more rigid than one made of LDPE, this rigidity tends to make an HDPE cap more difficult to penetrate than one made of LDPE. It should be understood that the vial 1100 and cap 1200 may be comprised of a combination of resins, including, for example, a mixture of LDPE and HDPE, preferably in a mixture range of about 20% LDPE:80% HDPE to about 50% LDPE:50% HDPE by volume. In addition, the amounts of LDPE and HDPE used to form each of the vial 1100 and cap 1200 may be the same or different. In various embodiments, at least a portion of the cap 1200 is formed from an opaque material having low to no autofluorescense characteristics. Also, in certain embodiments, the portion of the cap 1200 formed from an opaque material having low to no autofluorescense characteristics is at least the lower portion 1221 thereof, including the inner surface 1232 of the lower portion 1221 of the cap 1200.

Regardless of the type or mixture of resins chosen, the vial 1100 and cap 1200 are preferably injection molded as unitary pieces using procedures well-known to those skilled in the art of injection molding, including a multi-gate process for facilitating uniform resin flow into the receptacle and cap cavities used to form the shapes thereof. Uniform resin flow is desirable for achieving consistency in thickness, which is important for a variety of reasons, including for the penetrable bottom 1245 of the cap 1200; to ensure a secure, such as an air-tight, engagement of the cap 1200 and vial 1100; to ensure a predictable engagement of the cap 1200 with the receptacle transport mechanism 422; and to ensure maximal contact of the vial 1100 with a receptacle well of a receptacle holder.

The second module 400 may include "vial present" sensors. The vial present senor is used as a process control measure to verify that a vial is attached to the cap. The substance transfer pipettor 410 (front arm 408) and the vial transfer arm 418 (back arm 416) will detect when a cap is attached to the arm. One way substance transfer pipettor 410 or the vial transfer arm 418 will detect when a cap is present is by a strip sleeve on the probe 422. When the cap is picked by the probe, the upper rim of the cap pushes on and raises the sleeve (e.g., a few millimeters), and this movement may be detected by a sensor. However, pipettors often cannot detect if a vial is attached to the cap. In one exemplary embodiment, the vial present sensor is an optical sensor (or multiple sensors) that either arm 408, 416 can move past/ through as it transports a capped vial into or out of the centrifuge 588. The vial present sensor will trigger on the vial (if present) as the arm moves past the sensor.

Bulk Reagent Container Compartment and Bulk Reagent Container Transport

In one exemplary embodiment, the bulk reagent container compartment 500 is configured to hold a plurality of bulk reagent containers. Each bulk reagent container can hold a reagent for use in multiple reaction receptacles. In some embodiments, the bulk reagent containers are bottles or any other container suitable for containing reagents in bulk. In some embodiments, the bulk reagents within the bulk reagent containers can include a sample preparation reagent (e.g., target capture reagent (TCR), a wash solution, an elution reagent, or any other sample preparation reagent), a reconstitution reagent, or any other required bulk reagent. In some embodiments, the bulk reagent containers hold a quantity of the bulk reagent sufficient to perform between about 50 to 2000 assays. In some embodiments, the bulk reagent containers hold a quantity of the bulk reagent sufficient to perform between about 250 to 1000 assays. In some embodiments, the bulk reagent containers hold a quantity of the bulk reagent sufficient to perform less than about 250 assays, or more than about 1000 assays. In some embodiments, the bulk reagents are for performing isothermal nucleic acid amplification reactions, for example, a transcription-based amplification reaction such as TMA.

In some embodiments, the bulk reagent container compartment 500 can be configured to hold two elution buffer containers, two oil containers, and four reconstitution fluid containers. The bulk reagent container compartment 500 may be opened by an operator to load containers. For example, bulk reagent container compartment 500 may be a drawer that is slid out from the main body of diagnostic system 10. In some embodiments, once closed, the bulk reagent container transport 550 moves the elution buffer containers into the first module 100 to a location in which a substance transfer mechanism, for example, a robotic pipettor, can access the containers. In some embodiments, the bulk oil containers and the bulk reconstitution fluid containers remain in the bulk reagent container compartment 500, where they are accessible to the substance transfer pipettor 410.

Containers carried on the bulk reagent container compartment 500 may be identified by machine-readable code, such as RFID. An indicator panel 507 having visible (e.g., red and green LEDs) and/or audible indicators provides feedback to the operator regarding container status.

The bulk reagent container compartment 500 and bulk reagent container transport 550 are shown in FIGS. 5-10. In some embodiments, the bulk reagent container compartment 500 is located on the amplification processing deck 430 adjacent the tip compartments 580 and may be accessed from the front of the second module 400. The bulk reagent container compartment 500 may be pulled out to enable an operator to place two containers 502, 504 containing an elution buffer as well as a number of bulk containers, or other types of fluid containers, containing other reagents, such as, for example, oil or reconstitution buffer, into the drawer 500. The number of containers accommodated by the drawer 500 is dictated by considerations of intended throughput and desired time period between required restocking of supplies.

A door or cover panel, which is either part of the bulk reagent container compartment 500 or the housing of diagnostic system 10 is opened to access the bulk reagent container compartment 500 behind it. The door or cover panel can provide an esthetically pleasing appearance to the front of the second module 400. Automated locks, controlled by the system controller, may be provided to prevent the bulk reagent container compartment 500 from being pulled open when the second module 400 is operating. In some embodiments, visible and/or audible warning signals may be provided to indicate that the bulk reagent container compartment 500 is not closed properly.

When the bulk reagent container compartment 500 is closed, the containers 502, 504 are moved to the far end of the drawer 500, where they are positioned in operative engagement with the bulk reagent container transport 550 extending laterally from an end of the drawer 500 into the first module 100. Upon closing the bulk reagent container compartment 500, the bulk reagent container transport 550 is activated to move the containers 502, 504 into the first module 100 to a position at which the robotic pipettor of the first module 100 can access the containers 502, 504. The bulk reagent container transport 550 may be activated manually by an operator (e.g., pressing a button or switch) or automatically by the system controller upon receipt of an input signal indicating that the bulk reagent container compartment 500 has been fully closed, thereby placing the containers 502, 504 into operative position with respect to the bulk reagent container transport 550.

Figure 9:
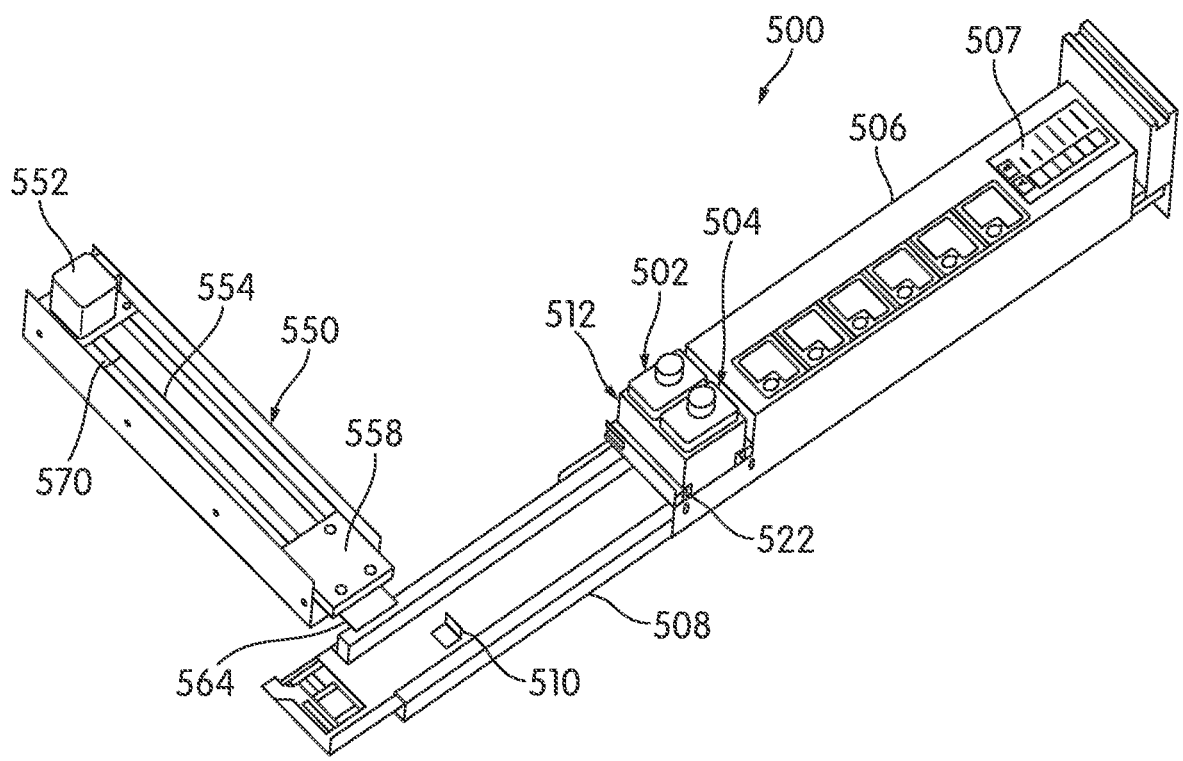
FIG. 9 is a top perspective view of the bulk reagent container compartment and bulk reagent container transport of the second module, with the bulk reagent container compartment in an open position according to an embodiment.
Figure 10:
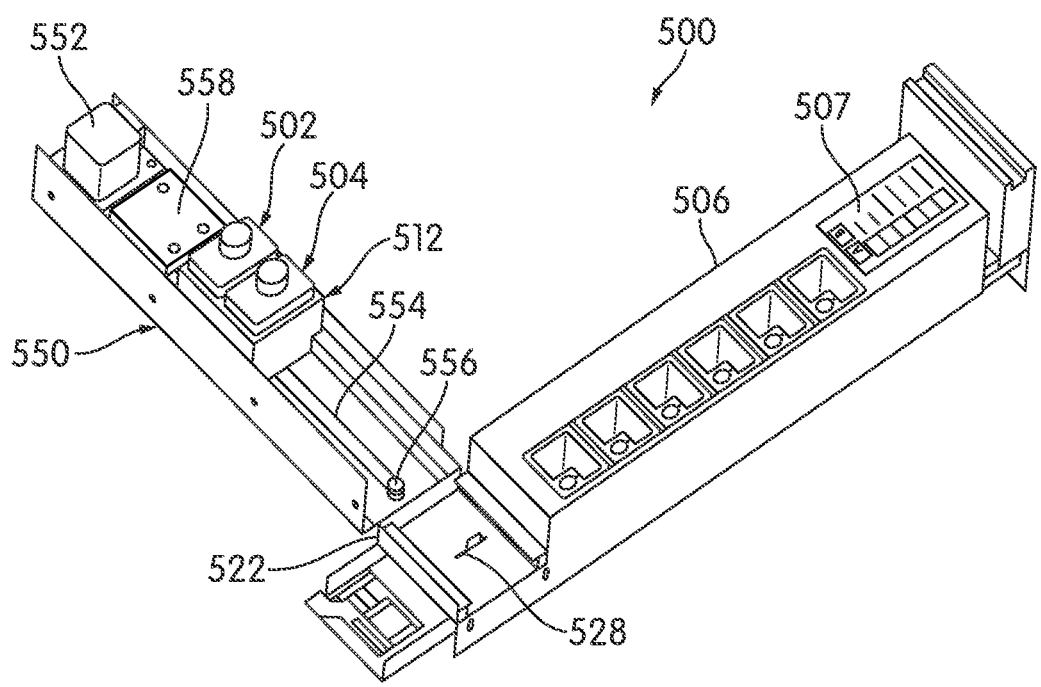
FIG. 10 is a top perspective view of the bulk reagent container compartment and bulk reagent container transport of the second module, with the bulk reagent container compartment in a closed position and elution containers transported to an end of the bulk reagent container transport according to an embodiment.

Details of the bulk reagent container compartment 500 are shown in FIGS. 9-13. In some embodiments, the bulk reagent container compartment 500 includes a container tray 506 configured to hold the plurality of reagent containers, and a container carriage 512 disposed at the end of the container tray 506 and configured to carry elution reagent containers 502, 504. In some embodiments, the container tray 506 and the container carriage 512 are moveable along a track 508 between a withdrawn position as shown in FIG. 9 (see also FIG. 7) and a closed position as shown in FIG. 10 (see also FIG. 8).

Figure 11:
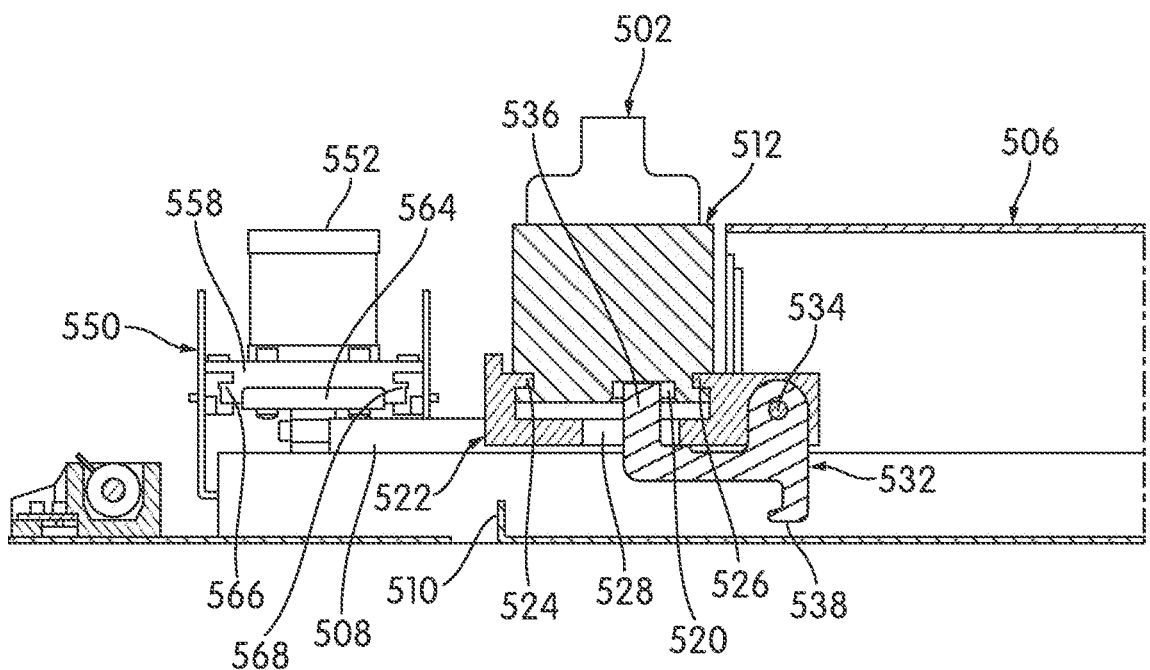
FIG. 11 is a partial cross-sectional view of bulk reagent container compartment, with the bulk reagent container compartment in an open position according to an embodiment.
Figure 12:
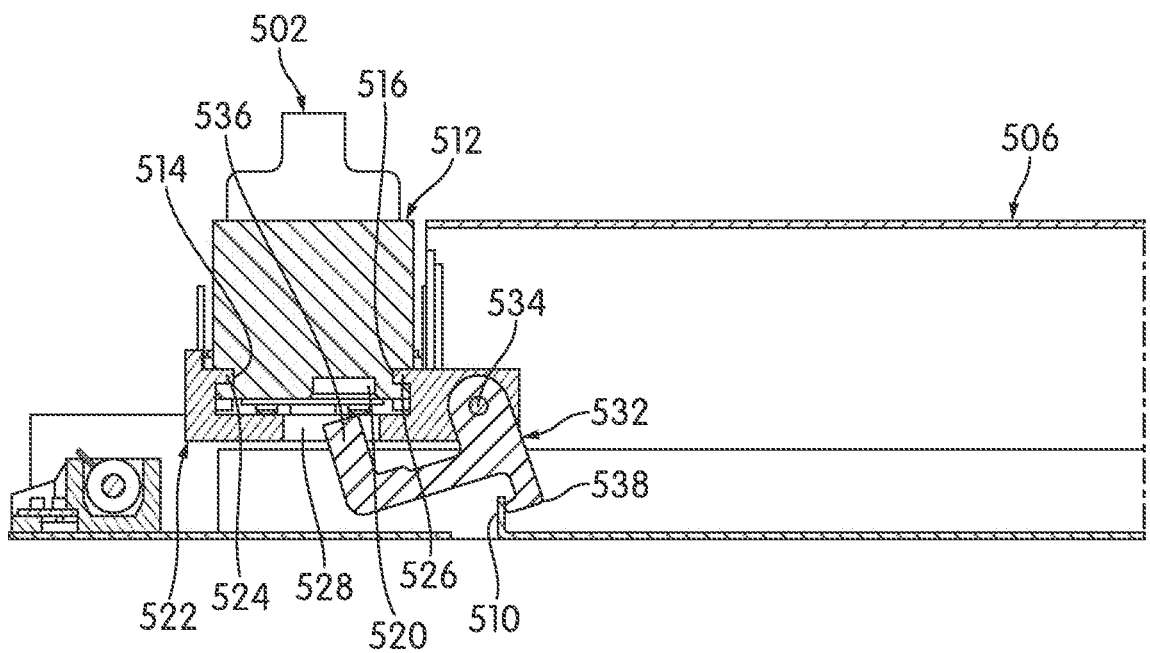
FIG. 12 is a partial cross-sectional view of bulk reagent container compartment and the bulk reagent container transport, with the bulk reagent container compartment in a closed position according to an embodiment.

The container carriage 512 is carried on a carriage transport 522 configured to be movable with the container tray 506 along the track 508. As shown in FIGS. 11 and 12, the carriage transport 522 includes horizontal carriage rails 524 and 526 that engage rail slots 514, 516, respectively, formed in the container carriage 512 to retain the container carriage 512 within the carriage transport 522.

Figure 7:
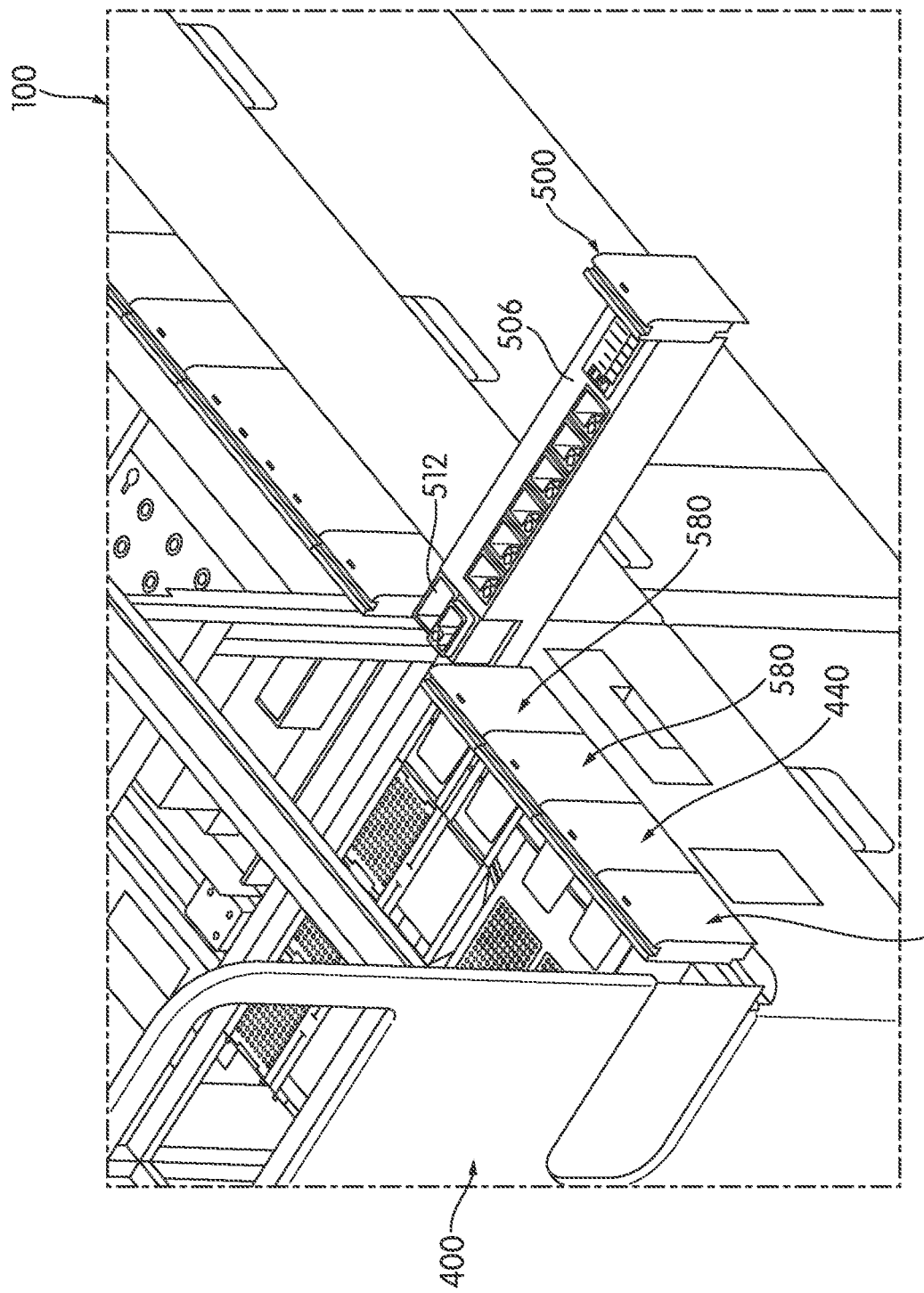
FIG. 7 is a partial, front perspective view of the second module with a bulk reagent container compartment in an open position according to an embodiment.
Figure 8:
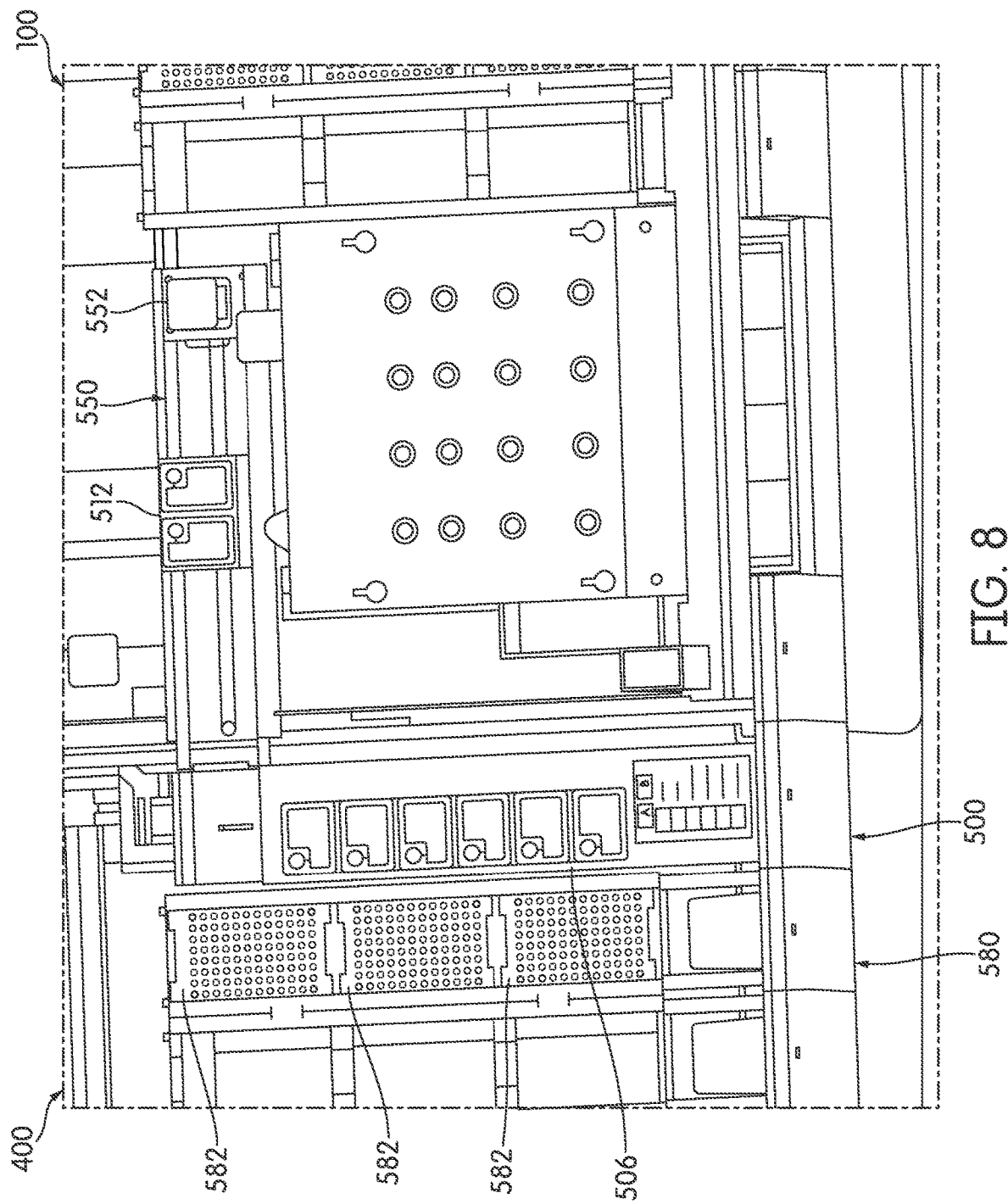
FIG. 8 is a partial, top plan view of the second module and first module showing the bulk reagent container compartment in a closed position according to an embodiment.

The bulk reagent container compartment 500 is configured to permit an operator to place reagent containers 502, 504 within the container carriage 512 when the drawer is in the open position, as shown in FIGS. 7 and 9. Upon closing the drawer, to the position shown in FIGS. 8 and 10, the reagent container carriage 512 can be released from the carriage transport 522 and engaged by the bulk reagent container transport 550 to pull the carriage 512 to a lateral position with respect to the track 508 of the container tray 506, as shown in FIG. 10. In this manner, it is possible to transfer bulk reagents from the second module 400 to the first module 100.

More particularly, the carriage transport 522 moves along the track 508 as the container tray 506 is moved into the open or closed positions. As shown in FIG. 11, the carriage transport 522 includes a pivoting carriage lock 532 configured to pivot about pivot pin 534 and including a locking leg 536 that extends upwardly through an opening 528 formed in the bottom of the carriage transport 522 and into a lock recess 520 formed in the bottom of the container carriage 512. A trigger leg 538 extends below the carriage transport 522. As the container tray 506 is moved into the closed position (to the left in FIG. 11) the trigger leg 538 of the pivoting carriage lock 532 engages a lock trigger 510 projecting upwardly from the track 508, thereby causing the carriage lock 532 to pivot counterclockwise, as shown in FIG. 12, to withdraw the end of the locking leg 536 from the lock recess 520 of the container carriage 512. With the trigger leg 538 withdrawn from the lock recess 520, the container carriage 512 and the containers 502, 504 carried therein, are able to slide laterally out of the carriage transport 522 and onto the bulk reagent container transport 550.

Figure 13:
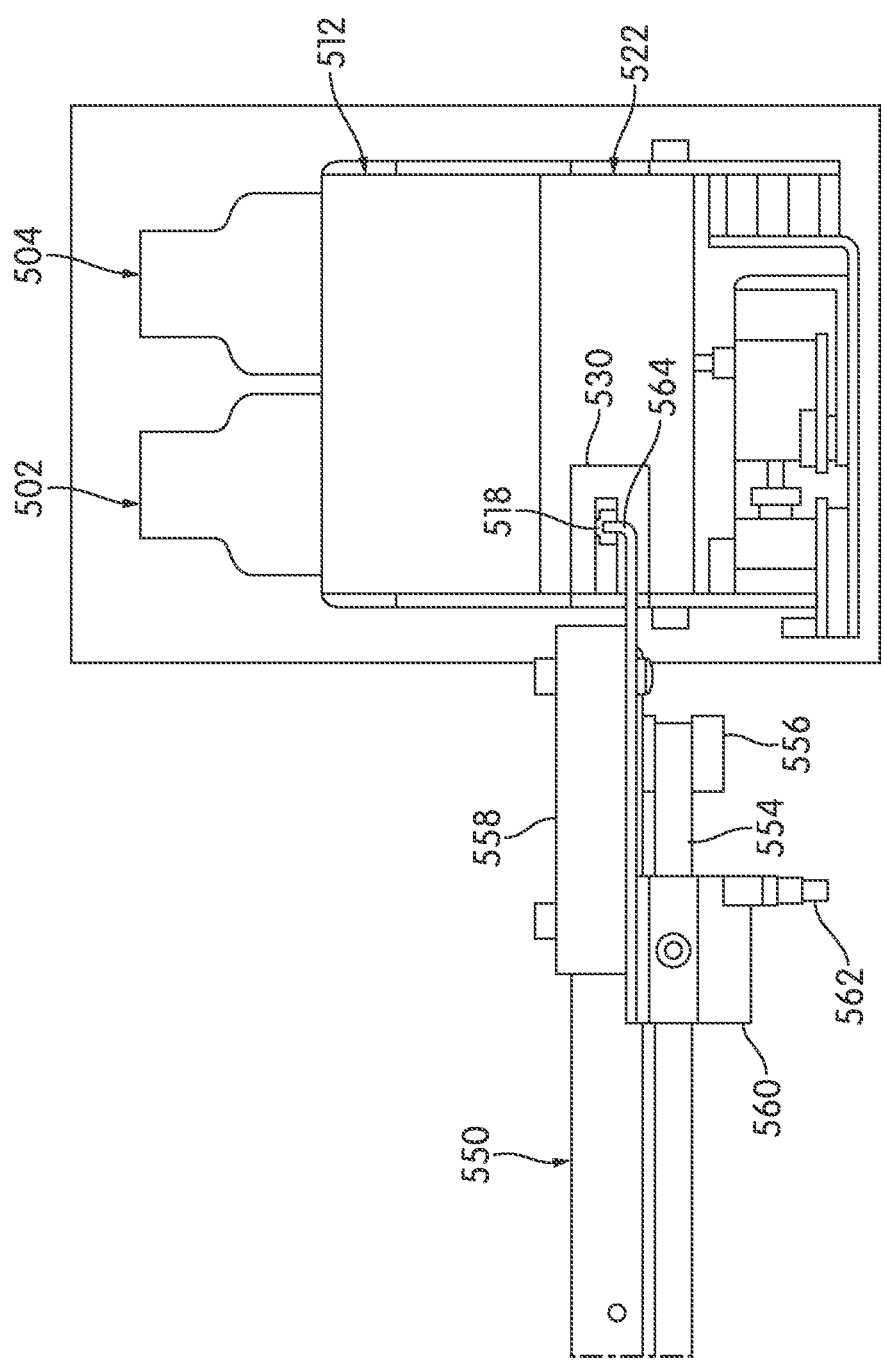
FIG. 13 is a partial end view of bulk reagent container compartment, with the bulk reagent container compartment in a closed position according to an embodiment.

The bulk reagent container transport 550 includes a powered carriage transport mechanism for moving the container carriage 512 and containers 502, 504. In one exemplary embodiment, as shown in FIGS. 9, 10, and 13, the carriage transport comprises motor 552 and a continuous belt 554 disposed over the output shaft of the motor and an idler wheel 556 located on an opposite end of the container transport 550 from the motor 552. Motor 552 may comprise a stepper motor and may include a rotary encoder for monitoring and controlling, via control signals and feedback data, the position of the motor.

The carriage transport mechanism further includes a sled 558 with a carriage hook 564 extending therefrom. The belt 554 is attached to a portion of the sled 558 so that movement of the belt by the motor 552 causes a corresponding translation of the sled 558 in one direction or the other along the transport 550.

As shown in FIGS. 12 and 13, as the container tray 506 is moved to a closed position in which the trigger leg 538 of the pivoting carriage lock 532 engages the lock trigger 510 to withdraw the locking leg 536 from the lock recess 520, the carriage hook 564 passes into a carriage hook slot 530 formed in the carriage transport 522 and engages a hook catch 518 formed in the container carriage 512. The sled 558 and carriage hook 564 may then be translated laterally along the container transport 550 by the belt 554 to pull the container carriage 512 off of the carriage transport 522 and onto the bulk reagent container transport 550. As shown in FIG. 11, the bulk reagent container transport includes carriage rails 566, 568 that will engage the rail slots 514, 516, respectively, of the container carriage 512 as the container carriage 512 is pulled onto the bulk reagent container transport 550.

As shown in FIG. 13, a home flag 560 projects from the sled 558 and engages a slotted optical sensor 562 to indicate that the sled 558 and the carriage hook 564 are in the fully-extended position shown in FIG. 13. A second slotted optical sensor 570 is provided closer to the motor 552 (see FIG. 9). The second optical sensor 570 is engaged by the home flag 560 when the sled 558 and hook 564 are in the fully retracted position, as shown in FIG. 9. Signals from the sensors 562, 570 are communicated to a system controller to monitor the position of the sled 558. Alternatively, the bulk reagent container transport 550 may include limit switches (e.g., contact switches) to stop operation movement of the sled 558 at the fully extended and/or fully retracted positions, for example, by generating stop signals communicated to a controller which then sends stop commands or terminates power to the motor 552. Still other types of sensors may be used for indicating extended and retracted stop positions, including proximity sensors, magnetic sensors, capacitive sensors, etc.

Cycler/Signal Detector

Cycler deck 430 comprises a cycler/detector 432, such as, for example, a thermal cycler. The cycler 432 is used in nucleic acid amplification reactions and the selection of cycler type depends on the nature of the amplification reaction intended to be run on the second module 400. For purposes of the present disclosure, exemplification will be made using a thermal cycler. However, it is understood that the cycler type incorporated into the second module 400 depends on the amplification reaction intended to be run on the second module 400.

An exemplary embodiment of a thermal cycler 432 is disclosed by Buse et al. in U.S. Patent Application Publication No. 2014/0038192. An exemplary embodiment of a signal detector 432 is disclosed by Hagen et al. in U.S. Pat. No. 9,465,161, "Indexing Signal Detection Module," filed Mar. 7, 2014, which enjoys common ownership herewith.

In certain embodiments, the thermal cycler can have different thermal zones. Such thermal cyclers allow the system to run separate assays under different conditions. For example, in a two zone thermal cycler, a first assay can be run under a first set of time and temperature conditions and a second assay can be run under a second set of time and temperature conditions. It is contemplated that the multi-zone thermal cycler can have two, three, four, five, or even six or more separate thermal zones. Generally, to the extent that a multi-zone thermal cycler is implemented in the system, the number of zones for the multi-zone thermal cycler is evenly divisible into 96 (i.e., 2, 4, 6, 8, etc.)

Receptacle Holder

Figure 56:
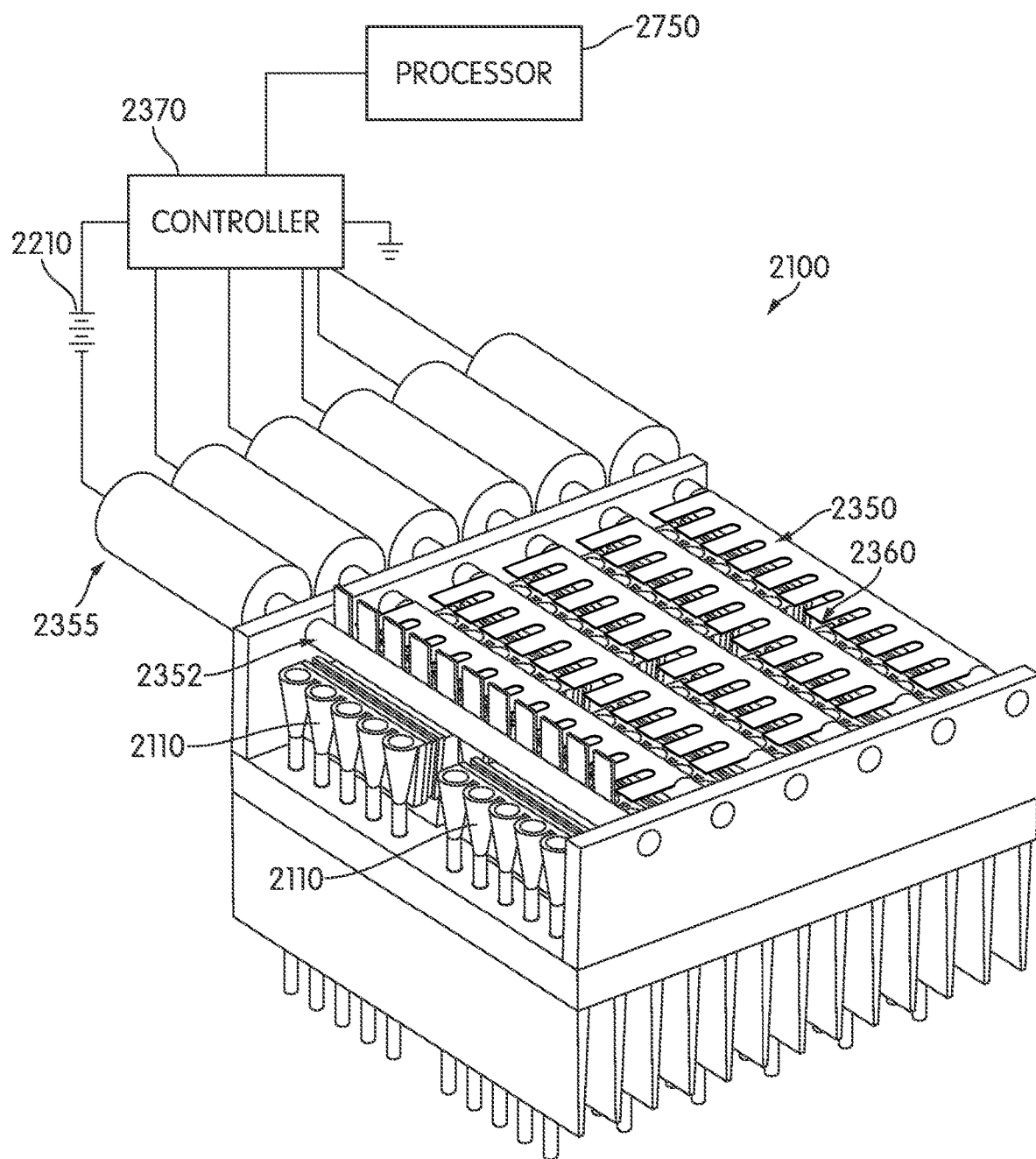
FIG. 56 shows an apparatus of the present disclosure.
Figure 57:
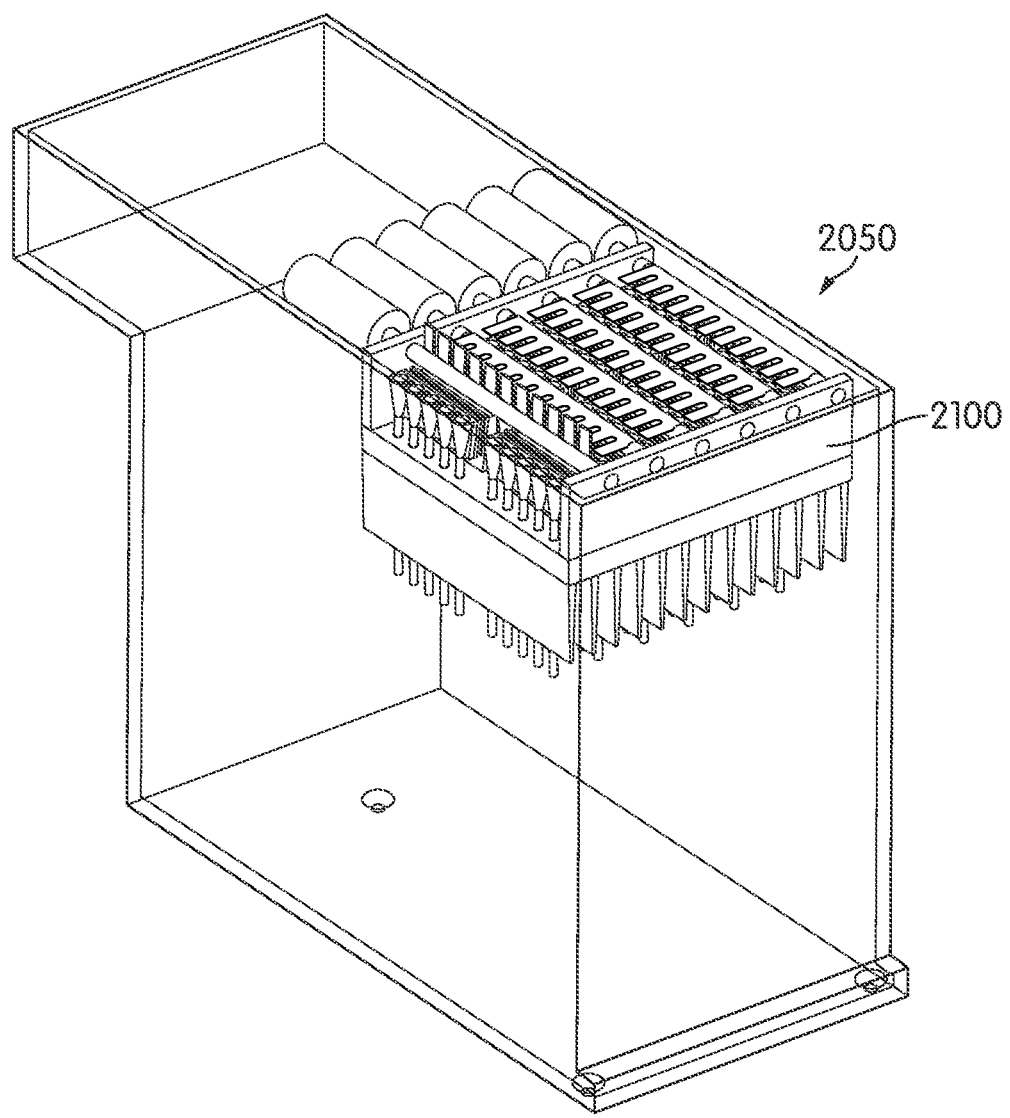
FIG. 57 shows an apparatus of the present disclosure mounted in a housing.

In an exemplary aspect, cycler 432 comprises an apparatus 2100 to perform the heating (i.e., isothermal or temperature cycling) necessary for a nucleic acid amplification assay. As shown in FIG. 56, the apparatus 2100 includes one or more (i.e., 1, 2, 3, 4, 5, 6, 7, 8, 9, 10, 11, 12, or any whole number between 1 and 20, or more) receptacle holders 2110 (see also FIGS. 57-61). In an exemplary embodiment, the apparatus 2100 includes two or more receptacle holders 2110. Such an apparatus may include a housing 2050 (see FIG. 57) within which the one or more receptacle holders 2110 are located. The housing 2050 may be made from any suitable structural material such as, for example, plastic or metal.

When multiple receptacle holders 2110 are provided in an apparatus described herein, each receptacle holder 2110 disposed within the apparatus may be disposed in alignment with one another to facilitate the automated processing steps involved in nucleic acid amplification assays. It should be understood that any alignment may be used in accordance with the size and shape of the apparatus. In an exemplary embodiment, the receptacle holders are disposed within the apparatus in one or more (i.e., 1, 2, 3, 4, 5, 6, 7, 8, 9, 10, or more) rows of two receptacle holders per row. Thus, two receptacle holders may be disposed in a row either in thermal connection with, or thermally separated from, one another. In an exemplary embodiment, the apparatus 2100 includes six rows of two receptacle holders per row.

Figure 58:
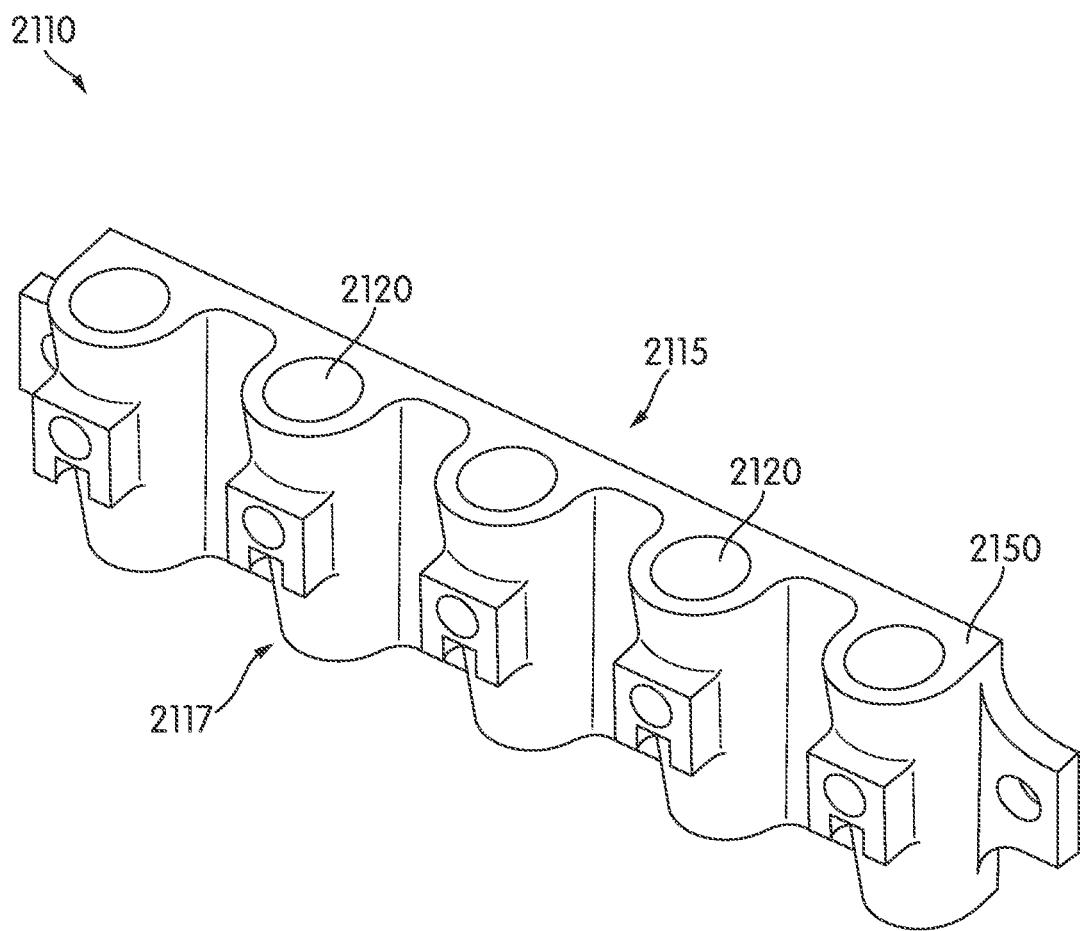
FIGS. 58-60 show a receptacle holder of the present disclosure.
Figure 59:
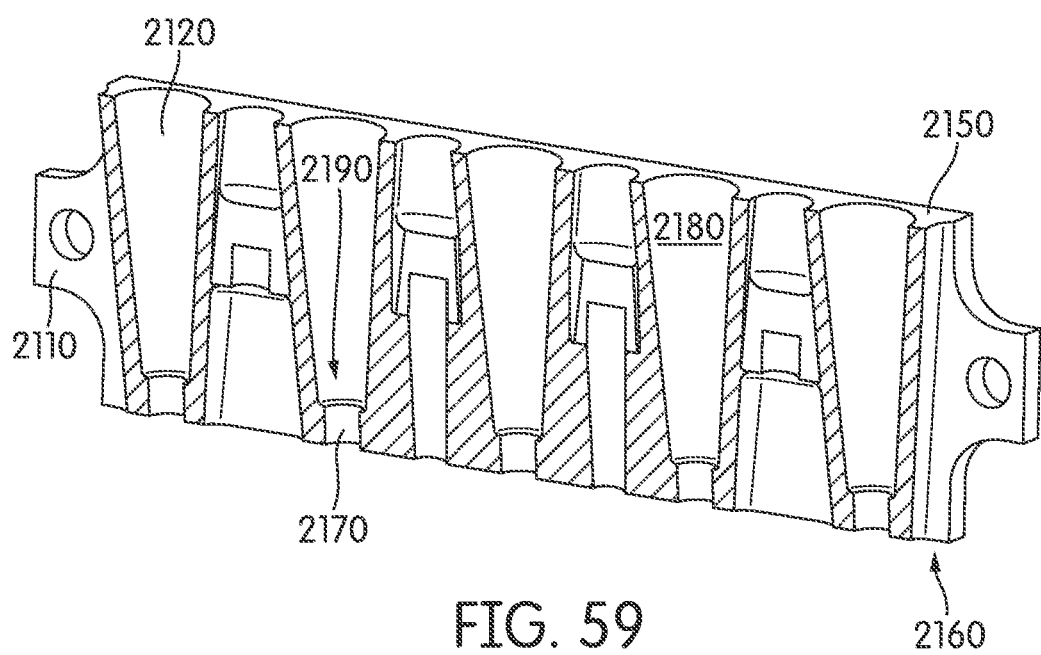
Figure 60:
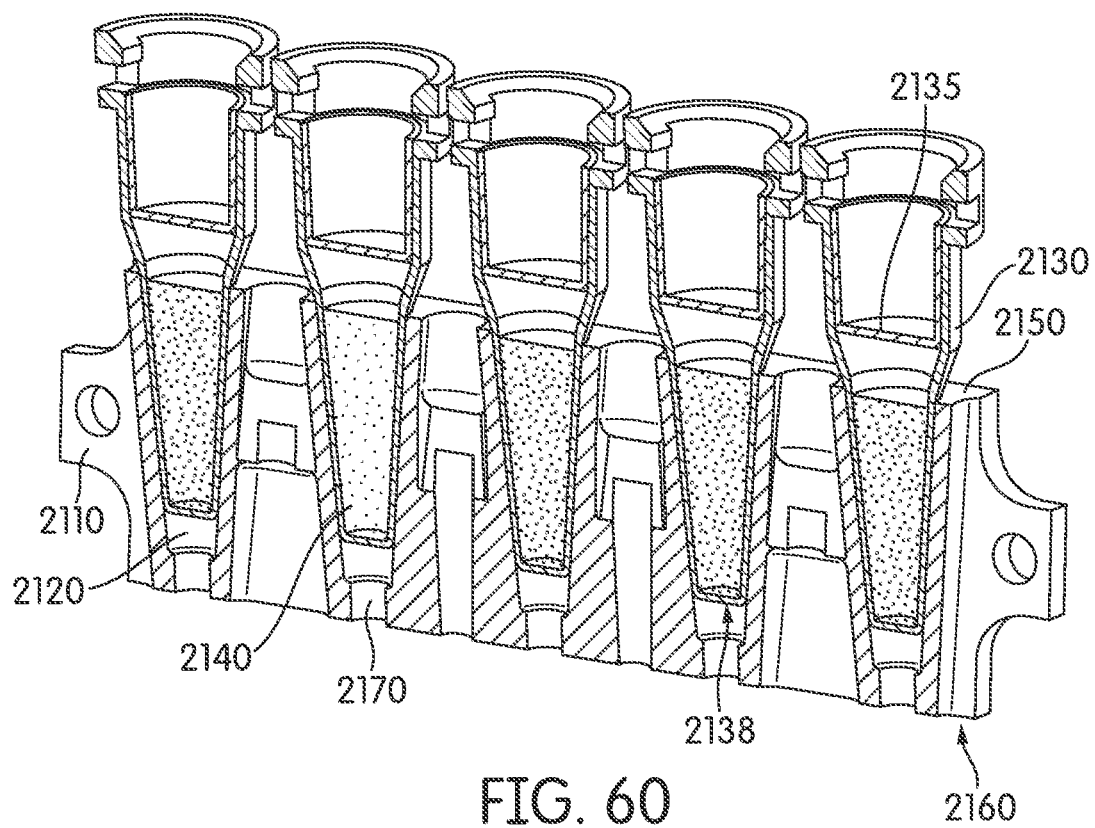

As shown in FIGS. 58-60, the receptacle holder 2110 includes a plurality (i.e., two or more) of receptacle wells 2120 that are configured to receive a receptacle 2130 (e.g., vial 464 or vial 1100) optionally containing a sample or reaction mixture 2140. For purposes of explanation, the surface of the receptacle holder into which the receptacles 2130 are inserted will be referred to as the "top surface" 2150 thereof. Likewise, the surface of the receptacle holder opposite to the surface into which the receptacles 2130 are inserted will be referred to as the "bottom surface" 2160. In an exemplary embodiment, each receptacle holder 2110 includes five or more (i.e., 5, 6, 7, 8, 9, 10, or any whole integer between 1 and 10, or more) receptacle wells 2120. In another exemplary embodiment, each receptacle holder 2110 includes one to ten receptacle wells. In another exemplary embodiment, each receptacle holder includes three to six receptacle wells. In yet another exemplary embodiment, each receptacle holder includes five receptacle wells. Each of the plurality of receptacle wells within a respective receptacle holder may be disposed in alignment with one another. In an exemplary embodiment, the receptacle wells 2120 are disposed in a row extending along the length of the top surface 2150 of the receptacle holder 2110.

Exemplary materials from which a receptacle holder may be made include, but are not limited to, aluminum, titanium, copper, steel, magnesium, metal composites, metal alloys, ceramics, plastics, plastic composites, or any suitable thermally-conductive material.

As used herein, a receptacle well of the receptacle holder that is "configured to receive" a particular size or shape of receptacle refers to a receptacle well whose dimensions are substantially similar to the size and shape of a receptacle 2130 (i.e., a sample tube) such that the receptacle 2130 fits snugly within the receptacle well 2120, thereby maximizing contact between the surface of the receptacle well 2120 and the receptacle 2130. In certain embodiments, this maximal contact refers to physical contact of the receptacle well 2120 with at least a portion of the receptacle 2130. In various embodiments, receptacles 2130 in accordance with the present disclosure are individual reaction vessels made from suitable rigid or flexible materials, and shaped and dimensioned to fit within the receptacle wells of the apparatus described herein. In other embodiments, two or more (i.e., 2, 3, 4, 5, or more) receptacles may be manufactured as a single unit configured to fit within a receptacle holder. Each receptacle 2130 may be closed or sealed to prevent contamination of and/or evaporation of the contents therein, and/or to facilitate handling or transport of each receptacle. Such seals may be permanent or semi-permanent and may be fluid-tight. In certain embodiments the seal comprises a cap or lid 2135.

Within each receptacle well 2120 is at least one through-hole 2170, which extends from an inner surface 2180 of the receptacle well to an outer surface of the receptacle holder. In an exemplary embodiment, the through-hole 2170 of a particular receptacle well 2120 extends from the bottom-center of inner surface 2180 of the receptacle well 2120 to the surface of the receptacle holder 2110 that is opposite to the surface of the receptacle holder within which the receptacles 2130 are inserted (i.e., in this embodiment, the through-hole extends from the bottom of the receptacle well 2120 to the bottom surface 2160 of the receptacle holder 2110). In certain embodiments the diameter of the through-hole 2170 is the same as that of the bottom 2190 of the inner surface 2180 of receptacle well 2120. In other embodiments, the through-hole 2170 comprises a hole or opening having dimensions smaller than the bottom 2190 of the inner surface 2180 of receptacle well 2120. In other embodiments, the through-hole 2170 comprises a hole or opening having dimensions the same size as, or larger than, the bottom 2190 of the inner surface 2180 of receptacle well 2120. The exact dimensions of the through-hole 2170 may vary, provided that the presence of the through-hole 2170 does not detrimentally affect the ability of the receptacle holder 2110 to efficiently transfer heat to and from a receptacle 2130 held within the receptacle well 2120.

Thermal Element

Figure 61:
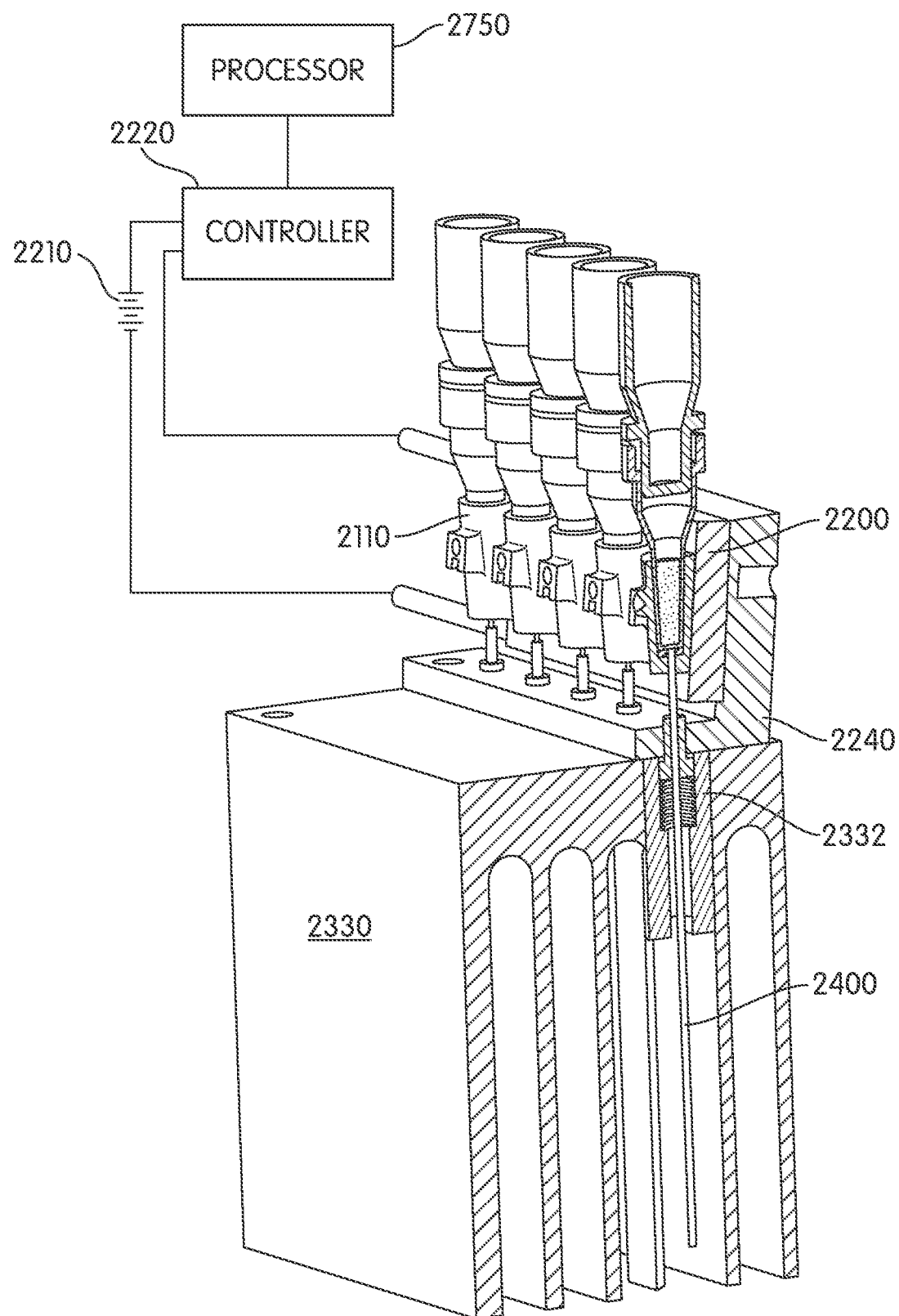
FIGS. 61 and 62 show a receptacle holder slidably mounted to a support. The support is mounted in thermal communication with a heat sink (FIG. 61). A cross-brace may be mounted to the support to exert a force onto a front surface the receptacle holder (FIG. 62).
Figure 62:
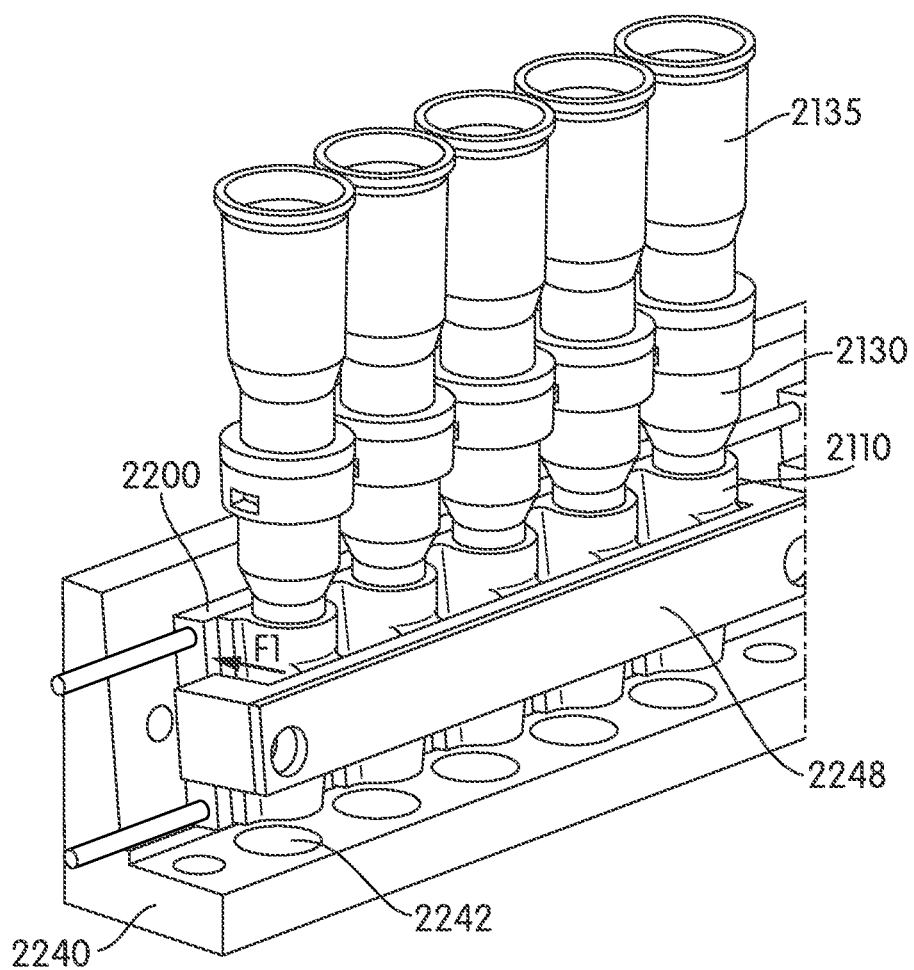

As shown in FIGS. 61 and 62, positioned proximal to the receptacle holder is one or more thermal elements 2200 for altering a temperature or temperatures of the receptacle holder 2110. As used herein, the term "thermal element" may include any known heating element for heating and cooling applications. In one embodiment, the thermal element is a resistive heating element, such as a thin metal film that is applied to the receptacle holder 2110 by using well-known methods such as sputtering or controlled vapor deposition. The heating element also can be provided as a molded or machined insert (e.g., such as a cartridge) for incorporation into the receptacle holder 2110.

In an exemplary embodiment, the thermal element 2200 is a thermoelectric device, such as a "Peltier device," which is generally constructed from electron-doped n-p semiconductor pairs that act as miniature heat pumps. When current is applied to the semiconductor pairs, a temperature difference is established, where one side becomes hot and the other cold. If the current direction is reversed, the hot and cold faces will be reversed. Usually an electrically nonconductive material layer, such as aluminum nitride or polyimide, is disposed over the substrate faces of the thermoelectric modules so as to allow for proper isolation of the semiconductor element arrays.

As used herein, "altered temperature or temperatures" of the receptacle holder refers to the increase or decrease of the temperature of the receptacle holder 2110. Often, the increase or decrease of the temperature is determined relative to the ambient temperature. Included in the term is the ability to individually adjust the temperature of one or more receptacle wells 2120, while separately adjusting the temperature of other receptacle wells within the same receptacle holder. Thus, the term may refer to uniformly raising/lowering the temperature of all receptacle wells 2120 within a receptacle holder 2110 or may refer to altering a subset of the receptacle wells 2120 within a single receptacle holder 2110. As used herein, "ambient temperature" refers to the temperature of a surrounding environment, which may include a fluid (e.g., air or liquid) or solid structure.

The thermal element 2200 may be electrically connected to a controllable power source 2210 for applying a current across the element to alter the temperature thereof. Control of the power source 2210 can be carried out by an appropriately programmed processor 2220 (such as a computer) which receives signals from one or more thermal sensors 2610 (see FIG. 61) in thermal communication with the receptacle holder 2110, as discussed below, and/or signals from another processor that controls the automated process steps involved with temperature cycling processes.

The thermal element 2200 may be held in contact with a side surface 2115 (see FIG. 58) of the receptacle holder 2110 by one or more supports 2240, which may be positioned in sliding engagement with the receptacle holder 2110. As used herein, being positioned "in sliding engagement" refers to a non-fixed contact between adjacent surfaces of different parts of the apparatus described herein. Thus, when the apparatus 2100 includes two or more receptacle holders 2110, each of the two or more receptacle holders are configured in sliding engagement with a support 2240. As used herein, the term "support" refers to a rigid structure, which can be thermally-conductive. Exemplary materials from which a support may be made include, but are not limited to, aluminum, titanium, copper, steel, magnesium, metal composites, metal alloys, ceramics, plastics, plastic composites, or any suitable rigid thermally-conductive material. Supports may also comprise a structure formed of, or from, a combination of materials, for example, plastic, metal (including alloys and composites), ceramic, or a combination of different types of one or more of these materials.

As is known in the art, thermal elements may require a specific force to achieve adequate thermal contact with a component that is to be heated. For example, certain Peltier devices require a mounting force of approximately 150-300 psi to effectively transfer thermal energy to a device. With reference to FIG. 62, the apparatus may include one or more cross-braces 2248 mounted to a support 2240, and exerting a force F1 onto a front surface 2117 of a receptacle holder 2110. Force F1 is sufficient to effect thermal transfer of energy from thermal element 2200 to receptacle holder 2110. In certain embodiments, the apparatus includes one cross-brace 2248 for each receptacle holder 2110. In other embodiments, the apparatus includes one cross-brace 2248 per row of receptacle holders 2110. In such embodiments, the cross-brace generally incorporates a portion or layer having low thermal conductivity as the portion that directly contacts the receptacle holder 2110. As discussed below, in other embodiments, a body 2300 having low thermal conductivity is used to exert the force required for thermal transfer of energy to the receptacle holder 2110.

Cover

Figure 63:
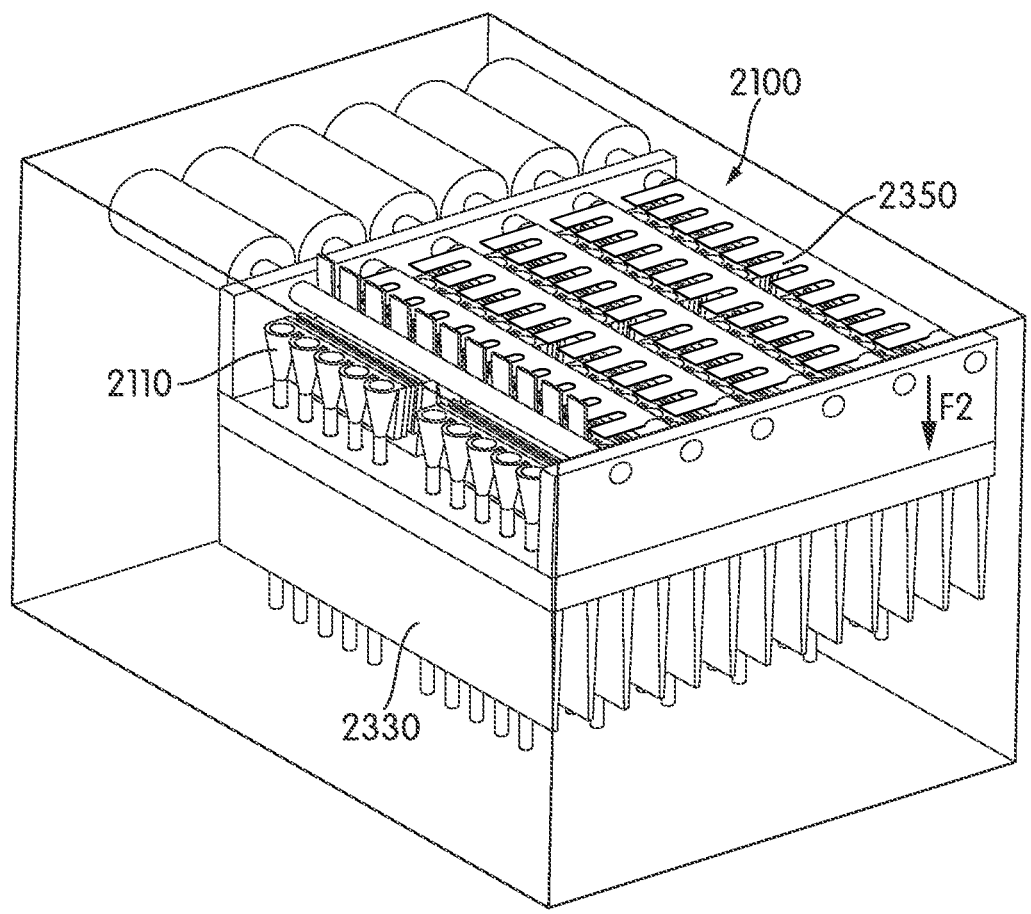
FIGS. 63-67 show exemplary covers and stripper plates disposed within the apparatus of the present disclosure.
Figure 64:
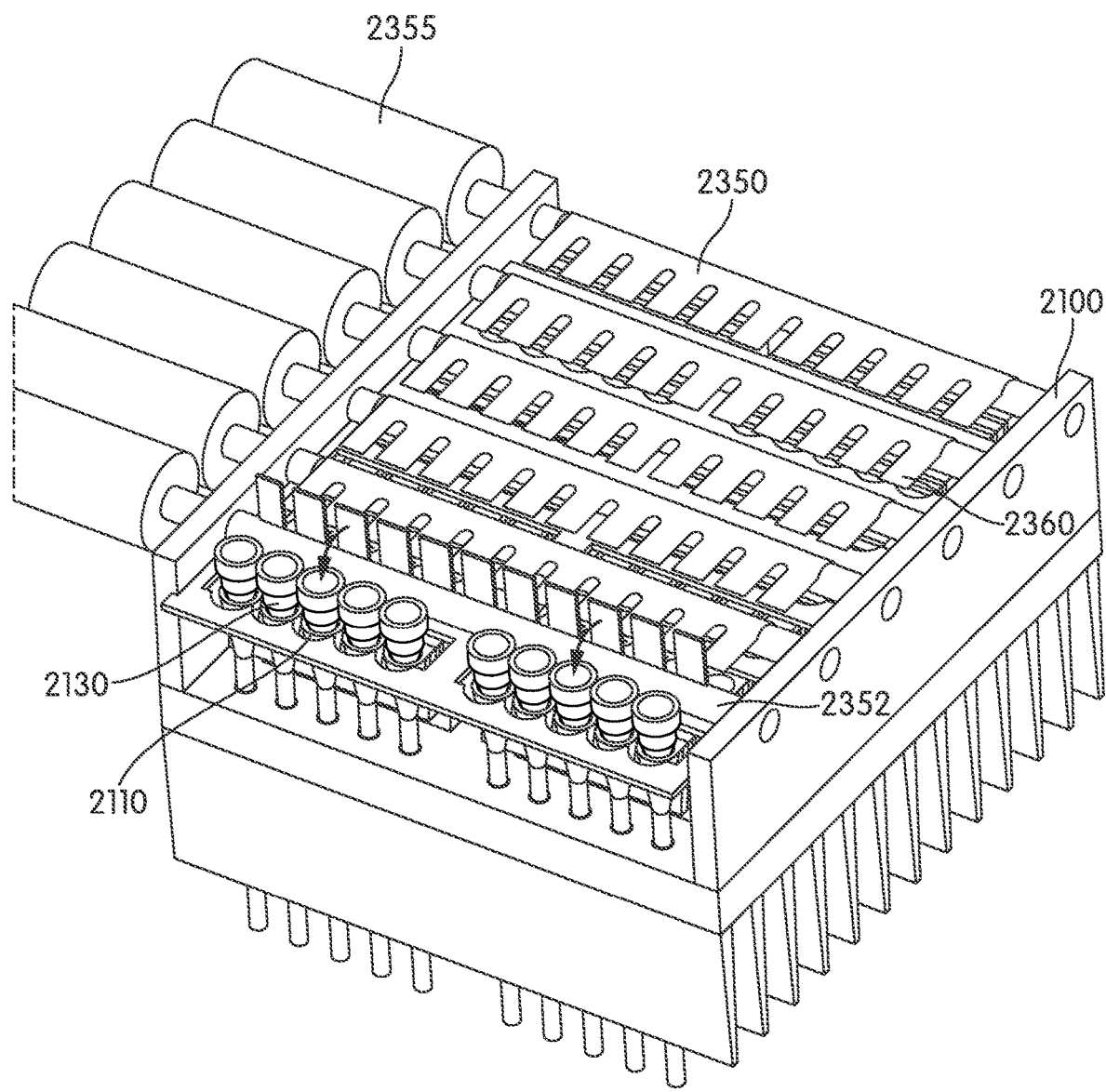
Figure 65:
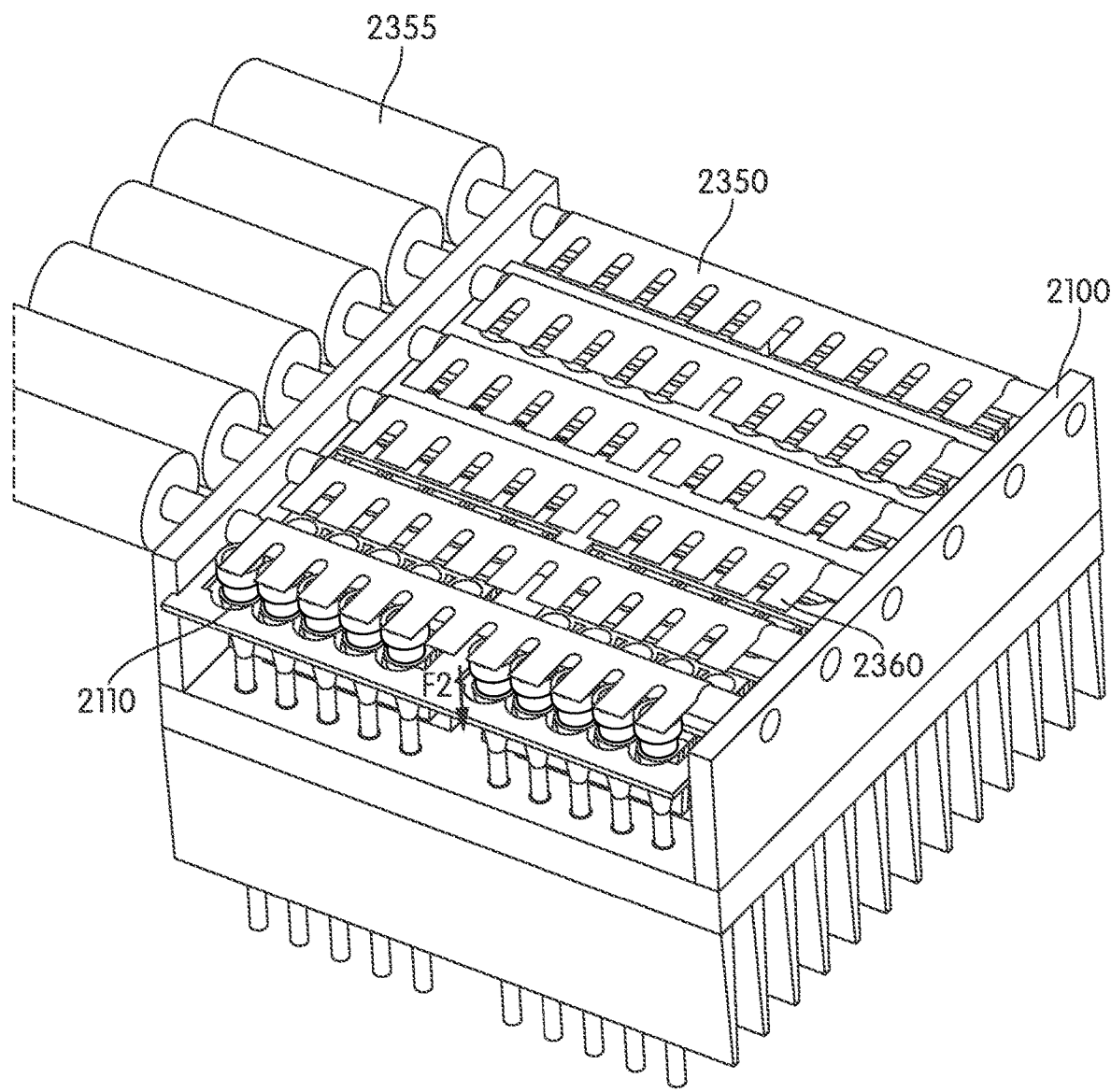
Figure 66:
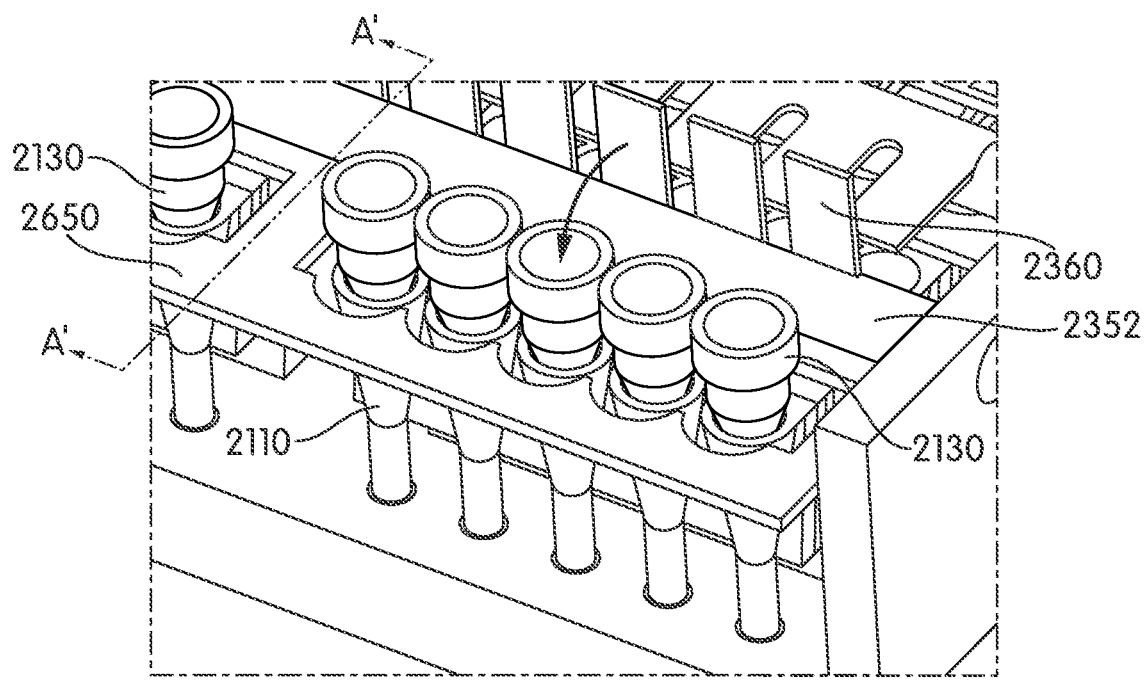

As shown in FIGS. 57, 58, and 64-68, the apparatus 2100 may also include a cover 2350 that is positioned in movable association with the receptacle holder 2110. As can be expected, the cover 2350 is movable between an open position (FIG. 64) and a closed position (FIG. 65) relative to the receptacle holder 2110, and may be moved to any position between open and closed, as necessary. In the open position, the cover 2350 does not obstruct access to the receptacle wells 2120 within the receptacle holder 2110 (see FIG. 63). When in the closed position, the cover 2350 will block and/or obstruct access to the receptacle wells 2120. In addition, when closed, the cover 2350 may exert a force F2 onto any receptacle within a receptacle well 2120 to seat or secure the receptacle 2130 in the receptacle well 2120 (see FIG. 65). As discussed above, because the receptacle well 2120 is configured to receive a receptacle 2130, the force F2 exerted by the cover 2350 serves to ensure that the receptacle 2130 fits snugly within the receptacle well 2120, thereby allowing maximal contact between the inner surface 2180 of the receptacle well 2120 and the receptacle 2130.

The cover 2350 may be made from any rigid or semi-rigid material suitable for exerting downward pressure onto a receptacle disposed within a receptacle well. Exemplary materials from which the cover may be made include, but are not limited to, beryllium copper, spring steel, chrome vanadium, chrome silicon, phosphor bronze, stainless steel, aluminum, titanium, tungsten, metal alloys, metal composites, plastic, or any suitable rigid or semi-rigid material.

Figure 67:
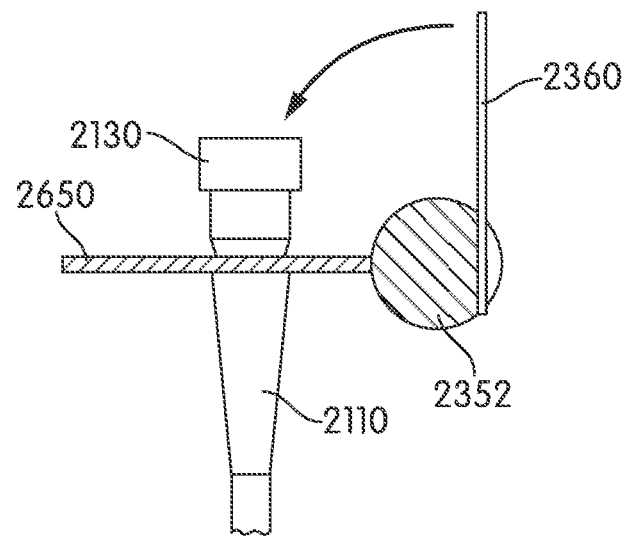

The cover 2350 may be movable by any suitable mechanical element included in the apparatus. In one embodiment, the cover 2350 is hingedly attached to the apparatus 2100 so as to enable movement between the open and closed positions. Attachment points include, but are not limited to any of the one or more supports of the apparatus or any suitable location within a housing containing the apparatus. As shown in FIG. 56, the cover 2350 may be fixedly attached to a rigid rotatable member 2352, which is in movable communication with one or more electric motors 2355. The rotatable member may be rotatably mounted to opposing sides of the housing 2050 of the apparatus or opposing sides of additional support members thereof, and span a length of the apparatus parallel to the orientation of one or more receptacle holders such that actuation of the rotatable member 2352 results in the cover 2350 being moved into the open or closed position relative to the one or more receptacle holders 2110. In an exemplary embodiment, the rotatable member 2352 is a cylindrical rod having a circular cross-section and an axis of rotation at the center thereof, as shown in FIG. 67, which is a sectional view taken along A'-A' in FIG. 66. Exemplary materials from which the rigid rotatable member may be made include, but are not limited to, steel, titanium, aluminum, or any suitable rigid material. As used herein, the term "rotatably mounted" refers to any mounting orientation that allows the rotatable member to rotate about its center axis.

The cover 2350 may comprise one or more (i.e., 1, 2, 3, 4, 5, 6, 7, 8, 9, 10, or more) flexible extensions 2360 attached to and extending laterally away from, the rigid rotatable member 2352. Such flexible extensions 2360 are configured to make contact with at least a portion of a receptacle 2130 disposed within the receptacle holder 2110 when the cover is in, approaching, or for a short distance after leaving, the closed position. As contact is made between the flexible extensions 2360 and at least a portion of the receptacle 2130, the flexible extensions 2360 flex while applying force F2 directly to at least a portion of the receptacle 2130. In an exemplary embodiment, the cover 2350 includes two or more (i.e., 2, 3, 4, 5, 6, 7, 8, 9, 10, or more) flexible extensions 2360 extending in the same direction away from the rigid rotatable member 2352. In certain embodiments, the flexible extensions 2360 extend laterally away from the hinged attachment of the cover 2350 to the apparatus 2100. In frequent embodiments, the cover 2350 includes one flexible extension 2360 per receptacle well 2120 of a receptacle holder 2110. Also in frequent embodiments, one flexible extension 2360 of the cover 2350 may contact at least a portion of more than one receptacle 2130 disposed within the receptacle holder 2110. Likewise, more than one flexible extension 2360 may contact at least a portion of more than one receptacle 2130 disposed within the receptacle holder 2110.

The cover 2350 of the present disclosure often comprises multiple components, such as flexible extensions 2360, a rotatable member 2352, or other elements, as a single molded cover unit, or in multiple elements comprising the entire cover unit. For example, the flexible extensions 2360 may be attached to the rotatable member 2352, or a single material may comprise the rotatable member 2352 and the flexible extensions 2360.

The apparatus 2100 may include a single cover 2350 in moveable association with all receptacle holders 2110 (not shown), or may include a single cover 2350 for each row of receptacle holders 2110, or may include a single cover 2350 for each individual respective receptacle holder 2110. Movement of each cover 2350 may be actuated by an electric motor 2355 disposed either within the apparatus 2100 or within the housing 2050 in which the apparatus is located. When the apparatus 2100 includes more than one cover 2350, each cover 2350 may be actuated by its own motor 2355, or more than one cover 2350 may be actuated by the same motor 2355. As such, when the apparatus 2100 includes more than one cover 2350, each cover 2350 may move independent of the next and/or more than one cover 2350 may be moved simultaneously. One of skill in the art would appreciate that independent movement of multiple covers utilizing a single motor may be provided through, for example, appropriate camming of its connection to each cover. The electric motor 2355 is electrically connected to a controllable power source 2210 for applying a current thereto. Control of the power source 2210 can be carried out by an appropriately programmed processor 2370 (such as a computer) which may receive signals from another processor that controls the automated process steps involved with temperature cycling processes.

Figure 68:
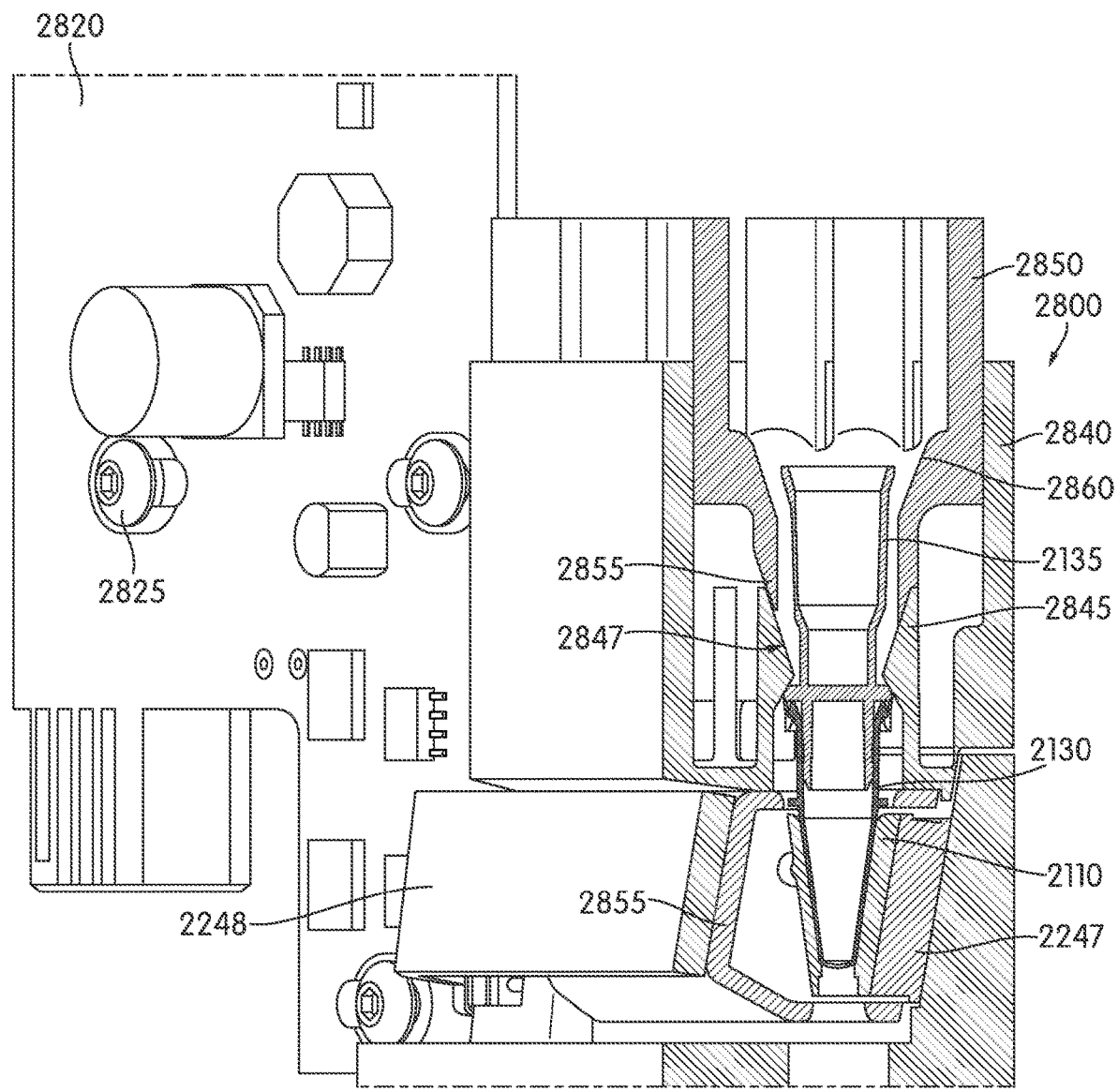
FIG. 68 show an exemplary embodiment of an apparatus of the present disclosure.
Figure 71:
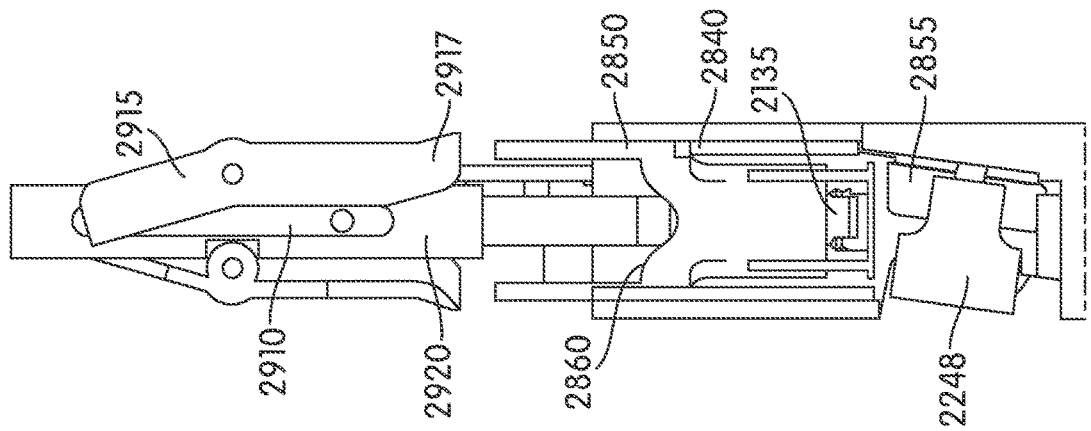
FIGS. 69-71 show a modified pipettor for use as a receptacle transport mechanism within a system of the present disclosure.

With reference now to FIG. 68, there is provided a second exemplary embodiment of an apparatus 2800 described herein. The description will be provided based on the differences from the first exemplary embodiment discussed above. As such any reference to like elements should be understood as described above.

As shown in FIG. 68, the apparatus 2800 may also include a primary cover 2840 that is fixedly positioned over the receptacle holder 2110. The primary cover 2840 may be formed with one or more (i.e., 1, 2, 3, 4, 5, 6, 7, 8, 9, 10, or more) securing arms 2845 in direct alignment with and circumventing each receptacle well 2120 of the receptacle holder 2110. In certain embodiments, the primary cover 2840 is formed with four securing arms 2845 in direct alignment with and disposed in a surrounding arrangement with each receptacle well 120 of the receptacle holder 2110. The securing arms 2840 are configured for securable attachment to at least a portion of the receptacle or cap 2135 that is attached to a receptacle 2130. Such securable attachment is analogous to the force F2 exerted by the cover 2350, as discussed above, for ensuring that the receptacle 2130 fits snugly within the receptacle well 2120, thereby allowing maximal contact between the inner surface 2180 of the receptacle well 2120 and the receptacle 2130. The securing arms can be made of any suitable material, including plastic, metal, or a metal composite.

The apparatus 2800 may further include a secondary cover 2850 fixedly positioned over the primary cover 2840. The secondary cover 2850 may be formed with one or more (i.e., 1, 2, 3, 4, 5, 6, 7, 8, 9, 10, or more) releasing arms 2855, each in direct alignment and in sliding contact with the securing arms 2845 of the primary cover. In various embodiments, the securing arms 2845 of the primary cover include an angled surface 2847 upon which the corresponding releasing arm 2855 of the secondary cover 2850 may slide when actuated during an automated process. The secondary cover 2850 may further include one or more (i.e., 1, 2, 3, 4, 5, 6, 7, 8, 9, 10, or more) actuators 2860 that are fixedly connected to the releasing arms 2855, and are positioned such that when a force is applied thereon, the force is transferred from the actuator 2860 to the releasing arms 2855, which in turn, press onto the angled surface 2847 of the primary cover 2840 and release the securable attachment to the cap 2135 that is attached to a receptacle 2130.

Figure 70:
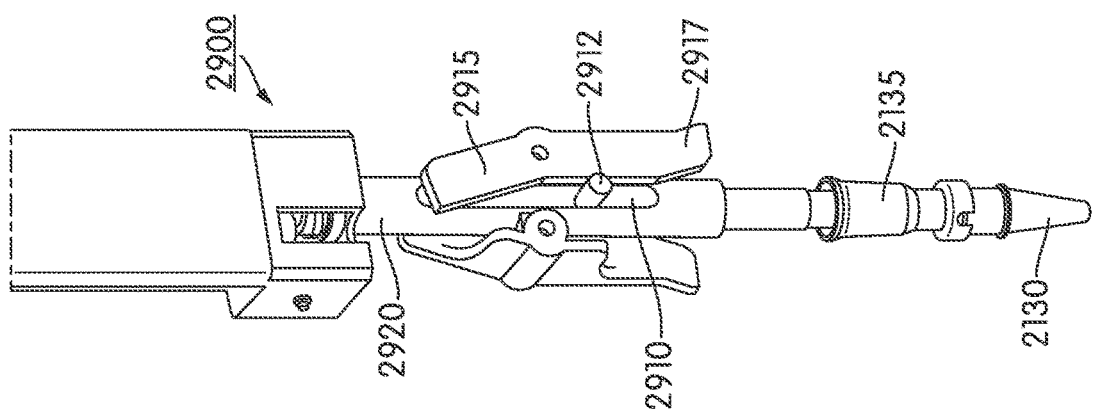
Figure 69:
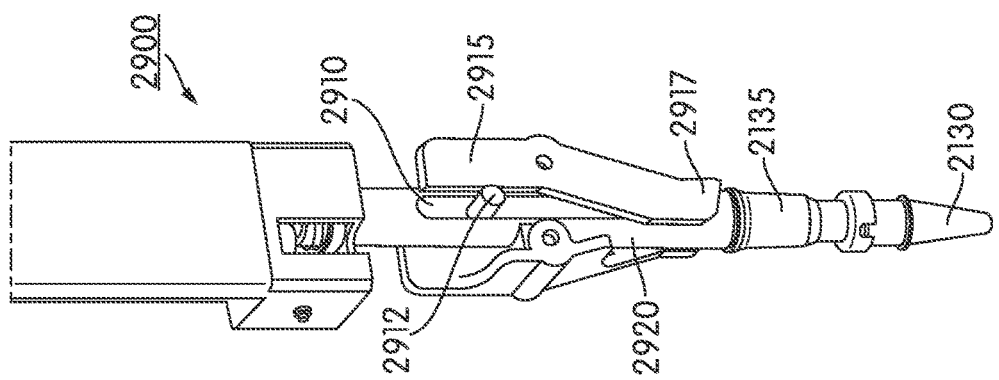

It is therefore contemplated that the housing 2050 within which the apparatus 2800 is located will include at least one modified pipettor 2900, as shown in FIGS. 69 and 70. As shown in FIG. 69, the modified pipettor 2900 is modified such that the plunger 2910 is slidingly connected to one or more limbs 2915, which are hingedly attached to the body 2920 of the modified pipettor 2900. Thus, when the modified pipettor 2900 causes the plunger 2910 to be in a first position (as shown in FIG. 69), the one or more limbs 2915 are in a retracted position such that a lower portions 2915 thereof are placed in close proximity to the body 2920. When the modified pipettor 2900 causes the plunger 2910 to be in a lowered second position (as shown in FIG. 70), the one or more limbs 2915 are then moved into an extended position such that the lower portions 2915 thereof are moved away from the body 2920.

This modified pipettor 2900 is useful for engaging the secondary cover 2850 and pressing on the secondary cover 2820 in a downward movement that actuates the release of the securing arms 2845 by the physical action of the releasing arms 2855. When the releasing arms 2855 are depressed in this manner, the securing arms 2845 are pulled axially away from the receptacle 2130 and cap 2135, permitting its unencumbered release and lifting out by the pipettor. In such circumstances it is advantageous that the securing arms maintain contact with, and depress in a radially outward manner, the releasing arms 2855 for the time period required for the pipettor plunger 2910 to frictionally engage the receptacle cap and to lift the receptacle and cap vertically clear of the securing arms 2845.

In certain embodiments, any of the apparatuses described herein will not include a cover or a mechanism to exert force F2 onto the capped receptacle 2130. In such embodiments, the receptacle 2130 fits snugly within the receptacle well 2120, thereby allowing maximal contact between the inner surface 2180 of the receptacle well 2120 and the receptacle 2130 without the need for a force F2.

Optical Fibers

Figure 72:
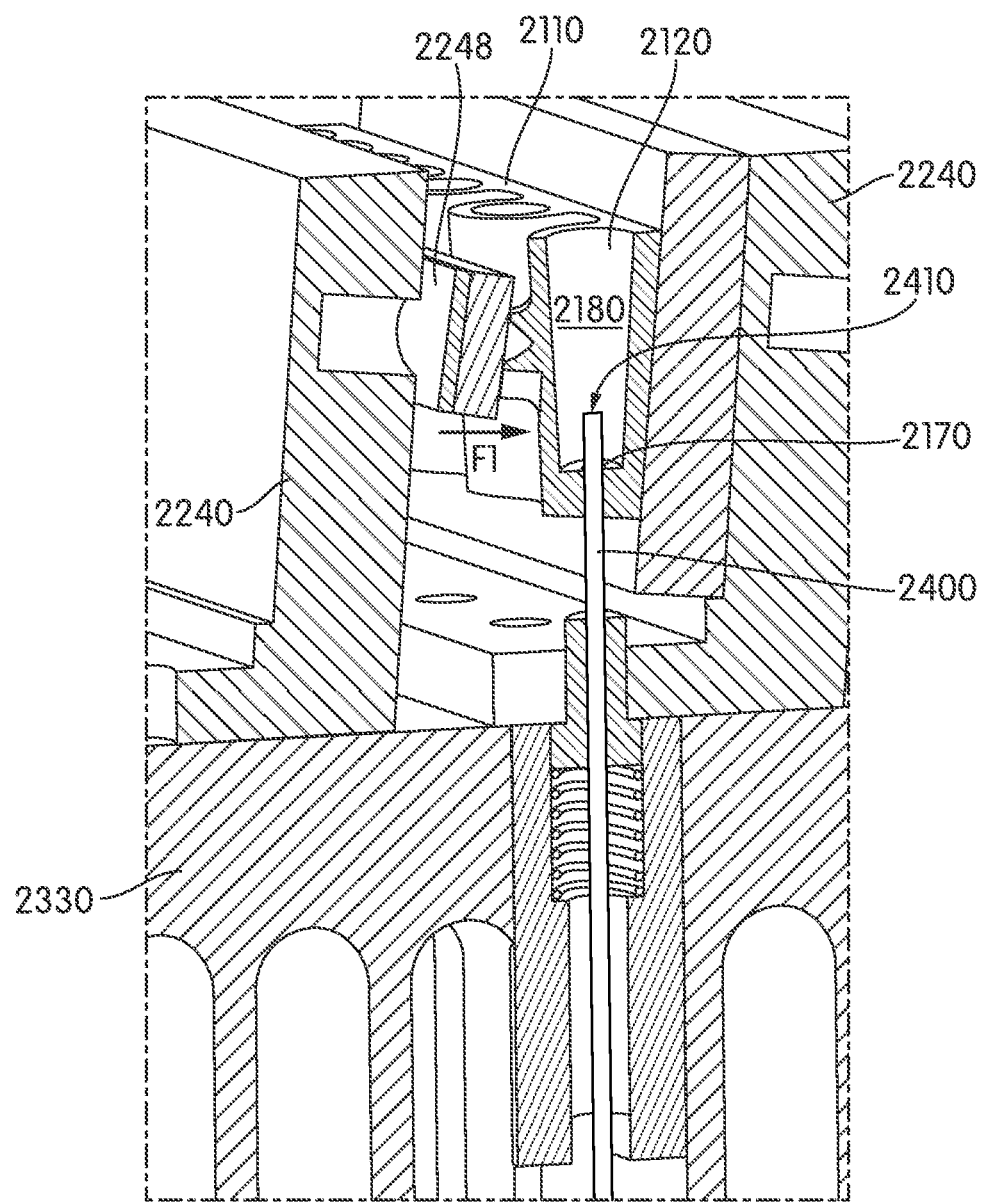
FIGS. 72-74 show an embodiment providing movement of the optical fibers of the apparatus of the present disclosure and the forces associated therewith prior to and after seating receptacles within the receptacle wells of a receptacle holder.
Figure 73:
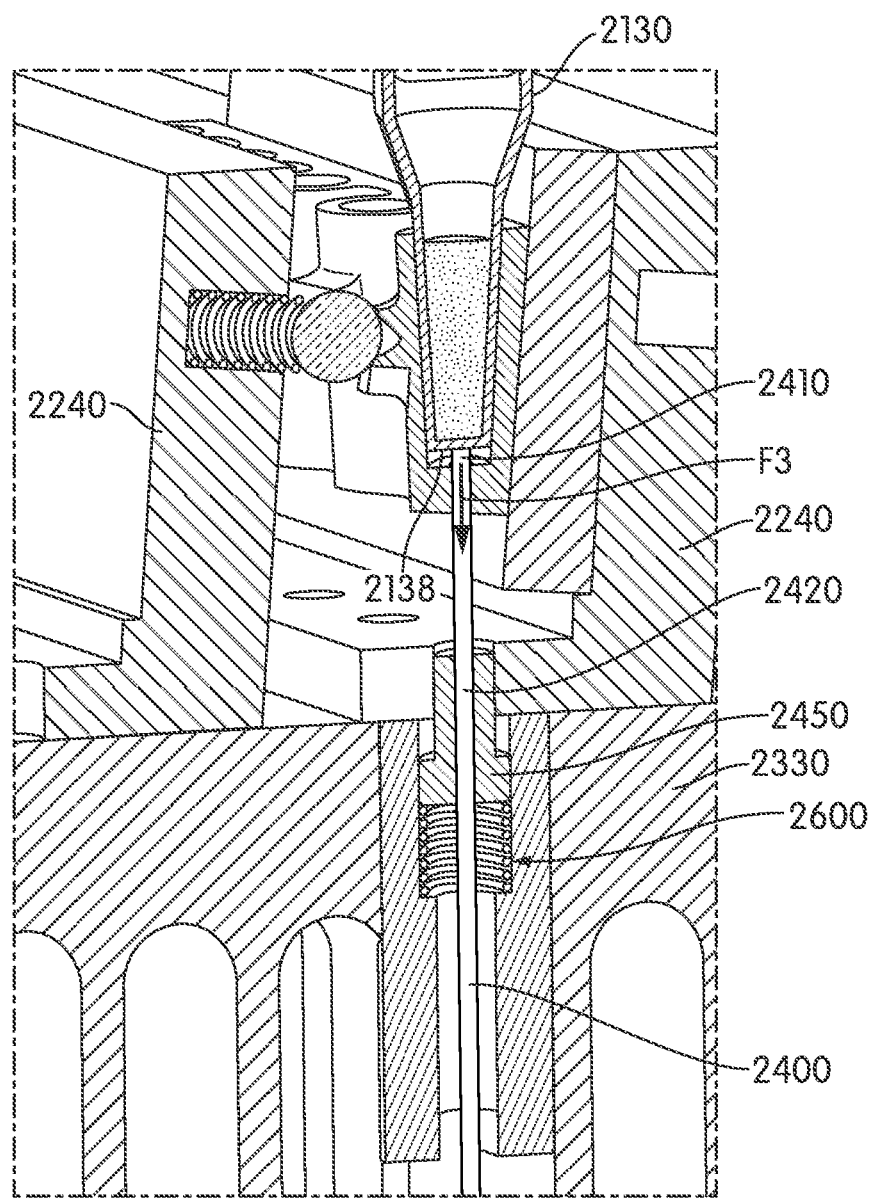
Figure 74:
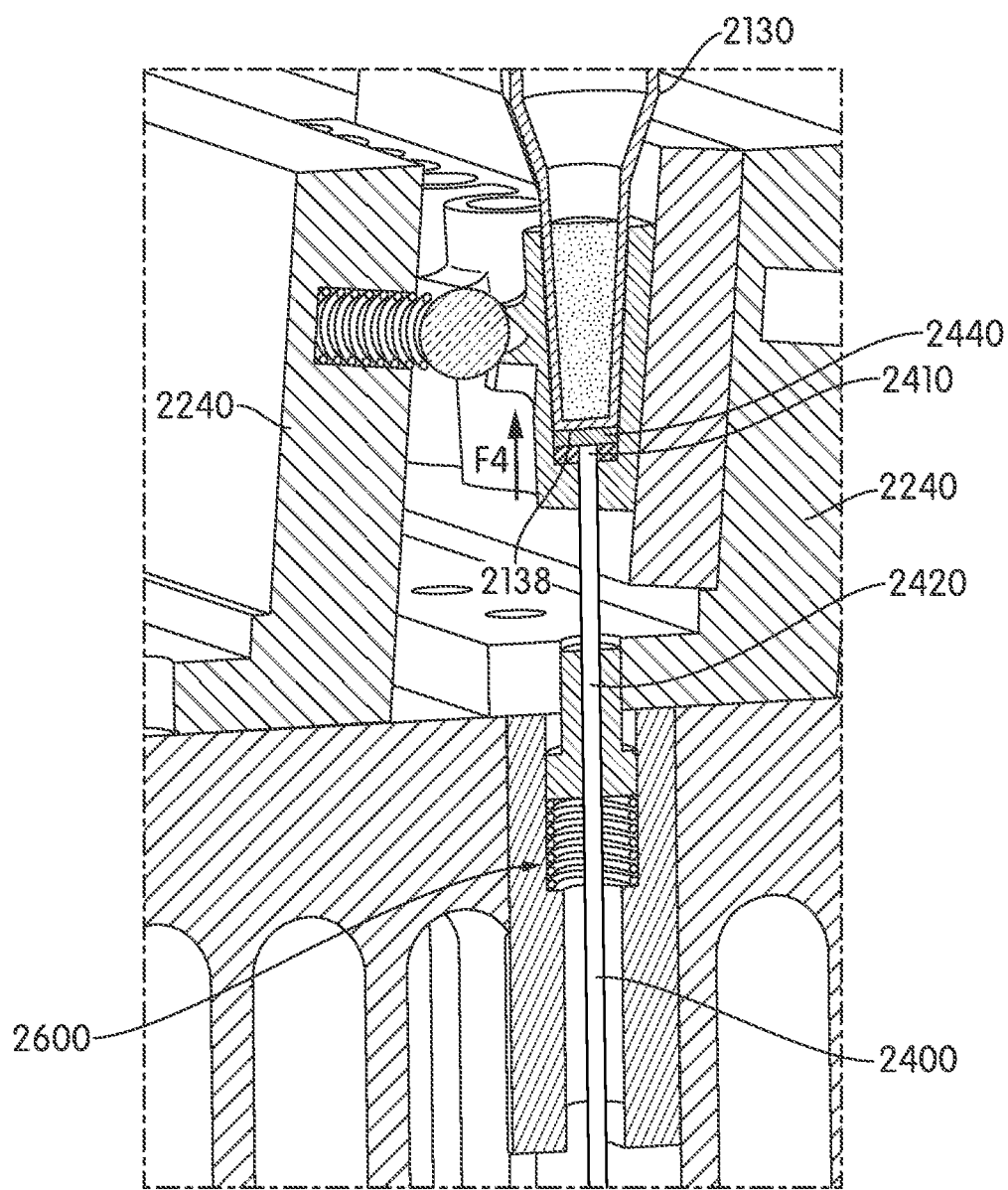
Figure 75:
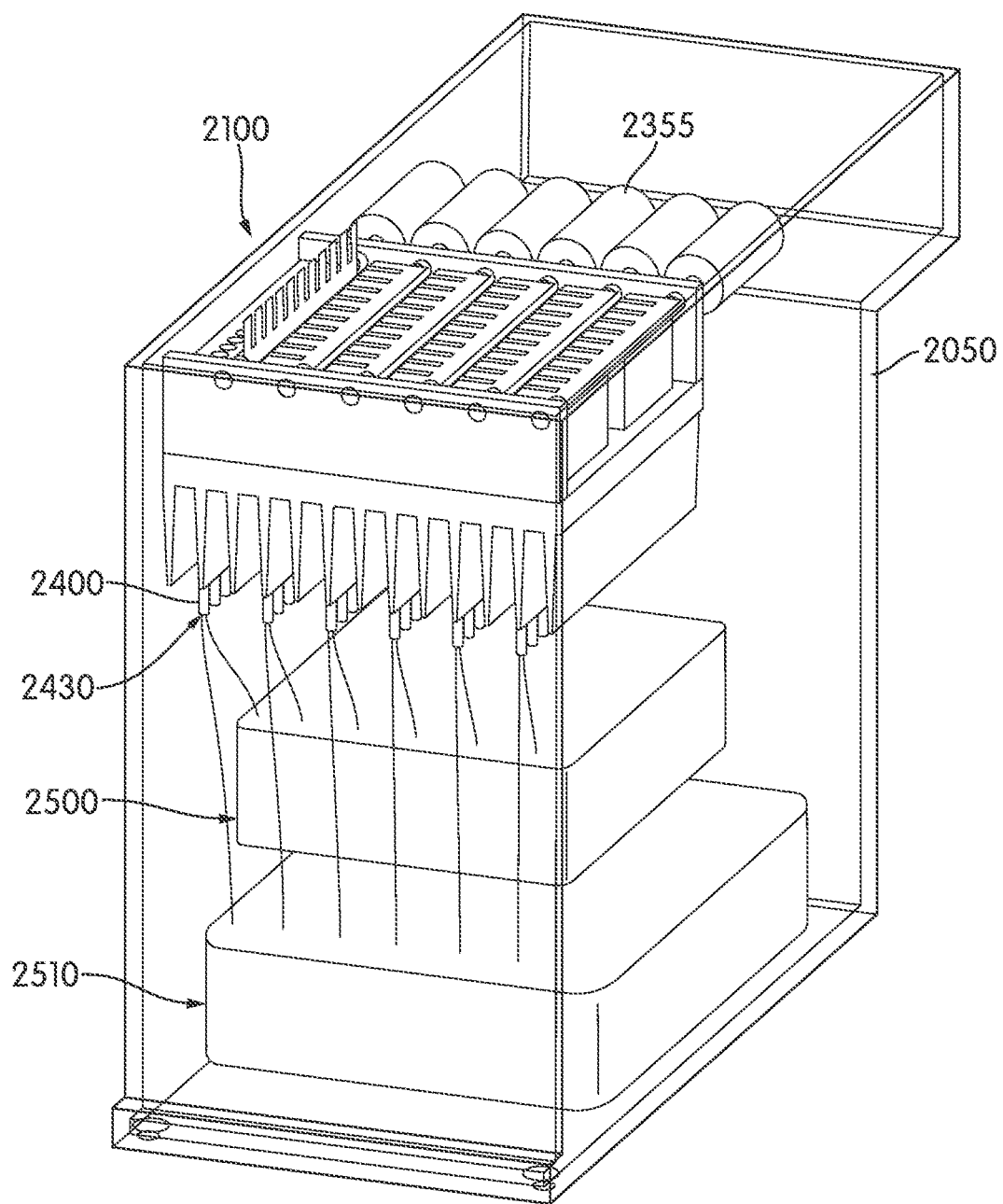
FIG. 75 shows an apparatus in optical communication with an excitation signal source and/or an emission signal detector within a housing of an instrument for performing a biochemical assay.

With reference now to FIGS. 72-74, the apparatus 2100 further includes a plurality of (i.e., more than one) optical fibers 2400 to provide optical communication of a receptacle well with at least one of an excitation signal source 2500 and an emission signal detector 2510 (see FIG. 75). In one embodiment, the apparatus 2100 includes one optical fiber 2400 per receptacle well 2120. Thus, when the apparatus 2100 includes ten receptacles wells 2120, at least ten optical fibers 2400 will be provided to establish optical communication between the receptacle well 2120 and one or more excitation signal sources 500 and/or one or more emission signal detectors 2510.

As used herein, an "optical fiber" refers to a flexible, transparent fiber made of glass or plastic that functions as a waveguide to transmit light between the two ends (i.e., the first end and the second end) of the fiber. Typically, optical fibers include a transparent core surrounded by an opaque cladding material with a lower index of refraction and low to no autofluorescence characteristics. It should be understood that an optical pathway or assembly comprising the optical fiber may optionally include one or more filters, lenses, etc., to modify and/or focus and excitation or emission signals passing therethrough. Optionally, the apparatus 2100 may include an optical interface 2440 between the first end 2410 of each optical fiber 2400 and the receptacle 2130 (see FIG. 75). Such optical interface 2440 may include a filter, lens, nose, cap, or any other element having desired optical properties. However, it should be understood that in various embodiments, the interface 2440 is not, and/or does not function as a lens. Exemplary interfaces 2440 useful in the apparatus include, but are not limited to, glass or plastic balls, noses or caps covering the first end 2410 of the optical fiber 2400, or any suitable optically clear material.

The first end 2410 of each of the plurality of optical fibers 2400 is disposed outside, within, or extending through a through-hole 2170 of the receptacle well 2110, thereby providing optical communication with a receptacle well 2120, and/or a receptacle 2130 disposed within the receptacle well 2120. When disposed within the receptacle well 2120, as shown in FIG. 72, the first end 2410 of the optical fiber 2400 may be moveable within the through-hole 2170 of the receptacle well 2120 relative to the inner surface 2180 thereof. In various exemplary embodiments, a variety of means of movement of the first end 2410 of the optical fiber 2400 within the through-hole 2170 are contemplated. For example, the first end 2410 of the optical fiber 2400 may extend into the receptacle well 2120, and when a receptacle 2130 is placed within the well 2120, the receptacle 2130 contacts the first end 2410 of the optical fiber 2400, thereby providing optical communication between the receptacle 2130 and the optical fiber 2400. In an exemplary embodiment, the presence of a receptacle 2130 within the receptacle well 2120 will cause the optical fiber 2400 to move within the through-hole 2170 (e.g., through the application of a direct force) in a direction opposite from the inner surface 2180 of the receptacle well 2120 such that the receptacle 2130 can make maximal contact with the inner surface 2180 of the receptacle well 2120 while maintaining optical communication with the optical fiber 2400, as shown in FIG. 74. In another embodiment, the downward force F2 exerted by the cover 2350 and/or the flexible extensions 2360 of the cover 2350 onto at least a portion of a receptacle 2130 disposed within a receptacle well 2120 causes the optical fiber 2400 to move within the through-hole 2170 when the receptacle 2130 contacts the optical fiber 2400. In such embodiments, the receptacle 2130 may apply a force F3 to the first end 2410 of optical fiber 2400 in substantially the same direction as the force F2 being applied to the receptacle, which is disposed within the well such that the end 2410 of the optical fiber 2400 moves within the well 2120.

As shown in FIG. 75, the system may further include one or more excitation signal sources 2500 and one or more emission signal detectors 2510 to which the second ends 2430 of the optical fibers 2400 of the apparatus 2100, 2800 included therein are in optical communication. Excitation signal sources 2500 and emission signal detectors 2510 contemplated by the present disclosure include, but are not limited to, fluorometers, luminometers, spectrophotometers, infrared detectors and charged-coupled devices. Each of these types of optical detection systems can be positioned within the housing of the apparatus 2100, 2800, within the housing of the system, or within the overall housing of the biochemical analysis instrument, as appropriate. Multiple types of signal sources 2500 and signal detectors 2510 may be movably mounted on a platform to facilitate different detection methods for different processes. The system may also include multiple detectors of the same or different types for detecting signals emitted from different receptacles 2130 simultaneously. As discussed above, though FIG. 75 depicts separate optical fibers branching out to the excitation signal source 2500 and emission signal detector 2510, certain embodiments of the present disclosure utilize a single optical fiber (e.g., a light pipe) between the excitation signal source 2500 and its corresponding emission signal detector 2510.

Methods of Establishing Optical Communication

Figure 76:
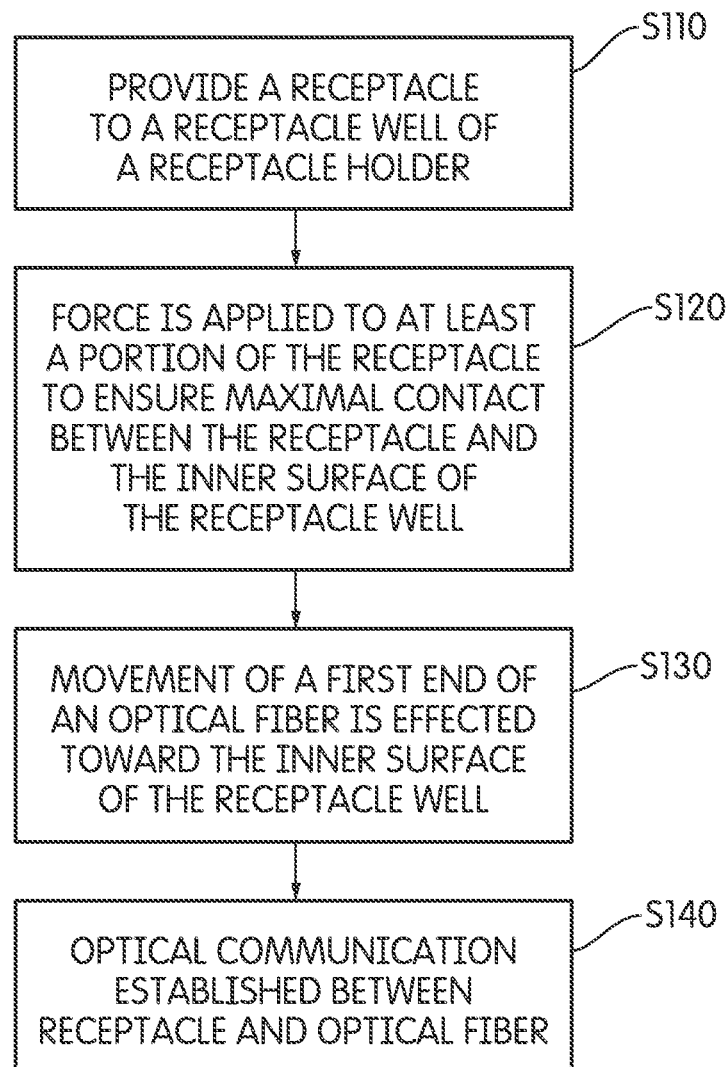
FIGS. 76 and 77 are flow charts showing exemplary steps involved in a method for establishing optical communication between a receptacle and an excitation signal source and/or an emission signal detector within a housing of the apparatus while allowing maximal contact between the surface of the receptacle well and the receptacle.

In another aspect, disclosed herein is provided a method for establishing optical communication between a receptacle and an excitation signal source and/or an emission signal detector within a housing of the apparatus while allowing maximal contact between the surface of the receptacle well and the receptacle (FIG. 76). As discussed in detail above, the method includes providing a receptacle 2130 to a receptacle well 2120 of a receptacle holder 2110 (step S110). Thereafter, a force F2 is applied to the receptacle 2130 or at least a portion of the receptacle 2130, such that the receptacle 2130 fits snugly within the receptacle well 2120, thereby allowing maximal contact between the inner surface 2180 of the receptacle well 2120 and the receptacle 2230 (step S120). While force F2 is being applied to at least a portion of the receptacle 2130, movement of a first end 2410 of an optical fiber 2400 is effected toward the inner surface 2180 of the receptacle well 2120 (step S130). In such embodiments, the receptacle 2130 may apply a force F3 to the optical fiber 2400 in substantially the same direction as the force F2 being applied to the receptacle 2130, to the first end 2410 of the optical fiber 2400, which is disposed within the receptacle well 2120 such that optical communication is established between the bottom 2138 of the receptacle 2130 and the first end 2410 of the optical fiber 2400 (step S140). As discussed above, movement of the first end 2410 of the optical fiber 2400 is coordinated with movement of cover 2350 into the closed position. As such, the method may further include movement of the cover 2350 in coordination with the movement of the first end 2410 of the optical fiber 2400.

Figure 77:
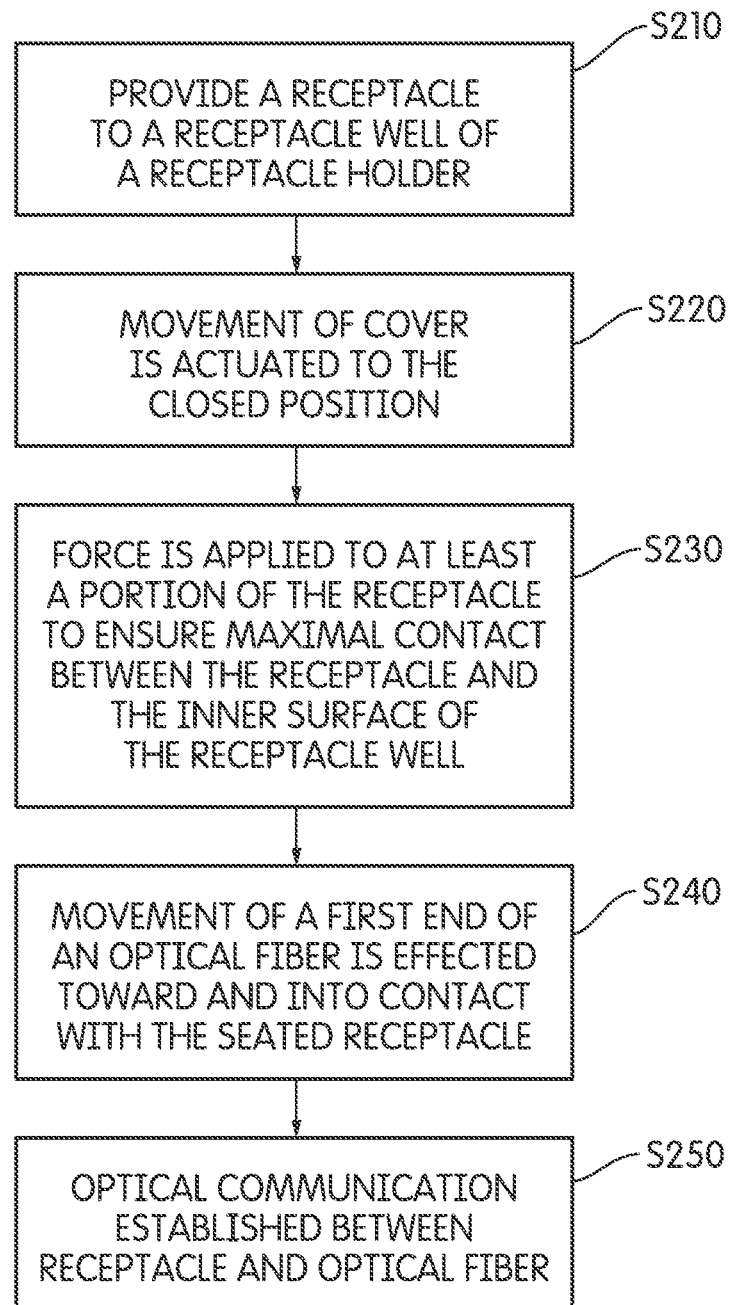

Another exemplary embodiment of the method for establishing optical communication between a receptacle and an excitation signal source and/or an emission signal detector within a housing of the apparatus while allowing maximal contact between the surface of the receptacle well and the receptacle is shown in FIG. 77. In this embodiment, the method includes providing a receptacle 2130 to a receptacle well 2120 of a receptacle holder 2110 (step S210). Thereafter, a cover 2350 is moved into the closed position (step S220), thereby exerting a force F2 onto the receptacle 130 or at least a portion of the receptacle 2130, such that the receptacle 2130 fits snugly within the receptacle well 2120, thereby allowing maximal contact between the inner surface 2180 of the receptacle well 2120 and the receptacle 2130 (step S230). Prior to, during, or after movement of the cover 2350 into the closed position, movement of a first end 2410 of an optical fiber 2400 is effected toward and into contact with the seated receptacle 2130 (step S240). Upon contact of the first end 2410 of the optical fiber 2400 with the closed end 2138 of the receptacle 2130, force F4 is exerted by the first end 2410 onto the receptacle 2130. In such embodiments, the receptacle 2130 may apply a force F3, which is greater than force F4, onto the first end 2410 of the optical fiber 2400 in substantially the same direction as the force F2. As such, optical communication is established between the first end 2410 of the optical fiber and the receptacle 2130, while ensuring maximal contact between the receptacle 2130 and the inner wall 2180 of the receptacle well 2120 (step S250). As discussed above, movement of the first end 2410 of the optical fiber 2400 is coordinated with movement of cover 2350 into the closed position.

Often, the first end 2410 of each of the plurality of optical fibers 2400, or an area 2420 proximal to the first end 2410 of each of the plurality of optical fibers 2400, is connected, directly or indirectly, to a respective through-hole 2170 of a receptacle well 2120 with a resilient element 2600, as discussed above. The resilient element 2600 thereby compresses and/or deforms as the optical fiber 2400 moves within the through-hole 2170, and returns to its uncompressed and/or original form when the optical fiber 2400 returns to its rest position.

Signal Detection Module

Figure 78:
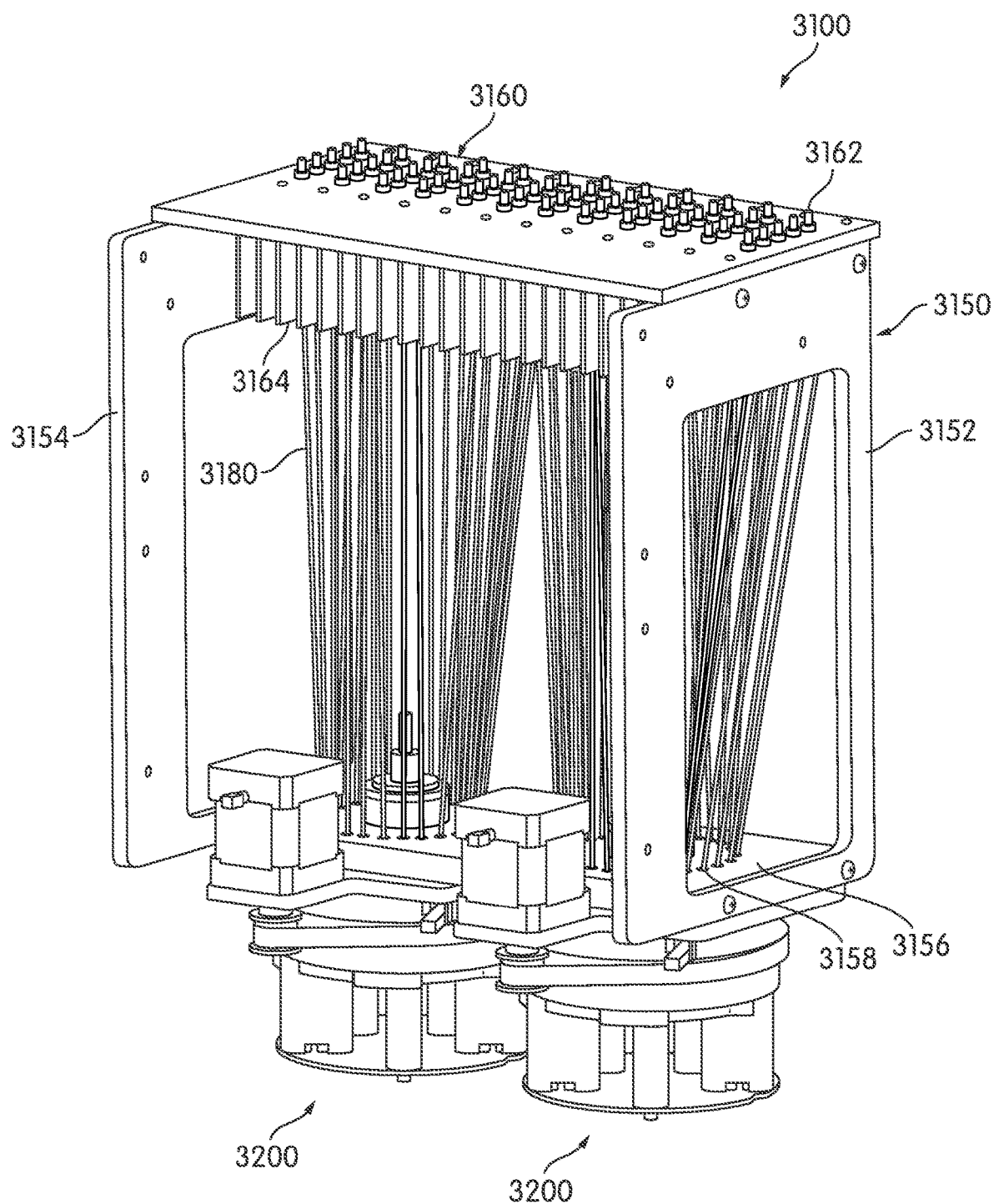
FIG. 78 is a perspective view of a signal detection module embodying aspects of the present disclosure.

Detection, and, optionally, measurement, of emission signals from emission signal sources, such as vials containing reaction materials undergoing amplification as described above can be performed in accordance with aspects of the present invention with a signal detection module. In an exemplary aspect, signal detector 432 comprises an a signal detection module indicated by reference number 3100 in FIG. 78. The signal detection module 3100 includes an upright reformatter frame 3150. Two signal detector heads 3200 are attached to a lower end of the reformatter frame 3150 and an interface plate 3160 is attached to an upper end of the reformatter frame 3150. In general, the reformatter frame includes sides 3152, 3154 which, in the illustrated embodiment, comprise generally vertical columns, and a base 3156 within which are formed a plurality of fiber-positioning holes 3158. Note that the designation of the reformatter frame 3150 as being upright or the sides 3152, 3154 as being vertical is merely to provide a convenient reference with respect to the orientation of the signal detection module 3100 as shown in FIG. 78, and such terms of orientation are not intended to be limiting. Accordingly, the signal detection module 3100 could be oriented at any angle, including vertical or horizontal, or any angle therebetween. The reformatter frame has a variety of purposes, including organizing and arranging a plurality of optical transmission fibers 3180 between an excitation/emission area and a detection area in an optimum optical pathway orientation. In particular embodiments the reformatter also provides for controlled orientation of a plurality of optical transmission fibers 3180 between the fins of a heat sink to a detection area.

Figure 79:
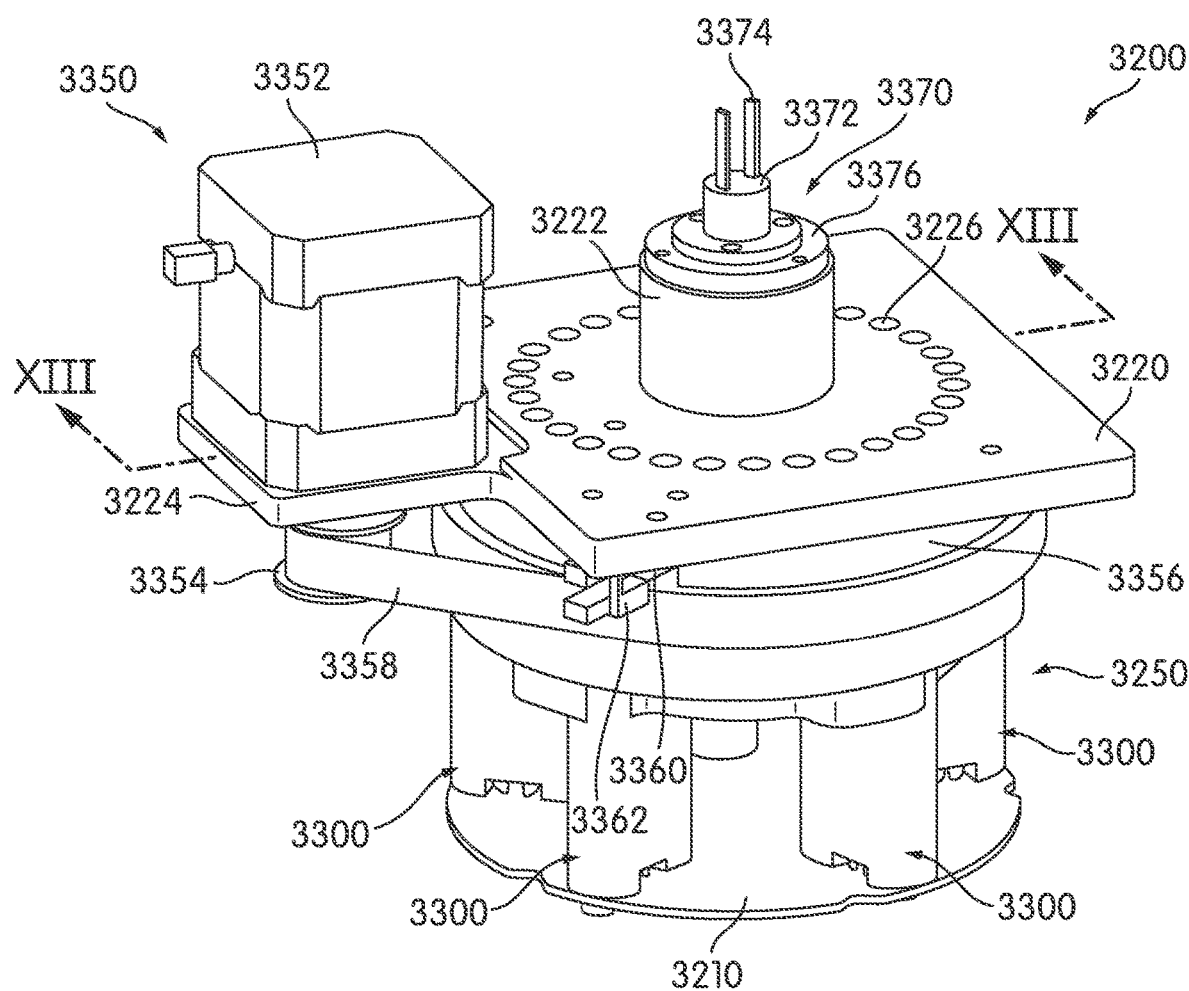
FIG. 79 is a perspective view of a signal detector head.

The signal detector head 3200 is shown in FIG. 79. The signal detector head 3200 may be attached to a reformatter frame 3150 and is constructed and arranged to index one or more signal detectors into operative positions with respect to each transmission fiber disposed in a fiber-positioning hole of the base of the reformatter frame. In the embodiment shown in FIG. 79, the signal detector head 3200 includes a base plate 3220 configured to be attached to the base 3156 of the reformatter frame 3150 and including a plurality of fiber tunnels 3226 arranged in a configuration corresponding to the spatial arrangement of fiber-positioning holes 3158 formed in the base 3156 of the reformatter frame 3150 so that each fiber tunnel 3226 will align with a corresponding one of the fiber-positioning holes 3158.

In general, the signal detector head is configured to move one or more signal detectors to sequentially place each signal detector into an operative position with respect to each transmission fiber 3180 to detect a signal transmitted by the transmission fiber. The signal detector head 3200 further includes a detector carrier 3250, which, in the illustrated embodiment, comprises a carousel that carries a plurality of signal detectors 3300 in a circular pattern. In the illustrated embodiment, the signal detector head 3200 includes six individual signal detectors 3300, each mounted on a printed circuit board 3210 and each configured to excite and detect a different emission signal or an emission signal having different characteristics.

Figure 80:
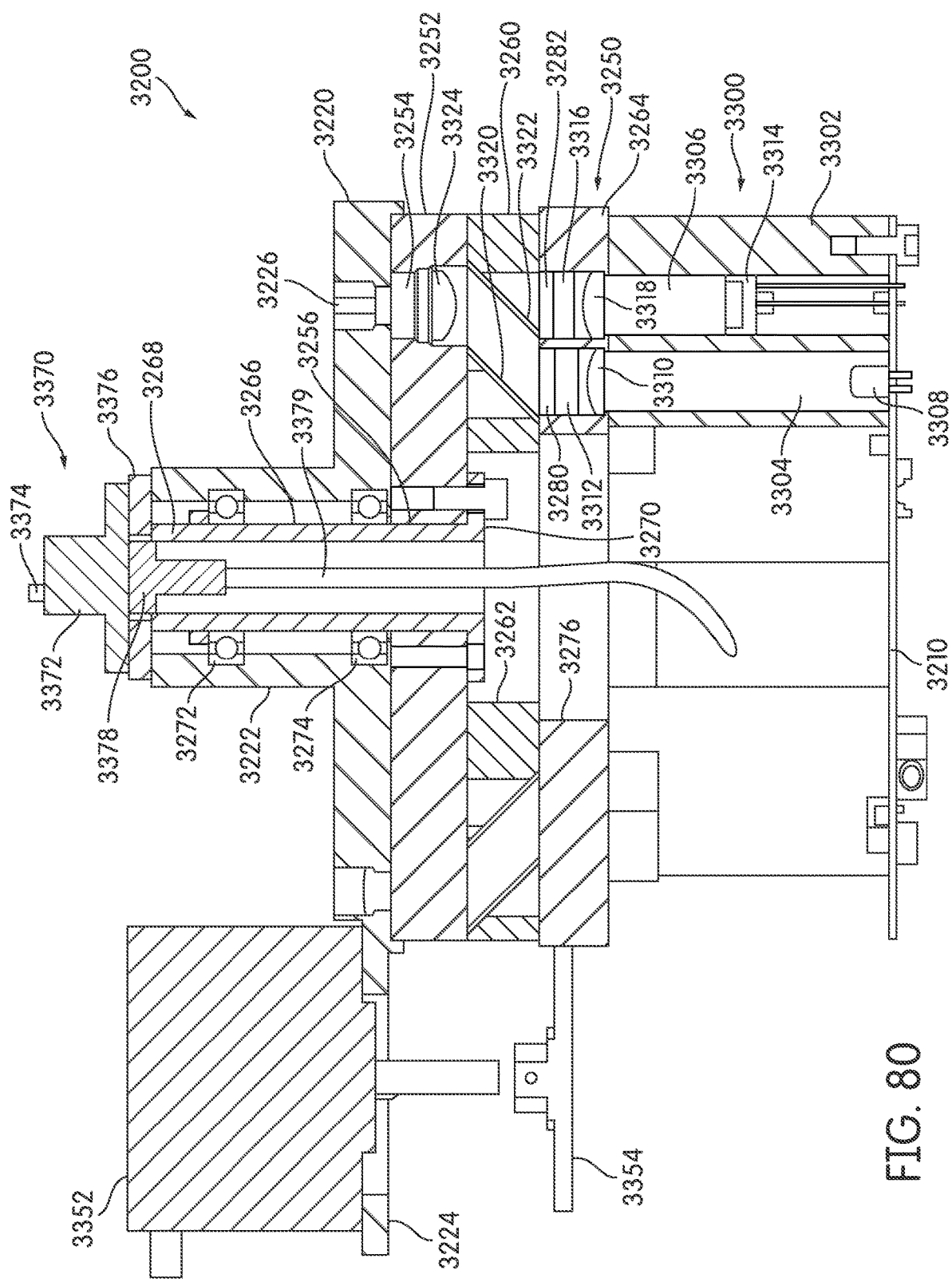
FIG. 80 is a transverse cross-section of the signal detector head along the line XIII-XIII in FIG. 79.

Further details of the signal detector head 3200 are shown in FIG. 80, which is a transverse cross-sectional view of the detector head 3200 along the line XIII-XIII in FIG. 79. Each signal detector 3300 includes a detector housing 3302 within which are formed an excitation channel 3304 and an emission channel 306, which, in the illustrated embodiment, are generally parallel to one another. An excitation source 3308, such as an LED, is mounted on the printed circuit board 3210 at the base of the excitation channel 3304. An emission detector 3314, such as a photodiode, is coupled to the printed circuit board 3210 and is disposed within the emission channel 3306.

The detector carrier 3350 further includes, positioned adjacent the signal detector housing 3302, a filter plate 3264 having a central opening 3276 formed therein and defining an annulus. Within the annulus, an emission filter opening 3282 and an excitation filter opening 3280 are formed in alignment with the emission channel 3306 and the excitation channel 3304, respectively, of each signal detector housing 3302. An excitation lens 3310 and an excitation filter 3312 are disposed in the excitation opening 3280. Although a single excitation lens 3310 and a single excitation filter 3312 are shown in FIG. 80, the signal detector 3300 may include multiple excitation filters and/or multiple excitation lenses. Similarly, an emission filter 3316 and an emission lens 3318 are disposed in the emission opening 3282. Although a single emission filter 3316 and a single emission lens 3318 are shown in FIG. 80, the signal detector 3300 may include multiple emission lenses and/or multiple emission filters.

The detector carrier 3250 further includes, adjacent the filter plate 3264, a mirror plate 3260 having a central opening 3262 and defining an annulus. The annulus of the mirror plate 3260 has formed therein openings aligned with the emission opening 3282 and the excitation opening 3280 formed in the filter plate 3264 for each signal detector 3300. A mirror 3320 is disposed in the mirror plate 3260 in general alignment with the excitation channel 3304, and a dichroic filter 3322 is disposed in the mirror plate 3260 in general alignment with the emission channel 3306. Mirror 3320 is oriented at an angle (e.g. 45°) with respect to the excitation channel 3304 so as to be configured to redirect a light beam.

The detector carrier 3250 further includes an objective lens plate 3252 having a central opening 3256 formed therein and defining an annulus. A lens opening 3254 is formed through the annulus of the objective lens plate 3252 in general alignment with the emission channel 3306 of each signal detector 3300. An objective lens 3324 is disposed within the lens opening 3254.

The base plate 3220 is disposed adjacent the objective lens plate 3252 and includes fiber tunnels 3226 formed about the perimeter thereof. Although base plate 3220 and objective lens plate 3252 are depicted as abutting one-another in FIG. 80, it is contemplated that there can be a designated distance, forming an air gap, between the base plate 3220 and the objective lens plate 3252. Also, while objective lens plate 3252 and mirror plate 3260 are depicted as abutting one-another in FIG. 80, it is contemplated that there can be a designated distance, forming an air gap, between the objective lens plate 3252 and the mirror plate 3260.

The detector carrier 3250, comprising the objective lens plate 3252, the mirror plate 3260, and the filter plate 3264, as well as the signal detectors 3300 carried thereon, are rotatable with respect to the base plate 3220 so that each objective lens 3324 associated with each of the signal detectors 3300 can be selectively placed into operative alignment with one of the fiber tunnels 3226 disposed in the base plate 3220. Thus, in the illustrated embodiment having six signal detectors 3300, at any given time, six of the fiber tunnels 3226 are in operative, optical alignment with one of the objective lenses 3324 and its corresponding signal detector 3300.

Figure 81:
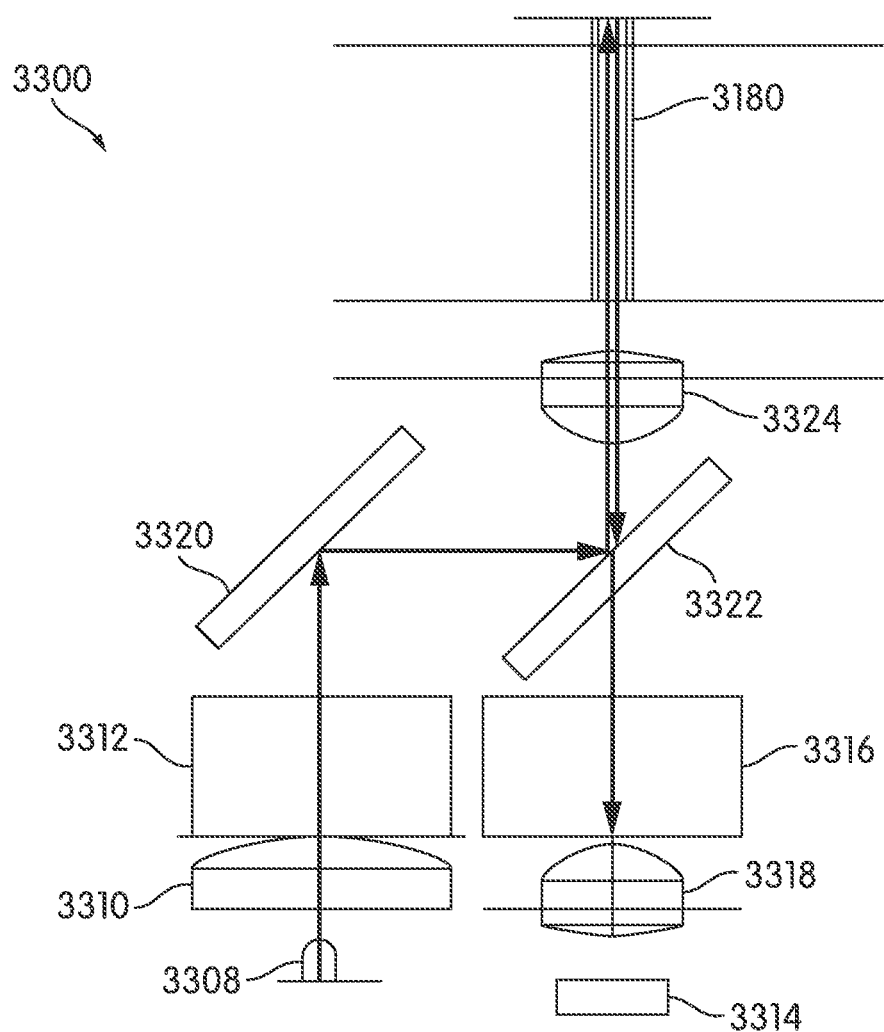
FIG. 81 is a schematic view of an embodiment of an exemplary optical path within a signal detector.

Operation of the signal detector 3300 in an exemplary embodiment is illustrated schematically in FIG. 81. The detector 3300 shown is a fluorometer that is constructed and arranged to generate an excitation signal of a particular, predetermined wavelength that is directed at the contents of a receptacle to determine if a probe or marker having a corresponding emission signal of a known wavelength is present. When the signal detector head 3200 includes multiple fluorometers—e.g., six—each fluorometer is configured to excite and detect an emission signal having a different wavelength to detect a different label associated with a different probe hybridized to a different target analyte. When a more frequent interrogation of a sample is desired for a particular emission signal, it may be desirable to incorporate two or more fluorometers configured to excite and detect a single emission signal on the signal detector head 3200.

Figure 82:
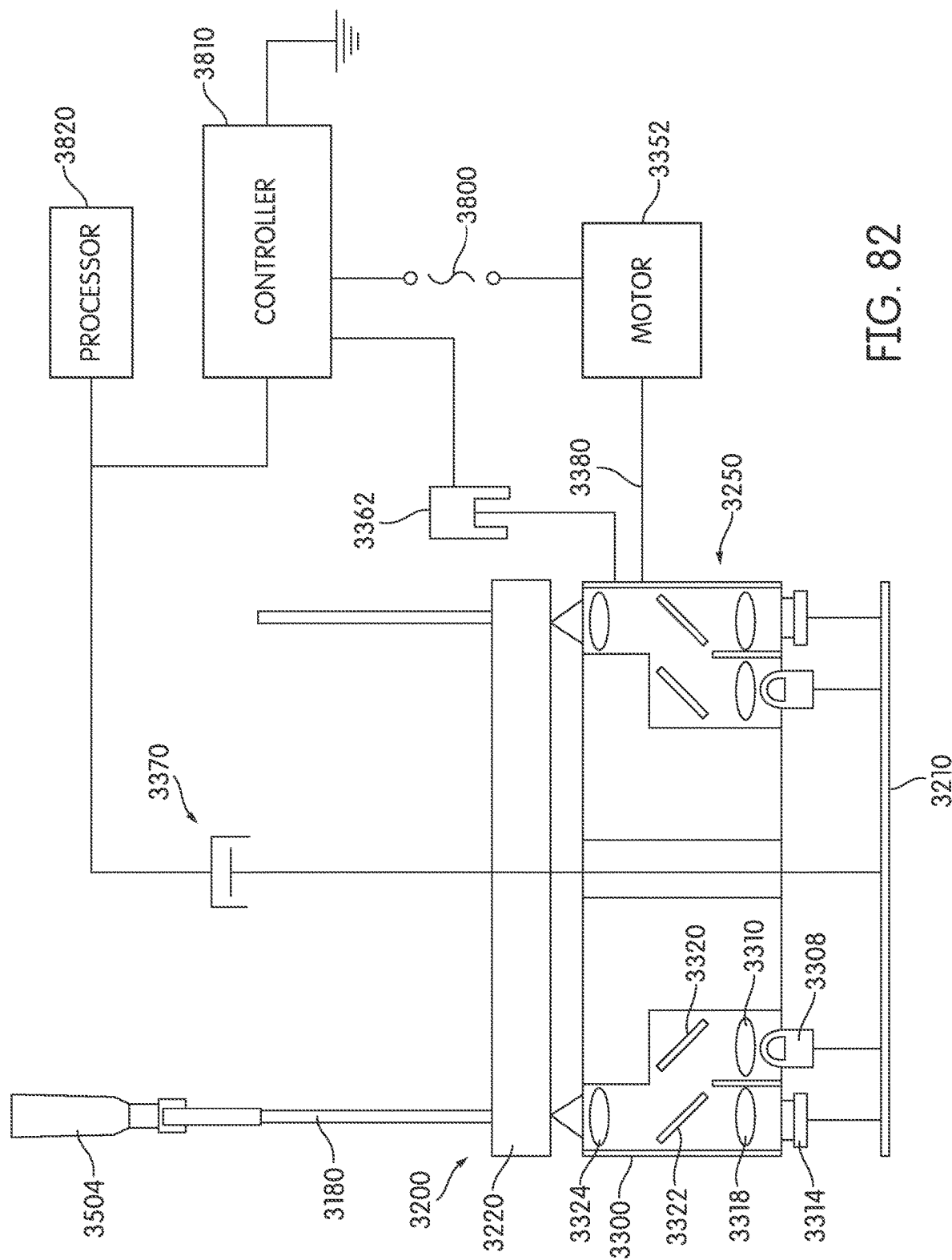
FIG. 82 is a schematic view of the signal detection module embodying aspects of the present disclosure and a power and data control system incorporated therewith.

An excitation signal is emitted by the excitation source 3308. As noted above, the excitation source may be an LED and may generate light at a predetermined wavelength, e.g. red, green, or blue light. Light from the source 3308 passes through and is focused by an excitation lens 3310 and then passes through the excitation filter 3312. As noted, FIG. 82 is a schematic representation of the signal detector 3300, and the focusing functionality provided by the excitation lens 3310 may be affected by one or more separate lenses disposed before and/or after the filter element 3312. Similarly, the filter functionality provided by the filter element 3312 may be affected by one or more individual filters disposed before and/or after the one or more lenses that provide the focusing functionality. Filter element 3312 may comprise a low band pass filter and a high band pass filter so as to transmit a narrow wavelength band of light therethrough. Light passing through the excitation lens 3310 and excitation filter element 3312 is reflected laterally by the mirror 3320 toward the dichroic 3322. The dichroic 3322 is constructed and arranged to reflect substantially all of the light that is within the desired excitation wavelength range toward the objective lens 3324. From the objective lens 3324, light passes into a transmission fiber 3180 and toward the receptacle at the opposite end thereof. The excitation signal is transmitted by the transmission fiber 3180 to a receptacle so as to expose the contents of the receptacle to the excitation signal.

A label that is present in the receptacle and is responsive to the excitation signal will emit an emission signal. At least a portion of any emission from the contents of the receptacle enters the transmission fiber 3180 and passes back through the objective lens 3324, from which the emission light is focused toward the dichroic 3322. Dichroic 3322 is configured to transmit light of a particular target emission wavelength range toward the emission filter 3316 and the emission lens 3318. Again, the filtering functionality provided by the emission filter 3316 may be affected by one or more filter elements and may comprise a high band pass and low band pass filter that together transmit a specified range of emission wavelength that encompasses a target emission wavelength. The emission light is focused by the emission lens 3318, which may comprise one or more lenses disposed before and/or after the filter elements represented in FIG. 81 by emission filter 3316. The emission lens 3318 thereafter focuses the emission light of the target wavelength at the detector 3314. In one embodiment, the detector 3314, which may comprise a photodiode, will generate a voltage signal corresponding to the intensity of the emission light at the prescribed target wavelength that impinges the detector.

Centrifuge

As shown in FIGS. 1, 5, and 6, centrifuge 588 can be located on the amplification processing deck 430 of the second module 400. In one exemplary embodiment, the centrifuge 588 will centrifuge one or more (up to five in one embodiment) capped processing vials 464, 1100 at a time. In an exemplary embodiment, each vial is centrifuged before PCR to ensure that sample material is concentrated primarily in the bottom of the processing vial 464, 1100 and to remove any air bubbles from the contents of the vial 464, 1100, which can affect heat transfer and optical transmission quality. The substance transfer pipettor 410 of the front arm 408 places the capped vial 464, 1100 into the centrifuge 588 at an access port indicated at reference number 589. After centrifuging is complete, the vial transfer arm 418 of the back arm 416 removes the capped vial 464, 1100 from the centrifuge 588 at an access port indicated at reference number 587 and places it in the thermal cycler 432. In an embodiment, the centrifuge configuration (e.g., by providing separate ports 587, 589) allows the substance transfer pipettor 410 (front arm 408) and the vial transfer arm 418 (back arm 416) to load/unload capped vials 464, 1100 simultaneously without colliding with each other. As such, in one embodiment, the centrifuge not only performs its function of providing centrifugation of loaded vials, but also functions as a vial transport mechanism by transporting capped vials 464, 1100 from a position 589 accessible to the substance transfer pipettor 410 to a position 587 where the capped vials 464, 1100 are accessible to the vial transfer arm 418. In certain embodiments the substance transfer pipettor 410 is unable to access position 587 and the vial transfer arm 418 is unable to access position 589.

In addition, the centrifuge 588 may be configured to track the position(s) of the loaded vial(s) within the centrifuge and determine when a vial is positioned at either access port 587, 589. For example, a turntable or other rotating structure on which the loaded vial(s) is (are) centrifuged may be driven by a stepper motor that may include a rotary encoder for precise movement of the turntable and tracking motor counts and/or the turntable or rotating structure may include a rotational position indicator, such as a home flag sensor, configured to indicate one or more rotational positions or reference points.

In one exemplary embodiment, the maximum revolution speed of the centrifuge is 3000 revolutions per minute, but other revolution speeds are contemplated based on, inter alia, the composition of the solution being centrifuged and the time period required to provide adequate centrifugation.

Receptacle Distribution System and Rotary Distributor

In one embodiment, the receptacle distributor, which is configured to move a receptacle onto the receptacle distributor at a first location on the second module, carry the receptacle from the first location to a second location on the second module that is different from the first location, and move the receptacle off the receptacle distributor at the second location on the second module, comprises a rotary distributor. In an exemplary embodiment, the rotary distributor of the receptacle distribution system does not constitute a robotic pipettor, such as substance transfer and handling device 402 described above, or other substance transfer device comprising a vial transfer arm that is supported on a structure for automatically moving the pipettor in different Cartesian directions (i.e., a x-y-z directions), but is also a 3-axis robot designed to transport MRDs 160 and reagent packs 760 between different components of the second module 400. In one exemplary embodiment, rotary distributor 312 works by a hook and rail system in which an extendible and retractable hook pulls or pushes MRDs 160 or reagent packs 760 into or from a distributor head of the rotary distributor 312. Within the distributor head, the MRD 160 or reagent pack 760 is supported and guided by rail and wall features within the head. The rotary position of the distributor head is controlled and monitored by a rotary encoder on the motor for position feedback and has a home sensor. The distributor hook may be belt driven with home and end of travel sensors (e.g., slotted optical sensors, limit switches, etc.) The rotary distributor 312 is also configured for powered, vertical (or z-axis) motion of the distributor head for vertical translation of an MRD 160 or reagent pack 760. In one exemplary embodiment, the rotary distributor 312 is configured to allow for at least 100 mm of z-axis travel. The distributor head may include an MRD/reagent pack presence sensor in the head. In one exemplary embodiment, the rotary distributor is configured to transfer an MRD 160 between any two modules of the second module 400 within four seconds. In certain embodiments, each axis can make a full travel move in approximately one second.

Figure 27:
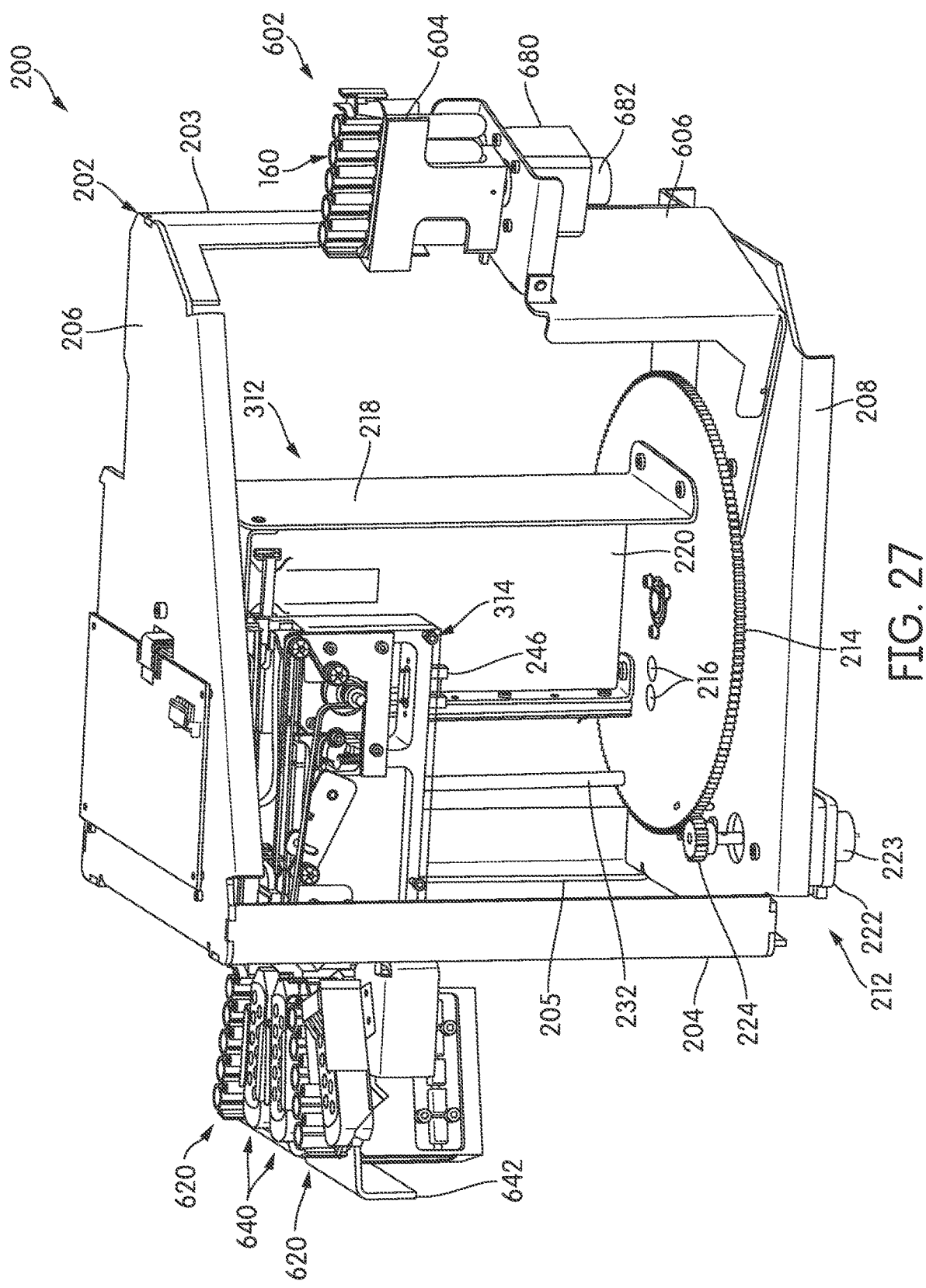
FIG. 27 is a top perspective view of an embodiment of a receptacle distribution module of the second module.
Figure 28:
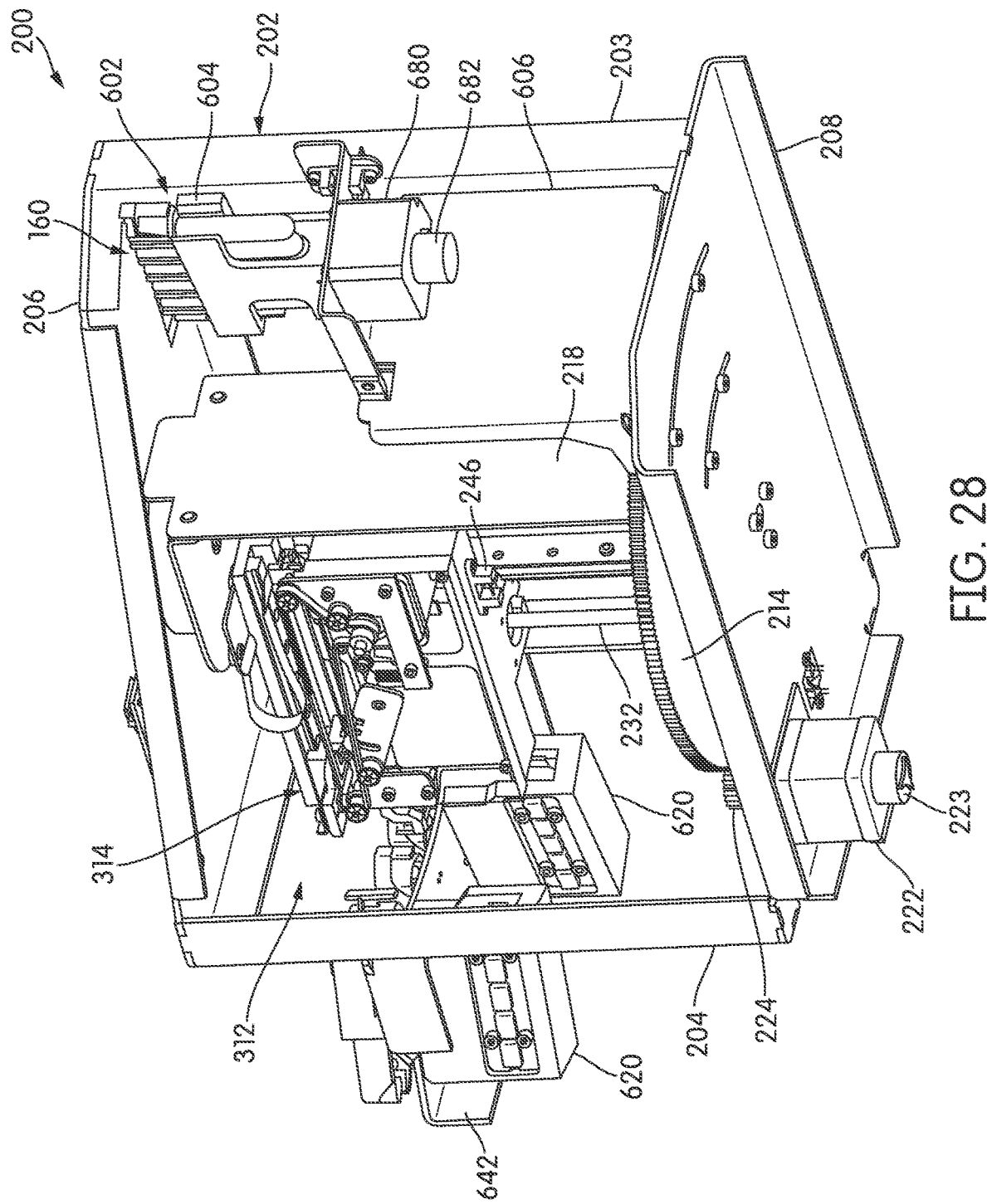
FIG. 28 is a bottom perspective view of the receptacle distribution module according to an embodiment.

Details of an exemplary receptacle distribution system are shown in FIGS. 27 and 28. In the illustrated embodiment, a receptacle distribution system 200 includes a frame 202 comprising legs 203, 204 and 205 extending between a bottom panel 208 and a top panel 206. The receptacle handoff station 602 is mounted on a handoff station bracket 606 attached to the bottom panel 208 of frame 202 and will be discussed further below. Magnetic elution slots 620 and reagent pack loading stations 640 are supported on a bracket 642 attached to legs 204 and 205 of frame 202 and will be discussed further below. A rotary distributor 312 is supported on a first upright wall 218 and a second upright wall 220 within the frame 202.

Figure 29:
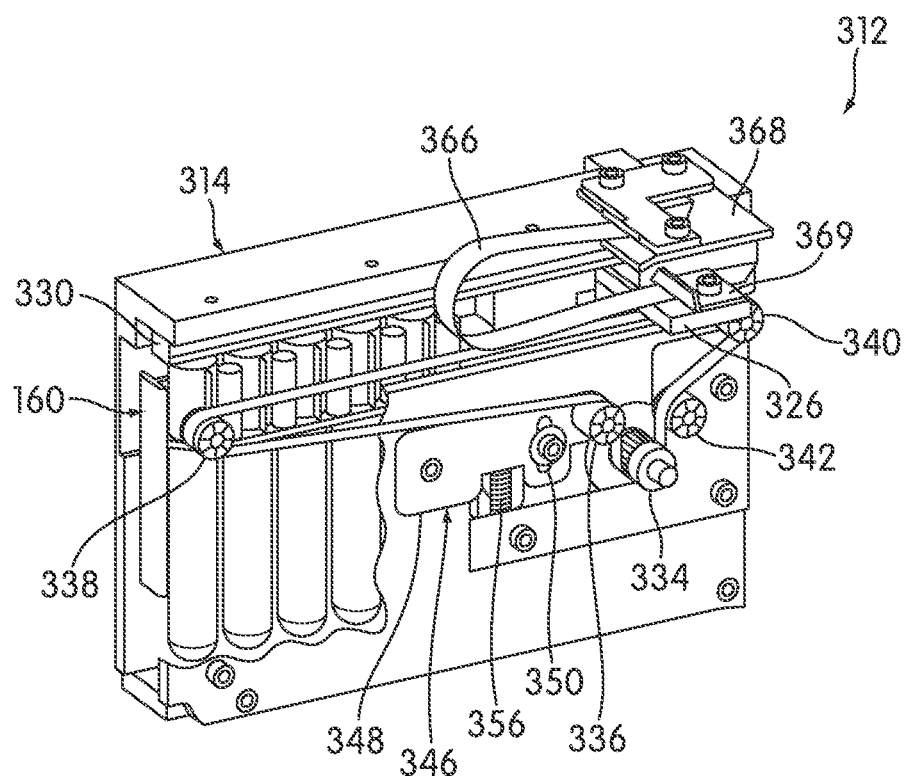
FIG. 29 is a perspective view of an embodiment of a distributor head of a rotary distributor of the receptacle distribution module with a receptacle hook in a retracted position.
Figure 30:
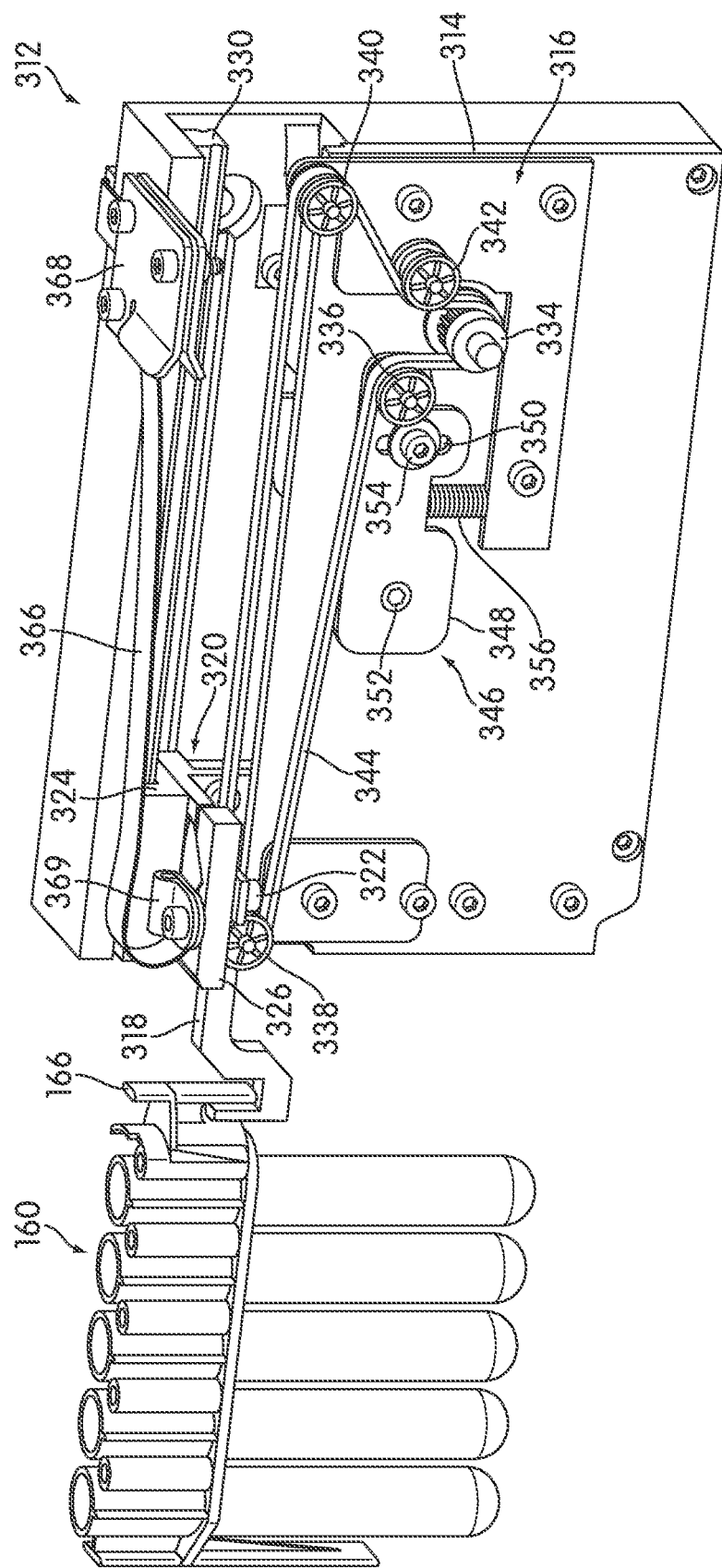
FIG. 30 is a perspective view of the distributor head with the receptacle hook in an extended position according to an embodiment.
Figure 31:
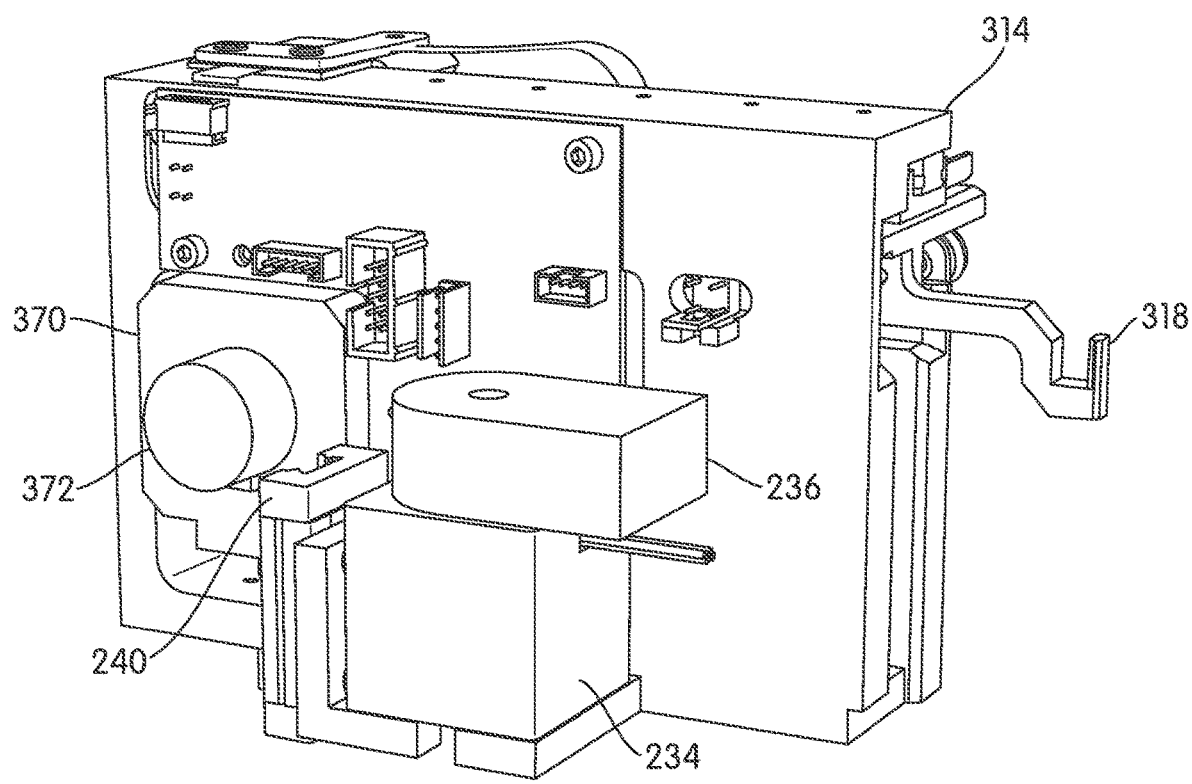
FIG. 31 is an opposite side perspective view of the distributor head according to an embodiment.

Details of an exemplary rotary distributor 312 are shown in FIGS. 29-31. The exemplified rotary distributor 312 includes a distributor head 314 defining a partial enclosure for holding an MRD 160 or reagent pack 760 and a receptacle hook 318 configured to engage the manipulating structure 166 of an MRD 160 or the manipulating hook 764 of the reagent pack 760.

A hook actuator system 316 linearly translates the receptacle hook 318 with respect to the distributor head 314 between an extended position, as exemplified in FIG. 30, and a retracted position, as exemplified in FIG. 29. The exemplified hook actuator system 316 includes a hook carriage 320 to which the receptacle hook 318 is attached. A drive belt 344 is attached to the hook carriage 320 by a screw and bracket indicated at 322. Drive belt 344 is carried on a drive wheel 334 and idler wheels 336, 338, 340, 342. Although exemplified using a drive belt-based system, it is understood that other mechanisms, such as screw-drive systems and linear piston actuators, are equally suited for the hook actuator system.

Referring to FIG. 31, which is a prospective of an opposite side of the distributor head 314, a drive belt motor 370 having a rotary encoder 372 is attached to the distributor head 314. Drive belt motor 370 is coupled to the drive wheel 334 that drives the drive belt 344 of the hook actuator system 316.

The hook actuator system 316 can include a belt tensioner 346 for maintaining proper tension in the belt 344. Belt tensioner 346 includes a pivoting idler wheel bracket 348 to which idler wheel 336 is attached and which is pivotally attached to the distributor head 314 by a pivot screw 352. A slot 350 is formed in an end of the pivoting idler wheel bracket 348, and a position lock screw 354 extends through the slot 350 into the distributor head 314. A spring 356 bears against a portion of the pivoting idler wheel bracket 348. Tension in the belt 344 can be adjusted by loosening the position lock screw 354, thereby allowing the spring 356 to pivot the pivoting idler wheel bracket 348 and thus urge the idler wheel 336 upwardly to create the proper tension in the drive belt 344. When proper tension is achieved in the drive belt 344, the position lock screw 354 can thereafter be retightened.

The hook carriage 320 includes a rail channel 324 that translates along a hook carriage guide rail 330 attached to an upper, internal portion of the distributor head 314. The receptacle hook 318 is attached to a mount 326 disposed between the rail channel 324 and the hook 318.

A hook home sensor, e.g., a slotted optical sensor or limit switch, may be provided to indicate when the hook 318 is in the retracted, or "home," position when a sensor flag extending from the mount 326 extends into the slotted optical sensor. Other types of sensors may be used for indicating a home position, such as proximity sensors, magnetic sensors, capacitive sensors, etc. The receptacle hook 318 and hook carriage 320 are operatively coupled for electronic communication with the remainder of the rotary distributor 312 by means of a flexible cable 366 attached at one end to the hook carriage 320 and at a printed circuit board or other connector located on the distributor head 314. Strain reliefs 368 and 369 may be provided for securing the flexible cable 366 to the distributor head 314 and the hook carriage 320, respectively.

Figure 32:
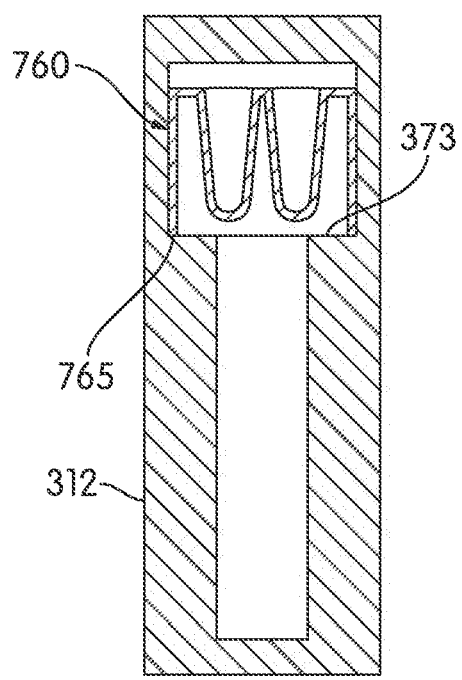
FIG. 32 is a transverse cross-section of the rotary distributor with a reagent pack disposed therein according to an embodiment.

FIG. 32 illustrates a manner in which a reagent pack 760 may be transported within the module 400 by means of the rotary distributor 312. As shown in FIG. 32, the rotary distributor 312 may be configured to receive and hold a reagent pack 760 that is pulled into the distributor 312 by the manipulating hook of the rotary distributor 312 with the bottom edge 765 of the pack 760 supported on a rail 373 formed on the inner walls of the distributor 312.

Figure 33:
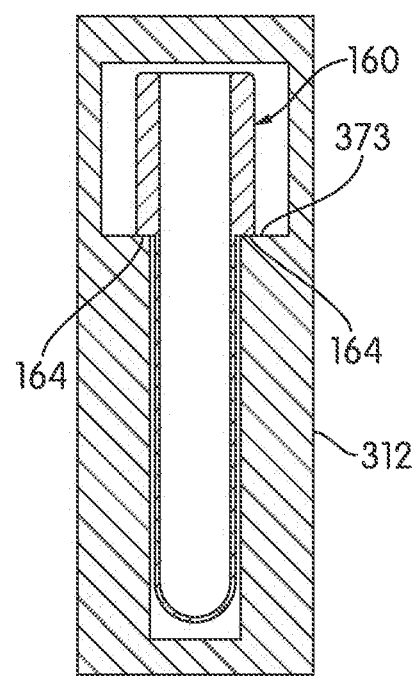
FIG. 33 is a transverse cross-section of the rotary distributor with an MRD disposed therein according to an embodiment.

Similarly, FIG. 33 illustrates a manner in which an MRD 160 may be transported within the module 400 by the rotary distributor 312. As shown in FIG. 33, the rotary distributor 312 may be configured to receive and hold an MRD 160 that is pulled into the distributor 312 by the manipulating hook of the rotary distributor 312 with the connecting rib structure 164 of the MRD 160 supported on a rail 373 formed on the inner walls of the distributor 312.

The receptacle distribution system 200 includes a distributor moving device configured to move the distributor head 314 in a circular path or in a vertical, linear path. More specifically, in one exemplary embodiment, the distributor moving device includes a rotary drive system 212 configured to move the distributor head 314 in a circular path and an elevation system 230 configured to move the distributor head 314 in a vertical direction.

Details of an exemplary rotary drive system 212 are shown in FIGS. 27, 28, 34, and 35. Although in certain embodiments, it is contemplated that the rotary drive system 212 is configured to freely rotate in 360°, it is understood that in at least certain embodiments the rotary drive system 212 is configured to rotate 180° between the two respective loading positions.

The first upright wall 218 and the second upright wall 220, on which the distributor head 314 is supported, are mounted onto a turntable 214 that is mounted for rotation about its central axis on the bottom panel 208 of the frame 202. A motor 222, attached to the bottom panel 208 and having a rotary drive 224, such as a rotary drive gear, extending above the bottom panel 208, engages peripheral teeth of the turntable 214 so that powered rotation of the motor 222 effects rotation of the turntable 214, as well as the first and second upright walls 218, 220 and the distributor head 314 supported thereon. Although exemplified as having teeth configured to engage each other, it is understood that the rotary drive 224 and the turntable 214 can engage each other without having teethed parts. In such an embodiment, both the rotary drive and the turntable can be wheels with rubberized outer surfaces to facilitate traction. Rotary motor 222 is preferably a stepper motor for providing precise control of the rotation of the turntable 214 and preferably includes a rotary encoder 223 for providing rotational position feedback to a control system controlling the rotary motor 222. Other means for rotationally coupling the distributor head 314 to the motor 222 are encompassed within this disclosure and include, for example, belt(s) and pulley(s), gear trains comprising one or more gears, drive shafts and worm gears, etc.

Figure 35:
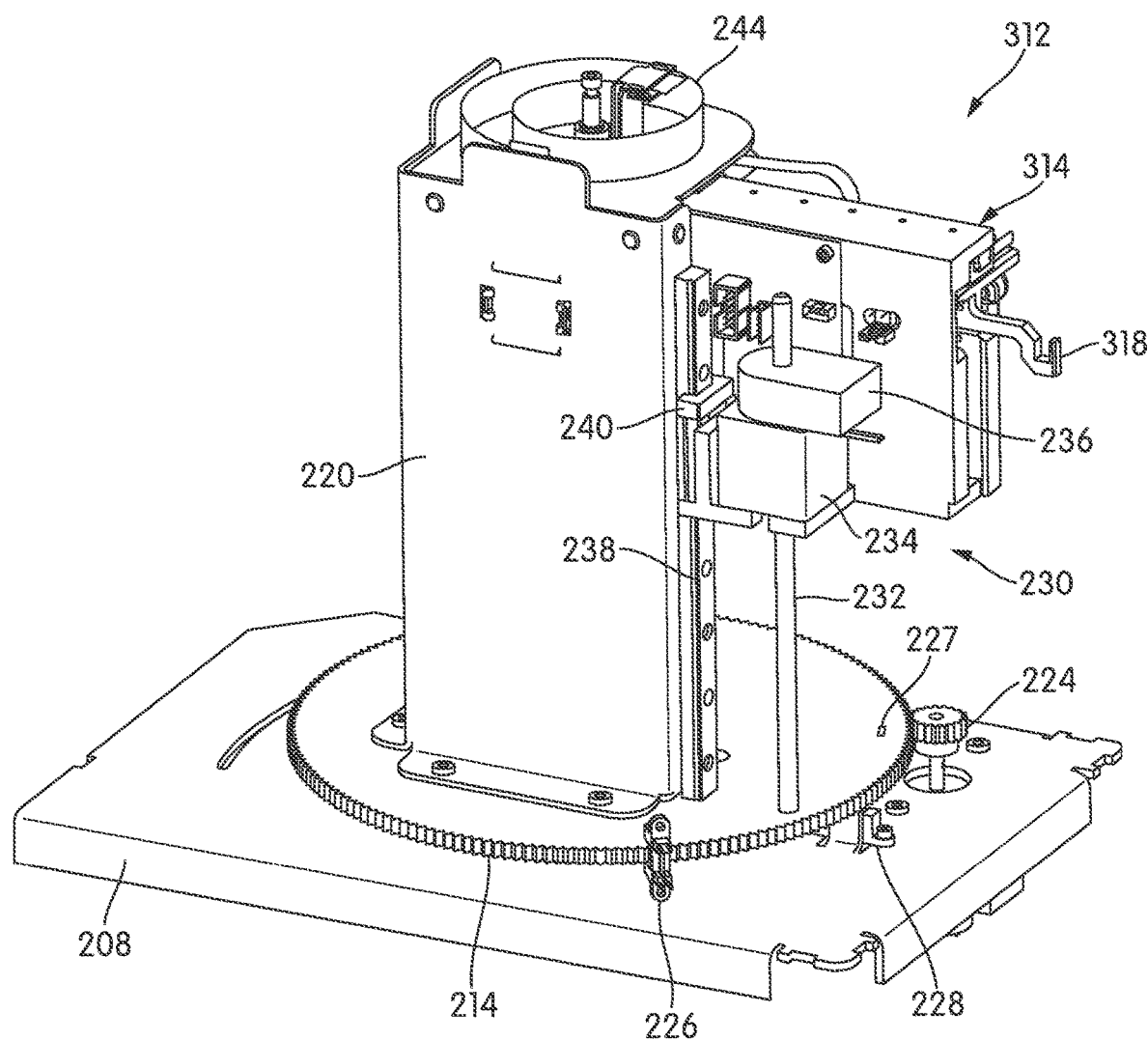
FIG. 35 is a top rear perspective view of the distributor moving system.

As shown in FIG. 35, a positional sensor 226, which may comprise a slotted optical sensor including an optical transmitter-receiver pair, provides a rotational position feedback signal of the turntable 214. Optical sensor 226 may be configured to detect a passing of one or more positional flags on the turntable 214 for indicating one or more specific rotational positions. Sensor 226 includes prongs, or portions, located above and below the turntable 214 and thus the positional flag(s) may comprise one or more openings (e.g., 227) formed through the turntable. Passage of an opening between the portions of sensor 226 located above and below the turntable 214 complete the optical signal transmission between the transmitter and receiver portions of the sensor 226 and thus generate a signal corresponding to the passage of the opening. Other types of sensors may be used for indicating particular rotational positions, including proximity sensors, magnetic sensors, capacitive sensors, etc.

A second optical sensor 228 may be provided below the turntable 214. Sensor 228 may comprise a slotted optical sensor including an optical transmitter-receiver pair for detecting the passage of one or more sensor flags (not shown) extending beneath the turntable 214 for indicating a rotational position. Other types of sensors may be used for indicating a home position, including proximity sensors, magnetic sensors, capacitive sensors, etc.

Details of a distributor elevation system 230 are shown primarily in FIG. 35. The depicted elevation system 230 includes a threaded rod 232 extending upwardly from the turntable 214 through a motor 234 and internal thread drive 236 mounted to the distributor head 314 (see also FIG. 31). Rotation of the internal thread drive 236 by the motor 234 causes the motor and the distributor head 314 to which it is attached to translate up or down the threaded rod 232. A guide rail 238 extends vertically up one edge of the second upright wall 220, and the motor 234 is coupled to the guide rail 238 by a rail coupling 240. Alternatives to the threaded rod and the internal thread drive for moving the distributor head 314 vertically are encompassed in this disclosure and include, for example, a rack and pinion or a belt drive system.

Figure 34:
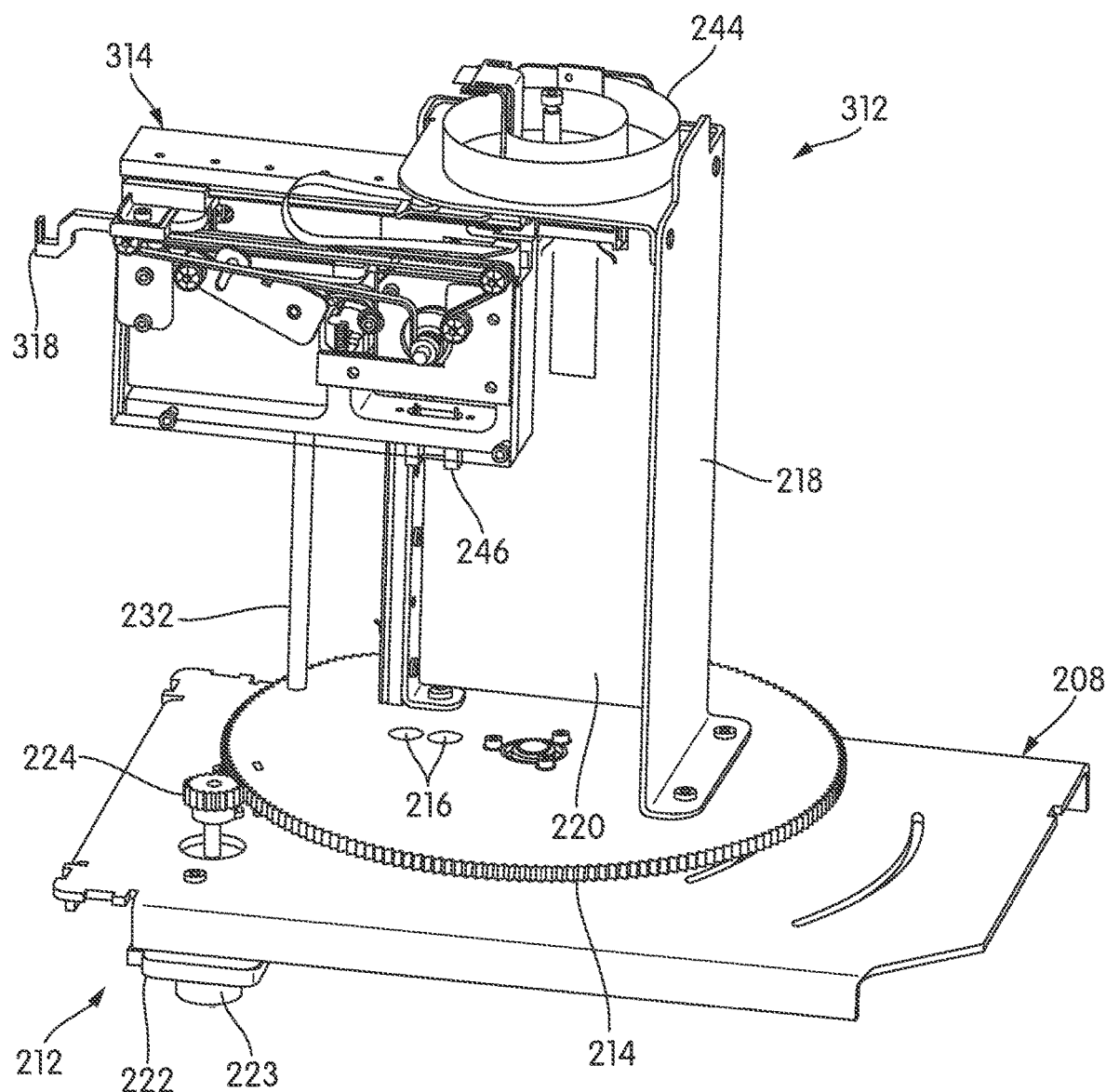
FIG. 34 is a top front perspective view of an embodiment of a distributor moving system of the receptacle distribution module.

Referring to the embodiment of FIGS. 27, 28, and 34, a sensor 246 extends below the distributor head 314. As the distributor head 314 is lowered by the elevation system 230, separate prongs of the sensor 246 extend into openings 216 formed in the turntable 214. Sensor 246 may be a slotted optical sensor with the prongs thereof forming a transmitted-receiver pair. An optical signal between the spaced prongs is broken when the prongs enter the openings 216, thereby sending a signal to a control system that the distributor head 314 is at its lowermost position. Other types of sensors may be used for indicating a down position for the distributor head 314, including, for example, proximity sensors, magnetic sensors, capacitive sensors, etc.

Data and power are communicated between the rotary distributor 312 and the module 400 by means of a coiled cable 244 that can accommodate rotation of the rotary distributor 312 with respect to the frame 202 by, for example, 180° in either direction.

To transfer an MRD 160, the distributor head 314 is rotated a few degrees by the rotary drive system 212 of the rotary distributor 312, the hook 318 is extended by the hook actuator system 316, and the head 314 is rotated in an opposite direction to engage the manipulating structure 166 of the MRD 160. The distributor hook 318 is then retracted, and the MRD 160 is coupled to the distributor head 314. Similarly, to transfer a reagent pack 760, the distributor head 314 is rotated a few degrees by the rotary drive system 212, the hook is extended by the hook actuator system 316, and the head 314 is then rotated in the opposite direction to engage the manipulating hook 764 of the reagent pack 760. The distributor hook 318 is then retracted, and the reagent pack 760 is pulled into the distributor head 314.

Receptacle Handoff Device

The receptacle handoff device 602 is configured to transfer a receptacle, such as the MRD 160, between the receptacle distributor 150 of the first module 100 and the rotary distributor 312 of the second module 400. Both the receptacle distributor 150 of the first module 100 and the rotary distributor 312 of the second module 400 manipulate the MRD 160 using a hook or other similar device to engage the manipulating structure 166 of the MRD 160. Therefore, after the MRD 160 is disengaged by the receptacle distributor 150 of the first module 100, the MRD 160 is positioned and oriented in such a manner as to present the manipulating structure 166 to the rotary distributor 312 of the second module 400. The handoff device 602 performs this function.

Details of the handoff device 602 are shown in FIGS. 27, 28, 39, 40. The receptacle handoff device 602 comprises a receptacle yoke 604 configured to receive and hold an MRD 160 placed into the yoke 604 by the receptacle distributor 150 of the first module 100. The yoke 604 is mounted on a handoff device bracket 606, attached to and extending from the bottom panel 208 of the frame 202, so as to be rotatable about a vertical axis of rotation. In one exemplary embodiment, the yoke 604 is coupled to a handoff device motor 680 attached to the bracket 606. Motor 680 may be a stepper motor for precise motion control and may include a rotary encoder 682 for providing rotational position feedback of the receptacle yoke 604 to a controller. A sensor 684, which may be a slotted optical sensor comprising an optical transmitter-receiver pair, is mounted to the bracket 606 and detects a home flag 686 extending from the yoke 604 for providing rotational position feedback. Other types of sensors may be used for providing position or orientation feedback, including proximity sensors, magnetic sensors, capacitive sensors, etc. After the MRD 160 is placed in the yoke 604 by the receptacle distributor 150 of the first module 100 and the receptacle distributor 150 disengages the MRD 160, the housing 604 is rotated to present the manipulating structure 166 of the MRD 160 to the rotary distributor 312 of the second module 400.

Alternatively, the handoff device 602 may be passively actuated by the rotary distributor 312. For example, the handoff device rotation may be tied to the rotation of the rotary distributor 312 (e.g., via a cable, belt, gear, or other means) such that when the rotary distributor 312 rotates to the handoff position, the handoff device 602 would spin around to face the rotary distributor 312. When the rotary distributor 312 rotates away from the handoff device 602, the handoff device 602 would rotate back toward the receptacle distributor 150 of the first module 100.

MRD Storage Station

As shown in FIG. 14, the MRD storage stations 608, 610, 612 are located on the receptacle processing deck 600 of the second module 400 and serve as temporary locations for MRDs in the second module 400. Storage stations 608, 610, 612 include a number of slots 614, each configured to receive an MRD 160. The storage stations 608, 610, 612 are arranged in an arc, thereby accommodating the rotational path of motion of the rotary distributor 312. Providing additional storage for MRDs within second module 400 provides the advantage of enhancing workflow by permitting flexibility in the timing that any particular MRD, or contents thereof, is/are utilized within second module 400. This permits MRDs that may arrive in second module 400 later to be processed out of order, for example, to address urgent needs in a laboratory.

Although exemplified as having three MRD storage stations 608, 610, 612, it is understood that embodiments can be constructed having two or more such storage stations. Similarly, although exemplified as being configured in an arc arrangement, it is understood that the distributor 312 in certain embodiments does not rotate about an arc and that the arc arrangement is convenient for the rotary distributor 312 embodiment. To the extent that an alternate configuration of the distributor 312 is implemented, the MRD storage stations similarly would match the alternate arrangement to maximize workflow of the system.

Magnetic Elution Slots/Reagent Pack Loading Stations

The magnetic elution slots 620 (two in the illustrated embodiment) and the reagent pack loading stations 640 are supported on a bracket 642 attached to frame 202. The purpose of each magnetic elution slot 620 is to hold an MRD 160 and apply magnetic force to the contents of the MRD to pull the magnetic beads to the side walls of each receptacle 162 while the substance transfer pipettor 410 aspirates the eluate fluid from the receptacles 162.

Figure 36:
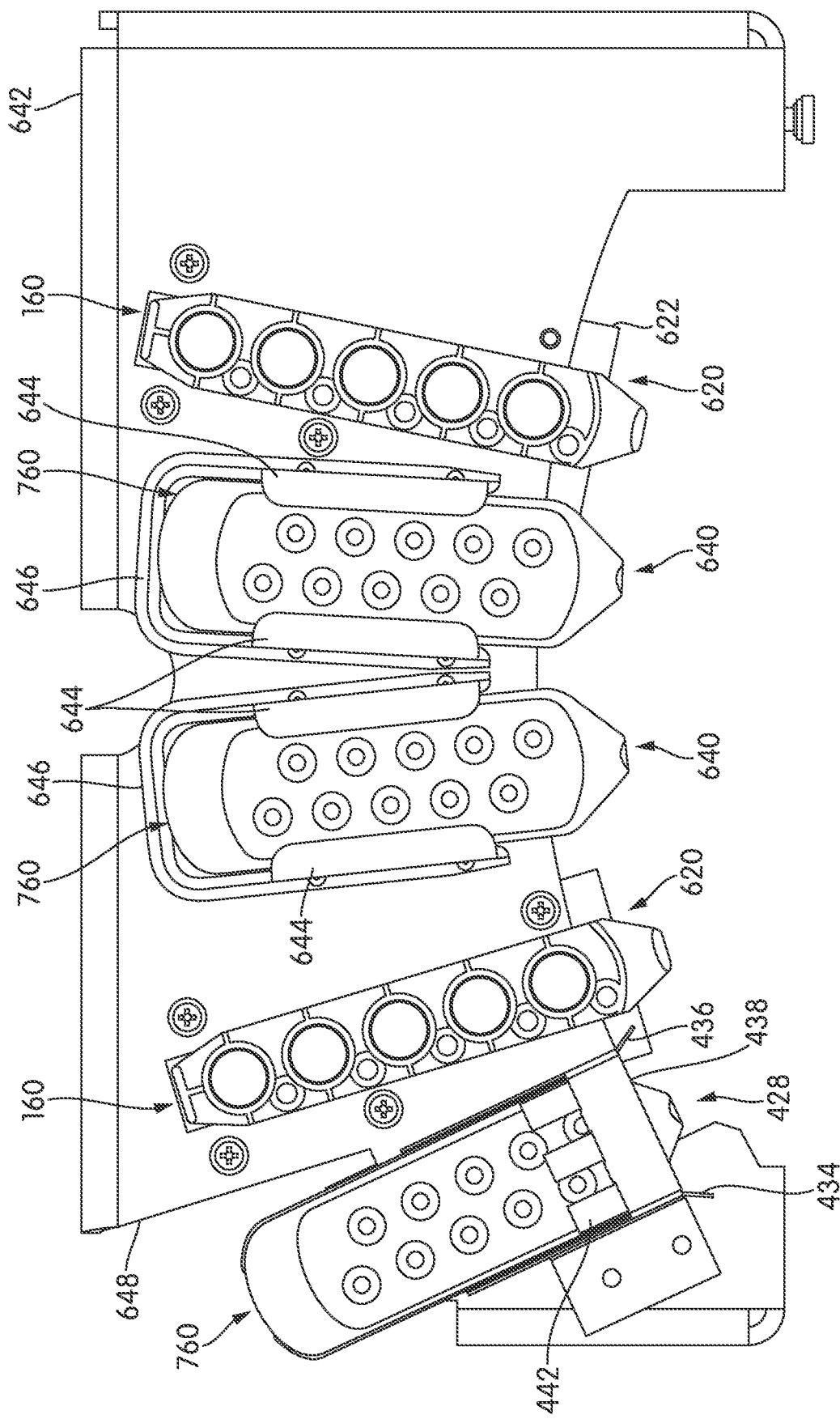
FIG. 36 is a top plan view of an embodiment of magnetic elution slots and reagent pack loading stations of the second module.
Figure 37:
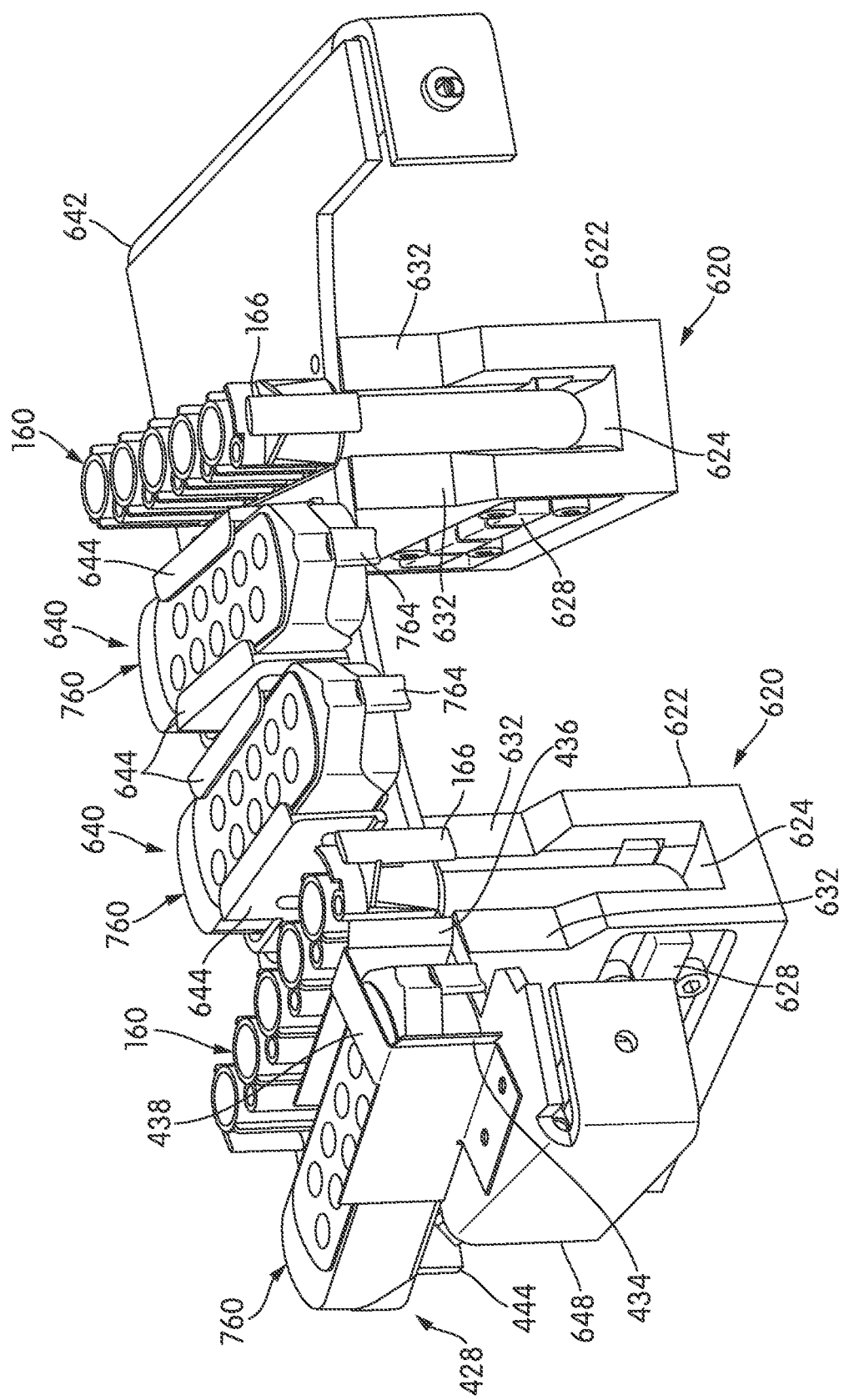
FIG. 37 is a front end perspective view of the magnetic elution slots and reagent pack loading stations according to an embodiment.
Figure 38:
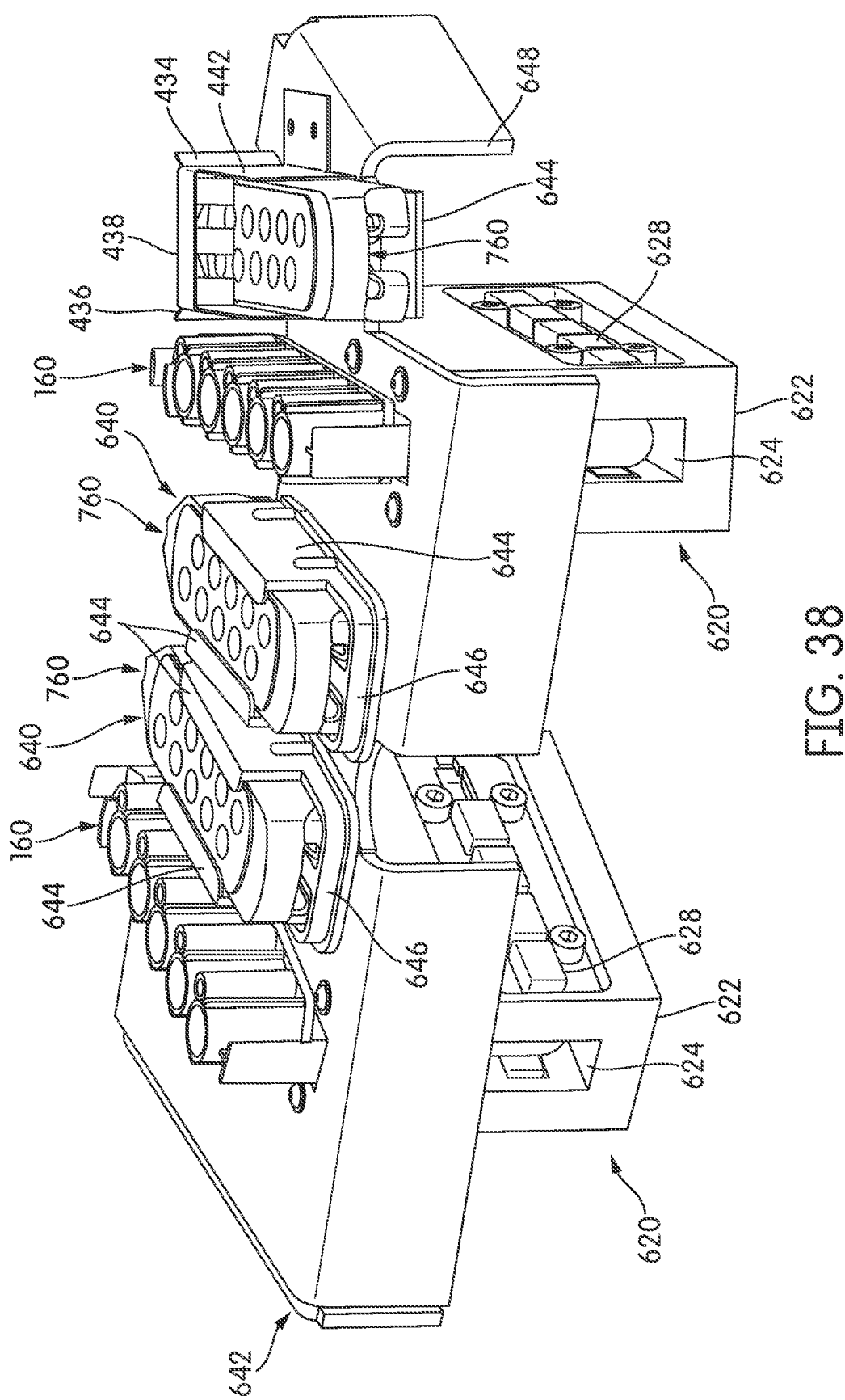
FIG. 38 is a back end perspective view of the magnetic elution slots and reagent pack loading stations according to an embodiment.
Figure 39:
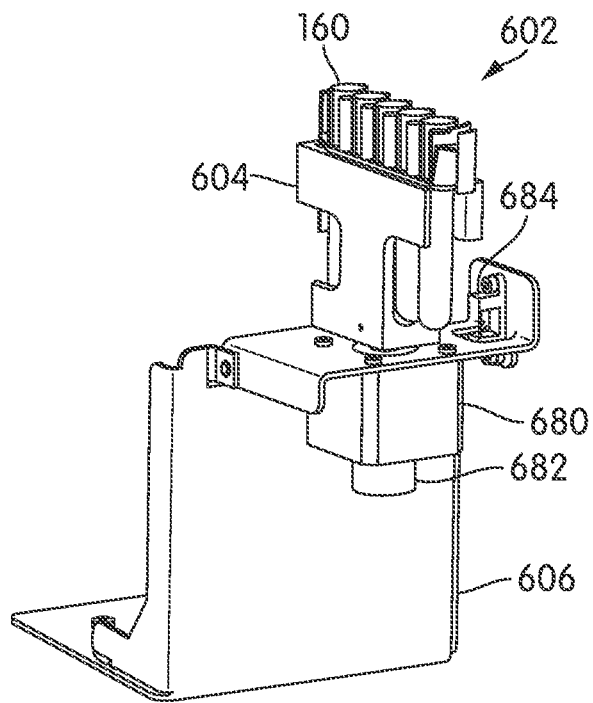
FIGS. 39 and 40 are perspective views of an embodiment of an MRD handoff device of the second module.
Figure 40:
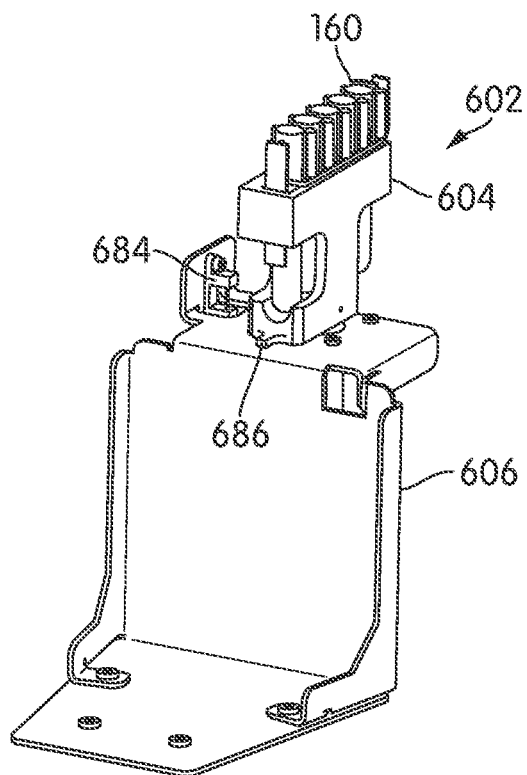

Details of the magnetic elution slots 620 and the reagent pack loading stations 640 are shown in FIGS. 36-38. Each magnetic elution slot 620 comprises a block 622 within which is formed a slotted opening 624. An MRD 160 placed within the slotted opening 624 is supported within the opening 624 by the connecting rib structure 164 of the MRD 160 resting on the top of bracket 642. The manipulating structure 166 extends out of the opening 624, and a cutout 632 in each side wall of the block 622 enables the hook 318 of the rotary distributor 312 to move laterally into or laterally out of the MRD manipulating structure 166 of an MRD 160 located within the slotted opening 624. The top of the MRD is uncovered, thus enabling pipettor access to the receptacles 162 of the MRD 160 held within the elution slot 620. Magnets 628 are attached to or embedded within one or both walls defining the slotted opening 624. Individual magnets 628 may be provided for each receptacle 162 of the MRD 160, as shown in FIGS. 37 and 38, or a single magnet may be provided for a receptacle that comprises one or more individual receptacles.

The reagent pack loading stations 640 are defined by spaced-apart, hold-down features 644 extending above the bracket 642 and a backstop 646 defining a back end of each reagent pack loading station 640. A reagent pack 760 is inserted between the hold-down features 644, under a lateral flange, and is pushed into the loading station 640 until the back end of the reagent pack 760 contacts the backstop 646.

Reagent Pack Trash Chute

A reagent pack trash chute 428 is supported on the bracket 642. In an exemplary embodiment, reagent pack trash chute 428 includes an entrance structure, defined by side walls 434, 436 and a top panel 438, through which a reagent pack 760 is inserted into the trash chute 428. Sidewalls 434, 436 are attached to the top of the bracket 642 and are bent or flared outwardly at their forward edges to provide a funneling entrance to the trash chute 428. Resilient tabs 442 extend down from the top panel 438.

To discard a reagent pack 760, the rotary distributor 312 inserts the pack 760 into the trash chute 428 between the side walls 434, 436. When the reagent pack 760 is inserted into the trash chute 428, there is a clearance between the top panel 438 and the top of the reagent pack 760. The resilient tabs 442 bear against the top of the reagent pack 760 and hold the reagent pack 760 down within the trash chute 428. The angle the resilient tabs 442 permits the reagent pack 760 to be pushed into the of the trash chute 428, but resists movement of the reagent pack 760 out of the trash chute.

When a subsequent reagent pack 760 is inserted into the reagent pack trash chute, it is pushed against the reagent pack 760 previously inserted into the trash chute 428, thereby pushing the previously-inserted pack further into the trash chute 428. A cut-out 648 is formed in the bracket 642, so the previously-inserted pack 760 eventually falls from the trash chute 428 and, guided by a guide ramp 444 extending down from the bracket 642, into a trash bin located below the trash chute 428.

Reagent Pack Changer

Figure 15:
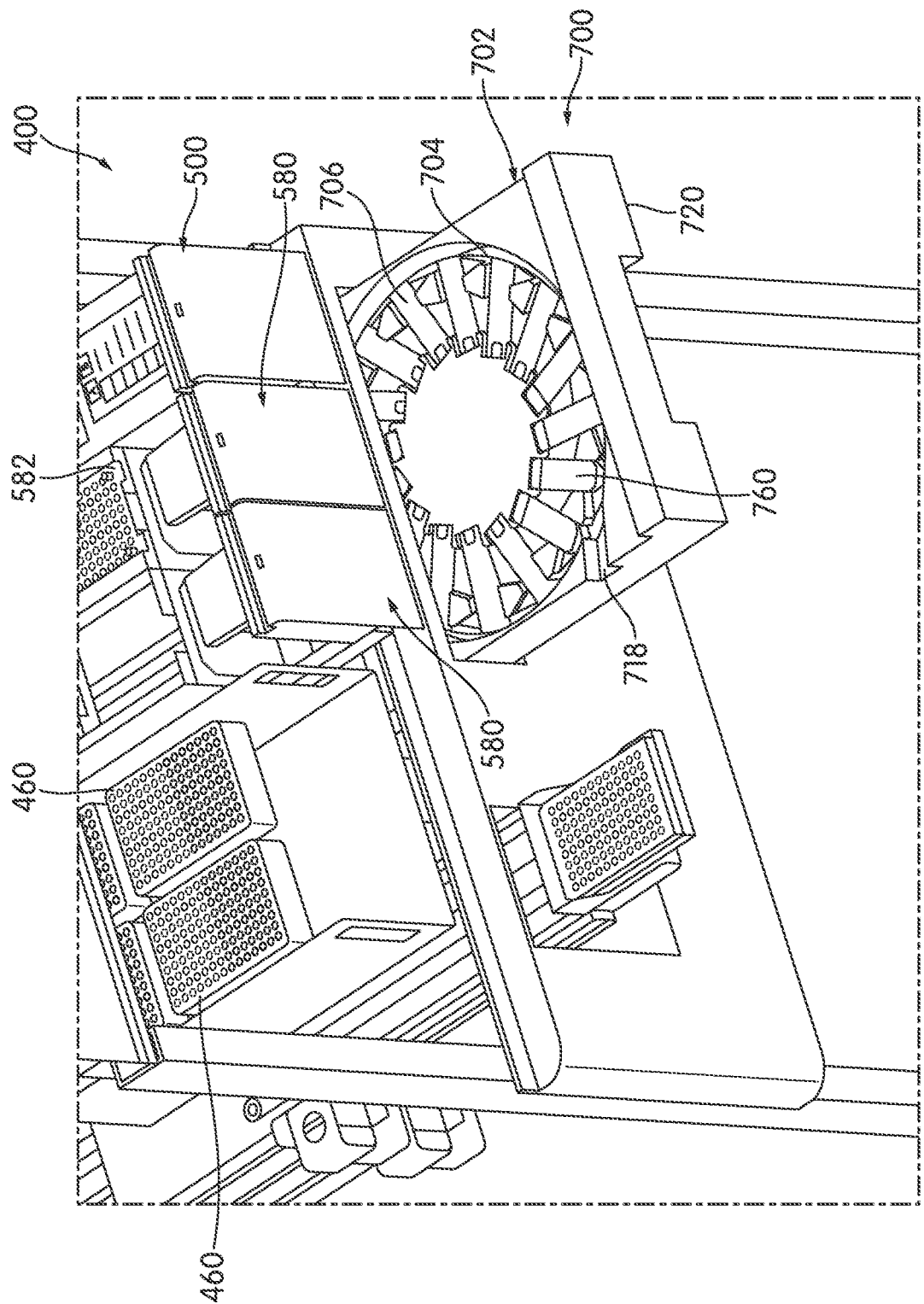
FIG. 15 is a partial, front perspective view of the second module with a carousel compartment of a reagent pack changer in an open position according to an embodiment.
Figure 16:
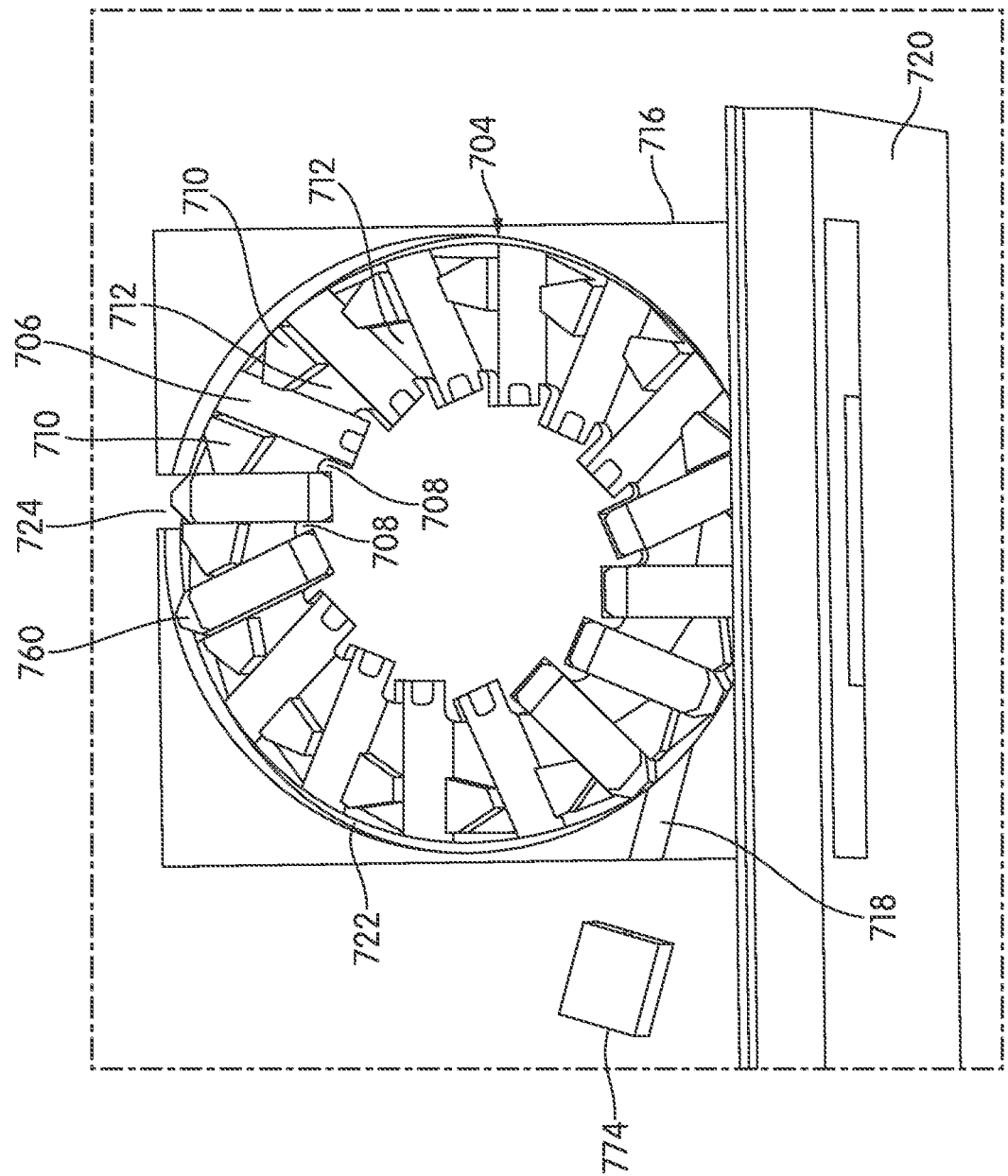
FIG. 16 is a partial, top perspective view of the pack carousel compartment according to an embodiment.
Figure 17:
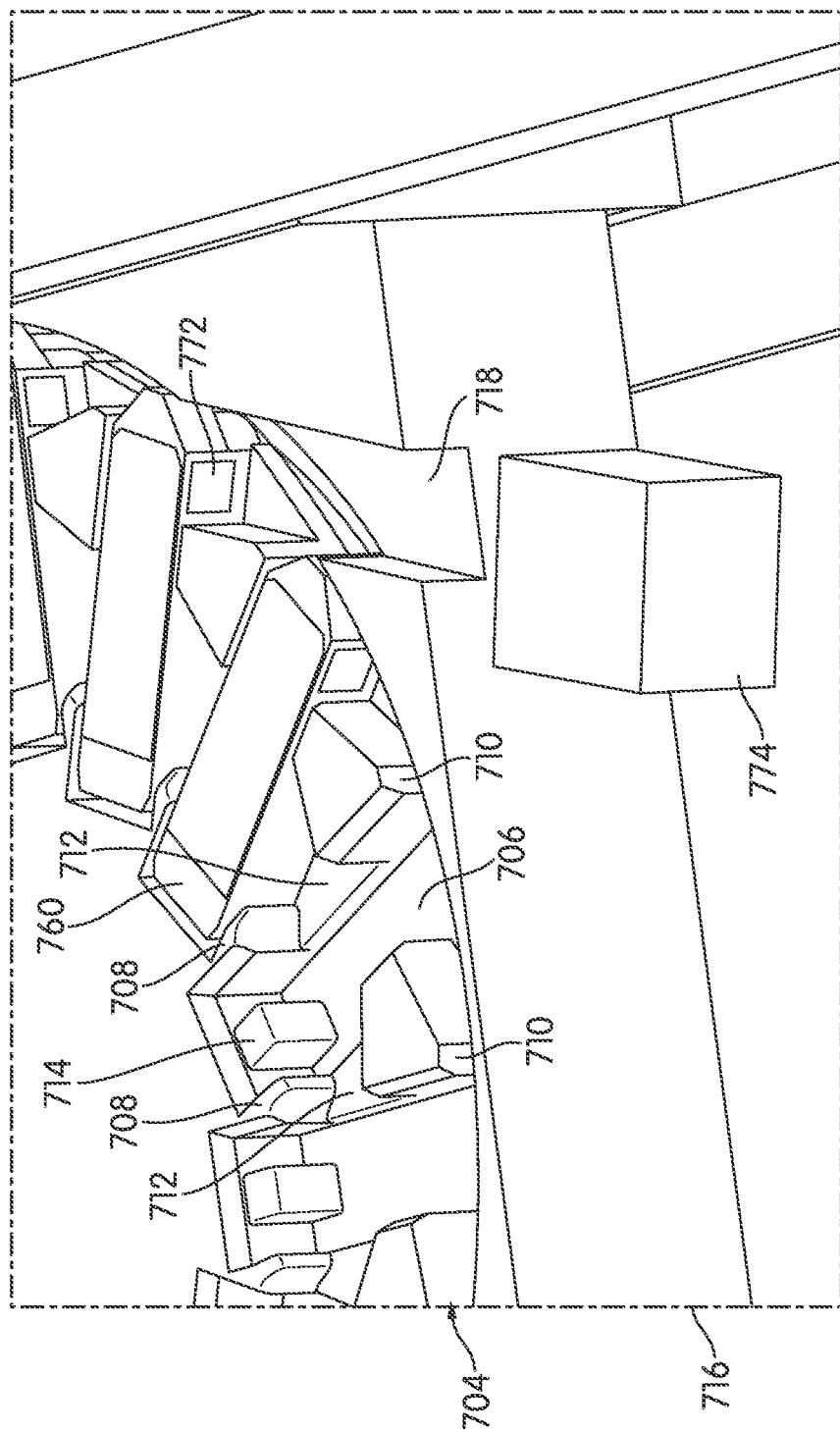
FIG. 17 is a partial, side perspective view of the pack carousel compartment according to an embodiment.

Details of an exemplary reagent pack changer 700 are shown in FIGS. 15-17. The purpose of the reagent pack changer 700 is to provide fully independent reagent pack loading and test execution whereby an operator may place reagent packs in a reagent pack input device and/or remove reagent packs 760 from the reagent pack input device while previously loaded reagent packs 760 are stored within a storage compartment, which may be temperature controlled, and are available for access by the instrument independently of the status of the reagent pack input device. The reagent pack changer is configured to move reagent packs 760 between the reagent pack input device and the storage compartment.

As shown in FIGS. 15-17, in one exemplary embodiment, the reagent pack input device comprises a reagent pack carousel compartment 702 which may be pulled open from the second module 400 and which contains a rotatable reagent pack carousel 704. The pack carousel 704 includes a number of reagent pack stations 706, each of which is adapted to receive and carry a reagent pack 760 and which are defined by radially inner dividers 708 and radially outer dividers 710. As can be seen in FIGS. 15-17, the reagent pack stations 706 of the reagent pack carousel 704 are arranged about the outer perimeter of the reagent pack carousel 704, but the elongated reagent pack stations 706, and reagent packs 760 carried thereby, are not oriented in a radial direction with respect to the center of the reagent pack carousel 704. Each reagent pack station 706 is oriented at an angle (e.g. 5-20°) with respect to a true radial orientation. This configuration of reagent packs optimizes the placement of reagent packs 760 on the carousel 704, thereby enabling the reagent pack carousel 704 to carry the maximum number of reagent packs 760 and providing access of identifiable indicia present on each reagent pack 760 to the barcode reader 774.

A gap 712 between each inner divider 708—outer divider 710 pair enables an operator to insert his or her fingers into the gap 712 to thereby grasp the sides of the reagent pack 760 for placing the reagent pack 760 into the reagent pack station 706 or for removing the reagent pack 760 from the reagent pack station 706. Each reagent pack station 706 of the reagent pack carousel 704 also includes an alignment block 714 at a radially inner end of the reagent pack station 706. The alignment block within the rear recess 770 of the reagent pack 760 helps to maintain the proper alignment and position of the reagent pack 760 within the reagent pack station 706.

In some embodiments, the reagent pack carousel compartment 702 includes a carousel frame 716, preferably disposed on a track that enables the frame 716 to be slid into or out of the module 400 as a drawer. The frame 716 includes a drawer front 720. The reagent pack carousel 704 is rotatably disposed within the frame 716, which may include a circular recess 722 shaped so as to conform to the reagent carousel 704.

The reagent pack carousel 704 is motorized to effect powered rotation of the carousel. In one exemplary embodiment, the reagent pack carousel compartment 702 may include a motor (not shown) that is coupled, for example by a belt and pulley arrangement (not shown), to the reagent pack carousel 704 for powered rotation of the reagent pack carousel 704. The motor may be mounted to the reagent pack carousel frame 716 and move in and out with the reagent pack carousel compartment 702, connected to the module 400 by a flex cable. The reagent pack carousel compartment 702 may include one or more position sensors for detecting when the carrousel is in an open or closed position and communicating a corresponding signal to the system controller. Such sensor(s) may include optical sensors, proximity sensors, magnetic sensors, capacitive sensors, etc.

The reagent pack carousel compartment 702 may also include a software-controlled lock.

The reagent pack carousel compartment 702 can also include one or more sensors for tracking the positions of the reagent pack station 706. For example, the reagent pack carousel 704 may include a home flag, such as a tab and an optical sensor that detects the position of the tab at a specified rotational position of the reagent pack carousel 704. Other types of sensors may be used for indicating a home position, including proximity sensors, magnetic sensors, capacitive sensors, etc. Furthermore, the motor driving the reagent pack carousel 704 may be a stepper motor including a rotary encoder for generating signals corresponding to a rotational position of the reagent pack carousel 704.

The second module 400 may include a machine pack reader configured to read a machine code provided on each reagent pack 760 providing information regarding the reagent pack 760, such as the identity of the assay reagents carried within the reagent pack 760, manufacturer, lot number, expiration date, etc. The machine code may also include a unique identifier specifically identifying that particular reagent pack 760. The machine code reader device may comprise a barcode reader 774 configured to read a barcode label 772 disposed on the reagent pack 760. Barcode label 772 may be a two dimensional or one dimensional barcode. A scanning slot 718 formed in the carousel frame 716 provides an opening through which the barcode reader 774 may read a label 772 on the reagent pack 760. Similarly, the orientation of the reagent pack 760 carried in the pack station 706 of the pack carrousel 704, may be set at an angle with respect to a true radial orientation, and the shape of the outer dividers 710, being generally trapezoidal in shape, creates a clearance opening through which the barcode reader 774 can read the barcode label 772 disposed on the reagent pack 760. Together with the rotary encoder, the barcode reader 772 provides an indication where each reagent pack 760 is positioned within each reagent pack station 706 of the reagent pack carrousel 704. Although a barcode scanner is exemplified, the use of other technologies such as RFID and QR codes are contemplated.

Each reagent pack station 706 may include a station empty barcode disposed on a side of each outer divider 710 that will be read by the barcode reader 774 if a reagent pack 760 is not positioned within the reagent pack station 706.

Figure 18:
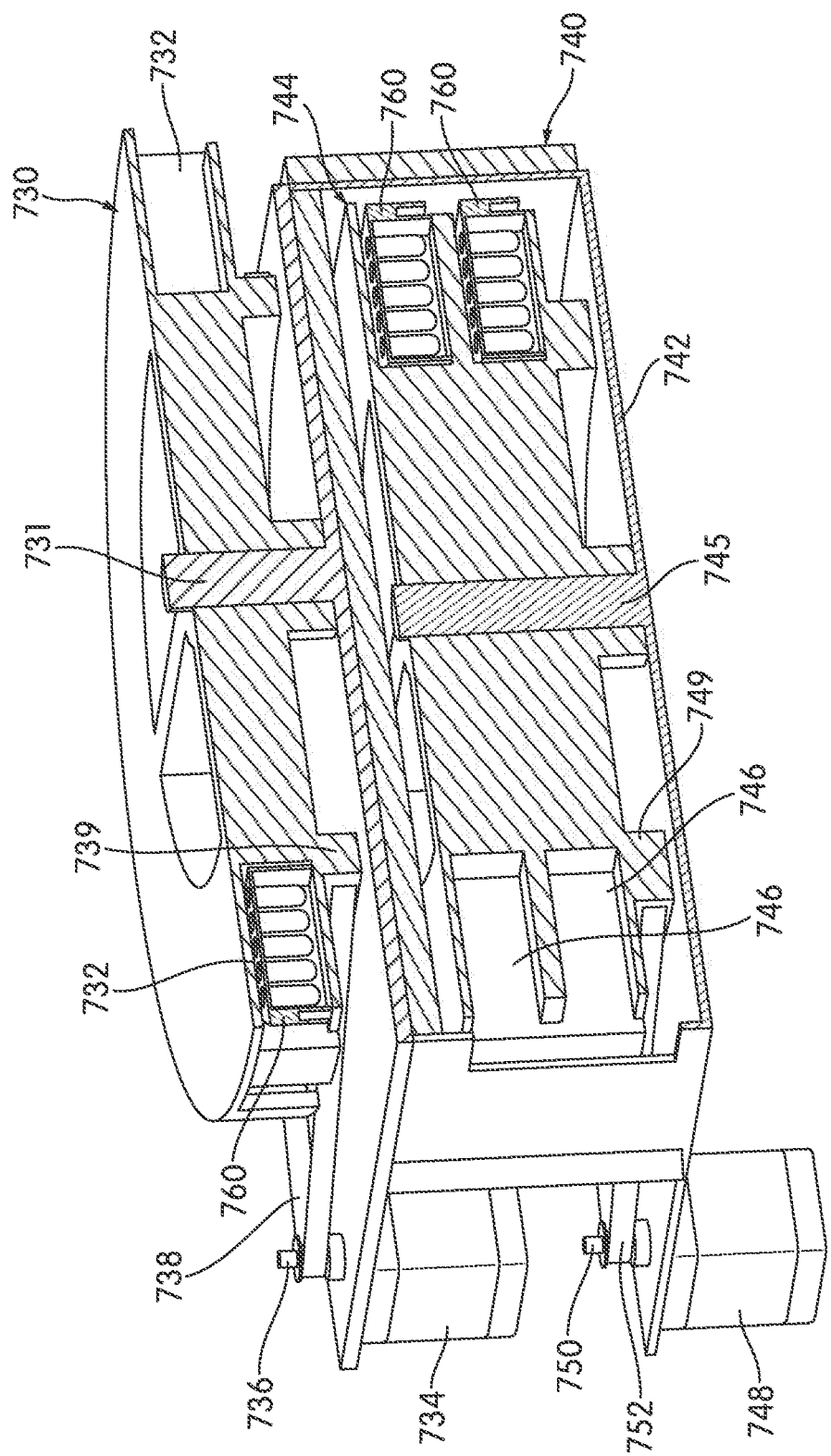
FIG. 18 is a cross-sectional, rear perspective view of an alternative embodiment of a reagent pack changer and a reagent pack storage compartment.

In another exemplary embodiment, the reagent pack input device comprises an alternative reagent pack carousel 730 shown in FIG. 18. Reagent pack carousel 730 is not carried on drawer be pulled out of the module 400, but instead, includes radially oriented reagent pack stations 732 arranged about the perimeter of the reagent pack carousel 730 and is accessible through a slot in front of the second module 400 which may be covered by a door that is openable by the operator. Powered rotation of the reagent pack carousel 730 may be provided by a carousel drive system that may include a motor 734 having an output drive wheel 736 that is coupled to a drive pulley 739 of the carousel 730 by means of a drive belt 738. Motor 734 may comprise a stepper motor having a rotary encoder, and a home flag may be provided on the carousel 730 to detect and monitor the rotational position of the reagent pack carousel 730 and thus each reagent pack station 732.

FIG. 18 also shows an exemplary embodiment of a reagent pack storage compartment represented by reference number 740. The storage compartment 740 is disposed beneath the reagent pack carousel 730. In the embodiments described above, the reagent pack carousel compartment 702 would be disposed within the module 400 above the storage compartment 740 and would be movable with respect thereto.

In some embodiments, storage compartment 740 includes a housing 742 that defines a temperature controlled chamber therein. The desired storage temperature may be as low as 4° C., but could be any temperature at or below ambient temperature, for example, 15° C. In some embodiments, the chamber of the storage compartment 740 further has a humidity control module configured to control the humidity level of the air circulating within the temperature controlled chamber. As part of this process, the humidity control module is optionally equipped to collect condensed water, and route it outside the cooled storage area for disposal.

Housing 742 may be insulated and may be cooled by Peltier devices that can be mounted directly onto the housing 742 or by Peltier devices coupled to a heat cools a fluid, such as water or a refrigerant, which is circulated around the housing 742. In one embodiment the storage compartment 740 is cooled by two separate Peltier devices mounted directly onto the housing 742, each at different temperatures or temperature ranges. In this embodiment the first Peltier device is held at a temperature close to the freezing temperature of water. The second Peltier device is provided at a location within the storage compartment 740 distant or adjacent to that of the first Peltier device and is provided at a temperature higher than that of the first Peltier device, e.g., 15° C. The second Peltier device is in operable communication with a temperature sensor within the storage compartment 740, positioned near the top of the storage compartment 740. The second Peltier device would operate based on the measured temperature to maintain a predetermined temperature in the storage compartment 740. In this embodiment a fan may be provided within the storage compartment 740 to cause air circulation within the storage compartment 740 through the fan, and past the first and second Peltier device s. When air passes the first Peltier device, which is held at a very low temperature, the air will cool, thus decreasing its capacity to hold moisture which moisture will condensate on the Peltier device or another designated element. Therefore, this dual Peltier device embodiment provides both a temperature and humidity controlled environment, which is beneficial for increasing the shelf-life of lyophilized reagents which are vulnerable to rapid degradation in the presence of increased temperatures and atmospheric moisture.

Other ways to cool and/or dehumidify the storage compartment 740 are contemplated and the disclosure is not limited to the exemplified embodiments.

The housing 742 should be provided with a liquid collection and/or drainage system for handling condensing liquid inside the housing 742. Such a system may, for example, include piping for directing the collected condensate away from the housing 742 and to a drain or an evaporator.

A storage carousel 744 is rotatably mounted within the housing 742, for example, on shaft 745. Storage carousel 744 includes a plurality of pack stations 746 disposed around the perimeter thereof and positioned on one or more levels of the carousel 744. In the illustrated embodiment, storage carousel 744 includes pack stations 746 on two levels, one above the other.

A carousel drive can power rotation of the storage carousel 744 within the storage compartment 740. The carousel drive may include a motor 748, which may be a stepper motor, having an output drive wheel 750 coupled by means of a drive belt 752 to a drive pulley 749 of the pack carousel 744. Motor 748 may be located outside the housing 742—to keep heat generated by the motor 748 from heating the storage compartment 740—and the drive belt 752 may extend through an opening in the housing 742. Alternatively, a drive pulley coupled to the carousel 744 may be located outside the housing 740. The motor 748 may include a rotary encoder, and the reagent pack carousel 744 may include a home flag for monitoring the rotational position of each of the reagent pack stations 746 of the pack carousel 744.

Operation of the reagent pack changer 700 will now be described.

After the reagent packs 760 are placed in the reagent pack carousel 704 or reagent pack carousel 730 of the pack input device, the barcode of each reagent pack 760 is read by a barcode reader 774 and the identity and other information provided by the barcode is associated with a particular reagent pack station 706,732 of the reagent pack carousel 704. Alternatively, the reagent packs 760 may be scanned externally of the module 400, for example, by a hand operated barcode scanner, before the reagent pack 760 being placed into the pack input device.

After reagent packs 760 have been placed into the reagent pack input device, such as reagent pack carousel 704 or reagent pack carousel 730, pack carousel compartment 702 is shut or a door in front of the carousel access opening is closed. Next, the rotary distributor 312 removes one or more reagent packs 760 from the reagent pack carousel 704, 730 and moves the reagent pack 760 into a pack station 746 of the storage carousel 744 of the storage compartment 740. As shown in FIG. 16, the carousel frame 716 of the reagent pack carousel compartment 702 includes a reagent pack access slot 724 through which the rotary distributor 312 can access the manipulating hook 764 of a reagent pack 760 disposed within the reagent pack station 706. To enable the rotary distributor 312 to transfer reagent pack 760 between the reagent pack input carousel 704 or 730, to the one or more levels of the storage carousel 744 of the storage compartment 740, the rotary distributor 312 provides powered and controlled vertical, i.e., z-axis, motion. It is preferable that access to the reagent pack access slot 724 by the rotary distributor 312 is controlled by a door when the reagent carousel 704 or 730 is temperature controlled.

Once a reagent pack 760 is present in the storage compartment 740, it is available to be utilized in an amplification assay, for example, a PCR assay. When a sample is present requiring a particular assay, the carousel of the storage compartment 740 rotates to a position where a reagent pack 760 containing the specific unit dose reagents for that particular assay are accessible by the rotary distributor 312. Generally, such access will be through a door to maintain a tightly controlled temperature environment in the storage compartment 740. The distributor 312 will access the reagent pack 760 through the door and move it to a reagent pack loading station 640 for reconstitution of one or more lyophilized reagents contained on the reagent pack 760. When the reagent pack 760 is empty, or when the reagents of one or more wells on the reagent pack 760 have been reconstituted and removed, the distributor 312 will again move the reagent pack 760. If there are reagents remaining in the reagent pack 760, the distributor 312 will transfer the reagent pack 760 back to the storage compartment 740. If the reagent pack 760 contains no more reagents, or is otherwise designated as inappropriate for continued use (e.g., contaminated or expired reagents), the distributor 312 will transfer the reagent pack 760 to either a waste chute 426 or back to the reagent pack input carousel 704 or 730 for removal.

A further alternative for scanning each reagent pack 760 is for the distributor 312 to present each reagent pack 760 to a barcode scanner as each reagent pack is removed from the reagent pack input carousel and before placing the reagent pack 760 into the storage carousel 744.

Reagent identity control is maintained after the bar code (or other machine code) is read on the reagent pack 760 by monitoring the position of each reagent pack station 706, 732 of carousel 704, 730 and each reagent pack station 746 on the storage carousel 744 and associating the reagent pack 760 identity—from the bar code—with the reagent pack station position.

The reagent pack carousels 704, 730 rotate independently of the storage carousel 744 of the storage compartment 740 to allow an operator to load and unload reagent packs 760 from the reagent pack carousel 704, 730 while the module 400 (i.e., rotary distributor 312) independently accesses reagent packs 760 stored in the storage carousel 744 for assay processing.

The reagent pack changer 700 preferably stores at least 28 to 30 or more reagent packs 760.

The second module 400 may further include an electrostatic generator to impart an electrostatic charge for positioning and holding the lyophilized reagent 768 present in the reagent pack 760 at the bottom of each of the mixing wells 762 of the reagent pack 760. Though the reagent 768 may be held at the bottom of the associated mixing well 768 with a previously-imparted electrostatic charge, as noted above, the inclusion of a mechanism, such as an electrostatic generator, to actively pull the lyophilized reagent 768 down to the bottom of the mixing well 762 at the time that the reagent is reconstituted will ensure its positioning in the correct spot in the mixing well during reconstitution. In an embodiment, the electrostatic generator is positioned below the reagent pack loading station 640, 730. Alternatively, or in addition, an electrostatic generator could be provided in the reagent pack carousel 704, 730 present in the reagent pack loading drawer and/or the storage carousel 744 present in the storage compartment 740. In such an embodiment, the electrostatic generator may be located under or operatively coupled to the reagent pack station 706, 732 or the reagent pack station 746 below the reagent pack 760, as providing an electrostatic generator within the storage compartment 740 will have an enhanced electrostatic effect due to the lower temperature and low humidity.

Storage/Expansion Module

Details of compartment 590 for storing accessories or to accommodate possible expansion of the second module 400 are shown in FIGS. 5, 6, 14, and 15. In one exemplary embodiment, compartment 590 can house a standard 96 well plate. The plate is located such that both pipettor arms 408, 416 can access the 96 well plate location. The expansion space has access to the front (via a drawer mechanism) so that the operator can load and unload the plate. The expansion space can also be accessed from the side of the instrument. A drive system comprising, for example, a motor-driven belt, may be provided for translating a well plate or other container or component into or out of the second module 400. Compartment 590 can be utilized as an area for collecting cap/vial assemblies that have undergone a PCR and/or melting assay to provide for the ability to perform additional assays (e.g., ELISAs) on the sample contained in the cap/vial assembly. (A procedure for performing a thermal melt analysis is disclosed by Wittwer et al. in U.S. Pat. No. 8,343,754.) In certain embodiments an arrangement of cap/vial assemblies in the format of a 96 well plate has advantages if further processing of the samples is desired since the 96 well plate size is compatible with a variety of known sample processing and molecular assay instruments.

Instrument Theory of Operation

The first module 100 is used for the sample preparation portion of the amplification assay (i.e., minimally the steps for isolating and purifying a target nucleic acid that may be present in a sample). Samples and TCR, which may include a magnetically-responsive solid supports, are loaded onto the first module 100. Elution buffer containers 502, 504 are loaded on the second module 400. The second module 400 then automatically moves these containers into a space within the first module 100 that can be accessed by a substance transfer device, for example, a reagent pipettor (not shown in FIG. 1), of the first module 100. Through information provided to the first module 100 by, for example, an operator via a user interface or through automated, machine-readable information, such as a bar code, provided on the sample container (not shown in FIG. 1), the first module recognizes that a particular amplification assay will be initiated. To process samples, the receptacle distributor 150 of the first module 100 pulls a new MRD 160 from an input queue 102 and places it into a sample dispense position within the first module 100. TCR and sample are transferred from a reagent container and sample tube, respectively, to each receptacle 162 the MRD 160 by a pipettor within the first module 100. The contents of the MRD 160 are then incubated for a prescribed period at a prescribed temperature before the MRD 160 is transferred to a magnetic separation wash station 118, 120 for a magnetic wash procedure.

After the target capture process, the MRD 160 is moved by the receptacle distributor 150 to an amplification reagent dispense position in the first module 100. The substance transfer device of the first module 100 then adds elution fluid to each receptacle 162 of the MRD 160 to separate target (sample) material from the magnetic particles, and the first module 100 mixes the contents of each receptacle 162 before sending the MRD 160 to the second module 400. The second module 400 places the MRD 160 into one of a series of slots configured to hold MRD 160. When signaled by the system controller, the second module 400 moves the MRD 160 to a magnetic elution slot 620 to separate the eluted nucleic acid material from the magnetic particles. The substance transfer device 402, for example, a robotic pipettor, then initiates the amplification process. The pipettor 402 first dispenses oil to all processing vials 464, 1100 queued for use in testing. The pipettor 402 then aspirates eluate/sample from the MRD 160, and then aspirates a reconstitution reagent solution from a reconstitution reagent cartridge or reservoir, dispensing them into a lyophilized-reagent well of reagent pack 760. The reconstitution reagent and a lyophilized amplification reagent in the reagent well of reagent pack 760 may be drawn into and released from the pipette tip one or more times to ensure adequate and rapid reconstitution. The reconstituted amplification reagent is pipetted to the processing vial 464, 1100 and is then capped. The reconstituted amplification reagent, sample, and oil may be drawn into and released from the pipette tip one or more times to ensure adequate mixing. The capped vial 464, 1100 is transferred to the centrifuge and then to the thermal cycler 432, such as thermal cycler 432 for PCR amplification and fluorometric detection.

Results may be displayed on an instrument monitor or user interface and either printed or communicated to the LIS.

In an embodiment, the first module 100 is configured to perform one or more isothermal nucleic acid amplification reactions on nucleic acid material contained within an MRD 160. In one embodiment, such an isothermal process may be performed on the contents of the MRD 160 before transporting the MRD 160 to the second module 400 to perform PCR on a portion of the MRD content material, as discussed above. Alternatively, after the MRD 160 is processed in the second module 400 and an amount of eluate/sample is transferred from the MRD to one or more vials 464, 1100 for performing PCR or other process(es) that the second module 400 is configured to perform. The MRD 160 may be transported back to the first module 100 to perform an isothermal nucleic acid amplification reaction on the remaining contents of the MRD 160.

Exemplary Processes

Figure 41:
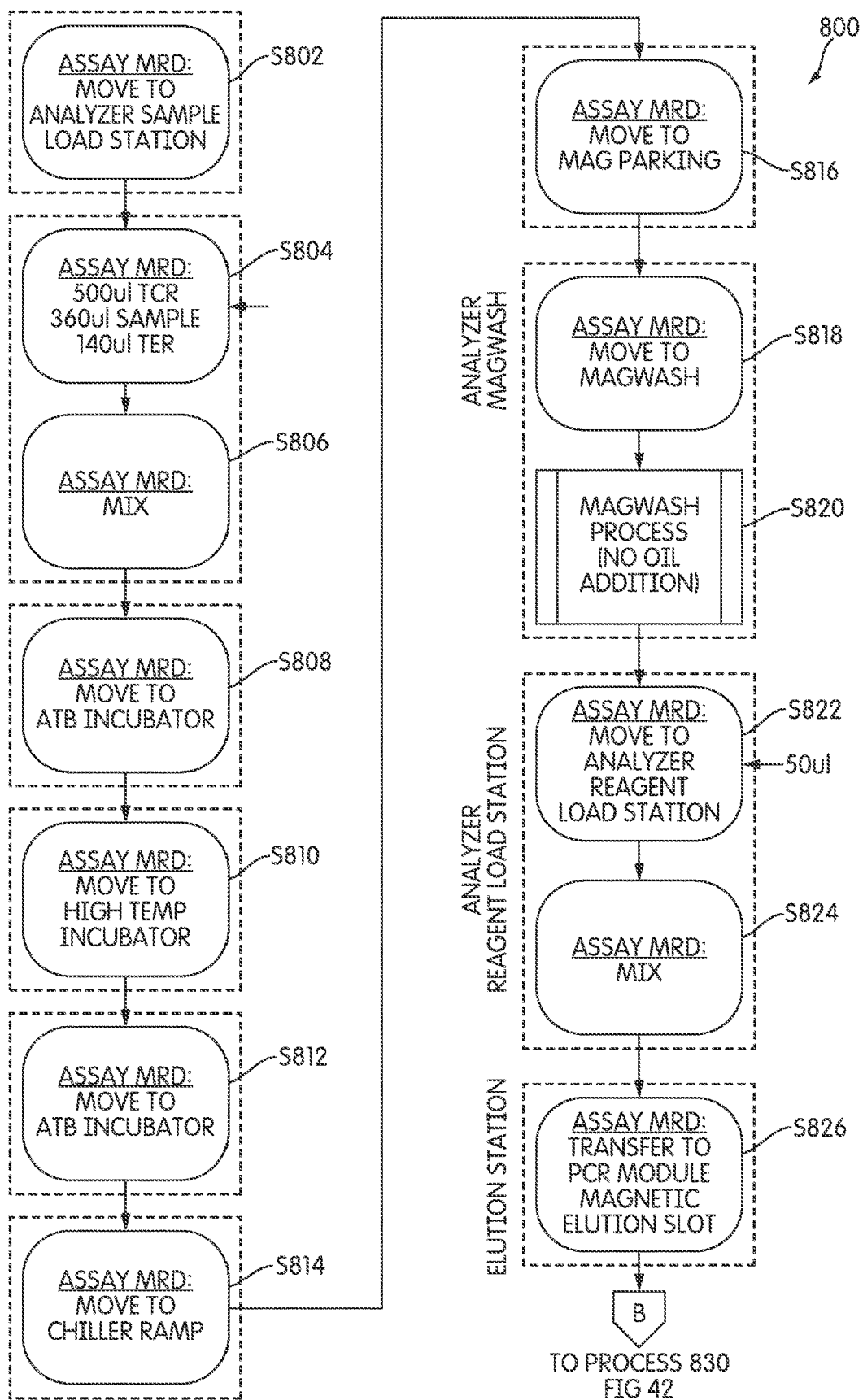
FIG. 41 is a flowchart illustrating the steps of a sample eluate preparation process according to an embodiment.
Figure 42:
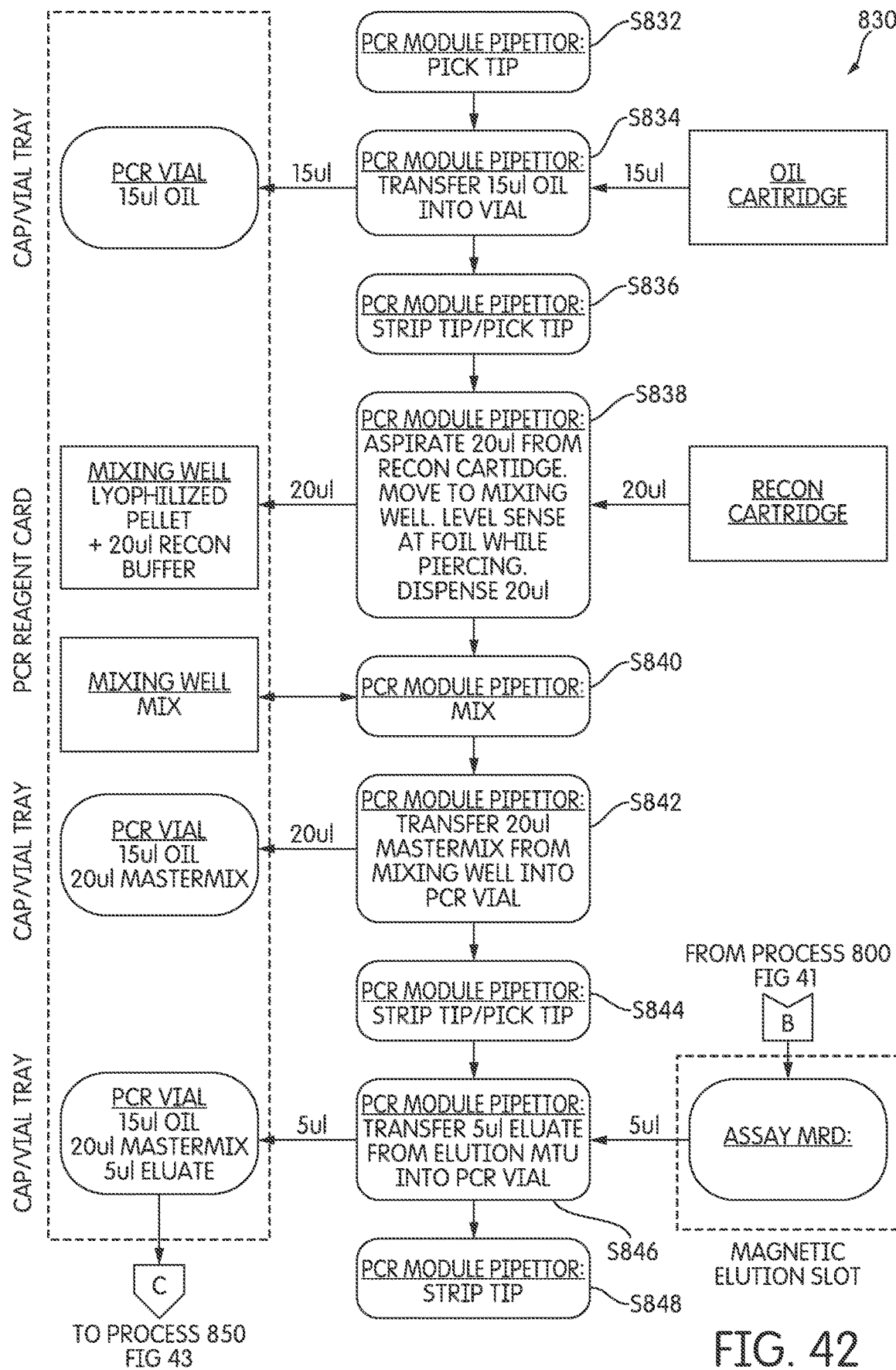
FIG. 42 is a flowchart illustrating the steps of a reaction mixture preparation process according to an embodiment.
Figure 43:
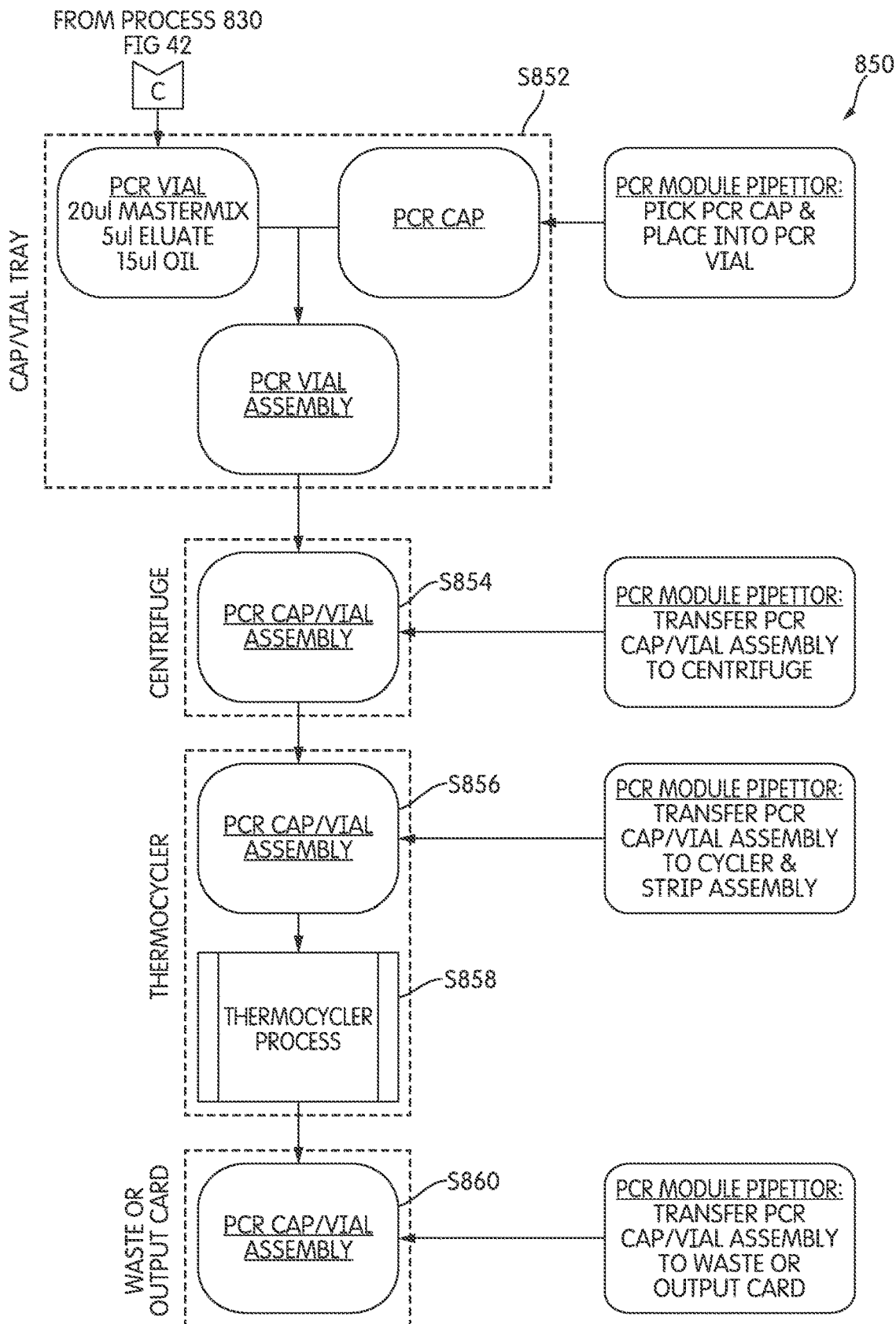
FIG. 43 is a flowchart illustrating the steps of a process for performing an automated nucleic acid amplification reaction, such as PCR, according to an embodiment.

Details of operation and a process embodying aspects of the present disclosure are shown in the flow charts of FIGS. 41-43. The following processes are exemplary. Other processes may be performed and/or the processes shown herein and described below may be modified, e.g., by omitting and/or reordering certain steps.

A sample eluate preparation process that can be performed using the first module 100 and the second module 400 described above is represented by flow chart 800 in FIG. 41. In step S802 of method 800, a reaction receptacle is moved to a location at which reaction materials can be added to the receptacle. See, e.g., Clark et al. in U.S. Pat. No. 8,309,036. For example, the receptacle distributor 150 of the first module 100 moves an MRD 160 from the input device 102 to one of the load stations 104, 106 or 108. See, e.g., Hagen et al. in U.S. Patent Application Publication No. 2012/0128451.

In step S804 a substance transfer device of the first module 100 transfers reaction materials to the receptacle. See, e.g., Buse et al. in U.S. Provisional Application No. 61/783,670. For example, a robotic pipettor of the first module 100 transfers a target capture reagent ("TCR") (e.g., 500 µL), sample fluid (e.g., 360 µL), and target enhancer reagent ("TER") (e.g., 140 µL) into each receptacle 162 of the MRD 160.

In step S806, the reaction materials added to the receptacle in step S804 are mixed. For example, the TCR, sample fluid, and TER added to the receptacles 162 of the MRD 160 are mixed by, for example, oscillating the MRD 160 at a high frequency (e.g., 60 seconds at 16 Hz).

In step S808, the receptacle is moved into an environment that will promote the desired reaction. For example, the receptacle distributor 150 removes the MRD 160 from the load station 104 and transfers the MRD 160 to one of the incubators 112, 114, 116 (referred to as the AT Binding Incubator "ATB Incubator" in FIG. 41) to incubate the contents of the MRD 160 at a prescribed temperature for a prescribed period of time (e.g., 1800 seconds at 63° C.). Before moving the MRD 160 to an incubator, the MRD 160 may first be placed in one of the temperature ramping stations 110 (e.g., 300 seconds at 65° C.) to elevate the temperature of the MRD 160 and its contents to a temperature that is closer to that of the incubator into which the MRD 160 will be transferred so as to minimize temperature fluctuations within the incubator.

The desired reaction may require two or more incubations at different temperatures. Thus, in accordance with one implementation of the disclosure, in step S810, the receptacle distributor 150 removes the MRD 160 from one of the incubators and transfers the MRD 160 to another incubator (referred to as the "High Temp Incubator" in FIG. 41) that is at a different (e.g., higher or lower) temperature than the first incubator to continue to incubate the contents of the MRD 160 at a prescribed temperature for a prescribed period of time (e.g., 600 seconds at 43.7° C.).

In step S812, the receptacle distributor 150 removes the MRD 160 from the second temperature incubator and returns the MRD 160 to another incubator at a different temperature, which may be the same incubator (e.g., the "ATB Incubator") the MRD 160 was placed into in step S808.

At the conclusion of the incubation step(s), it may be desirable to cool the temperature of the contents of the receptacle, for example to terminate any reaction occurring within the receptacle. Thus, in one example, in step S814, the receptacle distributor 150 may remove the MRD 160 from the incubator and transfer the MRD 160 to a chiller module 122 (referred to as a "Chiller Ramp" in FIG. 41), maintained at a predetermined temperature.

Next, assuming the reaction performed within the receptacle includes immobilizing a target nucleic acid on a magnetic-responsive solid support, a magnetic separation procedure is performed on the contents of the receptacle. Thus, in step S816, the receptacle distributor 150 removes the MRD 160 from a chiller module 122 after a predetermined period of time (e.g., 830 seconds), and transfers the MRD 160 to a magnetic parking station comprising magnets for attracting magnetically-responsive solid support within each receptacle 162 to the walls of the receptacles 162 to pull the solid support out of suspension. See, e.g., Davis et al. in U.S. Pat. No. 8,276,762. In step S818, after a prescribed period of time within the magnetic parking station (e.g., 300 seconds), the receptacle distributor 150 removes the MRD 160 from the magnetic parking station and transfers the MRD 160 to a magnetic separation wash station 118 or 120. See, e.g., Hagen et al. in U.S. Patent Application Publication No. 2010/0288395. In step S820, a magnetic wash procedure is performed on the contents of the MRD 160 placed into the magnetic wash station 118 or 120. One exemplary embodiment of the magnetic separation procedure involves a number magnetic dwells during which the contents of the receptacle are exposed to a magnetic force for a predetermined period of time, and after each magnetic dwell, while the contents are still exposed to the magnetic force, the fluid contents are aspirated from the receptacle, leaving the magnetic particles behind in the receptacle. In one exemplary embodiment, three magnetic dwells of 120 seconds each are performed. At the conclusion of each magnetic dwell, the magnetic force is removed from the contents of the receptacle. After each magnetic dwell, except the last magnetic dwell, an amount of wash fluid (e.g., 1000 µL of wash buffer) is added to the receptacle to re-suspend the magnetic particles before beginning the next magnetic dwell.

After the magnetic wash process is complete (e.g., after the last magnetic dwell followed by an aspiration of the non-magnetic fluid contents of the receptacle), in step S822, the receptacle distributor 150 retrieves the MRD 160 from the magnetic separation wash station 118 or 120 and moves the MRD 160 to one of the load stations 104, 106 or 108. In the load station, an amount of elution buffer (e.g., 50-110 µL) is transferred by, for example, a substance transfer device such as a robotic pipettor, from one of the elution containers 502, 504 transferred into the first module 100 by the bulk reagent container transport 550 of the bulk reagent container compartment 500 of the second module 400.

In some embodiments, it may be desirable to heat or incubate the contents of the MRD 160 to improve the efficiency of the nucleic acid elution.

In step S824, following the addition of the elution buffer, the contents of the MRD 160 are mixed by agitating the MRD 160.

In step S826, the MRD 160 is transferred from the first module 100 to a magnetic elution slot 620 in the second module 400. First, the receptacle distributor 150 of the first module 100 retrieves the MRD 160 from the load station 104, 106 or 108 and transfers the MRD 160 to an end of the transport track assembly 154 closest to the second module 400. The distribution head 152 of the receptacle distributor 150 places the MRD into the receptacle handoff device 602 of the second module 400. The receptacle handoff device 602 then rotates the MRD 160 and presents it to the rotary distributor 312. The rotary distributor 312 extends its hook 318 and engages the manipulation structure 166 of the MRD 160 by rotating a few degrees to place the hook 318 into the manipulation structure 166 and then withdraws the hook 318 to pull the MRD 160 into the distributor head 314 of the rotary distributor 312. The rotary distributor 312 then rotates to align the MRD 160 carried therein with one of the magnetic elution slots 620 of the second module 400 (or optionally MRD storage 608). The rotary distributor 312 then extends its hook 318 to push the MRD 160 into the magnetic elution slot 620 and rotates a few degrees to remove the hook 318 from the manipulation structure 166.

The process next proceeds to process 830 shown in FIG. 42.

Referring to FIG. 42, a reaction mixture preparation process is represented by flow chart 830. One or more of the steps of process 830 may proceed in parallel with one or more of the steps of process 800 shown in FIG. 41.

At step S832 the substance transfer pipettor 410 of the second module 400 picks up a disposable tip 584 from a disposable tip tray 582 carried in one of the tip compartments 580.

In step S834, the substance transfer pipettor 410 transfers an amount of oil (e.g., 15 µL) from an oil container carried in the bulk reagent container compartment 500 to one or more processing vials 464 held in the cap/vial trays 460 of the processing cap/vial compartment 440.

In step S836, the substance transfer pipettor 410 moves to a trash chute 426 to strip the disposable pipette tip 584 therefrom and discard the tip into the trash chute 426. Substance transfer pipettor 410 then returns to the disposable tip tray 582 and picks up another disposable pipette tip 584.

In step S838, substance transfer pipettor 410 transfers an amount of reconstitution reagent (e.g., 20 µL) from a reconstitution reagent container held in the bulk reagent container compartment 500 to a mixing well 762 of a PCR reagent pack 760 that was previously transferred by the rotary distributor 312 from the storage compartment 740 to a reagent pack loading station 640. In one embodiment, before the reconstitution reagent is dispensed into the mixing well 762, the pipettor 410 performs a level sense at the foil 766 before piercing the foil 766 with the pipette tip 584. The level-sense performed on the foil of the reagent pack 760 to "calibrate" the height of the reagent pack 760 relative to the pipettor. Generally, the pipettor 410 is configured to extend the pipette tip to the bottom of the mixing well for more accurate reagent aspiration.

In step S840, the fluid within the mixing well 762 is mixed to dissolve the lyophilized reagent 768. In one example, the substance transfer pipettor 410 mixes the fluid within the mixing well 762 by alternately aspirating the fluid into the pipette tip 584 and dispensing the fluid back in the well 762 one or more times to dissolve the lyophilized reagent 768.

In step S842, the substance transfer pipettor 410 transfers an amount, (e.g., 20 µL) of the reconstituted reagent from the mixing well 762 of the PCR reagent pack 760 (referred to as "Mastermix" in FIG. 42), into a vial 464. A PCR master mix provides the key ingredients necessary for performing PCR in a premixed and optimized format. Included in the master mix are Taq DNA polymerase, deoxynucleoside triphosphates (dNTPs), and magnesium chloride ($MgCl_2$). Not typically included are the forward and reverse primers.

In step S844, the substance transfer pipettor 410 moves to the trash chute 426 and strips the pipettor tip 584 into the trash chute. The substance transfer pipettor 410 then moves to the disposable tip tray 582 and picks up a new disposable pipette tip 584.

Block "B" in FIG. 42 represents the integration of process 800 shown in FIG. 41 with process 830 shown in FIG. 42. An MRD 160 containing a sample mixture (which, in this exemplary embodiment, was purified in a magnetic separation procedure) and an elution buffer is held in a magnetic elution slot 620, having been placed there in step S826 of process 800. In one embodiment, the MRD 160 is held in the magnetic elution slot 620 for dwell period of at least 120 seconds.

In step S846 of process 830, the substance transfer pipettor 410 transfers an amount of eluate (e.g., 5 µL) from the MRD 160 held in the elution slot 620 to the processing vial 464 to which oil and reagent were added in steps S834 and S842, respectively.

In step S848, the substance transfer pipettor 410 moves back to the trash chute 426 and strips the disposable pipette tip 584 into the trash chute.

The process now proceeds to process 850 shown in FIG. 43.

Referring to FIG. 43, a process for performing an automated biological process, such as a PCR reaction, is represented by flow chart 850. Block "C" in FIG. 43 represents the integration of process 830 shown in FIG. 43 with process 850 shown in FIG. 43.

In step S852, the substance transfer pipettor 410 picks up a processing vial cap 476 from the cap well 440 of the cap/vial tray 460 by inserting the pipettor probe 422 (without a disposable pipette tip thereon) into the cap 476 as shown in FIG. 23 (see FIG. 26, which shows an alternative cap 1200 and vial 1100 combination). The substance transfer pipettor 410 then picks up the cap 476, which is held onto the pipettor probe 422 by friction, and inserts the cap 476 into the processing vial 464 held in the processing vial well 474 until the cap 476 locks with the vial 464 to form a cap/vial assembly (see FIG. 25).

In step S854, the substance transfer pipettor 410 transfers the cap/vial assembly held to the pipettor probe 422 by friction to the centrifuge 588, where a stripping device removes the cap/vial assembly from the pipettor probe 422 to deposit the cap/vial assembly into the centrifuge 588.

In Step 856, following a specified period of time in the centrifuge, the vial transfer arm 418 inserts its pipettor probe 422 into the cap 476 of the cap/vial assembly held in the centrifuge 588 and removes the cap/vial assembly from the centrifuge 588 and transfers the cap/vial assembly to an incubator module, such as the thermal cycler 432. A stripping device removes the cap/vial assembly from the pipettor probe 422 of the vial transfer arm 418.

In step S858, an incubation process is performed. The incubation process may include PCR thermal cycling comprising multiple cycles of temperatures varying between 95° C. for denaturation, 55° C. for annealing, and 72° C. for synthesis. During the thermal cycler process an emission signal from the contents of the processing vial may be monitored. For example, fluorescence monitoring at one or more colored wavelengths during each PCR cycle may be measured using a signal detecting device, such as a fluorometer, operatively integrated with the thermal cycler 432. Periodic fluorescence intensity measurements at each wavelength may be made at regular intervals to generating fluorescence time series data for later processing and analysis.

In step S860, following the PCR process of step S858, the vial transfer arm 418 retrieves the cap/vial assembly from the thermal cycler 432 and transfers the cap/vial assembly to a trash chute 424 where the cap/vial assembly is stripped from the pipettor probe 422 into the trash chute 424, or the cap/vial assembly is transported to an output reagent pack 760 in the storage/expansion module.

Figure 44:
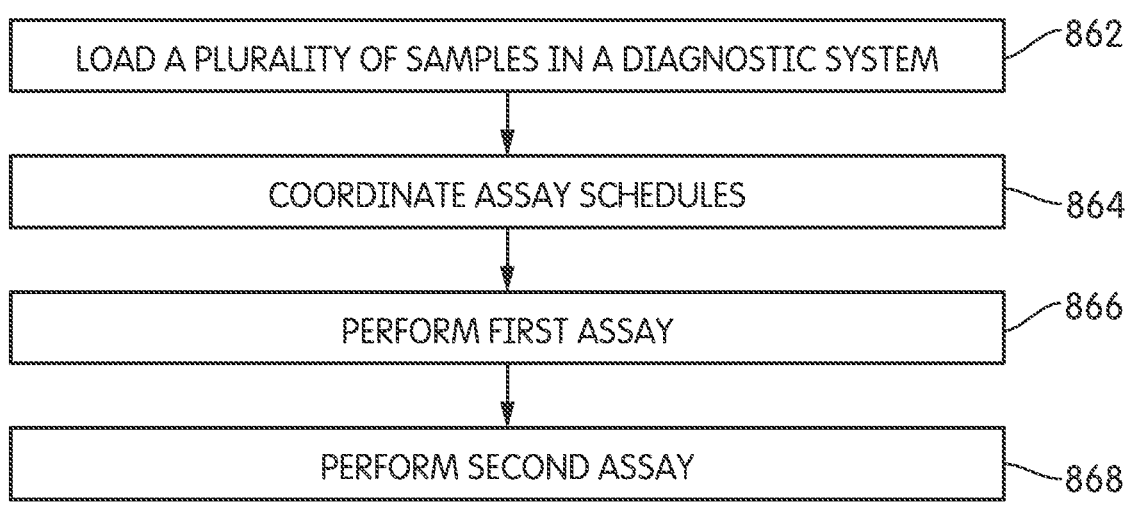
FIG. 44 is a flowchart illustrating a method of using diagnostic system according to one such embodiment.
Figure 45:
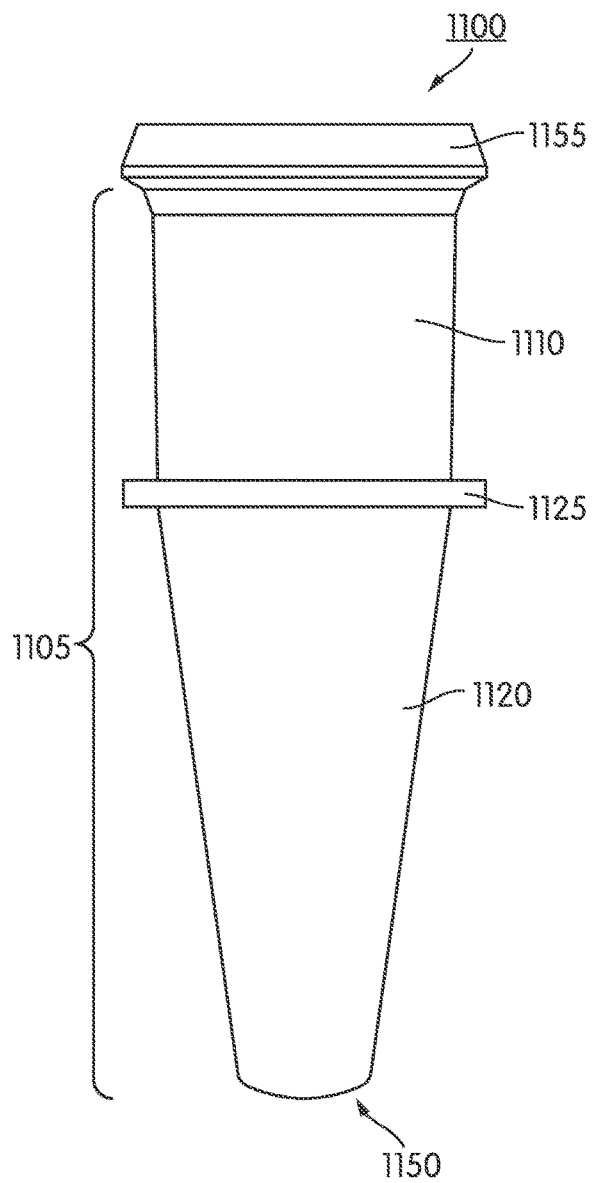
FIGS. 45-48 show a receptacle of the present disclosure.
Figure 46:
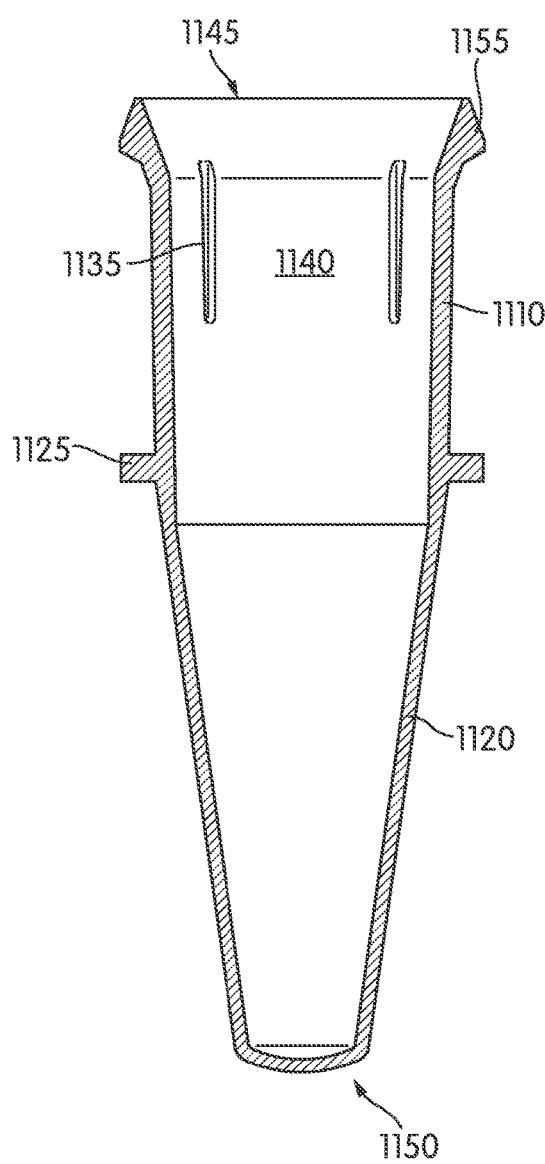
Figure 47:
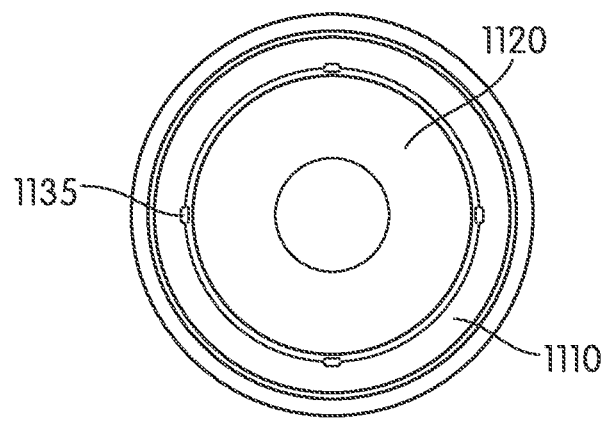
Figure 48:
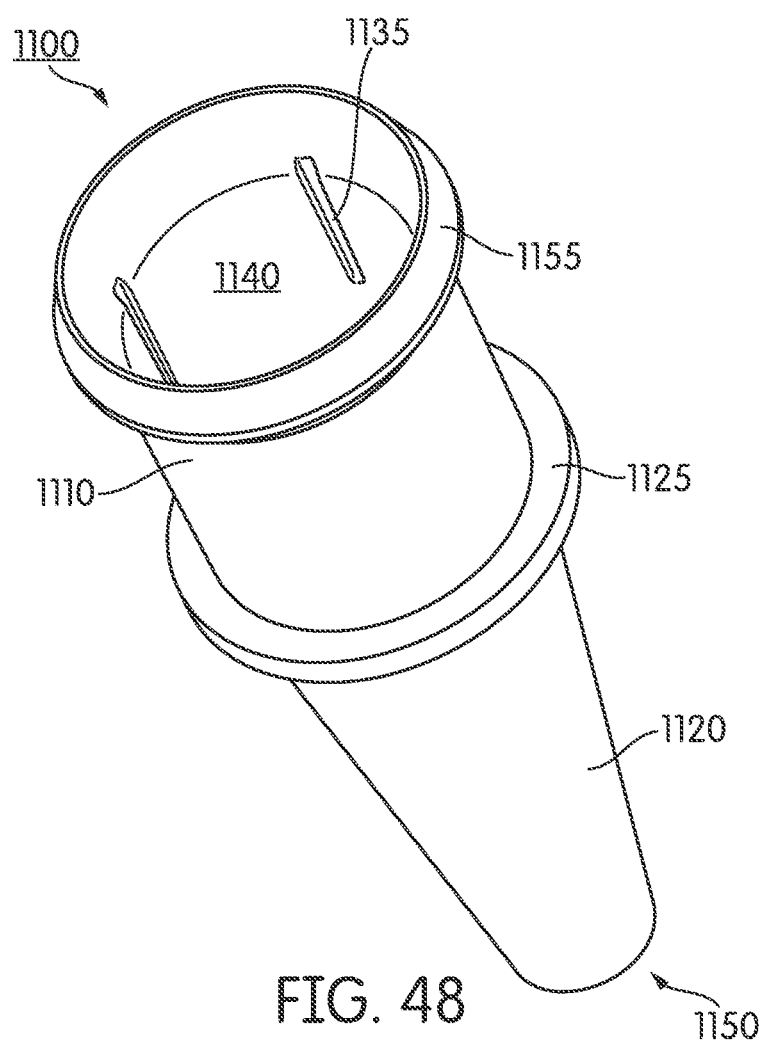

In some embodiments, diagnostic system 10 can be used to perform two or more assays that include nucleic acid amplification reactions that require different reagents, including one or more unit-dose reagents. FIG. 44 illustrates a method of using diagnostic system 10, which includes first module 100 and second module 400, according to one such embodiment.

At step 862, a plurality of samples is loaded in diagnostic system 10. A first sample subset of the plurality of samples has been designated for at least one assay, and a second sample subset of the plurality of samples has been designated for at least one different assay. In some embodiments, barcodes on the sample receptacles indicate the appropriate assay, and in other embodiments, the assay is entered manually into the system by an operator using a user-interface of diagnostic system 10.

In some embodiments, a first assay comprising a first nucleic amplification reaction has been designated for the first sample subset. For example, the first nucleic amplification reaction can be PCR, and the target nucleic acid can be a nucleic acid associated with a particular virus or organism, for example. In some embodiments, the first nucleic amplification reaction uses a unit-dose reagent stored and operatively accessible within the diagnostic system 10. For example, the first nucleic amplification reaction can be PCR or any other desired thermal cycling reaction that can be performed by second module 400 of diagnostic system 10.

In some embodiments, a second assay comprising a second nucleic amplification reaction will be designated for the second sample subset. The second nucleic amplification reaction may be the same or a different nucleic acid amplification reaction than the first nucleic acid amplification reaction of the first assay, but the reagent used in the second nucleic amplification reaction may target a different nucleic acid than the target of the first reagent used in the first assay in some embodiments. In some embodiments, the second nucleic amplification reaction can be PCR or any other desired thermal cycling reaction that is performed, for example, by second module 400 of diagnostic system 10. In some embodiments, the second nucleic amplification reaction is TMA or any other isothermal reaction that is performed, for example, by first module 100 of diagnostic system 10. The reagent used for the second assay can be a unit-dose reagent different than the unit-dose reagent used for the first assay, a bulk reagent, or both. For example, if the second nucleic amplification reaction is PCR, the second reagent used in the second assay can be a unit-dose reagent, and if the second nucleic amplification reaction is TMA, the second reagent used in the second assay can be a bulk reagent. In some embodiments, the second unit-dose reagent, the first bulk reagent, or both are stored and operatively accessible within diagnostic system 10.

Each of the first and second assays has a temporal workflow schedule associated with the respective assay. In some embodiments, at step 864, the diagnostic system 10 coordinates the schedule for performing the first assay with the schedule for performing the second assay such that use of resources of the diagnostic system is maximized. For example, the first assay schedule may require use of one of the substance transfer devices, and the second assay schedule may also require use of the same substance transfer device. Diagnostic system 10 can be configured to shift one or both of schedules such that once the first assay is finished with the substance transfer device, the substance transfer device can be used for the second assay. Such coordination increases throughput and minimizes processing time.

At step 866, diagnostic system 10 performs the first assay on the first sample subset. At step 868, diagnostic system 10 begins to perform the second assay on the second sample subset. Accordingly, diagnostic system 10, which stores and provides operative access to the first unit-dose reagent used in the first assay and at least one of the second unit-dose reagent or the first bulk reagent used in the second assay, performs both steps 866 and 868 according to an embodiment. In some embodiments, step 868 starts while step 866 is being performed—the diagnostic system can simultaneously perform the first assay and the second assay. In some embodiments, during steps 866 and 868 when the respective assays require a unit-dose reagent, for example, for a PCR assay, diagnostic system 10 verifies whether a reagent pack 760 containing the required reagent is positioned at one of the loading stations 640. If not, the distributor system replaces a reagent pack 706 located at the loading station 640 with a reagent pack 760 containing the unit-dose reagent needed for the requested assay. In some embodiments, step 868 starts after step 866 is completed. And in some embodiments, although step 868 can start after step 866, step 868 can be completed before step 866 is completed.

In some embodiments, diagnostic system 10 can alternate between step 866 and 868. For example, diagnostic system 10 can perform the first assay on a first sample of the first sample subset, and then perform the second assay on a first sample of the second sample subset. Diagnostic system 10 can then switch back to step 866 and perform the first assay on a second sample of the first sample subset.

In some embodiments, the first assay and the second assay each comprise preparing the respective sample subsets using a second bulk reagent different than the first bulk reagent that may be used in the second nucleic acid amplification reaction. For example, each sample of the first and second sample subsets can be prepared according to process 800 described above referencing FIG. 41.

In some embodiments, the first sample subset and the second sample subset comprise different samples. In some embodiments, the first sample subset and the second sample subset comprise the same samples. In such embodiments, multiple assays, for example, the first and second assays explained above, are performed on the same samples.

In some embodiments, steps 866 and 868 are performed without additional equipment preparation (for example, wiping down the equipment of diagnostic system 10), reagent preparation (replacing reagent bottles stored in diagnostic system 10), and consumable preparation (replacing empty tip trays).

Hardware and Software

Aspects of the disclosure are implemented via control and computing hardware components, user-created software, data input components, and data output components. Hardware components include computing and control modules (e.g., system controller(s)), such as microprocessors and computers, configured to effect computational and/or control steps by receiving one or more input values, executing one or more algorithms stored on non-transitory machine-readable media (e.g., software) that provide instruction for manipulating or otherwise acting on the input values, and output one or more output values. Such outputs may be displayed or otherwise indicated to an operator for providing information to the operator, for example information as to the status of the instrument or a process being performed thereby, or such outputs may comprise inputs to other processes and/or control algorithms Data input components comprise elements by which data is input for use by the control and computing hardware components. Such data inputs may comprise positions sensors, motor encoders, as well as manual input elements, such as graphic user interfaces, keyboards, touch screens, microphones, switches, manually-operated scanners, voice-activated input, etc. Data output components may comprise hard drives or other storage media, graphic user interfaces, monitors, printers, indicator lights, or audible signal elements (e.g., buzzer, horn, bell, etc.).

Software comprises instructions stored on non-transitory computer-readable media which, when executed by the control and computing hardware, cause the control and computing hardware to perform one or more automated or semi-automated processes.

While the present disclosure has been described and shown in considerable detail with reference to certain illustrative embodiments, including various combinations and sub-combinations of features, those skilled in the art will readily appreciate other embodiments and variations and modifications thereof as encompassed within the scope of the present disclosure. Moreover, the descriptions of such embodiments, combinations, and sub-combinations is not intended to convey that the disclosure requires features or combinations of features other than those expressly recited in the claims. Accordingly, the present disclosure is deemed to include all modifications and variations encompassed within the scope of the following appended claims.

The invention claimed is:

1. A system for performing a nucleic acid amplification assay, the system comprising:

a receptacle holder formed from a thermally-conductive material and comprising a receptacle well, wherein the receptacle well is configured to conform to an outer surface of a lower portion of a vial, and wherein the receptacle holder includes a through-hole extending from a bottom center of an inner surface of the receptacle well to a bottom outer surface of the receptacle holder;

a thermal element positioned proximal to the receptacle holder for altering a temperature of the receptacle holder;

a signal detection module in optical communication with the receptacle well via the through-hole of the receptacle well, wherein the signal detection module is configured to generate an excitation signal that is directed through the through-hole of the receptacle well and to detect an optical emission from a fluid contained in a vial supported by the receptacle well and through the through-hole of the receptacle well;

a capped vial comprising a cap and a vial containing a fluid comprising a sample and a nucleic acid amplification reagent; and a robotic pipettor; comprising a probe configured to be inserted into the cap;

wherein the receptacle well supports the capped vial, the cap of the capped vial comprising an opaque cap in a snap-fit relationship with the vial containing the fluid comprising the sample and the nucleic acid amplification reagent, the cap and the vial each being a single piece of plastic, wherein an upper portion of the cap is situated above the vial and defines a probe recess, a rim at a top end of the cap and fully circumscribing the upper portion of the cap, the upper portion of the cap being configured for frictional engagement with an end of the probe of the robotic pipettor when the end of the probe is inserted into the probe recess;

wherein a lower portion of the vial is contained within the receptacle well, and wherein the cap is situated above a top surface of the receptacle holder.

2. The system of claim 1, wherein an outer surface of a lower portion of the cap of the capped vial is in sealing contact with an inner surface of an upper portion of the vial.

3. The system of claim 2, wherein the vial comprises a lock collar and the cap comprises a corresponding latch collar, the latch collar including one or more locking members extending toward a lower portion of the cap, and wherein the one or more locking members are in inter-locking engagement with the lock collar.

4. The system of claim 1, wherein the thermal element is positioned proximal to a side surface of the receptacle holder, and wherein the thermal element provides thermal energy through the receptacle holder to the receptacle well.

5. The system of claim 1, wherein the thermal element is configured to cyclically vary the temperature of the receptacle holder.

6. The system of claim 1, wherein the signal detection module comprises an excitation signal source and an emission signal detector, and the system further comprises at least one optical fiber comprising a first end and a second end, the first end of the at least one optical fiber being in optical communication with the receptacle well through the through-hole of the receptacle well, and the second end of the at least one optical fiber being in optical communication with at least one of the excitation signal source and the emission signal detector.

7. The system of claim 6, wherein the excitation signal source is configured to generate an excitation signal at a predetermined wavelength.

8. The system of claim 7, wherein the emission signal detector is configured to detect the optical emission signal by receiving an optical emission from the fluid contained in the vial and generating a voltage signal corresponding to an intensity of the received optical emission.

9. The system of claim 6, wherein the second end of the at least one optical fiber is in optical communication with the excitation signal source and the emission signal detector.

10. The system of claim 6, wherein the excitation signal source is configured to generate an excitation signal at a predetermined wavelength, and wherein the emission signal detector is configured to detect the optical emission signal by receiving an optical emission from the fluid contained in the vial and generating a voltage signal corresponding to an intensity of the received optical emission.

11. The system of claim 1, wherein the system does not include a cover configured to move between a first position blocking access of the robotic pipettor to the capped vial and a second position allowing the robotic pipettor to access the capped vial.

12. The system of claim 1, further comprising a centrifuge configured to receive the capped vial, wherein the robotic pipettor is configured to transfer the capped vial to a first location of the centrifuge when the end of the probe of the robotic pipettor is frictionally engaged with the upper portion of the cap.

13. The system of claim 12, the robotic pipettor further comprising a vial transfer arm comprising the probe configured for frictional engagement with the upper portion of the cap when the probe is inserted into the probe recess, the vial transfer arm being further configured to transfer the capped vial from a second location of the centrifuge to the receptacle well, the first and second locations of the centrifuge being different locations.

14. The system of claim 12, wherein the robotic pipettor is further configured to transfer the capped vial from a second location of the centrifuge to the receptacle well, the first and second locations of the centrifuge being different locations.

15. The system of claim 2, wherein the vial comprises a pair of opposed latch hooks and the cap comprises a latch collar, the latch hooks in inter-locking engagement with the latch collar, where the latch collar is situated beneath the latch hooks.

16. The system of claim 15, wherein the cap further comprises an annular collar and a lower portion situated beneath the annular collar, the lower portion of the cap being frictionally fit within the upper portion of the vial.

17. The system of claim 16, wherein the lower portion of the cap comprises a plug having a closed end that extends into the upper portion of the vial.

18. The system of claim 17, wherein the plug comprises a seal ring that is in contact with the inner surface of the upper portion of the vial, thereby providing the sealing contact.

19. The system of claim 16, wherein the plug has a convex distal end surface.

20. The system of claim 1, wherein the nucleic acid amplification reagent includes a polymerase and nucleoside triphosphates, and wherein the fluid further comprises a detection reagent including a detection probe having interacting labels, the interacting labels including an emission moiety and a quencher moiety.

21. The system of claim 20, wherein the signal detection module is configured to periodically detect emissions from the emission moiety during a nucleic acid amplification reaction performed in the fluid contained in the capped vial.

22. The system of claim 21, wherein the emission moiety is a fluorescent moiety.

23. The system of claim 3, wherein the cap further comprises a lower portion having a closed lower end, the closed lower end defining a plug that extends into the upper portion of the vial, and wherein an annular rib on an outer surface of the plug is in contact with the inner surface of the upper portion of the vial, thereby providing the sealing sealing contact.

24. The system of claim 23, wherein the plug extends beneath the latch collar.

25. The system of claim 24, wherein vial further comprises a ring formed on an outer surface of the vial, the ring sitting on a top surface of the receptacle holder, and wherein the plug terminates at a position between the ring and the latch collar.

* * * * *